US012104196B2

(12) United States Patent
Lavoie et al.

(10) Patent No.: US 12,104,196 B2
(45) Date of Patent: Oct. 1, 2024

(54) INFLUENZA VIRUS HEMAGGLUTININ MUTANTS

(71) Applicant: MEDICAGO INC., Quebec (CA)

(72) Inventors: Pierre-Olivier Lavoie, Quebec (CA); Aurelien Lorin, Quebec (CA); Alain Doucet, Quebec (CA); Marc-Andre D'Aoust, Quebec (CA); Manon Couture, Quebec (CA)

(73) Assignee: ARAMIS BIOTECHNOLOGIES INC., Quebec (CA)

( * ) Notice: Subject to any disclaimer, the term of this patent is extended or adjusted under 35 U.S.C. 154(b) by 399 days.

(21) Appl. No.: 17/255,526

(22) PCT Filed: Jun. 27, 2019

(86) PCT No.: PCT/CA2019/050893

§ 371 (c)(1),
(2) Date: Dec. 23, 2020

(87) PCT Pub. No.: WO2020/000101

PCT Pub. Date: Jan. 2, 2020

(65) Prior Publication Data

US 2021/0221853 A1 Jul. 22, 2021

Related U.S. Application Data

(60) Provisional application No. 62/690,780, filed on Jun. 27, 2018.

(51) Int. Cl.

| | |
|---|---|
| ***C07K 14/005*** | (2006.01) |
| ***A61K 39/145*** | (2006.01) |
| ***A61P 31/16*** | (2006.01) |
| ***A61P 37/04*** | (2006.01) |
| ***C07K 14/11*** | (2006.01) |
| ***C07K 16/10*** | (2006.01) |
| ***C12N 7/00*** | (2006.01) |
| ***C12N 15/82*** | (2006.01) |
| ***C12P 21/02*** | (2006.01) |
| *A61K 38/00* | (2006.01) |
| *A61K 39/00* | (2006.01) |

(52) U.S. Cl.

CPC ............ *C12P 21/02* (2013.01); *A61K 39/145* (2013.01); *A61P 31/16* (2018.01); *A61P 37/04* (2018.01); *C07K 14/005* (2013.01); *C07K 14/11* (2013.01); *C07K 16/10* (2013.01); *C07K 16/1018* (2013.01); *C12N 7/00* (2013.01); *C12N 15/8257* (2013.01); *C12N 15/8258* (2013.01); *A61K 38/00* (2013.01); *A61K 2039/5258* (2013.01); *C12N 2760/16023* (2013.01); *C12N 2760/16033* (2013.01); *C12N 2760/16122* (2013.01); *C12N 2760/16123* (2013.01); *C12N 2760/16134* (2013.01); *C12N 2760/16152* (2013.01)

(58) Field of Classification Search

None

See application file for complete search history.

(56) References Cited

U.S. PATENT DOCUMENTS

| | | | |
|---|---|---|---|
| 2013/0315955 A1 | 11/2013 | Holtz et al. | |
| 2016/0122777 A1 | 5/2016 | Couture et al. | |
| 2017/0189519 A1 | 7/2017 | Nabel et al. | |
| 2021/0162037 A1 | 6/2021 | Jasny et al. | |

FOREIGN PATENT DOCUMENTS

| | | | |
|---|---|---|---|
| EP | 2570484 | A1 | 3/2013 |
| JP | 2016514674 | A | 5/2016 |
| JP | 2021528971 | A | 10/2021 |
| JP | 2021528972 | A | 10/2021 |
| WO | WO2009009876 | A1 | 1/2009 |
| WO | WO2009076778 | A1 | 6/2009 |
| WO | WO2010003225 | A1 | 1/2010 |
| WO | WO2010003235 | A1 | 1/2010 |
| WO | WO2010006452 | A1 | 1/2010 |
| WO | WO2010148511 | A1 | 12/2010 |
| WO | WO2011035422 | A1 | 3/2011 |
| WO | 2013044390 | A1 | 4/2013 |

(Continued)

OTHER PUBLICATIONS

Eshaghi et al. Genetic characterization of seasonal influenza A (H3N2) viruses in Ontario during 2010-2011 influenza season: high prevalence of mutations at antigenic sites, Influenza Journal, 2014, vol. 8, No. 2, pp. 250-256.*

(Continued)

*Primary Examiner* — Benjamin P Blumel

(74) *Attorney, Agent, or Firm* — RAPHAEL BELLUM PLLC; Stephen C. Bellum

(57) ABSTRACT

The present invention relates to the production of modified influenza viral proteins in plants. More specifically, the present invention relates to producing and increasing influenza virus-like particle (VLP) production in plants, wherein the VLPs comprise the modified influenza viral proteins, such as modified influenza hemagglutinin (HA). The HA protein may comprising an amino acid sequence comprising at least one substitution when compared to a corresponding wildtype amino acid sequence. Further provided are nucleic acid encoding the modified HA protein. Furthermore methods of producing an influenza virus like particle (VLP) and methods of increasing yield of production of an influenza virus like particle (VLP) in a plant, portion of a plant, or a plant cell, are also provided.

15 Claims, 21 Drawing Sheets

Specification includes a Sequence Listing.

(56) References Cited

FOREIGN PATENT DOCUMENTS

| | | | |
|---|---|---|---|
| WO | WO2013079473 | A1 | 6/2013 |
| WO | WO2013177444 | A2 | 11/2013 |
| WO | 2014151488 | A1 | 9/2014 |
| WO | WO2014153674 | A1 | 10/2014 |
| WO | WO2014191435 | A1 | 12/2014 |
| WO | WO2015020913 | A2 | 2/2015 |
| WO | 2017/191258 | A1 | 11/2017 |
| WO | WO2018073340 | A1 | 4/2018 |
| WO | 2018078053 | A1 | 5/2018 |
| WO | 2020/000100 | A1 | 1/2020 |
| WO | 2020000101 | A1 | 1/2020 |

OTHER PUBLICATIONS

Garten et al. Hemagglutinin Influenza A virus (A/California/07/2009 (H1N1)) GenBank Accession ACP44119, Jun. 1, 2009.*
Ha, Y., et al. H5 avian and H9 swine influenza virus haemagglutinin structures: possible origin of influenza subtypes. The EMBO Journal (2002) 21(5): 865-875.
Castelan-Vega et al. The hemagglutinin of the infuenza A(H1N1)pdm09 is mutating towards stability. (Adv Appl Bioinform Chem. 2014;7:37-44).
Cotter, Christopher et al. A single amino acid in the stalk region of the H1N1pdm Influenza Virus HA protein affects viral fusion, stability and infectivity. (PLoS Pathog. 2014; 10(1):e1003831.
Antanasijevic et al. (J Biol Chem. 2014;289(32):22237-45).
Lu, Yuan, et al. Production and stabilization of the trimeric influenza hemagglutinin stem domain for potentially broadly protective influenza vaccines. (Proc Natl Acad Sci USA. 2014; 111(1):125-30).
Holtz, Kathleen M., et al. Modifications of cystine residues in the transmembrane cytoplasmic domains of a recombinant hemagglutinin protein prevent cross-linked multimer formation and potency loss. (BMC Biotechnology. 2014;14:111.
Air, Gillian. Sequence relationships among the hemagglutinin genes of 12 subtypes of influenza A Virus. Pros. Nat'l Academy of Sciences USA. (1981) vol. 78:12, 7639-7643.
Suzuki, Yoshiyuki, and NEI, Masatoshi Origin and Evolution of Influenza Virus Hemagglutinin Genes. Mol. Biol. Evol. 2002, 19:501-509.
Fouchier, Ron A.M., et al., Characterization of a novel influenza A virus Hemagglutinin subtype (H16) obtaind from Black-headed gulls. J Virol. Mar. 2005; 79(5):2814-22.
Ben-Bassat, Arie, et al. Processing of the Initiation methionine from proteins: properties of the *Escherichia coli* methionine aminopeptidase and its gene structure. (J. Bacteriol, 169:751-757, 1987).
O'Regan, Michael et al. Cloning and nucleotide sequence of the phosphoenolpyruvate carboxylase-coding gene of Corynebacterium glutamicum ATCC13032. (Gene, 77:237-251, 1989).
Sahin-Toth, Miklos et al. Cysteine scanning mutagenesis of the N-terminal 32 amino acid residues in the lactose permease of *Escherichia coli*. (Protein Scl, 3:240-247, 1994).
Hochuli, E., et al Genetic approach to facilitate purification of recombinant proteins with a novel metal chelate adsorbent. Nature Biotechnology, 6:1321-1325, 1988).
Henikoff, Steven, et al., Amino acid substitution matrices from protein blocks. Proc. Natl. Acad. Sci. USA, 89:10915-10919, 1992.
Yang et al. (Structural stability of influenza A(H1N1)pdm09 virus hemagglutinins, J. Virol.2014;88(9):4828-4838).
Clark, Amelia, et al. Antigenicity of the 2015-2016 seasonal H1N1 human influenza virus HA and HA proteins. PLOS one 2017, pp. 1-27.
GenBank accession A0A1D8H6M7. May 23, 2018.
UniProt Accession AOA1P7ZM40. Apr. 12, 2017.
UniProt Accession A0A1I9TUY4. Feb. 15, 2017.
Thyagarajan, Bargavi, et al. The inherent mutational tolerance and antigenic evolvability of influenza hemagglutinin. eLife Jul. 8, 2014, pp. 1-26.
GenBank AOZ84818.1.
Brooke, C.D. Biological activities of "noninfectious" influenza A virus particles. Future Virol. 2014, vol. 9(1), pp. 41-51.
Zhang, S., et al. Comparative characterization of the glycosylation profiles of an influenza hemagglutinin produced in plant and insect hosts. Proteomics, 2012 12(8), pp. 1269-1288.

* cited by examiner

Figure 1

```
HA0_A-Bang-3007-15_H3N2        QKIPGNDNSTATLCLGHHAVPNGTIVKTITNDRIEVTNATELVQNSSIGEICDSPHQILD 60
HA0_A-HK-4801-14_H3N2          QKIPGNDNSTATLCLGHHAVPNGTIVKTITNDRIEVTNATELVQNSSIGEICDSPHQILD 60
HA0_A-Minn-40-15_H3N2          QKIPGNDNSTATLCLGHHAVPNGTIVKTITNDRIEVTNATELVQNSSIGEICDSPHQILD 60
HA0_A-SAus-1-16_H3N2           QKIPGNDNSTATLCLGHHAVPNGTIVKTITNDRIEVTNATELVQNSSIGEICDSPHQILD 60
HA0_A-Penn-09-15_H3N2          QKLPGNDNSTATLCLGHHAVPNGTIVKTITNDRIEVTNATELVQNSSIGEICDSPHQILD 60
HA0_A-Switz-9715293-13_H3N2    QKLPGNDNSTATLCLGHHAVPNGTIVKTITNDRIEVTNATELVQNSSIGEICDSPHQILD 60
HA0_A-Miss-16-16_H3N2          QKLPGNDNSTATLCLGHHAVPNGTIVKTITNDRIEVTNATELVQNSSIGEICDSPHQILD 60
                               **:*********************************************************

HA0_A-Bang-3007-15_H3N2        GENCTLIDALLGDPQCDGFQNKKWDLFVERSKAYSNCYPYDVPDYASLRSLVASSGTLEF 120
HA0_A-HK-4801-14_H3N2          GENCTLIDALLGDPQCDGFQNKKWDLFVERSKAYSNCYPYDVPDYASLRSLVASSGTLEF 120
HA0_A-Minn-40-15_H3N2          GENCTLIDALLGDPQCDGFQNKKWDLFVERSKAYSNCYPYDVPDYASLRSLVASSGTLEF 120
HA0_A-SAus-1-16_H3N2           GENCTLIDALLGDPQCDGFQNKKWDLFVERSKAYSNCYPYDVPDYASLRSLVASSGTLEF 120
HA0_A-Penn-09-15_H3N2          GKNCTLIDALLGDPQCDGFQNKRWDLFVERSKAYSNCYPYDVPDYASLRSLVASSGTLEF 120
HA0_A-Switz-9715293-13_H3N2    GENCTLIDALLGDPQCDGFQNKKWDLFVERSKAYSNCYPYDVPDYASLRSLVASSGTLEF 120
HA0_A-Miss-16-16_H3N2          GENCTLIDALLGDPQCDGFQNKKWDLFVERSRAYSNCYPYDVPDYASLRSLVASSGTLEF 120
                               *:********************:********:****************************

HA0_A-Bang-3007-15_H3N2        NNESFNWTGVTQNGTSSACIRKSSSSFFSRLNWLTHLNYTYPALNVTVPNNEQFDKLYIW 180
HA0_A-HK-4801-14_H3N2          NNESFNWTGVTQNGTSSACIRRSSSSFFSRLNWLTHLNYTYPALNVTMPNNEQFDKLYIW 180
HA0_A-Minn-40-15_H3N2          NNESFNWTGVTQNGTSSACIRRSSSSFFSRLNWLTHLNYTYPALNVTMPNKEQFDKLYIW 180
HA0_A-SAus-1-16_H3N2           KNESFNWTGVTQNGTSSACIRRSSSSFFSRLNWLTHLNYTYPALNVTMPNKEQFDKLYIW 180
HA0_A-Penn-09-15_H3N2          NDESFNWAGVTQNGTSSACIRGSNSSFFSRLNWLTHSNFKYPALNVTMPNNEQFDKLYIW 180
HA0_A-Switz-9715293-13_H3N2    NNESFNWAGVTQNGTSSSCIRGSNSSFFSRLNWLTHLNSKYPALNVTMPNNEQFDKLYIW 180
HA0_A-Miss-16-16_H3N2          NNESFNWAGVTQNGTSSSCIRGSNSSFFSRLNWLTHLNSKYPALNVTMPNNEQFDKLYIW 180
                               ::*****:*********:*** *.************ * .*******:**:*********

HA0_A-Bang-3007-15_H3N2        GVHHPGTDKDQIFLYARSSGRITVSTKRSQQAVIPNIGSRPRIRDIPSRISIYWTIVKPG 240
HA0_A-HK-4801-14_H3N2          GVHHPGTDKDQIFLYAQSSGRITVSTKRSQQAVIPNIGSRPRIRDIPSRISIYWTIVKPG 240
HA0_A-Minn-40-15_H3N2          GVHHPGTDKDQIFLYAQSSGRITVSTKRSQQAVIPNIGSRPRIRDIPSRISIYWTIVKPG 240
HA0_A-SAus-1-16_H3N2           GVHHPGTDKDQIFLYAQSSGRITVSTKRSQQAVIPNIGSRPRIRDIPSRISIYWTIVKPG 240
HA0_A-Penn-09-15_H3N2          GVHHPGTDKDQIFLYAQSSGRITVSTKRSQQAVIPNIGSRPRIRNIPSRISIYWTIVKPG 240
HA0_A-Switz-9715293-13_H3N2    GVHHPGTDKDQIFLYAQSSGRITVSTKRSQQAVIPNIGSRPRIRDIPSRISIYWTIVKPG 240
HA0_A-Miss-16-16_H3N2          GVHHPGTDKDQIFLYAKPSGRITVSTKRSQQAVIPNIGSRPRIRDIPSRISIYWTIVKPG 240
                               ****************: *************************:****************

HA0_A-Bang-3007-15_H3N2        DILLINSTGNLIAPRGYFKIRSGKSSIMRSDAPIGKCKSECITPNGSIPNDKPFQNVNRI 300
HA0_A-HK-4801-14_H3N2          DILLINSTGNLIAPRGYFKIRSGKSSIMRSDAPIGKCKSECITPNGSIPNDKPFQNVNRI 300
HA0_A-Minn-40-15_H3N2          DILLINSTGNLIAPRGYFKIRSGKSSIMRSDAPIGKCKSECITPNGSIPNDKPFQNVNRI 300
HA0_A-SAus-1-16_H3N2           DILLINSTGNLIAPRGYFKIRSGKSSIMRSDAPIGKCKSECITPNGSIPNDKPFQNVNRI 300
HA0_A-Penn-09-15_H3N2          DILLINSTGNLIAPRGYFKIQSGKSSIMRSDAPIGKCKSECITPNGSIPNDKPFQNVNRI 300
HA0_A-Switz-9715293-13_H3N2    DILLINSTGNLIAPRGYFKIRSGKSSIMRSDAPIGKCKSECITPNGSIPNDKPFQNVNRI 300
HA0_A-Miss-16-16_H3N2          DILLINSTGNLIAPRGYFKIRSGKSSIMRSDAPIGKCKSECITPNGSIPNDKPFQNVNRI 300
                               ********************:***************************************
```

Continuation of Fig 1

```
HA0_A-Bang-3007-15_H3N2        TYGACPRYVKHSTLKLATGMRNVPEKQTRGIFGAIAGFIENGWEGMVDGWYGFRHQNSEG   360
HA0_A-HK-4801-14_H3N2          TYGACPRYVKHSTLKLATGMRNVPEKQTRGIFGAIAGFIENGWEGMVDGWYGFRHQNSEG   360
HA0_A-Minn-40-15_H3N2          TYGACPRYVKHSTLKLATGMRNVPEKQTRGIFGAIAGFIENGWEGMVDGWYGFRHQNSEG   360
HA0_A-SAus-1-16_H3N2           TYGACPRYVKHSTLKLATGMRNVPEKQTRGIFGAIAGFIENGWEGMVDGWYGFRHQNSEG   360
HA0_A-Penn-09-15_H3N2          TYGACPRYVKQSTLKLATGMRNVPEKQTRGIFGAIAGFIENGWEGMKDGWYGFRHQNSEG   360
HA0_A-Switz-9715293-13_H3N2    TYGACPRYVKQSTLKLATGMRNVPERQTRGIFGAIAGFIENGWEGMVDGWYGFRHQNSEG   360
HA0_A-Miss-16-16_H3N2          TYGACPRYVKQNTLKLATGMRNVPERQTRGIFGAIAGFIENGWEGMVDGWYGFRHQNSEG   360
                               **********:.*************:******************** *************

HA0_A-Bang-3007-15_H3N2        RGQAADLKSTQAAIDQINGKLNRLIGKTNEKFHQIEKEFSEVEGRIQDLEKYVEDTKIDL   420
HA0_A-HK-4801-14_H3N2          RGQAADLKSTQAAIDQINGKLNRLIGKTNEKFHQIEKEFSEVEGRIQDLEKYVEDTKIDL   420
HA0_A-Minn-40-15_H3N2          RGQAADLKSTQAAIDQINGKLNRLIGKTNEKFHQIEKEFSEVEGRVQDLEKYVEDTKIDL   420
HA0_A-SAus-1-16_H3N2           RGQAADLKSTQAAIDQINGKLNRLIGKTNEKFHQIEKEFSEVEGRVQDLEKYVEDTKIDL   420
HA0_A-Penn-09-15_H3N2          RGQAADLKSTQAAIDQINGKLNRLIGKTNEKFHQIEKEFSEVEGRIQDLEKYVEDTKIDL   420
HA0_A-Switz-9715293-13_H3N2    RGQAADLKSTQAAIDQINGKLNRLIGKTNEKFHQIEKEFSEVEGRIQDLEKYVEDTKIDL   420
HA0_A-Miss-16-16_H3N2          RGQAADLKSTQAAIDQINGKLNRLIGKTNEKFHQIEKEFSEVEGRIQDLEKYVEDTKIDL   420
                               *********************************************:**************

HA0_A-Bang-3007-15_H3N2        WSYNAELLVALENQHTIDLTDSEMNKLFEKTKKQLRENAEDMGNGCFKIYHKCDNACIGS   480
HA0_A-HK-4801-14_H3N2          WSYNAELLVALENQHTIDLTDSEMNKLFEKTKKQLRENAEDMGNGCFKIYHKCDNACIGS   480
HA0_A-Minn-40-15_H3N2          WSYNAELLVALENQHTIDLTDSEMNKLFEKTKKQLRENAEDMGNGCFKIYHKCDNACIGS   480
HA0_A-SAus-1-16_H3N2           WSYNAELLVALENQHTIDLTDSEMNKLFEKTKKQLRENAEDMGNGCFKIYHKCDNACIGS   480
HA0_A-Penn-09-15_H3N2          WSYNAELLVALENQHTIDLTDSEMNKLFEKTKKQLRENAEDMGNGCFKIYHKCDNACIGS   480
HA0_A-Switz-9715293-13_H3N2    WSYNAELLVALENQHTIDLTDSEMNKLFEKTKKQLRENAEDMGNGCFKIYHKCDNACIGS   480
HA0_A-Miss-16-16_H3N2          WSYNAELLVALENQHTIDLTDSEMNKLFEKTKKQLRENAEDMGNGCFKIYHKCDNACIGS   480
                               ************************************************************

HA0_A-Bang-3007-15_H3N2        IRNGTYDHNVYRDEALNNRFQIKGVELKSGYKDWILWISFAISCFLLCVALLGFIMWACQ   540
HA0_A-HK-4801-14_H3N2          IRNGTYDHNVYRDEALNNRFQIKGVELKSGYKDWILWISFAISCFLLCVALLGFIMWACQ   540
HA0_A-Minn-40-15_H3N2          IRNETYDHNVYRDEALNNRFQIKGVELKSGYKDWILWISFAISCFLLCVALLGFIMWACQ   540
HA0_A-SAus-1-16_H3N2           IRNETYDHNVYRDEALNNRFQIKGVELKSGYKDWILWISFAISCFLLCVALLGFIMWACQ   540
HA0_A-Penn-09-15_H3N2          IRNGTYDHDVYRDEALNNRFQIKGVELKSGYKDWILWISFAISCFLLCVALLGFIMWACQ   540
HA0_A-Switz-9715293-13_H3N2    IRNGTYDHDVYRDEALNNRFQIKGVELKSGYKDWILWISFAISCFLLCVALLGFIMWACQ   540
HA0_A-Miss-16-16_H3N2          IRNGTYDHDVYRDEALNNRFQIKGVELKSGYKDWILWISFAISCFLLCVALLGFIMWACQ   540
                               *** ****:***************************************************

HA0_A-Bang-3007-15_H3N2        KGNIRCNICI 550
HA0_A-HK-4801-14_H3N2          KGNIRCNICI 550
HA0_A-Minn-40-15_H3N2          KGNIRCNICI 550
HA0_A-SAus-1-16_H3N2           KGNIRCNICI 550
HA0_A-Penn-09-15_H3N2          KGNIRCNICI 550
HA0_A-Switz-9715293-13_H3N2    KGNIRCNICI 550
HA0_A-Miss-16-16_H3N2          KGNIRCNICI 550
                               **********
```

Figure 4A: Schematic representation of vector 3045
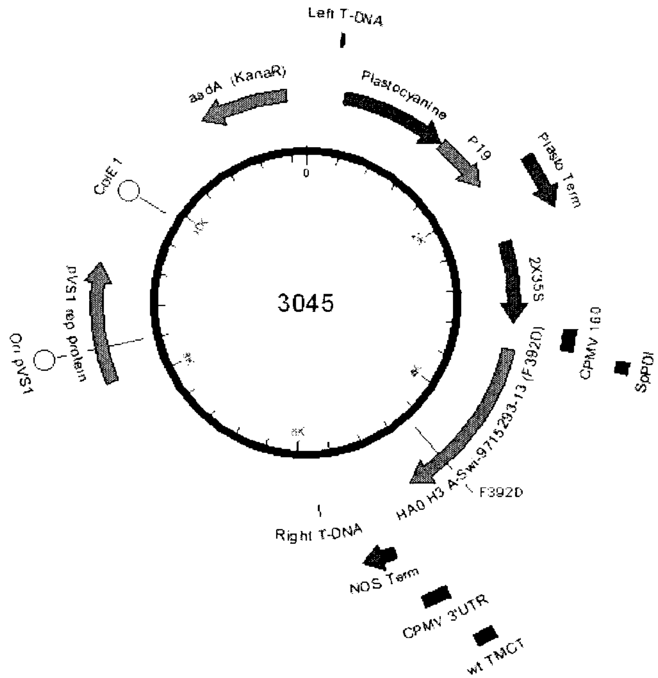
Figure 4B: Schematic representation of vector 3022
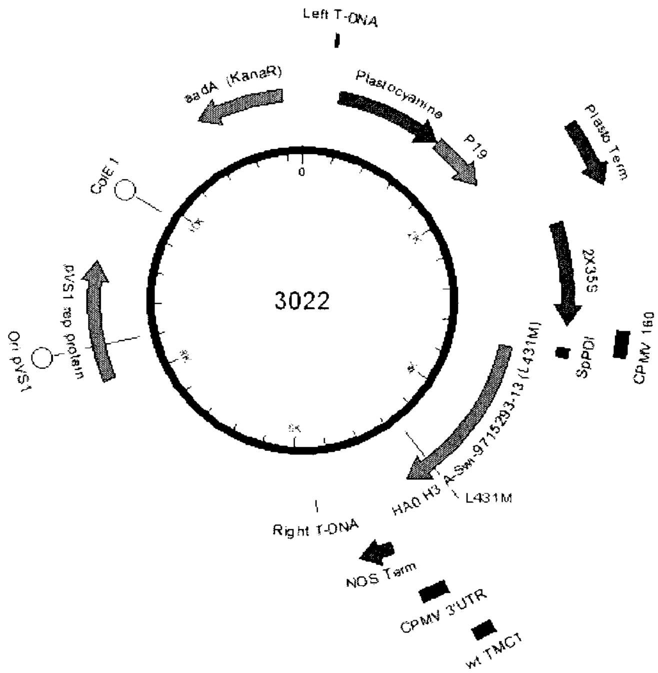

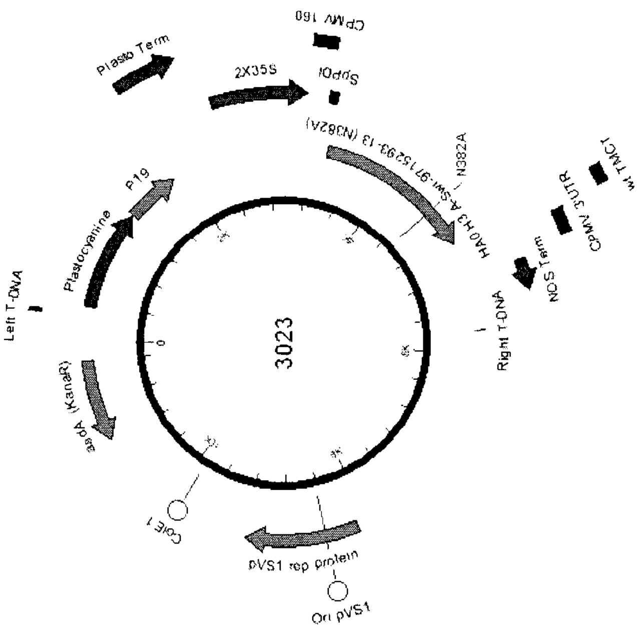
Figure 4C: Schematic representation of vector 3023
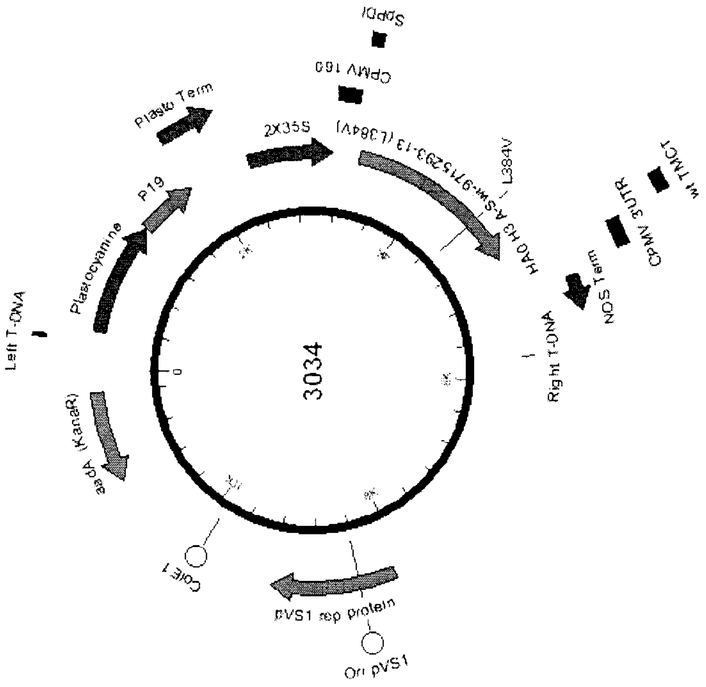
Figure 4D: Schematic representation of vector 3034

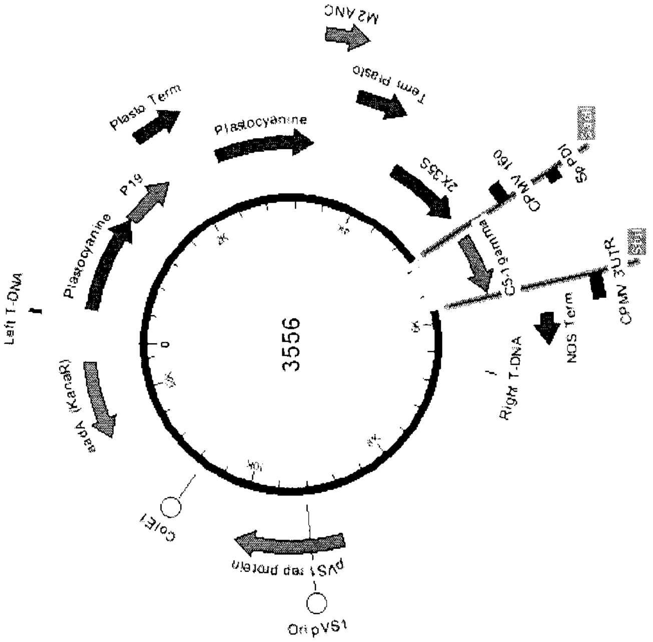
Figure 5A: Schematic representation of vector 3556
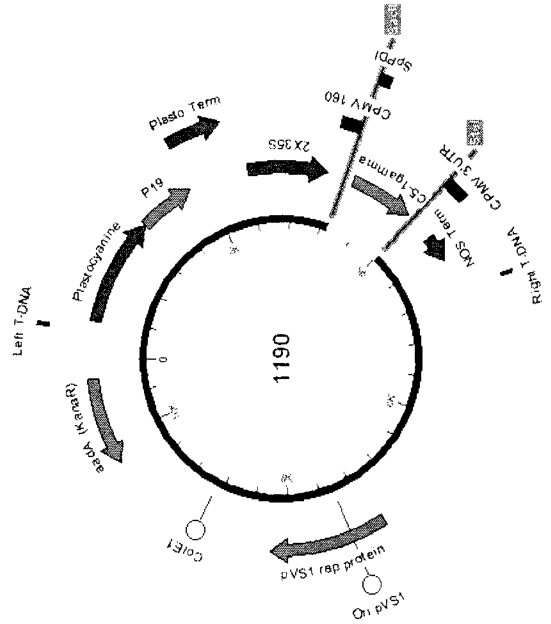
Figure 5B: Schematic representation of vector 1190

Figure 8B: Schematic representation of vector 3341
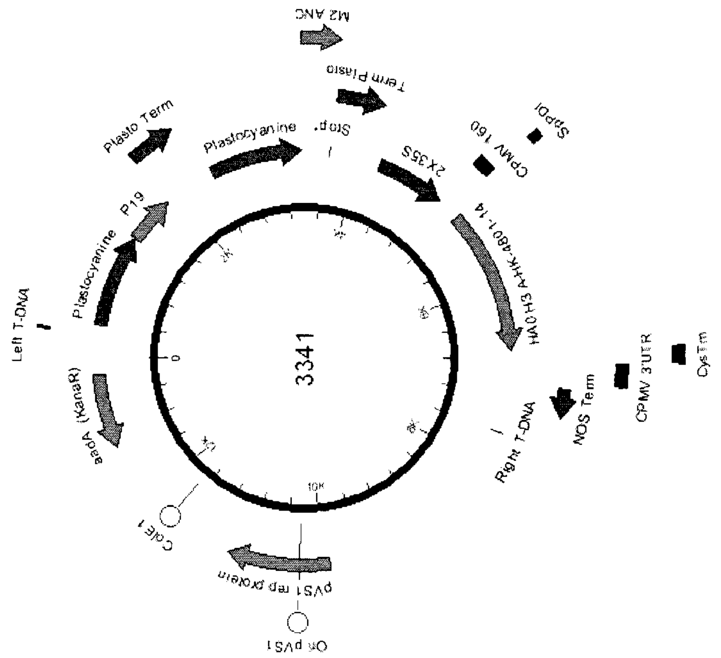
Figure 8A: Schematic representation of vector 3340
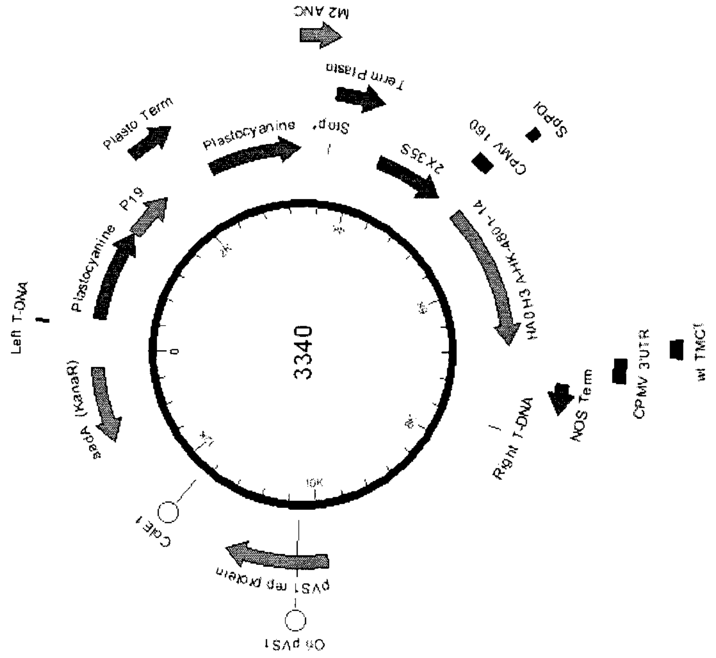

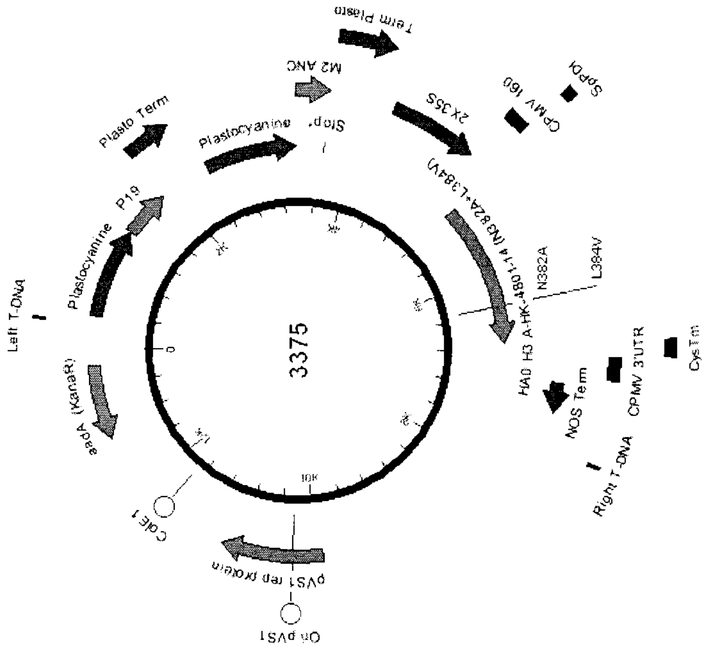
Figure 8C: Schematic representation of vector 3375
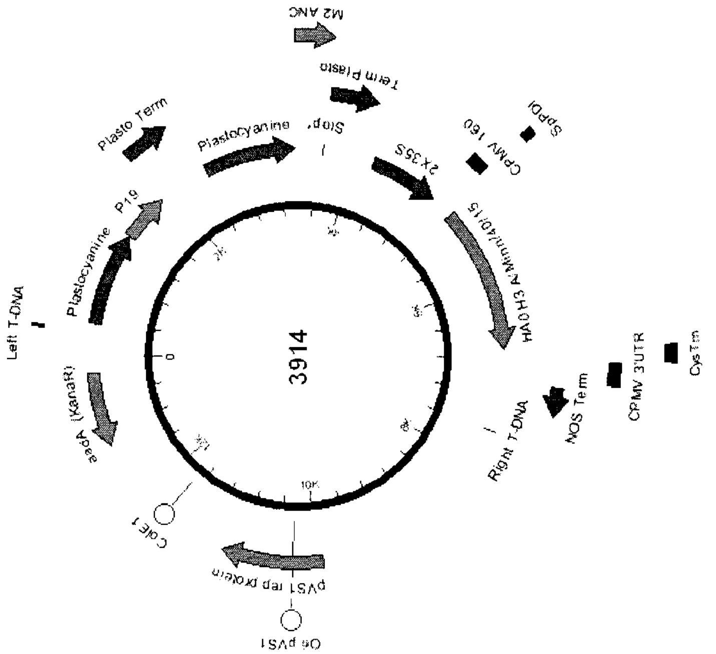
Figure 8D: Schematic representation of vector 3914

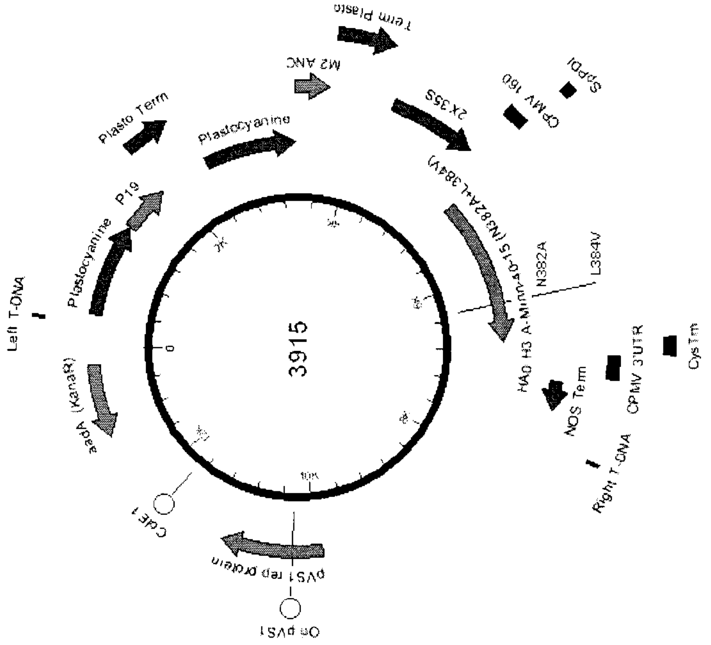
Figure 8E: Schematic representation of vector 3915
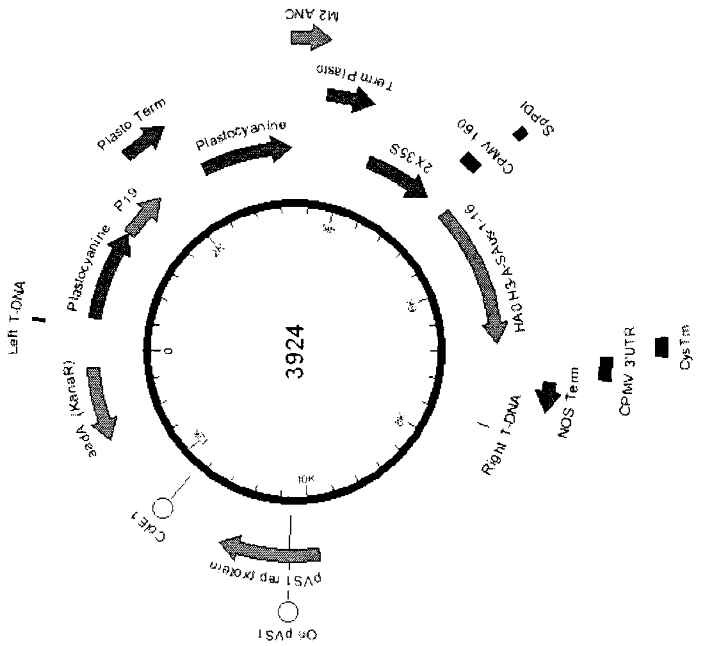
Figure 8F: Schematic representation of vector 3924

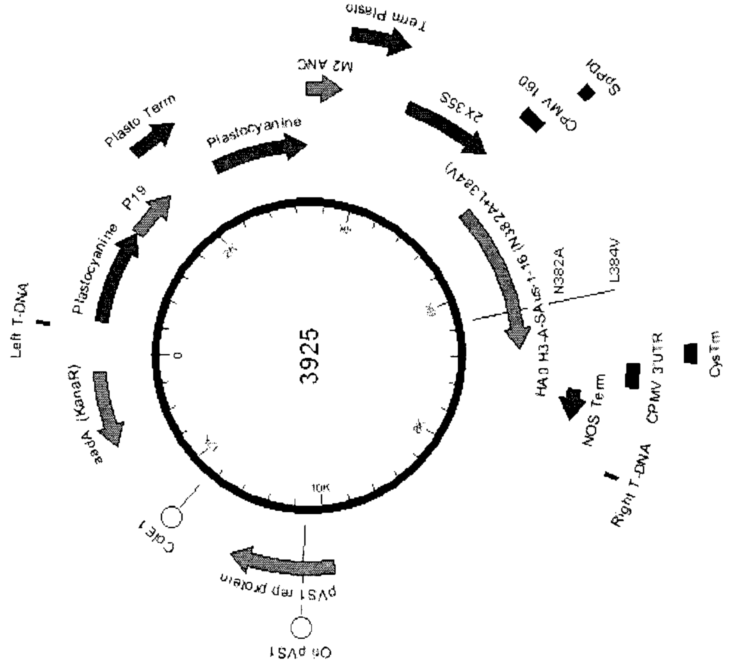
Figure 8G: Schematic representation of vector 3925
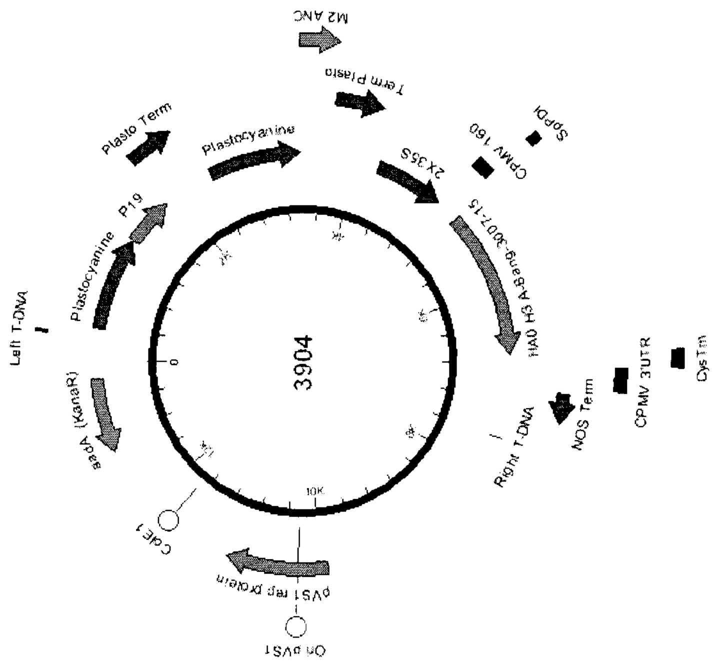
Figure 8H: Schematic representation of vector 3904

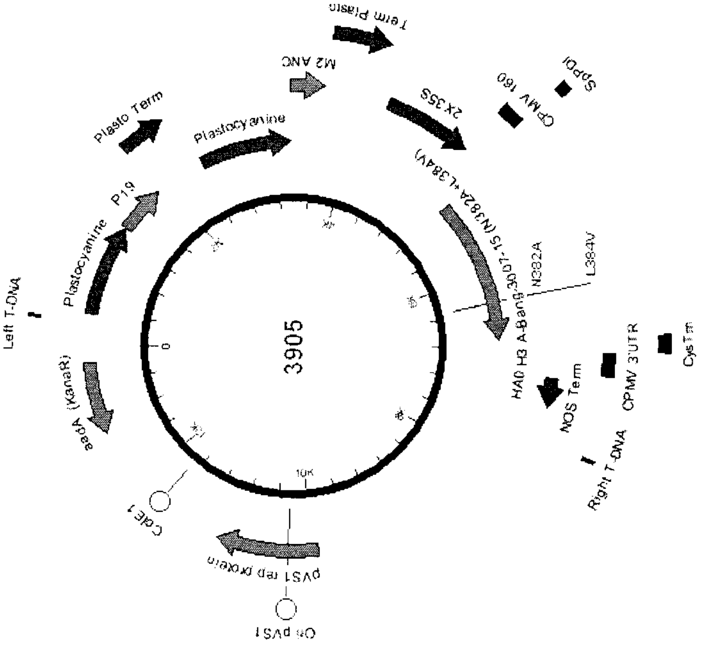
Figure 8I: Schematic representation of vector 3905
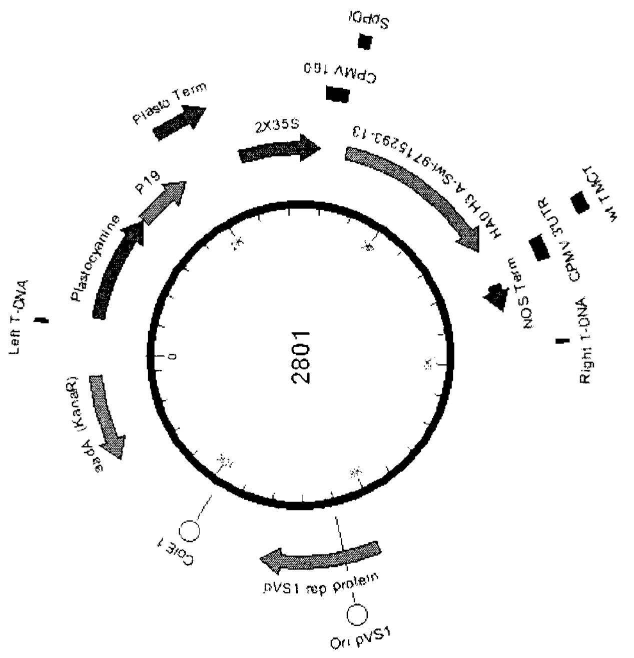
Figure 8J: Schematic representation of vector 2801

Figure 8K: Schematic representation of vector 2811
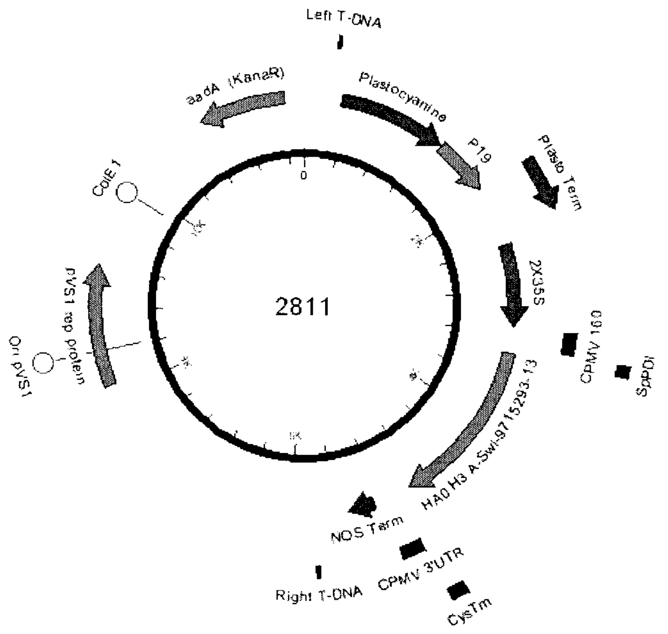
Figure 8L: Schematic representation of vector 3063
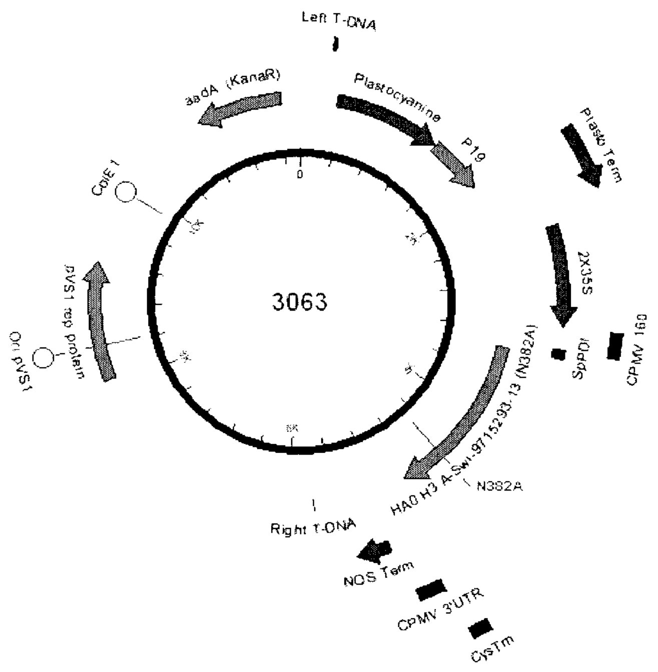

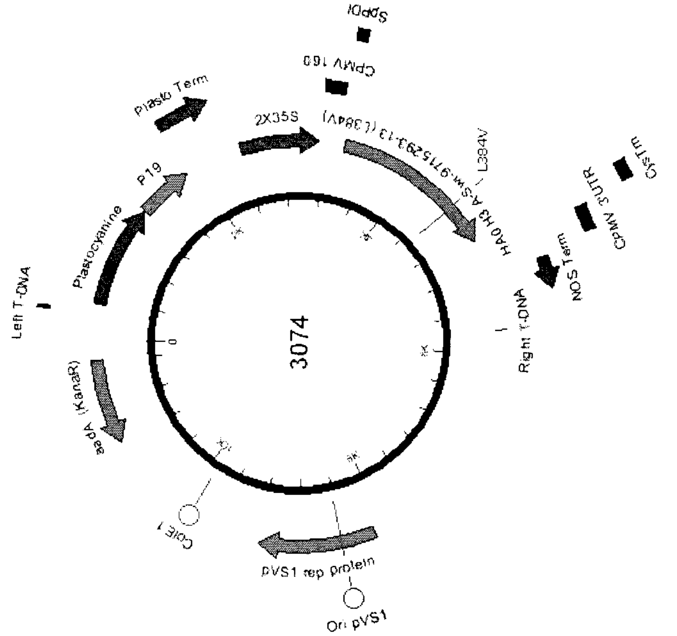
Figure 8M: Schematic representation of vector 3074
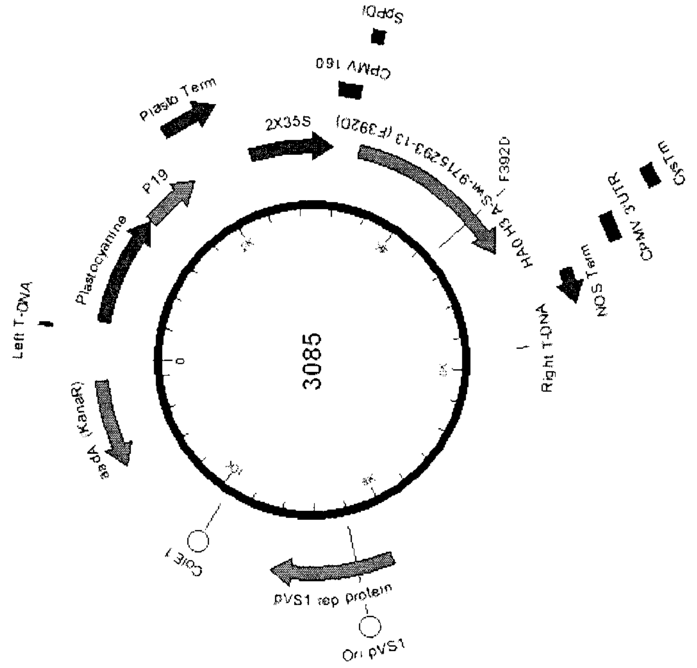
Figure 8N: Schematic representation of vector 3085

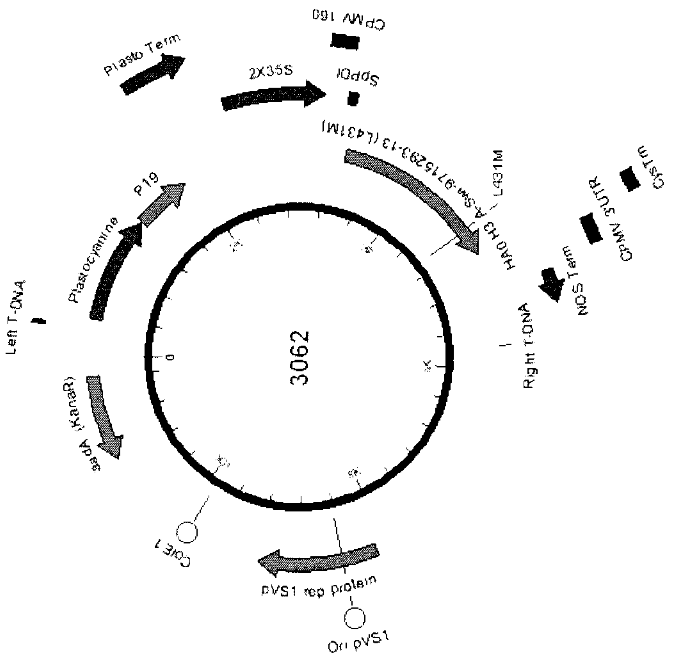
Figure 8O: Schematic representation of vector 3062
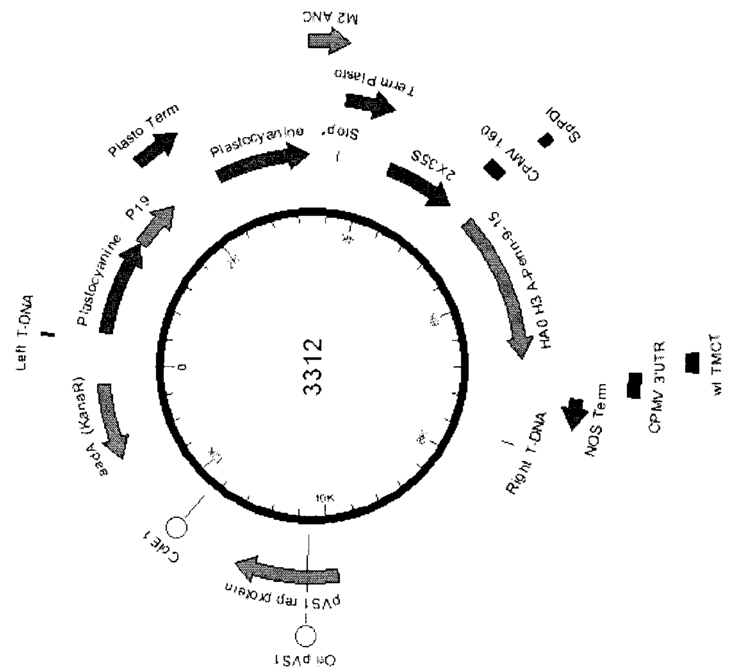
Figure 8P: Schematic representation of vector 3312

Figure 8Q: Schematic representation of vector 3313
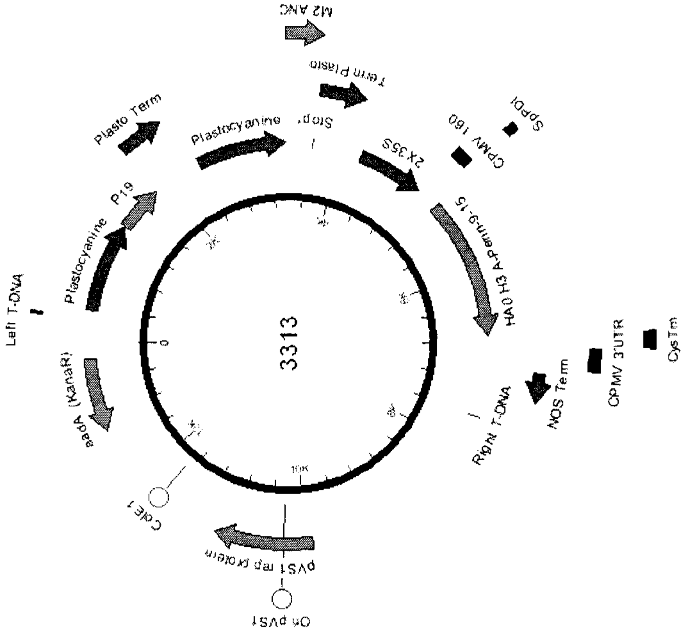

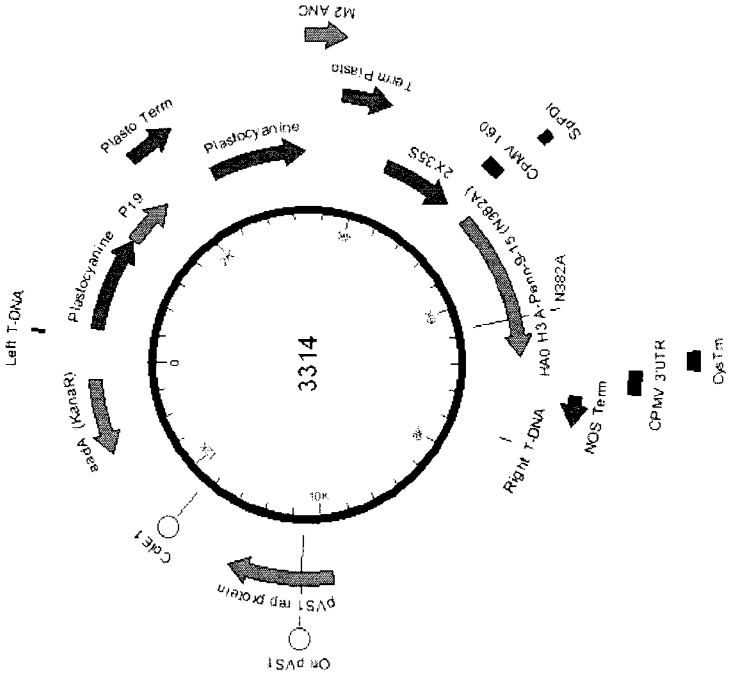
Figure 8R: Schematic representation of vector 3314
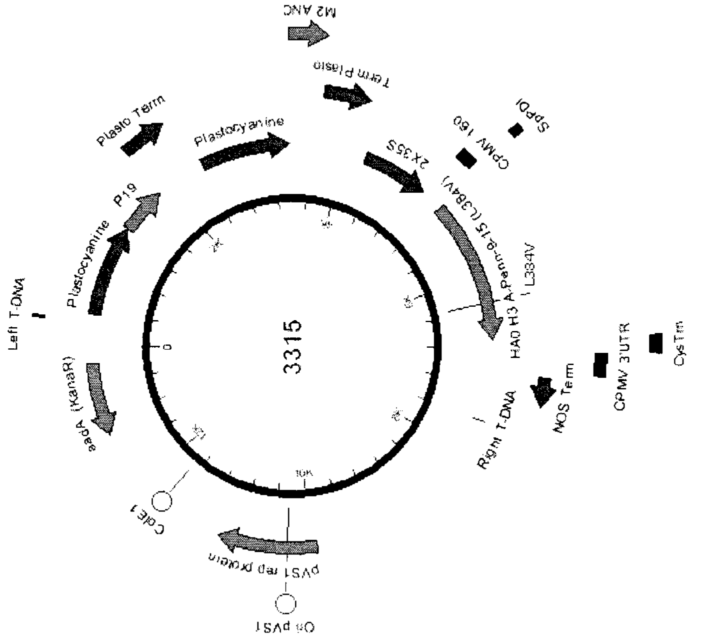
Figure 8S: Schematic representation of vector 3315

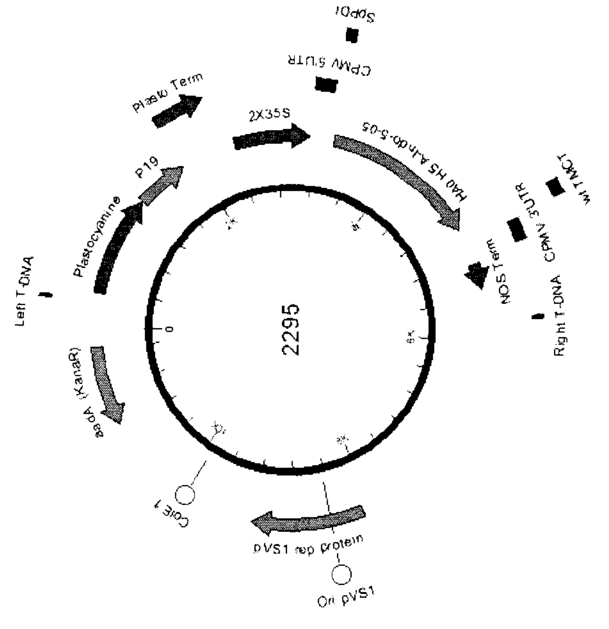
Figure 9A: Schematic representation of vector 2295
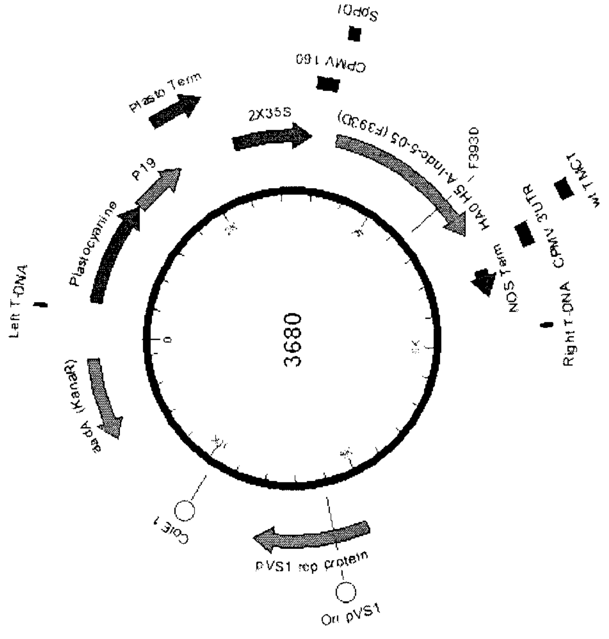
Figure 9B: Schematic representation of vector 3680

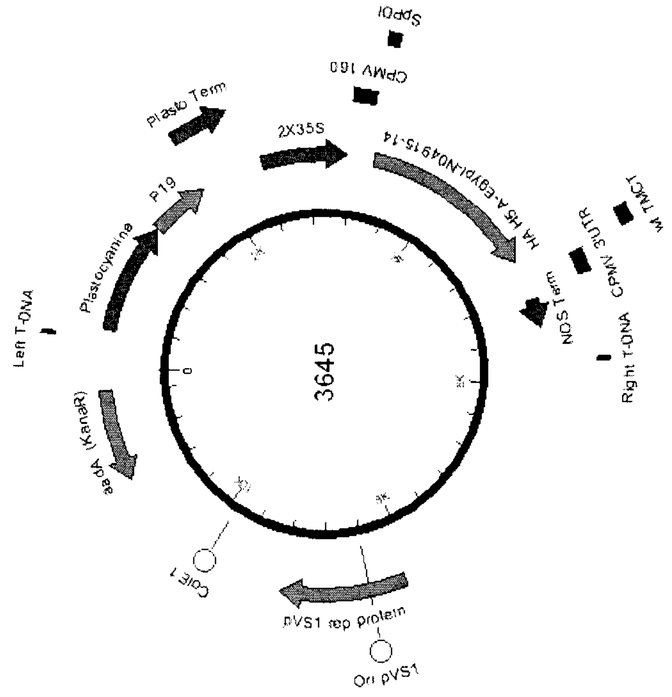
Figure 9C: Schematic representation of vector 3645
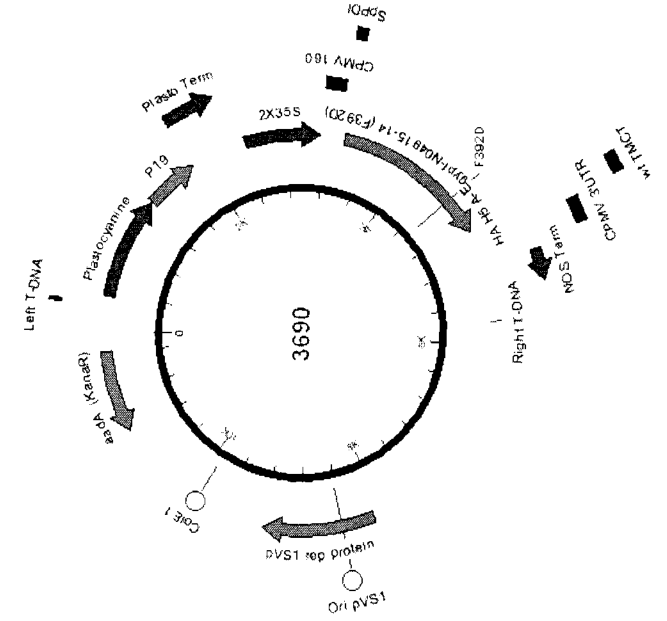
Figure 9D: Schematic representation of vector 3690

SEQUENCE LISTING

<160> NUMBER OF SEQ ID NOS: 105

<210> SEQ ID NO 1
<211> LENGTH: 1725
<212> TYPE: DNA
<213> ORGANISM: Artificial Sequence
<220> FEATURE:
<223> OTHER INFORMATION: PDI-H3 HK DNA

<400> SEQUENCE: 1
atggcgaaaa acgttgcgat tttcggctta ttgttttctc ttcttgtgtt ggttccttct 60
cagatcttcg cgcaaaaaat tcctggaaat gacaatagca cggcaacgct gtgccttggg 120
catcatgcag taccaaacgg aacgatagtg aaaacaatca cgaatgaccg aattgaagtt 180
actaatgcta ctgagctggt tcagaattcc tcaataggtg aaatatgcga cagtcctcat 240
cagatccttg atggagaaaa ctgcacacta atagatgctc tattgggaga ccctcagtgt 300
gatggctttc aaaataagaa atgggacctt tttgttgaac gaagcaaagc ctacagcaac 360
tgttaccctt atgatgtgcc ggattatgcc tcccttaggt cactagttgc ctcatccggc 420
acactggagt ttaacaatga aagcttcaat tggactggag tcactcaaaa cggaacaagt 480
tctgcttgca taaggagatc tagtagtagt ttctttagta gattaaattg gttgacccac 540
ttaaactaca catacccagc attgaacgtg actatgccaa acaatgaaca atttgacaaa 600

-continued

```
ttgtacattt ggggggttca ccacccgggt acggacaagg accaaatctt cctgtatgct    660

caatcatcag gaagaatcac agtatctacc aaaagaagcc aacaagctgt aatcccaaat    720

atcggatcta gacccagaat aagggatatc cctagcagaa taagcatcta ttggacaata    780

gtaaaaccgg gagacatact tttgattaac agcacaggga atctaattgc tcctaggggt    840

tacttcaaaa tacgaagtgg gaaaagctca ataatgagat cagatgcacc cattggcaaa    900

tgcaagtctg aatgcatcac tccaaatgga agcattccca atgacaaacc attccaaaat    960

gtaaacagga tcacatacgg ggcctgtccc agatatgtta agcatagcac tctgaaattg   1020

gcaacaggaa tgcgaaatgt accagagaaa caaactagag gcatatttgg tgcaatagcg   1080

ggtttcatag aaaatggttg ggagggaatg gtggatggtt ggtacggttt caggcatcaa   1140

aattctgagg gaagaggaca agcagcagat ctcaaaagca ctcaagcagc aatcgatcaa   1200

atcaatggga agctgaatcg attgatcggg aaaaccaacg agaaattcca tcagattgaa   1260

aaagaattct cagaagtaga aggaagaatt caggaccttg agaaatatgt tgaggacact   1320

aaaatagatc tctggtcata caacgcggag cttcttgttg ccctggagaa ccaacataca   1380

attgatctaa ctgactcaga aatgaacaaa ctgtttgaaa aaacaaagaa gcaactgagg   1440

gaaaatgctg aggatatggg caatggttgt ttcaaaatat accacaaatg tgacaatgcc   1500

tgcataggat caataagaaa tggaacttat gaccacaatg tgtacaggga tgaagcatta   1560

aacaaccggt tccagatcaa gggagttgag ctgaagtcag ggtacaaaga ttggatccta   1620

tggatttcct ttgccatatc atgtttttttg ctttgtgttg ctttgttggg gttcatcatg   1680

tgggcctgcc aaaagggcaa cattaggtgc aacatttgca tttga                   1725
```

<210> SEQ ID NO 2
<211> LENGTH: 574
<212> TYPE: PRT
<213> ORGANISM: Artificial Sequence
<220> FEATURE:
<223> OTHER INFORMATION: PDI-H3 HK AA

<400> SEQUENCE: 2

```
Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Ser Ser Ser Phe Phe Ser Arg Leu Asn
```

```
                165                 170                 175

Trp Leu Thr His Leu Asn Tyr Thr Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 3

<211> LENGTH: 1725
<212> TYPE: DNA
<213> ORGANISM: Artificial Sequence
<220> FEATURE:
<223> OTHER INFORMATION: PDI-H3 Minn DNA

<400> SEQUENCE: 3
atggcgaaaa acgttgcgat tttcggctta ttgttttctc ttcttgtgtt ggttccttct 60
cagatcttcg cgcaaaaaat tcctggaaat gacaatagca cggcaacgct gtgccttggg 120
caccatgcag taccaaacgg aacgatagtg aaaacaatca caaatgaccg aattgaagtt 180
actaatgcta ctgagttggt tcagaattcc tcaataggtg aaatatgcga cagtcctcat 240
cagatccttg atggagagaa ctgcacacta atagatgctc tattgggaga ccctcagtgt 300
gatggctttc aaaataagaa atgggacctt tttgttgaac gaagcaaagc ctacagcaac 360
tgttaccctt atgatgtgcc ggattatgcc tcccttaggt cactagttgc ctcatccggc 420
acactggagt ttaacaatga aagcttcaat tggactggag tcactcaaaa cggaacaagt 480
tctgcttgca taaggagatc tagtagtagt ttctttagta gattaaattg gttgacccac 540
ttaaactaca catatccagc attgaacgtg actatgccaa acaaggaaca atttgacaaa 600
ttgtacattt gggggttca ccacccgggt acggacaagg accaaatctt cctgtatgct 660
caatcatcag gaagaatcac agtatctacc aaaagaagcc aacaagctgt aatcccaaat 720
atcggatcta gacccagaat aagggatatc cctagcagaa taagcatcta ttggacaata 780
gtaaaaccgg gagacatact tttgattaac agcacaggga atctaattgc tcctaggggt 840
tacttcaaaa tacgaagtgg gaaaagctca ataatgagat cagatgcacc cattggcaaa 900
tgcaagtctg aatgcatcac tccaaatgga agcattccca atgacaaacc attccaaaat 960
gtaaacagga tcacatacgg ggcctgtccc agatatgtta agcatagcac tctgaaattg 1020
gcaacaggaa tgcgaaatgt accagagaaa caaactagag gcatatttgg cgcaatagcg 1080
ggtttcatag aaaatggttg ggagggaatg gtggatggtt ggtacggttt caggcatcaa 1140
aattctgagg gaagaggaca agcagcagat ctcaaaagca ctcaagcagc aatcgatcaa 1200
atcaatggga agctgaatcg gttgatcggg aaaaccaacg agaaattcca tcagattgaa 1260
aaagaattct cagaagtaga aggaagagtt caagaccttg agaaatatgt tgaggacact 1320
aaaatagatc tctggtcata caacgcggag cttcttgttg ccctggagaa ccaacataca 1380
attgatctaa ctgactcaga aatgaacaaa ctgtttgaaa aaacaaagaa gcaactgagg 1440
gaaaatgctg aggatatggg aaatggttgt ttcaaaatat accacaaatg tgacaatgcc 1500
tgcataggat caataagaaa tgaaacttat gaccacaatg tgtacaggga tgaagcatta 1560
aacaaccggt tccagatcaa gggagttgag ctgaagtcag ggtacaaaga ttggatccta 1620
tggatttcct ttgccatatc atgtttttg ctttgtgttg ctttgttggg gttcatcatg 1680
tgggcctgcc aaaagggcaa cattagatgc aacatttgca tttga 1725

<210> SEQ ID NO 4
<211> LENGTH: 574
<212> TYPE: PRT
<213> ORGANISM: Artificial Sequence
<220> FEATURE:
<223> OTHER INFORMATION: PDI-H3 Minn AA

<400> SEQUENCE: 4

Met Ala Lys Asn Val Ala Ile Phe Gly Leu Leu Phe Ser Leu Leu Val
1 5 10 15

-continued

```
Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Ser Ser Ser Phe Phe Ser Arg Leu Asn
                165                 170                 175

Trp Leu Thr His Leu Asn Tyr Thr Tyr Pro Ala Leu Asn Val Thr Met
            180                 185                 190

Pro Asn Lys Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Val Gln Asp
            420                 425                 430

Leu Glu Lys Tyr Val Glu Asp Thr Lys Ile Asp Leu Trp Ser Tyr Asn
```

```
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Glu Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570

<210> SEQ ID NO 5
<211> LENGTH: 1725
<212> TYPE: DNA
<213> ORGANISM: Artificial Sequence
<220> FEATURE:
<223> OTHER INFORMATION: PDI-H3 SAus DNA

<400> SEQUENCE: 5
atggcgaaaa acgttgcgat tttcggctta ttgttttctc ttcttgtgtt ggttccttct      60
cagatcttcg cgcaaaaaat tcctggaaat gacaatagca cggcaacgct gtgccttggg     120
caccatgcag taccaaacgg aacgatagtg aaaacaatca caaatgaccg aattgaagtt     180
actaatgcta ctgagttggt tcagaattcc tcaataggtg aaatatgcga cagtcctcat     240
cagatccttg atggagagaa ctgcacacta atagatgctc tattgggaga ccctcagtgt     300
gatggctttc aaaataagaa atgggacctt tttgttgaac gaagcaaagc ctacagcaac     360
tgttaccctt atgatgtgcc ggattatgcc tcccttaggt cactagttgc ctcatccggc     420
acactggagt ttaaaaatga aagcttcaat tggactggag tcactcaaaa cggaacaagt     480
tctgcttgca taaggagatc tagtagtagt ttctttagta gattaaattg gttgacccac     540
ttaaactaca catatccagc attgaacgtg actatgccaa acaaggaaca atttgacaaa     600
ttgtacattt ggggggttca ccacccgggt acggacaagg accaaatctt cctgtatgct     660
caatcatcag gaagaatcac agtatctacc aaaagaagcc aacaagctgt aatcccaaat     720
atcggatcta gacccagaat aagggatatc cctagcagaa taagcatcta ttggacaata     780
gtaaaaccgg gagacatact tttgattaac agcacaggga atctaattgc tcctaggggt     840
tacttcaaaa tacgaagtgg gaaaagctca ataatgagat cagatgcacc cattggcaaa     900
tgcaagtctg aatgcatcac tccaaatgga agcattccca atgacaaacc attccaaaat     960
gtaaacagga tcacatacgg ggcctgtccc agatatgtta agcatagcac tctgaaattg    1020
gcaacaggaa tgcgaaatgt accagagaaa caaactagag gcatatttgg cgcaatagcg    1080
ggtttcatag aaaatggttg ggagggaatg gtggatggtt ggtacggttt caggcatcaa    1140
aattctgagg gaagaggaca agcagcagat ctcaaaagca ctcaagcagc aatcgatcaa    1200
atcaatggga agctgaatcg gttgatcggg aaaaccaacg agaaattcca tcagattgaa    1260
aaagaattct cagaagtaga aggaagagtt caagaccttg agaaatatgt tgaggacact    1320
```

```
aaaatagatc tctggtcata caacgcggag cttcttgttg ccctggagaa ccaacataca   1380

attgatctaa ctgactcaga aatgaacaaa ctgtttgaaa aaacaaagaa gcaactgagg   1440

gaaaatgctg aggatatggg aaatggttgt ttcaaaatat accacaaatg tgacaatgcc   1500

tgcataggat caataagaaa tgaaacttat gaccacaatg tgtacaggga tgaagcatta   1560

aacaaccggt tccagatcaa gggagttgag ctgaagtcag ggtacaaaga ttggatccta   1620

tggatttcct ttgccatatc atgtttttg ctttgtgttg ctttgttggg gttcatcatg   1680

tgggcctgcc aaaagggcaa cattagatgc aacatttgca tttga                  1725
```

<210> SEQ ID NO 6
<211> LENGTH: 574
<212> TYPE: PRT
<213> ORGANISM: Artificial Sequence
<220> FEATURE:
<223> OTHER INFORMATION: PDI-H3 SAus AA

<400> SEQUENCE: 6

```
Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Lys Asn Glu Ser Phe Asn Trp Thr Gly Val Thr Gln Asn Gly Thr Ser
145                 150                 155                 160

Ser Ala Cys Ile Arg Arg Ser Ser Ser Ser Phe Phe Ser Arg Leu Asn
                165                 170                 175

Trp Leu Thr His Leu Asn Tyr Thr Tyr Pro Ala Leu Asn Val Thr Met
            180                 185                 190

Pro Asn Lys Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285
```

-continued

```
Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Val Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Glu Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 7
<211> LENGTH: 1725
<212> TYPE: DNA
<213> ORGANISM: Artificial Sequence
<220> FEATURE:
<223> OTHER INFORMATION: PDI-H3 Bang DNA

<400> SEQUENCE: 7

```
atggcgaaaa acgttgcgat tttcggctta ttgttttctc ttcttgtgtt ggttccttct      60

cagatcttcg cgcaaaaaat tcctggaaat gacaatagca cggcaacgct gtgccttggg     120

caccatgcag taccaaacgg aacgatagtg aaaacaatca caaatgaccg aattgaagtt     180

actaatgcta ctgagctggt tcagaattcc tcaataggtg aaatatgcga cagtcctcat     240

cagatccttg atggagaaaa ctgcacacta atagatgctc tattgggaga ccctcagtgt     300

gatggctttc aaaataagaa atgggacctt tttgttgaac gaagcaaagc ctacagcaac     360

tgttaccctt atgatgtgcc ggattatgcc tcccttaggt cactagttgc ctcatccggc     420

acactggagt ttaacaatga aagcttcaat tggactggag tcactcaaaa cggaacaagt     480
```

-continued

```
tctgcttgca taaggaaatc tagtagtagt ttctttagta gattaaattg gttgacccac    540

ttaaactaca catacccagc attgaacgtg actgtgccaa acaatgaaca atttgacaaa    600

ttgtacattt ggggggttca ccacccgggt acggacaagg accaaatctt cctgtatgct    660

cgatcatcag gaagaatcac agtatctacc aaaagaagcc aacaagctgt aatcccaaat    720

atcggatcta gacccagaat aagggatatc cctagcagaa taagcatcta ttggacaata    780

gtaaaaccgg gagacatact tttgattaac agcacaggga atctaattgc tcctaggggt    840

tacttcaaaa tacgaagtgg gaaaagctca ataatgagat cagatgcacc cattggcaaa    900

tgcaagtctg aatgcatcac tccaaatgga agcattccca atgacaaacc attccaaaat    960

gtaaacagga tcacatacgg ggcctgtccc agatatgtta agcatagcac tctgaaattg   1020

gcaacaggaa tgcgaaatgt accagagaaa caaactagag gcatatttgg cgcaatagcg   1080

ggtttcatag aaaatggttg ggagggaatg gtggatggtt ggtacggttt caggcatcaa   1140

aattctgagg gaagaggaca agcagcagat ctcaaaagca ctcaagcagc aatcgatcaa   1200

atcaatggga agctgaatcg attgatcggg aaaaccaacg agaaattcca tcagattgaa   1260

aaagaattct cagaagtaga aggaagaatt caggaccttg agaaatatgt tgaggacact   1320

aaaatagatc tctggtcata caacgcggag cttcttgttg ccctggagaa tcaacataca   1380

attgatctaa ctgactcaga aatgaacaaa ctgtttgaaa aaacaaagaa gcaactgagg   1440

gaaaatgctg aggatatggg aaatggttgt ttcaaaatat accacaaatg tgacaatgcc   1500

tgcataggat caataagaaa tggaacttat gaccacaatg tgtacaggga tgaagcatta   1560

aacaaccggt tccagatcaa gggagttgag ctgaagtcag ggtacaaaga ttggatccta   1620

tggatttcct ttgccatatc atgtttttttg ctttgtgttg ctttgttggg gttcatcatg   1680

tgggcctgcc aaaagggcaa cattaggtgc aacatttgca tttga                   1725
```

<210> SEQ ID NO 8
<211> LENGTH: 574
<212> TYPE: PRT
<213> ORGANISM: Artificial Sequence
<220> FEATURE:
<223> OTHER INFORMATION: PDI-H3 Bang AA

<400> SEQUENCE: 8

```
Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140
```

Asn Asn Glu Ser Phe Asn Trp Thr Gly Val Thr Gln Asn Gly Thr Ser
145 150 155 160

Ser Ala Cys Ile Arg Lys Ser Ser Ser Ser Phe Phe Ser Arg Leu Asn
165 170 175

Trp Leu Thr His Leu Asn Tyr Thr Tyr Pro Ala Leu Asn Val Thr Val
180 185 190

Pro Asn Asn Glu Gln Phe Asp Lys Leu Tyr Ile Trp Gly Val His His
195 200 205

Pro Gly Thr Asp Lys Asp Gln Ile Phe Leu Tyr Ala Arg Ser Ser Gly
210 215 220

Arg Ile Thr Val Ser Thr Lys Arg Ser Gln Gln Ala Val Ile Pro Asn
225 230 235 240

Ile Gly Ser Arg Pro Arg Ile Arg Asp Ile Pro Ser Arg Ile Ser Ile
245 250 255

Tyr Trp Thr Ile Val Lys Pro Gly Asp Ile Leu Leu Ile Asn Ser Thr
260 265 270

Gly Asn Leu Ile Ala Pro Arg Gly Tyr Phe Lys Ile Arg Ser Gly Lys
275 280 285

Ser Ser Ile Met Arg Ser Asp Ala Pro Ile Gly Lys Cys Lys Ser Glu
290 295 300

Cys Ile Thr Pro Asn Gly Ser Ile Pro Asn Asp Lys Pro Phe Gln Asn
305 310 315 320

Val Asn Arg Ile Thr Tyr Gly Ala Cys Pro Arg Tyr Val Lys His Ser
325 330 335

Thr Leu Lys Leu Ala Thr Gly Met Arg Asn Val Pro Glu Lys Gln Thr
340 345 350

Arg Gly Ile Phe Gly Ala Ile Ala Gly Phe Ile Glu Asn Gly Trp Glu
355 360 365

Gly Met Val Asp Gly Trp Tyr Gly Phe Arg His Gln Asn Ser Glu Gly
370 375 380

Arg Gly Gln Ala Ala Asp Leu Lys Ser Thr Gln Ala Ala Ile Asp Gln
385 390 395 400

Ile Asn Gly Lys Leu Asn Arg Leu Ile Gly Lys Thr Asn Glu Lys Phe
405 410 415

His Gln Ile Glu Lys Glu Phe Ser Glu Val Glu Gly Arg Ile Gln Asp
420 425 430

Leu Glu Lys Tyr Val Glu Asp Thr Lys Ile Asp Leu Trp Ser Tyr Asn
435 440 445

Ala Glu Leu Leu Val Ala Leu Glu Asn Gln His Thr Ile Asp Leu Thr
450 455 460

Asp Ser Glu Met Asn Lys Leu Phe Glu Lys Thr Lys Lys Gln Leu Arg
465 470 475 480

Glu Asn Ala Glu Asp Met Gly Asn Gly Cys Phe Lys Ile Tyr His Lys
485 490 495

Cys Asp Asn Ala Cys Ile Gly Ser Ile Arg Asn Gly Thr Tyr Asp His
500 505 510

Asn Val Tyr Arg Asp Glu Ala Leu Asn Asn Arg Phe Gln Ile Lys Gly
515 520 525

Val Glu Leu Lys Ser Gly Tyr Lys Asp Trp Ile Leu Trp Ile Ser Phe
530 535 540

Ala Ile Ser Cys Phe Leu Leu Cys Val Ala Leu Leu Gly Phe Ile Met
545 550 555 560

-continued

```
Trp Ala Cys Gln Lys Gly Asn Ile Arg Cys Asn Ile Cys Ile
                565                 570
```

<210> SEQ ID NO 9
<211> LENGTH: 1725
<212> TYPE: DNA
<213> ORGANISM: Artificial Sequence
<220> FEATURE:
<223> OTHER INFORMATION: PDI-H3 Switz DNA

<400> SEQUENCE: 9

```
atggcgaaaa acgttgcgat tttcggctta ttgttttctc ttcttgtgtt ggttccttct     60
cagatcttcg cgcaaaaact tcctggaaat gacaatagca cggcaacgct gtgccttggg    120
caccatgcag taccaaacgg aacgatagtg aaaacaatca cgaatgaccg aattgaagtt    180
actaatgcta ctgagctggt tcagaattcc tcaataggtg aaatatgcga cagtcctcat    240
cagatccttg atggagaaaa ctgcacacta atagatgctc tattgggaga ccctcagtgt    300
gatggctttc aaaataagaa atgggacctt tttgttgaac gaagcaaagc ctacagcaac    360
tgttaccctt atgatgtgcc ggattatgcc tcccttaggt cactagttgc ctcatccggc    420
acactggagt ttaacaatga aagcttcaat tgggctggag tcactcaaaa cggaacaagt    480
tcttcttgca taaggggatc taatagtagt ttctttagta gattaaattg gttgacccac    540
ttaaactcca aatacccagc attaaacgtg actatgccaa acaatgaaca atttgacaaa    600
ttgtacattt gggggttca ccacccgggt acggacaagg accaaatctt cctgtatgca     660
caatcatcag gaagaatcac agtatctacc aaaagaagcc aacaagctgt aatcccgaat    720
atcggatcta gacccagaat aagggatatc cctagcagaa taagcatcta ttggacaata    780
gtaaaaccgg gagacatact tttgattaac agcacaggga atctaattgc tcctaggggt    840
tacttcaaaa tacgaagtgg gaaaagctca ataatgagat cagatgcacc cattggcaaa    900
tgcaagtctg aatgcatcac tccaaatgga agcattccca atgacaaacc attccaaaat    960
gtaaacagga tcacatacgg ggcctgtccc agatatgtta agcaaagcac tctgaaattg   1020
gcaacaggaa tgcgaaatgt accagagaga caaactagag gcatatttgg cgcaatagcg   1080
ggtttcatag aaaatggttg ggagggaatg gtggatggtt ggtacggctt caggcatcaa   1140
aattctgagg gaagaggaca agcagcagat ctcaaaagca ctcaagcagc aatcgatcaa   1200
atcaatggga agctgaatcg attgatcggg aaaaccaacg agaaattcca tcagattgaa   1260
aaagaattct cagaagtaga agggagaatt caggaccttg agaaatatgt tgaggacaca   1320
aaaatagatc tctggtcata caacgcggag cttcttgttg ccctggagaa ccaacataca   1380
attgatctaa ctgactcaga aatgaacaaa ctgtttgaaa aaacaaagaa gcaactgagg   1440
gaaaatgctg aggatatggg caatggttgt ttcaaaatat accacaaatg tgacaatgcc   1500
tgcataggat caatcagaaa tggaacttat gaccacgatg tatacaggga tgaagcatta   1560
aacaaccggt tccagatcaa gggagttgag ctgaagtcag ggtacaaaga ttggatccta   1620
tggatttcct ttgccatatc atgtttttg ctttgtgttg ctttgttggg gttcatcatg    1680
tgggcctgcc aaaagggcaa cattaggtgc aacatttgca tttga                   1725
```

<210> SEQ ID NO 10
<211> LENGTH: 574
<212> TYPE: PRT
<213> ORGANISM: Artificial Sequence
<220> FEATURE:
<223> OTHER INFORMATION: PDI-H3 Switz AA

<400> SEQUENCE: 10

Met Ala Lys Asn Val Ala Ile Phe Gly Leu Leu Phe Ser Leu Leu Val
1 5 10 15

Leu Val Pro Ser Gln Ile Phe Ala Gln Lys Leu Pro Gly Asn Asp Asn
20 25 30

Ser Thr Ala Thr Leu Cys Leu Gly His His Ala Val Pro Asn Gly Thr
35 40 45

Ile Val Lys Thr Ile Thr Asn Asp Arg Ile Glu Val Thr Asn Ala Thr
50 55 60

Glu Leu Val Gln Asn Ser Ser Ile Gly Glu Ile Cys Asp Ser Pro His
65 70 75 80

Gln Ile Leu Asp Gly Glu Asn Cys Thr Leu Ile Asp Ala Leu Leu Gly
85 90 95

Asp Pro Gln Cys Asp Gly Phe Gln Asn Lys Lys Trp Asp Leu Phe Val
100 105 110

Glu Arg Ser Lys Ala Tyr Ser Asn Cys Tyr Pro Tyr Asp Val Pro Asp
115 120 125

Tyr Ala Ser Leu Arg Ser Leu Val Ala Ser Ser Gly Thr Leu Glu Phe
130 135 140

Asn Asn Glu Ser Phe Asn Trp Ala Gly Val Thr Gln Asn Gly Thr Ser
145 150 155 160

Ser Ser Cys Ile Arg Gly Ser Asn Ser Ser Phe Phe Ser Arg Leu Asn
165 170 175

Trp Leu Thr His Leu Asn Ser Lys Tyr Pro Ala Leu Asn Val Thr Met
180 185 190

Pro Asn Asn Glu Gln Phe Asp Lys Leu Tyr Ile Trp Gly Val His His
195 200 205

Pro Gly Thr Asp Lys Asp Gln Ile Phe Leu Tyr Ala Gln Ser Ser Gly
210 215 220

Arg Ile Thr Val Ser Thr Lys Arg Ser Gln Gln Ala Val Ile Pro Asn
225 230 235 240

Ile Gly Ser Arg Pro Arg Ile Arg Asp Ile Pro Ser Arg Ile Ser Ile
245 250 255

Tyr Trp Thr Ile Val Lys Pro Gly Asp Ile Leu Leu Ile Asn Ser Thr
260 265 270

Gly Asn Leu Ile Ala Pro Arg Gly Tyr Phe Lys Ile Arg Ser Gly Lys
275 280 285

Ser Ser Ile Met Arg Ser Asp Ala Pro Ile Gly Lys Cys Lys Ser Glu
290 295 300

Cys Ile Thr Pro Asn Gly Ser Ile Pro Asn Asp Lys Pro Phe Gln Asn
305 310 315 320

Val Asn Arg Ile Thr Tyr Gly Ala Cys Pro Arg Tyr Val Lys Gln Ser
325 330 335

Thr Leu Lys Leu Ala Thr Gly Met Arg Asn Val Pro Glu Arg Gln Thr
340 345 350

Arg Gly Ile Phe Gly Ala Ile Ala Gly Phe Ile Glu Asn Gly Trp Glu
355 360 365

Gly Met Val Asp Gly Trp Tyr Gly Phe Arg His Gln Asn Ser Glu Gly
370 375 380

Arg Gly Gln Ala Ala Asp Leu Lys Ser Thr Gln Ala Ala Ile Asp Gln
385 390 395 400

Ile Asn Gly Lys Leu Asn Arg Leu Ile Gly Lys Thr Asn Glu Lys Phe
405 410 415

-continued

```
His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 11
<211> LENGTH: 1725
<212> TYPE: DNA
<213> ORGANISM: Artificial Sequence
<220> FEATURE:
<223> OTHER INFORMATION: PDI-H3 Miss DNA

<400> SEQUENCE: 11

```
atggcgaaaa acgttgcgat tttcggctta ttgttttctc ttcttgtgtt ggttccttct      60

cagatcttcg cgcaaaaact tcctggaaat gacaatagca cggcaacgct gtgccttggg     120

caccatgcag taccaaacgg aacgatagtg aaaacaatca cgaatgaccg aattgaagtt     180

actaatgcta ctgagctggt tcagaattcc tcaataggtg aaatatgcga cagtcctcat     240

cagatccttg atggagaaaa ctgcacacta atagatgctc tattgggaga ccctcagtgt     300

gatggctttc aaaataagaa atgggacctt tttgttgaac gaagcagagc ctacagcaac     360

tgttaccctt atgatgtgcc ggattatgcc tcccttaggt cactagttgc ctcatccggc     420

acactggagt ttaacaatga aagcttcaat tgggctggag tcactcaaaa cggaacaagt     480

tcttcttgca taaggggatc taatagtagt ttctttagta gattaaattg gttgacccac     540

ttaaactcca aatacccagc attaaacgtg actatgccaa acaatgaaca atttgacaaa     600

ttgtacattt ggggggttca ccacccgggt acggacaagg accaaatctt cctgtatgca     660

aaaccatcag gaagaatcac agtatctacc aaaagaagcc aacaagctgt aatcccgaat     720

atcggatcta gacccagaat aagggatatc cctagcagaa taagcatcta ttggacaata     780

gtaaaaccgg gagacatact tttgattaac agcacaggga atctaattgc tcctaggggt     840

tacttcaaaa tacgaagtgg gaaaagctca ataatgagat cagatgcacc cattggcaaa     900

tgcaagtctg aatgcatcac tccaaatgga agcattccca atgacaaacc attccaaaat     960

gtaaacagga tcacatacgg ggcctgtccc agatatgtta agcaaaacac tctgaaattg    1020

gcaacaggaa tgcgaaatgt accagagaga caaactagag gcatatttgg cgcaatagcg    1080

ggtttcatag aaaatggttg ggagggaatg gtggatggtt ggtacggctt caggcatcaa    1140
```

```
aattctgagg gaagaggaca agcagcagat ctcaaaagca ctcaagcagc aatcgatcaa   1200

atcaatggga agctgaatcg attgatcggg aaaaccaacg agaaattcca tcagattgaa   1260

aaagaattct cagaagtaga agggagaatt caggaccttg agaaatatgt tgaggacaca   1320

aaaatagatc tctggtcata caacgcggag cttcttgttg ccctggagaa ccaacataca   1380

attgatctaa ctgactcaga aatgaacaaa ctgtttgaaa aaacaaagaa gcaactgagg   1440

gaaaatgctg aggatatggg caatggttgt ttcaaaatat accacaaatg tgacaatgcc   1500

tgcataggat caatcagaaa tggaacttat gaccacgatg tatacaggga tgaagcatta   1560

aacaaccggt tccagatcaa gggagttgag ctgaagtcag ggtacaaaga ttggatccta   1620

tggatttcct ttgccatatc atgttttttg ctttgtgttg ctttgttggg gttcatcatg   1680

tgggcctgcc aaaagggcaa cattaggtgc aacatttgca tttga                   1725
```

<210> SEQ ID NO 12
<211> LENGTH: 574
<212> TYPE: PRT
<213> ORGANISM: Artificial Sequence
<220> FEATURE:
<223> OTHER INFORMATION: PDI-H3 Miss AA

<400> SEQUENCE: 12

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Arg Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160

Ser Ser Cys Ile Arg Gly Ser Asn Ser Ser Phe Phe Ser Arg Leu Asn
                165                 170                 175

Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Lys Pro Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
```

```
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Asn
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 13
<211> LENGTH: 1725
<212> TYPE: DNA
<213> ORGANISM: Artificial Sequence
<220> FEATURE:
<223> OTHER INFORMATION: PDI-H3 Penn DNA

<400> SEQUENCE: 13

```
atggcgaaaa acgttgcgat tttcggctta ttgttttctc ttcttgtgtt ggttccttct      60

cagatcttcg cgcaaaaact tcctggaaat gacaatagca cggcaacgct gtgccttggg     120

caccatgcag taccaaacgg aacgatagtg aaaacaatca cgaatgaccg aattgaagtt     180

actaatgcta ctgagctggt tcagaattcc tcaataggtg aaatatgcga cagtcctcat     240

cagatccttg atggaaaaaa ctgcactcta atagatgctc tattgggaga ccctcagtgt     300
```

-continued

```
gatggctttc aaaataagag atgggacctt tttgttgaac gaagcaaagc ctacagcaac    360
tgttaccctt atgatgtgcc ggattatgcc tcccttaggt cactagttgc ctcatccggc    420
acactggagt ttaacgatga aagcttcaat tgggctggag tcactcaaaa cggaacaagt    480
tctgcttgca taaggggatc taatagtagt ttctttagta gattaaattg gttgacccac    540
tcaaacttca aatacccagc attgaacgtg actatgccaa acaatgaaca atttgacaaa    600
ttgtacattt gggggttca ccacccgggt acagacaagg accaaatctt cctgtacgct    660
caatcatcag gaagaatcac agtatctacc aaaagaagcc aacaagctgt aatcccgaat    720
atcggatcta gacccagaat aaggaatatc cctagcagaa taagcatcta ttggacaata    780
gtaaaaccgg gagacatact tttgattaac agcacaggga atctaattgc tcctaggggt    840
tacttcaaaa tacaaagtgg gaaaagctca ataatgagat cagatgcacc cattggcaaa    900
tgcaagtctg aatgcatcac tccaaatgga agcattccca atgacaaacc attccaaaat    960
gtaaacagga tcacatacgg ggcctgtccc agatatgtta agcaaagcac tctgaaattg   1020
gcaacaggaa tgcgaaatgt accagagaaa caaactagag gcatatttgg cgcaatagcg   1080
ggtttcatag aaaatggttg ggagggaatg aaggatggtt ggtacggttt caggcatcaa   1140
aattctgagg gaagaggaca agcagcagat ctcaaaagca ctcaagcagc aatcgatcaa   1200
atcaatggga agctgaatcg attgatcggg aaaaccaacg agaaattcca tcagattgaa   1260
aaagaattct cagaagtaga agggagaatt caggaccttg agaaatatgt tgaggacaca   1320
aaaatagatc tctggtcata caacgcggag cttcttgttg ccctggagaa ccaacataca   1380
attgatctaa ctgactcaga aatgaacaaa ctgtttgaaa aaacaaagaa gcaactgagg   1440
gaaaatgctg aggatatggg caatggttgt ttcaaaatat accacaaatg tgacaatgcc   1500
tgcataggat caatcagaaa tggaacttat gaccacgatg tatacaggga tgaagcttta   1560
aacaaccggt tccagatcaa gggagttgag ctgaagtcag ggtacaaaga ttggatccta   1620
tggatttcct ttgccatatc atgtttttttg ctttgtgttg ctttgttggg gttcatcatg   1680
tgggcctgcc aaaagggcaa cattaggtgc aacatttgca tttga                   1725
```

<210> SEQ ID NO 14
<211> LENGTH: 574
<212> TYPE: PRT
<213> ORGANISM: Artificial Sequence
<220> FEATURE:
<223> OTHER INFORMATION: PDI-H3 Penn AA

<400> SEQUENCE: 14

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Lys Asn Cys Thr Leu Ile Asp Ala Leu Leu Gly
                85                  90                  95

Asp Pro Gln Cys Asp Gly Phe Gln Asn Lys Arg Trp Asp Leu Phe Val
            100                 105                 110
```

-continued

```
Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asp Glu Ser Phe Asn Trp Ala Gly Val Thr Gln Asn Gly Thr Ser
145                 150                 155                 160

Ser Ala Cys Ile Arg Gly Ser Asn Ser Ser Phe Phe Ser Arg Leu Asn
                165                 170                 175

Trp Leu Thr His Ser Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Gln Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Lys Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
```

-continued

```
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570


<210> SEQ ID NO 15
<211> LENGTH: 49
<212> TYPE: DNA
<213> ORGANISM: Artificial Sequence
<220> FEATURE:
<223> OTHER INFORMATION: Primer IF-CPMV(fl5'UTR)_SpPDI.c

<400> SEQUENCE: 15

tcgtgcttcg gcaccagtac aatggcgaaa aacgttgcga ttttcggct                 49


<210> SEQ ID NO 16
<211> LENGTH: 46
<212> TYPE: DNA
<213> ORGANISM: Artificial Sequence
<220> FEATURE:
<223> OTHER INFORMATION: Primer IF-H1cTMCT.S1-4r

<400> SEQUENCE: 16

actaaagaaa ataggccttt aaatacatat tctacactgt agagac                    46


<210> SEQ ID NO 17
<211> LENGTH: 55
<212> TYPE: DNA
<213> ORGANISM: Artificial Sequence
<220> FEATURE:
<223> OTHER INFORMATION: Primer IF-H3A-Ala.r

<400> SEQUENCE: 17

actaaagaaa ataggccttc aaatgcaaat gttgcaccta atgttgccct tttgg          55


<210> SEQ ID NO 18
<211> LENGTH: 51
<212> TYPE: DNA
<213> ORGANISM: Artificial Sequence
<220> FEATURE:
<223> OTHER INFORMATION: Primer H3_Swi_SLVLL.r

<400> SEQUENCE: 18

agcaactaac agtacaaggg atgatatggc aaaggaaatc cataggatcc a              51


<210> SEQ ID NO 19
<211> LENGTH: 53
<212> TYPE: DNA
<213> ORGANISM: Artificial Sequence
<220> FEATURE:
<223> OTHER INFORMATION: H3_Swi_SLVLL.c

<400> SEQUENCE: 19

tcctttgcca tatcatccct tgtactgtta gttgctttgt tggggttcat cat            53


<210> SEQ ID NO 20
<211> LENGTH: 1725
<212> TYPE: DNA
<213> ORGANISM: Artificial Sequence
<220> FEATURE:
<223> OTHER INFORMATION: PDI-H3 HK-CysTm DNA

<400> SEQUENCE: 20

atggcgaaaa acgttgcgat tttcggctta ttgttttctc ttcttgtgtt ggttccttct     60
```

```
cagatcttcg cgcaaaaaat tcctggaaat gacaatagca cggcaacgct gtgccttggg    120
catcatgcag taccaaacgg aacgatagtg aaaacaatca cgaatgaccg aattgaagtt    180
actaatgcta ctgagctggt tcagaattcc tcaataggtg aaatatgcga cagtcctcat    240
cagatccttg atggagaaaa ctgcacacta atagatgctc tattgggaga ccctcagtgt    300
gatggctttc aaaataagaa atgggacctt tttgttgaac gaagcaaagc ctacagcaac    360
tgttaccctt atgatgtgcc ggattatgcc tcccttaggt cactagttgc ctcatccggc    420
acactggagt ttaacaatga aagcttcaat tggactggag tcactcaaaa cggaacaagt    480
tctgcttgca taaggagatc tagtagtagt ttctttagta gattaaattg gttgacccac    540
ttaaactaca catacccagc attgaacgtg actatgccaa acaatgaaca atttgacaaa    600
ttgtacattt ggggggttca ccacccgggt acggacaagg accaaatctt cctgtatgct    660
caatcatcag gaagaatcac agtatctacc aaaagaagcc aacaagctgt aatcccaaat    720
atcggatcta gacccagaat aagggatatc cctagcagaa taagcatcta ttggacaata    780
gtaaaaccgg gagacatact tttgattaac agcacaggga atctaattgc tcctaggggt    840
tacttcaaaa tacgaagtgg gaaaagctca ataatgagat cagatgcacc cattggcaaa    900
tgcaagtctg aatgcatcac tccaaatgga agcattccca atgacaaacc attccaaaat    960
gtaaacagga tcacatacgg ggcctgtccc agatatgtta agcatagcac tctgaaattg   1020
gcaacaggaa tgcgaaatgt accagagaaa caaactagag gcatatttgg tgcaatagcg   1080
ggtttcatag aaaatggttg ggagggaatg gtggatggtt ggtacggttt caggcatcaa   1140
aattctgagg gaagaggaca agcagcagat ctcaaaagca ctcaagcagc aatcgatcaa   1200
atcaatggga agctgaatcg attgatcggg aaaaccaacg agaaattcca tcagattgaa   1260
aaagaattct cagaagtaga aggaagaatt caggaccttg agaaatatgt tgaggacact   1320
aaaatagatc tctggtcata caacgcggag cttcttgttg ccctggagaa ccaacataca   1380
attgatctaa ctgactcaga aatgaacaaa ctgtttgaaa aaacaaagaa gcaactgagg   1440
gaaaatgctg aggatatggg caatggttgt ttcaaaatat accacaaatg tgacaatgcc   1500
tgcataggat caataagaaa tggaacttat gaccacaatg tgtacaggga tgaagcatta   1560
aacaaccggt tccagatcaa gggagttgag ctgaagtcag ggtacaaaga ttggatccta   1620
tggatttcct ttgccatatc atcccttgta ctgttagttg ctttgttggg gttcatcatg   1680
tgggcctgcc aaaagggcaa cattaggtgc aacatttgca tttga                   1725
```

```
<210> SEQ ID NO 21
<211> LENGTH: 574
<212> TYPE: PRT
<213> ORGANISM: Artificial Sequence
<220> FEATURE:
<223> OTHER INFORMATION: PDI-H3 HK-CysTm AA

<400> SEQUENCE: 21

Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60
```

-continued

```
Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Ser Ser Ser Phe Phe Ser Arg Leu Asn
                165                 170                 175

Trp Leu Thr His Leu Asn Tyr Thr Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
```

-continued

```
                485                 490                 495

Cys Asp Asn Ala Cys Ile Gly Ser Ile Arg Asn Gly Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570


<210> SEQ ID NO 22
<211> LENGTH: 48
<212> TYPE: DNA
<213> ORGANISM: Artificial Sequence
<220> FEATURE:
<223> OTHER INFORMATION: Primer H3_HK480114(N382A+L384V).r

<400> SEQUENCE: 22

ttggttttcc cgatcactcg agccagcttc ccattgattt gatcgatt                  48


<210> SEQ ID NO 23
<211> LENGTH: 48
<212> TYPE: DNA
<213> ORGANISM: Artificial Sequence
<220> FEATURE:
<223> OTHER INFORMATION: Primer H3_HK480114(N382A+L384V).c

<400> SEQUENCE: 23

gggaagctgg ctcgagtgat cgggaaaacc aacgagaaat tccatcag                  48


<210> SEQ ID NO 24
<211> LENGTH: 1725
<212> TYPE: DNA
<213> ORGANISM: Artificial Sequence
<220> FEATURE:
<223> OTHER INFORMATION: PDI-H3 HK-N382A+L384V-CysTm DNA

<400> SEQUENCE: 24

atggcgaaaa acgttgcgat tttcggctta ttgttttctc ttcttgtgtt ggttccttct      60

cagatcttcg cgcaaaaaat tcctggaaat gacaatagca cggcaacgct gtgccttggg     120

catcatgcag taccaaacgg aacgatagtg aaaacaatca cgaatgaccg aattgaagtt     180

actaatgcta ctgagctggt tcagaattcc tcaataggtg aaatatgcga cagtcctcat     240

cagatccttg atggagaaaa ctgcacacta atagatgctc tattgggaga ccctcagtgt     300

gatggctttc aaaataagaa atgggacctt tttgttgaac gaagcaaagc ctacagcaac     360

tgttaccctt atgatgtgcc ggattatgcc tcccttaggt cactagttgc ctcatccggc     420

acactggagt ttaacaatga aagcttcaat tggactggag tcactcaaaa cggaacaagt     480

tctgcttgca taaggagatc tagtagtagt ttctttagta gattaaattg gttgacccac     540

ttaaactaca catacccagc attgaacgtg actatgccaa acaatgaaca atttgacaaa     600

ttgtacattt ggggggttca ccacccgggt acggacaagg accaaatctt cctgtatgct     660

caatcatcag gaagaatcac agtatctacc aaaagaagcc aacaagctgt aatcccaaat     720

atcggatcta gacccagaat aagggatatc cctagcagaa taagcatcta ttggacaata     780

gtaaaaccgg gagacatact tttgattaac agcacaggga atctaattgc tcctaggggt     840
```

```
tacttcaaaa tacgaagtgg gaaaagctca ataatgagat cagatgcacc cattggcaaa    900

tgcaagtctg aatgcatcac tccaaatgga agcattccca atgacaaacc attccaaaat    960

gtaaacagga tcacatacgg ggcctgtccc agatatgtta agcatagcac tctgaaattg   1020

gcaacaggaa tgcgaaatgt accagagaaa caaactagag gcatatttgg tgcaatagcg   1080

ggtttcatag aaaatggttg ggagggaatg gtggatggtt ggtacggttt caggcatcaa   1140

aattctgagg gaagaggaca agcagcagat ctcaaaagca ctcaagcagc aatcgatcaa   1200

atcaatggga agctggctcg agtgatcggg aaaaccaacg agaaattcca tcagattgaa   1260

aaagaattct cagaagtaga aggaagaatt caggaccttg agaaatatgt tgaggacact   1320

aaaatagatc tctggtcata caacgcggag cttcttgttg ccctggagaa ccaacataca   1380

attgatctaa ctgactcaga aatgaacaaa ctgtttgaaa aaacaaagaa gcaactgagg   1440

gaaaatgctg aggatatggg caatggttgt ttcaaaatat accacaaatg tgacaatgcc   1500

tgcataggat caataagaaa tggaacttat gaccacaatg tgtacaggga tgaagcatta   1560

aacaaccggt tccagatcaa gggagttgag ctgaagtcag ggtacaaaga ttggatccta   1620

tggatttcct ttgccatatc atcccttgta ctgttagttg ctttgttggg gttcatcatg   1680

tgggcctgcc aaaagggcaa cattaggtgc aacatttgca tttga                   1725
```

```
<210> SEQ ID NO 25
<211> LENGTH: 574
<212> TYPE: PRT
<213> ORGANISM: Artificial Sequence
<220> FEATURE:
<223> OTHER INFORMATION: PDI-H3 HK-N382A+L384V-CysTm AA

<400> SEQUENCE: 25

Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Ser Ser Ser Phe Phe Ser Arg Leu Asn
                165                 170                 175

Trp Leu Thr His Leu Asn Tyr Thr Tyr Pro Ala Leu Asn Val Thr Met
            180                 185                 190

Pro Asn Asn Glu Gln Phe Asp Lys Leu Tyr Ile Trp Gly Val His His
        195                 200                 205
```

```
Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Ala Arg Val Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 26
<211> LENGTH: 1725
<212> TYPE: DNA
<213> ORGANISM: Artificial Sequence
<220> FEATURE:
<223> OTHER INFORMATION: PDI-H3 Minn-CysTm DNA

<400> SEQUENCE: 26

```
atggcgaaaa acgttgcgat tttcggctta ttgttttctc ttcttgtgtt ggttccttct      60
cagatcttcg cgcaaaaaat tcctggaaat gacaatagca cggcaacgct gtgccttggg     120
caccatgcag taccaaacgg aacgatagtg aaaacaatca caaatgaccg aattgaagtt     180
actaatgcta ctgagttggt tcagaattcc tcaataggtg aaatatgcga cagtcctcat     240
cagatccttg atggagagaa ctgcacacta atagatgctc tattgggaga ccctcagtgt     300
gatggctttc aaaataagaa atgggacctt tttgttgaac gaagcaaagc ctacagcaac     360
tgttaccctt atgatgtgcc ggattatgcc tcccttaggt cactagttgc ctcatccggc     420
acactggagt ttaacaatga aagcttcaat tggactggag tcactcaaaa cggaacaagt     480
tctgcttgca taaggagatc tagtagtagt ttctttagta gattaaattg gttgacccac     540
ttaaactaca catatccagc attgaacgtg actatgccaa acaaggaaca atttgacaaa     600
ttgtacattt ggggggttca ccacccgggt acggacaagg accaaatctt cctgtatgct     660
caatcatcag gaagaatcac agtatctacc aaaagaagcc aacaagctgt aatcccaaat     720
atcggatcta gacccagaat aagggatatc cctagcagaa taagcatcta ttggacaata     780
gtaaaaccgg gagacatact tttgattaac agcacaggga atctaattgc tcctaggggt     840
tacttcaaaa tacgaagtgg gaaaagctca ataatgagat cagatgcacc cattggcaaa     900
tgcaagtctg aatgcatcac tccaaatgga agcattccca atgacaaacc attccaaaat     960
gtaaacagga tcacatacgg ggcctgtccc agatatgtta agcatagcac tctgaaattg    1020
gcaacaggaa tgcgaaatgt accagagaaa caaactagag gcatatttgg cgcaatagcg    1080
ggtttcatag aaaatggttg ggagggaatg gtggatggtt ggtacggttt caggcatcaa    1140
aattctgagg gaagaggaca agcagcagat ctcaaaagca ctcaagcagc aatcgatcaa    1200
atcaatggga agctgaatcg gttgatcggg aaaaccaacg agaaattcca tcagattgaa    1260
aaagaattct cagaagtaga aggaagagtt caagaccttg agaaatatgt tgaggacact    1320
aaaatagatc tctggtcata caacgcggag cttcttgttg ccctggagaa ccaacataca    1380
attgatctaa ctgactcaga aatgaacaaa ctgtttgaaa aaacaaagaa gcaactgagg    1440
gaaaatgctg aggatatggg aaatggttgt ttcaaaatat accacaaatg tgacaatgcc    1500
tgcataggat caataagaaa tgaaacttat gaccacaatg tgtacaggga tgaagcatta    1560
aacaaccggt tccagatcaa gggagttgag ctgaagtcag ggtacaaaga ttggatccta    1620
tggatttcct ttgccatatc atcccttgta ctgttagttg ctttgttggg gttcatcatg    1680
tgggcctgcc aaaagggcaa cattagatgc aacatttgca tttga                   1725
```

<210> SEQ ID NO 27
<211> LENGTH: 574
<212> TYPE: PRT
<213> ORGANISM: Artificial Sequence
<220> FEATURE:
<223> OTHER INFORMATION: PDI-H3 Minn-CysTm AA

<400> SEQUENCE: 27

```
Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60
```

```
Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Ser Ser Ser Phe Phe Ser Arg Leu Asn
                165                 170                 175

Trp Leu Thr His Leu Asn Tyr Thr Tyr Pro Ala Leu Asn Val Thr Met
            180                 185                 190

Pro Asn Lys Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Val Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480
```

-continued

```
Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Glu Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570


<210> SEQ ID NO 28
<211> LENGTH: 60
<212> TYPE: DNA
<213> ORGANISM: Artificial Sequence
<220> FEATURE:
<223> OTHER INFORMATION: Primer H3Minn(N382A+L384V).r

<400> SEQUENCE: 28

gttggttttc ccgatcaccc gagccagctt cccattgatt tgatcgattg ctgcttgagt     60


<210> SEQ ID NO 29
<211> LENGTH: 56
<212> TYPE: DNA
<213> ORGANISM: Artificial Sequence
<220> FEATURE:
<223> OTHER INFORMATION: Primer H3Minn(N382A+L384V).c

<400> SEQUENCE: 29

aatcaatggg aagctggctc gggtgatcgg gaaaaccaac gagaaattcc atcaga         56


<210> SEQ ID NO 30
<211> LENGTH: 1725
<212> TYPE: DNA
<213> ORGANISM: Artificial Sequence
<220> FEATURE:
<223> OTHER INFORMATION: PDI-H3 Minn-N382A+L384V-CysTm DNA

<400> SEQUENCE: 30

atggcgaaaa acgttgcgat tttcggctta ttgttttctc ttcttgtgtt ggttccttct     60

cagatcttcg cgcaaaaaat tcctggaaat gacaatagca cggcaacgct gtgccttggg    120

caccatgcag taccaaacgg aacgatagtg aaaacaatca caaatgaccg aattgaagtt    180

actaatgcta ctgagttggt tcagaattcc tcaataggtg aaatatgcga cagtcctcat    240

cagatccttg atggagagaa ctgcacacta atagatgctc tattgggaga ccctcagtgt    300

gatggctttc aaaataagaa atgggacctt tttgttgaac gaagcaaagc ctacagcaac    360

tgttaccctt atgatgtgcc ggattatgcc tcccttaggt cactagttgc ctcatccggc    420

acactggagt ttaacaatga aagcttcaat tggactggag tcactcaaaa cggaacaagt    480

tctgcttgca taaggagatc tagtagtagt ttctttagta gattaaattg gttgacccac    540

ttaaactaca catatccagc attgaacgtg actatgccaa acaaggaaca atttgacaaa    600

ttgtacattt ggggggttca ccacccgggt acggacaagg accaaatctt cctgtatgct    660

caatcatcag gaagaatcac agtatctacc aaaagaagcc aacaagctgt aatcccaaat    720

atcggatcta gacccagaat aagggatatc cctagcagaa taagcatcta ttggacaata    780

gtaaaaccgg gagacatact tttgattaac agcacaggga atctaattgc tcctaggggt    840
```

tacttcaaaa tacgaagtgg gaaaagctca ataatgagat cagatgcacc cattggcaaa 900
tgcaagtctg aatgcatcac tccaaatgga agcattccca atgacaaacc attccaaaat 960
gtaaacagga tcacatacgg ggcctgtccc agatatgtta agcatagcac tctgaaattg 1020
gcaacaggaa tgcgaaatgt accagagaaa caaactagag gcatatttgg cgcaatagcg 1080
ggtttcatag aaaatggttg ggagggaatg gtggatggtt ggtacggttt caggcatcaa 1140
aattctgagg gaagaggaca agcagcagat ctcaaaagca ctcaagcagc aatcgatcaa 1200
atcaatggga agctggctcg ggtgatcggg aaaaccaacg agaaattcca tcagattgaa 1260
aaagaattct cagaagtaga aggaagagtt caagaccttg agaaatatgt tgaggacact 1320
aaaatagatc tctggtcata caacgcggag cttcttgttg ccctggagaa ccaacataca 1380
attgatctaa ctgactcaga aatgaacaaa ctgtttgaaa aaacaaagaa gcaactgagg 1440
gaaaatgctg aggatatggg aaatggttgt ttcaaaatat accacaaatg tgacaatgcc 1500
tgcataggat caataagaaa tgaaacttat gaccacaatg tgtacaggga tgaagcatta 1560
aacaaccggt tccagatcaa gggagttgag ctgaagtcag ggtacaaaga ttggatccta 1620
tggatttcct ttgccatatc atcccttgta ctgttagttg ctttgttggg gttcatcatg 1680
tgggcctgcc aaaagggcaa cattagatgc aacatttgca tttga 1725

<210> SEQ ID NO 31
<211> LENGTH: 574
<212> TYPE: PRT
<213> ORGANISM: Artificial Sequence
<220> FEATURE:
<223> OTHER INFORMATION: PDI-H3 Minn-N382A+L384V-CysTm AA

<400> SEQUENCE: 31

Met Ala Lys Asn Val Ala Ile Phe Gly Leu Leu Phe Ser Leu Leu Val
1 5 10 15

Leu Val Pro Ser Gln Ile Phe Ala Gln Lys Ile Pro Gly Asn Asp Asn
20 25 30

Ser Thr Ala Thr Leu Cys Leu Gly His His Ala Val Pro Asn Gly Thr
35 40 45

Ile Val Lys Thr Ile Thr Asn Asp Arg Ile Glu Val Thr Asn Ala Thr
50 55 60

Glu Leu Val Gln Asn Ser Ser Ile Gly Glu Ile Cys Asp Ser Pro His
65 70 75 80

Gln Ile Leu Asp Gly Glu Asn Cys Thr Leu Ile Asp Ala Leu Leu Gly
85 90 95

Asp Pro Gln Cys Asp Gly Phe Gln Asn Lys Lys Trp Asp Leu Phe Val
100 105 110

Glu Arg Ser Lys Ala Tyr Ser Asn Cys Tyr Pro Tyr Asp Val Pro Asp
115 120 125

Tyr Ala Ser Leu Arg Ser Leu Val Ala Ser Ser Gly Thr Leu Glu Phe
130 135 140

Asn Asn Glu Ser Phe Asn Trp Thr Gly Val Thr Gln Asn Gly Thr Ser
145 150 155 160

Ser Ala Cys Ile Arg Arg Ser Ser Ser Ser Phe Phe Ser Arg Leu Asn
165 170 175

Trp Leu Thr His Leu Asn Tyr Thr Tyr Pro Ala Leu Asn Val Thr Met
180 185 190

Pro Asn Lys Glu Gln Phe Asp Lys Leu Tyr Ile Trp Gly Val His His
195 200 205

-continued

```
Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Ala Arg Val Ile Gly Lys Thr Asn Glu Lys Phe
                405                 410                 415

His Gln Ile Glu Lys Glu Phe Ser Glu Val Glu Gly Arg Val Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Glu Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 32
<211> LENGTH: 1725
<212> TYPE: DNA
<213> ORGANISM: Artificial Sequence
<220> FEATURE:
<223> OTHER INFORMATION: PDI-H3 SAus-CysTm DNA

<400> SEQUENCE: 32

```
atggcgaaaa acgttgcgat tttcggctta ttgttttctc ttcttgtgtt ggttccttct      60
cagatcttcg cgcaaaaaat tcctggaaat gacaatagca cggcaacgct gtgccttggg     120
caccatgcag taccaaacgg aacgatagtg aaaacaatca caaatgaccg aattgaagtt     180
actaatgcta ctgagttggt tcagaattcc tcaataggtg aaatatgcga cagtcctcat     240
cagatccttg atggagagaa ctgcacacta atagatgctc tattgggaga ccctcagtgt     300
gatggctttc aaaataagaa atgggacctt tttgttgaac gaagcaaagc ctacagcaac     360
tgttaccctt atgatgtgcc ggattatgcc tcccttaggt cactagttgc ctcatccggc     420
acactggagt ttaaaaatga aagcttcaat tggactggag tcactcaaaa cggaacaagt     480
tctgcttgca taaggagatc tagtagtagt ttctttagta gattaaattg gttgacccac     540
ttaaactaca catatccagc attgaacgtg actatgccaa acaaggaaca atttgacaaa     600
ttgtacattt gggggttca ccacccgggt acggacaagg accaaatctt cctgtatgct      660
caatcatcag gaagaatcac agtatctacc aaaagaagcc aacaagctgt aatcccaaat     720
atcggatcta gacccagaat aagggatatc cctagcagaa taagcatcta ttggacaata     780
gtaaaaccgg gagacatact tttgattaac agcacaggga atctaattgc tcctaggggt     840
tacttcaaaa tacgaagtgg gaaaagctca ataatgagat cagatgcacc cattggcaaa     900
tgcaagtctg aatgcatcac tccaaatgga agcattccca atgacaaacc attccaaaat     960
gtaaacagga tcacatacgg ggcctgtccc agatatgtta agcatagcac tctgaaattg    1020
gcaacaggaa tgcgaaatgt accagagaaa caaactagag gcatatttgg cgcaatagcg    1080
ggtttcatag aaaatggttg ggagggaatg gtggatggtt ggtacggttt caggcatcaa    1140
aattctgagg gaagaggaca agcagcagat ctcaaaagca ctcaagcagc aatcgatcaa    1200
atcaatggga agctgaatcg gttgatcggg aaaaccaacg agaaattcca tcagattgaa    1260
aaagaattct cagaagtaga aggaagagtt caagaccttg agaaatatgt tgaggacact    1320
aaaatagatc tctggtcata caacgcggag cttcttgttg ccctggagaa ccaacataca    1380
attgatctaa ctgactcaga aatgaacaaa ctgtttgaaa aaacaaagaa gcaactgagg    1440
gaaaatgctg aggatatggg aaatggttgt ttcaaaatat accacaaatg tgacaatgcc    1500
tgcataggat caataagaaa tgaaacttat gaccacaatg tgtacaggga tgaagcatta    1560
aacaaccggt tccagatcaa gggagttgag ctgaagtcag ggtacaaaga ttggatccta    1620
tggatttcct ttgccatatc atcccttgta ctgttagttg ctttgttggg gttcatcatg    1680
tgggcctgcc aaaagggcaa cattagatgc aacatttgca tttga                    1725
```

<210> SEQ ID NO 33
<211> LENGTH: 574
<212> TYPE: PRT
<213> ORGANISM: Artificial Sequence
<220> FEATURE:
<223> OTHER INFORMATION: PDI-H3 SAus-CysTm AA

<400> SEQUENCE: 33

```
Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
```

-continued

```
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Lys Asn Glu Ser Phe Asn Trp Thr Gly Val Thr Gln Asn Gly Thr Ser
145                 150                 155                 160

Ser Ala Cys Ile Arg Arg Ser Ser Ser Ser Phe Phe Ser Arg Leu Asn
                165                 170                 175

Trp Leu Thr His Leu Asn Tyr Thr Tyr Pro Ala Leu Asn Val Thr Met
            180                 185                 190

Pro Asn Lys Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Val Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480
```

```
Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Glu Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 34
<211> LENGTH: 1725
<212> TYPE: DNA
<213> ORGANISM: Artificial Sequence
<220> FEATURE:
<223> OTHER INFORMATION: PDI-H3 SAus-N382A+L384V-CysTm DNA

<400> SEQUENCE: 34

```
atggcgaaaa acgttgcgat ttcggctta ttgttttctc ttcttgtgtt ggttccttct     60

cagatcttcg cgcaaaaaat tcctggaaat gacaatagca cggcaacgct gtgccttggg    120

caccatgcag taccaaacgg aacgatagtg aaaacaatca caaatgaccg aattgaagtt    180

actaatgcta ctgagttggt tcagaattcc tcaataggtg aaatatgcga cagtcctcat    240

cagatccttg atggagagaa ctgcacacta atagatgctc tattgggaga ccctcagtgt    300

gatggctttc aaaataagaa atgggacctt tttgttgaac gaagcaaagc ctacagcaac    360

tgttaccctt atgatgtgcc ggattatgcc tcccttaggt cactagttgc ctcatccggc    420

acactggagt ttaaaaatga aagcttcaat tggactggag tcactcaaaa cggaacaagt    480

tctgcttgca taaggagatc tagtagtagt ttctttagta gattaaattg gttgacccac    540

ttaaactaca catatccagc attgaacgtg actatgccaa acaaggaaca atttgacaaa    600

ttgtacattt ggggggttca ccacccgggt acggacaagg accaaatctt cctgtatgct    660

caatcatcag gaagaatcac agtatctacc aaaagaagcc aacaagctgt aatcccaaat    720

atcggatcta gacccagaat aagggatatc cctagcagaa taagcatcta ttggacaata    780

gtaaaaccgg gagacatact tttgattaac agcacaggga atctaattgc tcctaggggt    840

tacttcaaaa tacgaagtgg gaaaagctca ataatgagat cagatgcacc cattggcaaa    900

tgcaagtctg aatgcatcac tccaaatgga agcattccca atgacaaacc attccaaaat    960

gtaaacagga tcacatacgg ggcctgtccc agatatgtta agcatagcac tctgaaattg   1020

gcaacaggaa tgcgaaatgt accagagaaa caaactagag gcatatttgg cgcaatagcg   1080

ggtttcatag aaaatggttg ggagggaatg gtggatggtt ggtacggttt caggcatcaa   1140

aattctgagg gaagaggaca agcagcagat ctcaaaagca ctcaagcagc aatcgatcaa   1200

atcaatggga agctggctcg ggtgatcggg aaaaccaacg agaaattcca tcagattgaa   1260

aaagaattct cagaagtaga aggaagagtt caagaccttg agaaatatgt tgaggacact   1320

aaaatagatc tctggtcata caacgcggag cttcttgttg ccctggagaa ccaacataca   1380

attgatctaa ctgactcaga aatgaacaaa ctgtttgaaa aaacaaagaa gcaactgagg   1440

gaaaatgctg aggatatggg aaatggttgt ttcaaaatat accacaaatg tgacaatgcc   1500
```

```
tgcataggat caataagaaa tgaaacttat gaccacaatg tgtacaggga tgaagcatta   1560

aacaaccggt tccagatcaa gggagttgag ctgaagtcag ggtacaaaga ttggatccta   1620

tggatttcct ttgccatatc atcccttgta ctgttagttg ctttgttggg gttcatcatg   1680

tgggcctgcc aaaagggcaa cattagatgc aacatttgca tttga                   1725


<210> SEQ ID NO 35
<211> LENGTH: 574
<212> TYPE: PRT
<213> ORGANISM: Artificial Sequence
<220> FEATURE:
<223> OTHER INFORMATION: PDI-H3 SAus-N382A+L384V-CysTm AA

<400> SEQUENCE: 35

Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Lys Asn Glu Ser Phe Asn Trp Thr Gly Val Thr Gln Asn Gly Thr Ser
145                 150                 155                 160

Ser Ala Cys Ile Arg Arg Ser Ser Ser Ser Phe Phe Ser Arg Leu Asn
                165                 170                 175

Trp Leu Thr His Leu Asn Tyr Thr Tyr Pro Ala Leu Asn Val Thr Met
            180                 185                 190

Pro Asn Lys Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
```

```
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Ala Arg Val Ile Gly Lys Thr Asn Glu Lys Phe
                405                 410                 415

His Gln Ile Glu Lys Glu Phe Ser Glu Val Glu Gly Arg Val Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Glu Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 36
<211> LENGTH: 1725
<212> TYPE: DNA
<213> ORGANISM: Artificial Sequence
<220> FEATURE:
<223> OTHER INFORMATION: PDI-H3 Bang-CysTm DNA

<400> SEQUENCE: 36

```
atggcgaaaa acgttgcgat tttcggctta ttgttttctc ttcttgtgtt ggttccttct     60

cagatcttcg cgcaaaaaat tcctggaaat gacaatagca cggcaacgct gtgccttggg    120

caccatgcag taccaaacgg aacgatagtg aaaacaatca caaatgaccg aattgaagtt    180

actaatgcta ctgagctggt tcagaattcc tcaataggtg aaatatgcga cagtcctcat    240

cagatccttg atggagaaaa ctgcacacta atagatgctc tattgggaga ccctcagtgt    300

gatggctttc aaaataagaa atgggacctt tttgttgaac gaagcaaagc ctacagcaac    360

tgttaccctt atgatgtgcc ggattatgcc tcccttaggt cactagttgc ctcatccggc    420

acactggagt ttaacaatga aagcttcaat tggactggag tcactcaaaa cggaacaagt    480

tctgcttgca taaggaaatc tagtagtagt ttctttagta gattaaattg gttgacccac    540

ttaaactaca catacccagc attgaacgtg actgtgccaa acaatgaaca atttgacaaa    600

ttgtacattt ggggggttca ccacccgggt acggacaagg accaaatctt cctgtatgct    660
```

-continued

```
cgatcatcag gaagaatcac agtatctacc aaaagaagcc aacaagctgt aatcccaaat    720

atcggatcta gacccagaat aagggatatc cctagcagaa taagcatcta ttggacaata    780

gtaaaaccgg gagacatact tttgattaac agcacaggga atctaattgc tcctaggggt    840

tacttcaaaa tacgaagtgg gaaaagctca ataatgagat cagatgcacc cattggcaaa    900

tgcaagtctg aatgcatcac tccaaatgga agcattccca atgacaaacc attccaaaat    960

gtaaacagga tcacatacgg ggcctgtccc agatatgtta agcatagcac tctgaaattg   1020

gcaacaggaa tgcgaaatgt accagagaaa caaactagag gcatatttgg cgcaatagcg   1080

ggtttcatag aaaatggttg ggagggaatg gtggatggtt ggtacggttt caggcatcaa   1140

aattctgagg gaagaggaca agcagcagat ctcaaaagca ctcaagcagc aatcgatcaa   1200

atcaatggga agctgaatcg attgatcggg aaaaccaacg agaaattcca tcagattgaa   1260

aaagaattct cagaagtaga aggaagaatt caggaccttg agaaatatgt tgaggacact   1320

aaaatagatc tctggtcata caacgcggag cttcttgttg ccctggagaa tcaacataca   1380

attgatctaa ctgactcaga aatgaacaaa ctgtttgaaa aaacaaagaa gcaactgagg   1440

gaaaatgctg aggatatggg aaatggttgt ttcaaaatat accacaaatg tgacaatgcc   1500

tgcataggat caataagaaa tggaacttat gaccacaatg tgtacaggga tgaagcatta   1560

aacaaccggt tccagatcaa gggagttgag ctgaagtcag ggtacaaaga ttggatccta   1620

tggatttcct ttgccatatc atcccttgta ctgttagttg ctttgttggg gttcatcatg   1680

tgggcctgcc aaaagggcaa cattaggtgc aacatttgca tttga                   1725
```

<210> SEQ ID NO 37
<211> LENGTH: 574
<212> TYPE: PRT
<213> ORGANISM: Artificial Sequence
<220> FEATURE:
<223> OTHER INFORMATION: PDI-H3 Bang-CysTm AA

<400> SEQUENCE: 37

```
Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Lys Ser Ser Ser Ser Phe Phe Ser Arg Leu Asn
                165                 170                 175
```

-continued

```
Trp Leu Thr His Leu Asn Tyr Thr Tyr Pro Ala Leu Asn Val Thr Val
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Arg Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 38
<211> LENGTH: 1725
<212> TYPE: DNA

<213> ORGANISM: Artificial Sequence
<220> FEATURE:
<223> OTHER INFORMATION: PDI-H3 Bang-N382A+L384V-CysTm DNA

<400> SEQUENCE: 38

```
atggcgaaaa acgttgcgat tttcggctta ttgttttctc ttcttgtgtt ggttccttct      60

cagatcttcg cgcaaaaaat tcctggaaat gacaatagca cggcaacgct gtgccttggg     120

caccatgcag taccaaacgg aacgatagtg aaaacaatca caaatgaccg aattgaagtt     180

actaatgcta ctgagctggt tcagaattcc tcaataggtg aaatatgcga cagtcctcat     240

cagatccttg atggagaaaa ctgcacacta atagatgctc tattgggaga ccctcagtgt     300

gatggctttc aaaataagaa atgggacctt tttgttgaac gaagcaaagc ctacagcaac     360

tgttaccctt atgatgtgcc ggattatgcc tcccttaggt cactagttgc ctcatccggc     420

acactggagt ttaacaatga aagcttcaat tggactggag tcactcaaaa cggaacaagt     480

tctgcttgca taaggaaatc tagtagtagt ttctttagta gattaaattg gttgacccac     540

ttaaactaca catacccagc attgaacgtg actgtgccaa acaatgaaca atttgacaaa     600

ttgtacattt ggggggttca ccacccgggt acggacaagg accaaatctt cctgtatgct     660

cgatcatcag gaagaatcac agtatctacc aaaagaagcc aacaagctgt aatcccaaat     720

atcggatcta gacccagaat aagggatatc cctagcagaa taagcatcta ttggacaata     780

gtaaaaccgg gagacatact tttgattaac agcacaggga atctaattgc tcctaggggt     840

tacttcaaaa tacgaagtgg gaaaagctca ataatgagat cagatgcacc cattggcaaa     900

tgcaagtctg aatgcatcac tccaaatgga agcattccca atgacaaacc attccaaaat     960

gtaaacagga tcacatacgg ggcctgtccc agatatgtta agcatagcac tctgaaattg    1020

gcaacaggaa tgcgaaatgt accagagaaa caaactagag gcatatttgg cgcaatagcg    1080

ggtttcatag aaaatggttg ggagggaatg gtggatggtt ggtacggttt caggcatcaa    1140

aattctgagg gaagaggaca agcagcagat ctcaaaagca ctcaagcagc aatcgatcaa    1200

atcaatggga agctggctcg agtgatcggg aaaaccaacg agaaattcca tcagattgaa    1260

aaagaattct cagaagtaga aggaagaatt caggaccttg agaaatatgt tgaggacact    1320

aaaatagatc tctggtcata caacgcggag cttcttgttg ccctggagaa tcaacataca    1380

attgatctaa ctgactcaga aatgaacaaa ctgtttgaaa aaacaaagaa gcaactgagg    1440

gaaaatgctg aggatatggg aaatggttgt ttcaaaatat accacaaatg tgacaatgcc    1500

tgcataggat caataagaaa tggaacttat gaccacaatg tgtacaggga tgaagcatta    1560

aacaaccggt tccagatcaa gggagttgag ctgaagtcag ggtacaaaga ttggatccta    1620

tggatttcct ttgccatatc atcccttgta ctgttagttg ctttgttggg gttcatcatg    1680

tgggcctgcc aaaagggcaa cattaggtgc aacatttgca tttga                    1725
```

<210> SEQ ID NO 39
<211> LENGTH: 574
<212> TYPE: PRT
<213> ORGANISM: Artificial Sequence
<220> FEATURE:
<223> OTHER INFORMATION: PDI-H3 Bang-N382A+L384V-CysTm AA

<400> SEQUENCE: 39

```
Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30
```

-continued

```
Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Lys Ser Ser Ser Ser Phe Phe Ser Arg Leu Asn
                165                 170                 175

Trp Leu Thr His Leu Asn Tyr Thr Tyr Pro Ala Leu Asn Val Thr Val
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Arg Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Ala Arg Val Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445
```

-continued

```
Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 40
<211> LENGTH: 54
<212> TYPE: DNA
<213> ORGANISM: Artificial Sequence
<220> FEATURE:
<223> OTHER INFORMATION: Primer H3_Swi(F392D).r

<400> SEQUENCE: 40

```
ttttcaatct gatggtcttt ctcgttggtt ttcccgatca atcgattcag cttc           54
```

<210> SEQ ID NO 41
<211> LENGTH: 48
<212> TYPE: DNA
<213> ORGANISM: Artificial Sequence
<220> FEATURE:
<223> OTHER INFORMATION: Primer H3_Swi(F392D).c

<400> SEQUENCE: 41

```
tcgggaaaac caacgagaaa gaccatcaga ttgaaaaaga attctcag                  48
```

<210> SEQ ID NO 42
<211> LENGTH: 1725
<212> TYPE: DNA
<213> ORGANISM: Artificial Sequence
<220> FEATURE:
<223> OTHER INFORMATION: PDI-H3 Switz-F392D DNA

<400> SEQUENCE: 42

```
atggcgaaaa acgttgcgat tttcggctta ttgttttctc ttcttgtgtt ggttccttct     60

cagatcttcg cgcaaaaact tcctggaaat gacaatagca cggcaacgct gtgccttggg    120

caccatgcag taccaaacgg aacgatagtg aaaacaatca cgaatgaccg aattgaagtt    180

actaatgcta ctgagctggt tcagaattcc tcaataggtg aaatatgcga cagtcctcat    240

cagatccttg atggagaaaa ctgcacacta atagatgctc tattgggaga ccctcagtgt    300

gatggctttc aaaataagaa atgggacctt tttgttgaac gaagcaaagc ctacagcaac    360

tgttaccctt atgatgtgcc ggattatgcc tcccttaggt cactagttgc ctcatccggc    420

acactggagt ttaacaatga aagcttcaat tgggctggag tcactcaaaa cggaacaagt    480

tcttcttgca taaggggatc taatagtagt ttctttagta gattaaattg gttgacccac    540

ttaaactcca aatacccagc attaaacgtg actatgccaa acaatgaaca atttgacaaa    600

ttgtacattt ggggggttca ccacccgggt acggacaagg accaaatctt cctgtatgca    660
```

-continued

```
caatcatcag gaagaatcac agtatctacc aaaagaagcc aacaagctgt aatcccgaat     720

atcggatcta gacccagaat aagggatatc cctagcagaa taagcatcta ttggacaata     780

gtaaaaccgg gagacatact tttgattaac agcacaggga atctaattgc tcctaggggt     840

tacttcaaaa tacgaagtgg gaaaagctca ataatgagat cagatgcacc cattggcaaa     900

tgcaagtctg aatgcatcac tccaaatgga agcattccca atgacaaacc attccaaaat     960

gtaaacagga tcacatacgg ggcctgtccc agatatgtta agcaaagcac tctgaaattg    1020

gcaacaggaa tgcgaaatgt accagagaga caaactagag gcatatttgg cgcaatagcg    1080

ggtttcatag aaaatggttg ggagggaatg gtggatggtt ggtacggctt caggcatcaa    1140

aattctgagg gaagaggaca agcagcagat ctcaaaagca ctcaagcagc aatcgatcaa    1200

atcaatggga agctgaatcg attgatcggg aaaaccaacg agaaagacca tcagattgaa    1260

aaagaattct cagaagtaga agggagaatt caggaccttg agaaatatgt tgaggacaca    1320

aaaatagatc tctggtcata caacgcggag cttcttgttg ccctggagaa ccaacataca    1380

attgatctaa ctgactcaga aatgaacaaa ctgtttgaaa aaacaaagaa gcaactgagg    1440

gaaaatgctg aggatatggg caatggttgt ttcaaaatat accacaaatg tgacaatgcc    1500

tgcataggat caatcagaaa tggaacttat gaccacgatg tatacaggga tgaagcatta    1560

aacaaccggt tccagatcaa gggagttgag ctgaagtcag ggtacaaaga ttggatccta    1620

tggatttcct ttgccatatc atgtttttg ctttgtgttg ctttgttggg gttcatcatg    1680

tgggcctgcc aaaagggcaa cattaggtgc aacatttgca tttga                   1725
```

<210> SEQ ID NO 43
<211> LENGTH: 574
<212> TYPE: PRT
<213> ORGANISM: Artificial Sequence
<220> FEATURE:
<223> OTHER INFORMATION: PDI-H3 Switz-F392D AA

<400> SEQUENCE: 43

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160

Ser Ser Cys Ile Arg Gly Ser Asn Ser Ser Phe Phe Ser Arg Leu Asn
                165                 170                 175
```

-continued

```
Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Asp
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 44
<211> LENGTH: 50

-continued

<212> TYPE: DNA
<213> ORGANISM: Artificial Sequence
<220> FEATURE:
<223> OTHER INFORMATION: Primer H3_Swi(L431M).r

<400> SEQUENCE: 44
ttgtatgttg gttctccatg gcaacaagaa gctccgcgtt gtatgaccag 50

<210> SEQ ID NO 45
<211> LENGTH: 54
<212> TYPE: DNA
<213> ORGANISM: Artificial Sequence
<220> FEATURE:
<223> OTHER INFORMATION: Primer H3_Swi(L431M).c

<400> SEQUENCE: 45
ggagcttctt gttgccatgg agaaccaaca tacaattgat ctaactgact caga 54

<210> SEQ ID NO 46
<211> LENGTH: 1725
<212> TYPE: DNA
<213> ORGANISM: Artificial Sequence
<220> FEATURE:
<223> OTHER INFORMATION: PDI-H3 Switz-L431M DNA

<400> SEQUENCE: 46
atggcgaaaa acgttgcgat tttcggctta ttgttttctc ttcttgtgtt ggttccttct 60
cagatcttcg cgcaaaaact tcctggaaat gacaatagca cggcaacgct gtgccttggg 120
caccatgcag taccaaacgg aacgatagtg aaaacaatca cgaatgaccg aattgaagtt 180
actaatgcta ctgagctggt tcagaattcc tcaataggtg aaatatgcga cagtcctcat 240
cagatccttg atggagaaaa ctgcacacta atagatgctc tattgggaga ccctcagtgt 300
gatggctttc aaaataagaa atgggacctt tttgttgaac gaagcaaagc ctacagcaac 360
tgttaccctt atgatgtgcc ggattatgcc tcccttaggt cactagttgc ctcatccggc 420
acactggagt ttaacaatga aagcttcaat tgggctggag tcactcaaaa cggaacaagt 480
tcttcttgca taaggggatc taatagtagt ttctttagta gattaaattg gttgacccac 540
ttaaactcca aatacccagc attaaacgtg actatgccaa acaatgaaca atttgacaaa 600
ttgtacattt ggggggttca ccacccgggt acggacaagg accaaatctt cctgtatgca 660
caatcatcag gaagaatcac agtatctacc aaaagaagcc aacaagctgt aatcccgaat 720
atcggatcta gacccagaat aagggatatc cctagcagaa taagcatcta ttggacaata 780
gtaaaaccgg gagacatact tttgattaac agcacaggga atctaattgc tcctaggggt 840
tacttcaaaa tacgaagtgg gaaaagctca ataatgagat cagatgcacc cattggcaaa 900
tgcaagtctg aatgcatcac tccaaatgga agcattccca atgacaaacc attccaaaat 960
gtaaacagga tcacatacgg ggcctgtccc agatatgtta agcaaagcac tctgaaattg 1020
gcaacaggaa tgcgaaatgt accagagaga caaactagag gcatatttgg cgcaatagcg 1080
ggtttcatag aaaatggttg ggagggaatg gtggatggtt ggtacggctt caggcatcaa 1140
aattctgagg gaagaggaca agcagcagat ctcaaaagca ctcaagcagc aatcgatcaa 1200
atcaatggga agctgaatcg attgatcggg aaaaccaacg agaaattcca tcagattgaa 1260
aaagaattct cagaagtaga agggagaatt caggaccttg agaaatatgt tgaggacaca 1320
aaaatagatc tctggtcata caacgcggag cttcttgttg ccatggagaa ccaacataca 1380
attgatctaa ctgactcaga aatgaacaaa ctgtttgaaa aaacaaagaa gcaactgagg 1440

-continued

```
gaaaatgctg aggatatggg caatggttgt ttcaaaatat accacaaatg tgacaatgcc   1500

tgcataggat caatcagaaa tggaacttat gaccacgatg tatacaggga tgaagcatta   1560

aacaaccggt tccagatcaa gggagttgag ctgaagtcag ggtacaaaga ttggatccta   1620

tggatttcct ttgccatatc atgtttttttg ctttgtgttg ctttgttggg gttcatcatg   1680

tgggcctgcc aaaagggcaa cattaggtgc aacatttgca tttga                   1725


<210> SEQ ID NO 47
<211> LENGTH: 574
<212> TYPE: PRT
<213> ORGANISM: Artificial Sequence
<220> FEATURE:
<223> OTHER INFORMATION: PDI-H3 Switz-L431M AA

<400> SEQUENCE: 47

Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160

Ser Ser Cys Ile Arg Gly Ser Asn Ser Ser Phe Phe Ser Arg Leu Asn
                165                 170                 175

Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320
```

```
Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Met Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 48
<211> LENGTH: 1725
<212> TYPE: DNA
<213> ORGANISM: Artificial Sequence
<220> FEATURE:
<223> OTHER INFORMATION: PDI-H3 Switz-CysTm DNA

<400> SEQUENCE: 48

```
atggcgaaaa acgttgcgat tttcggctta ttgttttctc ttcttgtgtt ggttccttct      60

cagatcttcg cgcaaaaact tcctggaaat gacaatagca cggcaacgct gtgccttggg     120

caccatgcag taccaaacgg aacgatagtg aaaacaatca cgaatgaccg aattgaagtt     180

actaatgcta ctgagctggt tcagaattcc tcaataggtg aaatatgcga cagtcctcat     240

cagatccttg atggagaaaa ctgcacacta atagatgctc tattgggaga ccctcagtgt     300

gatggctttc aaaataagaa atgggacctt tttgttgaac gaagcaaagc ctacagcaac     360

tgttaccctt atgatgtgcc ggattatgcc tcccttaggt cactagttgc ctcatccggc     420

acactggagt ttaacaatga aagcttcaat tgggctggag tcactcaaaa cggaacaagt     480

tcttcttgca taaggggatc taatagtagt ttctttagta gattaaattg gttgacccac     540

ttaaactcca aatacccagc attaaacgtg actatgccaa acaatgaaca atttgacaaa     600
```

```
ttgtacattt ggggggttca ccacccgggt acggacaagg accaaatctt cctgtatgca    660

caatcatcag gaagaatcac agtatctacc aaaagaagcc aacaagctgt aatcccgaat    720

atcggatcta gacccagaat aagggatatc cctagcagaa taagcatcta ttggacaata    780

gtaaaaccgg gagacatact tttgattaac agcacaggga atctaattgc tcctaggggt    840

tacttcaaaa tacgaagtgg gaaaagctca ataatgagat cagatgcacc cattggcaaa    900

tgcaagtctg aatgcatcac tccaaatgga agcattccca atgacaaacc attccaaaat    960

gtaaacagga tcacatacgg ggcctgtccc agatatgtta agcaaagcac tctgaaattg   1020

gcaacaggaa tgcgaaatgt accagagaga caaactagag gcatatttgg cgcaatagcg   1080

ggtttcatag aaaatggttg ggagggaatg gtggatggtt ggtacggctt caggcatcaa   1140

aattctgagg gaagaggaca agcagcagat ctcaaaagca ctcaagcagc aatcgatcaa   1200

atcaatggga agctgaatcg attgatcggg aaaaccaacg agaaattcca tcagattgaa   1260

aaagaattct cagaagtaga agggagaatt caggaccttg agaaatatgt tgaggacaca   1320

aaaatagatc tctggtcata caacgcggag cttcttgttg ccctggagaa ccaacataca   1380

attgatctaa ctgactcaga aatgaacaaa ctgtttgaaa aaacaaagaa gcaactgagg   1440

gaaaatgctg aggatatggg caatggttgt ttcaaaatat accacaaatg tgacaatgcc   1500

tgcataggat caatcagaaa tggaacttat gaccacgatg tatacaggga tgaagcatta   1560

aacaaccggt tccagatcaa gggagttgag ctgaagtcag ggtacaaaga ttggatccta   1620

tggatttcct ttgccatatc atcccttgta ctgttagttg ctttgttggg gttcatcatg   1680

tgggcctgcc aaaagggcaa cattaggtgc aacatttgca tttga                   1725
```

<210> SEQ ID NO 49
<211> LENGTH: 574
<212> TYPE: PRT
<213> ORGANISM: Artificial Sequence
<220> FEATURE:
<223> OTHER INFORMATION: PDI-H3 Switz-CysTm AA

<400> SEQUENCE: 49

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160

Ser Ser Cys Ile Arg Gly Ser Asn Ser Ser Phe Phe Ser Arg Leu Asn
```

-continued

```
                165                 170                 175

Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 50

<211> LENGTH: 48
<212> TYPE: DNA
<213> ORGANISM: Artificial Sequence
<220> FEATURE:
<223> OTHER INFORMATION: Primer H3_Swi(N382A).r

<400> SEQUENCE: 50
tttcccgatc aatcgagcca gcttcccatt gatttgatcg attgctgc 48

<210> SEQ ID NO 51
<211> LENGTH: 54
<212> TYPE: DNA
<213> ORGANISM: Artificial Sequence
<220> FEATURE:
<223> OTHER INFORMATION: Primer H3_Swi(N382A).c

<400> SEQUENCE: 51
tcaaatcaat gggaagctgg ctcgattgat cgggaaaacc aacgagaaat tcca 54

<210> SEQ ID NO 52
<211> LENGTH: 1725
<212> TYPE: DNA
<213> ORGANISM: Artificial Sequence
<220> FEATURE:
<223> OTHER INFORMATION: PDI-H3 Switz-N382A-CysTm DNA

<400> SEQUENCE: 52
atggcgaaaa acgttgcgat tttcggctta ttgttttctc ttcttgtgtt ggttccttct 60
cagatcttcg cgcaaaaact tcctggaaat gacaatagca cggcaacgct gtgccttggg 120
caccatgcag taccaaacgg aacgatagtg aaaacaatca cgaatgaccg aattgaagtt 180
actaatgcta ctgagctggt tcagaattcc tcaataggtg aaatatgcga cagtcctcat 240
cagatccttg atggagaaaa ctgcacacta atagatgctc tattgggaga ccctcagtgt 300
gatggctttc aaaataagaa atgggacctt tttgttgaac gaagcaaagc ctacagcaac 360
tgttaccctt atgatgtgcc ggattatgcc tcccttaggt cactagttgc ctcatccggc 420
acactggagt ttaacaatga aagcttcaat tgggctggag tcactcaaaa cggaacaagt 480
tcttcttgca taaggggatc taatagtagt ttctttagta gattaaattg gttgacccac 540
ttaaactcca aatacccagc attaaacgtg actatgccaa acaatgaaca atttgacaaa 600
ttgtacattt ggggggttca ccacccgggt acggacaagg accaaatctt cctgtatgca 660
caatcatcag gaagaatcac agtatctacc aaaagaagcc aacaagctgt aatcccgaat 720
atcggatcta gacccagaat aagggatatc cctagcagaa taagcatcta ttggacaata 780
gtaaaaccgg gagacatact tttgattaac agcacaggga atctaattgc tcctaggggt 840
tacttcaaaa tacgaagtgg gaaaagctca ataatgagat cagatgcacc cattggcaaa 900
tgcaagtctg aatgcatcac tccaaatgga agcattccca atgacaaacc attccaaaat 960
gtaaacagga tcacatacgg ggcctgtccc agatatgtta agcaaagcac tctgaaattg 1020
gcaacaggaa tgcgaaatgt accagagaga caaactagag gcatatttgg cgcaatagcg 1080
ggtttcatag aaaatggttg ggagggaatg gtggatggtt ggtacggctt caggcatcaa 1140
aattctgagg gaagaggaca agcagcagat ctcaaaagca ctcaagcagc aatcgatcaa 1200
atcaatggga agctggctcg attgatcggg aaaaccaacg agaaattcca tcagattgaa 1260
aaagaattct cagaagtaga agggagaatt caggaccttg agaaatatgt tgaggacaca 1320
aaaatagatc tctggtcata caacgcggag cttcttgttg ccctggagaa ccaacataca 1380
attgatctaa ctgactcaga aatgaacaaa ctgtttgaaa aaacaaagaa gcaactgagg 1440

```
gaaaatgctg aggatatggg caatggttgt ttcaaaatat accacaaatg tgacaatgcc   1500

tgcataggat caatcagaaa tggaacttat gaccacgatg tatacaggga tgaagcatta   1560

aacaaccggt tccagatcaa gggagttgag ctgaagtcag ggtacaaaga ttggatccta   1620

tggatttcct ttgccatatc atcccttgta ctgttagttg ctttgttggg gttcatcatg   1680

tgggcctgcc aaaagggcaa cattaggtgc aacatttgca tttga                   1725


<210> SEQ ID NO 53
<211> LENGTH: 574
<212> TYPE: PRT
<213> ORGANISM: Artificial Sequence
<220> FEATURE:
<223> OTHER INFORMATION: PDI-H3 Switz-N382A-CysTm AA

<400> SEQUENCE: 53

Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160

Ser Ser Cys Ile Arg Gly Ser Asn Ser Ser Phe Phe Ser Arg Leu Asn
                165                 170                 175

Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
```

```
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Ala Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 54
<211> LENGTH: 48
<212> TYPE: DNA
<213> ORGANISM: Artificial Sequence
<220> FEATURE:
<223> OTHER INFORMATION: Primer H3_Swi(L384V).r

<400> SEQUENCE: 54
ttggttttcc cgatcactcg attcagcttc ccattgattt gatcgatt 48

<210> SEQ ID NO 55
<211> LENGTH: 48
<212> TYPE: DNA
<213> ORGANISM: Artificial Sequence
<220> FEATURE:
<223> OTHER INFORMATION: Primer H3_Swi(L384V).c

<400> SEQUENCE: 55
gggaagctga atcgagtgat cgggaaaacc aacgagaaat tccatcag 48

<210> SEQ ID NO 56
<211> LENGTH: 1725
<212> TYPE: DNA
<213> ORGANISM: Artificial Sequence
<220> FEATURE:
<223> OTHER INFORMATION: PDI-H3 Switz-L384V-CysTm DNA

<400> SEQUENCE: 56
atggcgaaaa acgttgcgat tttcggctta ttgttttctc ttcttgtgtt ggttccttct 60
cagatcttcg cgcaaaaact tcctggaaat gacaatagca cggcaacgct gtgccttggg 120
caccatgcag taccaaacgg aacgatagtg aaaacaatca cgaatgaccg aattgaagtt 180
actaatgcta ctgagctggt tcagaattcc tcaataggtg aaatatgcga cagtcctcat 240
cagatccttg atggagaaaa ctgcacacta atagatgctc tattgggaga ccctcagtgt 300
gatggctttc aaaataagaa atgggacctt tttgttgaac gaagcaaagc ctacagcaac 360
tgttaccctt atgatgtgcc ggattatgcc tcccttaggt cactagttgc ctcatccggc 420
acactggagt ttaacaatga aagcttcaat tgggctggag tcactcaaaa cggaacaagt 480
tcttcttgca taaggggatc taatagtagt ttctttagta gattaaattg gttgacccac 540
ttaaactcca aatacccagc attaaacgtg actatgccaa acaatgaaca atttgacaaa 600
ttgtacattt ggggggttca ccacccgggt acggacaagg accaaatctt cctgtatgca 660
caatcatcag gaagaatcac agtatctacc aaaagaagcc aacaagctgt aatcccgaat 720
atcggatcta gacccagaat aagggatatc cctagcagaa taagcatcta ttggacaata 780
gtaaaaccgg gagacatact tttgattaac agcacaggga atctaattgc tcctaggggt 840
tacttcaaaa tacgaagtgg gaaaagctca ataatgagat cagatgcacc cattggcaaa 900
tgcaagtctg aatgcatcac tccaaatgga agcattccca atgacaaacc attccaaaat 960
gtaaacagga tcacatacgg ggcctgtccc agatatgtta agcaaagcac tctgaaattg 1020
gcaacaggaa tgcgaaatgt accagagaga caaactagag gcatatttgg cgcaatagcg 1080
ggtttcatag aaaatggttg ggagggaatg gtggatggtt ggtacggctt caggcatcaa 1140
aattctgagg gaagaggaca agcagcagat ctcaaaagca ctcaagcagc aatcgatcaa 1200
atcaatggga agctgaatcg agtgatcggg aaaaccaacg agaaattcca tcagattgaa 1260
aaagaattct cagaagtaga agggagaatt caggaccttg agaaatatgt tgaggacaca 1320
aaaatagatc tctggtcata caacgcggag cttcttgttg ccctggagaa ccaacataca 1380
attgatctaa ctgactcaga aatgaacaaa ctgtttgaaa aaacaaagaa gcaactgagg 1440
gaaaatgctg aggatatggg caatggttgt ttcaaaatat accacaaatg tgacaatgcc 1500
tgcataggat caatcagaaa tggaacttat gaccacgatg tatacaggga tgaagcatta 1560
aacaaccggt tccagatcaa gggagttgag ctgaagtcag ggtacaaaga ttggatccta 1620
tggatttcct ttgccatatc atcccttgta ctgttagttg ctttgttggg gttcatcatg 1680
tgggcctgcc aaaagggcaa cattaggtgc aacatttgca tttga 1725

<210> SEQ ID NO 57
<211> LENGTH: 574
<212> TYPE: PRT
<213> ORGANISM: Artificial Sequence
<220> FEATURE:
<223> OTHER INFORMATION: PDI-H3 Switz-L384V-CysTm AA

<400> SEQUENCE: 57

Met Ala Lys Asn Val Ala Ile Phe Gly Leu Leu Phe Ser Leu Leu Val
1 5 10 15

Leu Val Pro Ser Gln Ile Phe Ala Gln Lys Leu Pro Gly Asn Asp Asn
20 25 30

-continued

```
Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160

Ser Ser Cys Ile Arg Gly Ser Asn Ser Ser Phe Phe Ser Arg Leu Asn
                165                 170                 175

Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Val Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
```

```
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570


<210> SEQ ID NO 58
<211> LENGTH: 1725
<212> TYPE: DNA
<213> ORGANISM: Artificial Sequence
<220> FEATURE:
<223> OTHER INFORMATION: PDI-H3 Switz-F392D-CysTm DNA

<400> SEQUENCE: 58

atggcgaaaa acgttgcgat tttcggctta ttgttttctc ttcttgtgtt ggttccttct     60

cagatcttcg cgcaaaaact tcctggaaat gacaatagca cggcaacgct gtgccttggg    120

caccatgcag taccaaacgg aacgatagtg aaaacaatca cgaatgaccg aattgaagtt    180

actaatgcta ctgagctggt tcagaattcc tcaataggtg aaatatgcga cagtcctcat    240

cagatccttg atggagaaaa ctgcacacta atagatgctc tattgggaga ccctcagtgt    300

gatggctttc aaaataagaa atgggacctt tttgttgaac gaagcaaagc ctacagcaac    360

tgttaccctt atgatgtgcc ggattatgcc tcccttaggt cactagttgc ctcatccggc    420

acactggagt ttaacaatga aagcttcaat tgggctggag tcactcaaaa cggaacaagt    480

tcttcttgca taaggggatc taatagtagt ttctttagta gattaaattg gttgacccac    540

ttaaactcca aatacccagc attaaacgtg actatgccaa acaatgaaca atttgacaaa    600

ttgtacattt ggggggttca ccacccgggt acggacaagg accaaatctt cctgtatgca    660

caatcatcag gaagaatcac agtatctacc aaaagaagcc aacaagctgt aatcccgaat    720

atcggatcta gacccagaat aagggatatc cctagcagaa taagcatcta ttggacaata    780

gtaaaaccgg gagacatact tttgattaac agcacaggga atctaattgc tcctaggggt    840

tacttcaaaa tacgaagtgg gaaaagctca ataatgagat cagatgcacc cattggcaaa    900

tgcaagtctg aatgcatcac tccaaatgga agcattccca atgacaaacc attccaaaat    960

gtaaacagga tcacatacgg ggcctgtccc agatatgtta agcaaagcac tctgaaattg   1020

gcaacaggaa tgcgaaatgt accagagaga caaactagag gcatatttgg cgcaatagcg   1080

ggtttcatag aaaatggttg ggagggaatg gtggatggtt ggtacggctt caggcatcaa   1140

aattctgagg gaagaggaca agcagcagat ctcaaaagca ctcaagcagc aatcgatcaa   1200

atcaatggga agctgaatcg attgatcggg aaaaccaacg agaaagacca tcagattgaa   1260

aaagaattct cagaagtaga agggagaatt caggaccttg agaaatatgt tgaggacaca   1320

aaaatagatc tctggtcata caacgcggag cttcttgttg ccctggagaa ccaacataca   1380
```

```
attgatctaa ctgactcaga aatgaacaaa ctgtttgaaa aaacaaagaa gcaactgagg   1440

gaaaatgctg aggatatggg caatggttgt ttcaaaatat accacaaatg tgacaatgcc   1500

tgcataggat caatcagaaa tggaacttat gaccacgatg tatacaggga tgaagcatta   1560

aacaaccggt tccagatcaa gggagttgag ctgaagtcag ggtacaaaga ttggatccta   1620

tggatttcct ttgccatatc atcccttgta ctgttagttg ctttgttggg gttcatcatg   1680

tgggcctgcc aaaagggcaa cattaggtgc aacatttgca tttga                    1725
```

<210> SEQ ID NO 59
<211> LENGTH: 574
<212> TYPE: PRT
<213> ORGANISM: Artificial Sequence
<220> FEATURE:
<223> OTHER INFORMATION: PDI-H3 Switz-F392D-CysTm AA

<400> SEQUENCE: 59

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160

Ser Ser Cys Ile Arg Gly Ser Asn Ser Ser Phe Phe Ser Arg Leu Asn
                165                 170                 175

Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300
```

-continued

```
Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Asp
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 60
<211> LENGTH: 1725
<212> TYPE: DNA
<213> ORGANISM: Artificial Sequence
<220> FEATURE:
<223> OTHER INFORMATION: PDI-H3 Switz-L431M-CysTm DNA

<400> SEQUENCE: 60

```
atggcgaaaa acgttgcgat tttcggctta ttgttttctc ttcttgtgtt ggttccttct      60

cagatcttcg cgcaaaaact tcctggaaat gacaatagca cggcaacgct gtgccttggg     120

caccatgcag taccaaacgg aacgatagtg aaaacaatca cgaatgaccg aattgaagtt     180

actaatgcta ctgagctggt tcagaattcc tcaataggtg aaatatgcga cagtcctcat     240

cagatccttg atggagaaaa ctgcacacta atagatgctc tattgggaga ccctcagtgt     300

gatggctttc aaaataagaa atgggacctt tttgttgaac gaagcaaagc ctacagcaac     360

tgttaccctt atgatgtgcc ggattatgcc tcccttaggt cactagttgc ctcatccggc     420

acactggagt ttaacaatga aagcttcaat tgggctggag tcactcaaaa cggaacaagt     480

tcttcttgca taaggggatc taatagtagt ttctttagta gattaaattg gttgacccac     540
```

-continued

```
ttaaactcca aatacccagc attaaacgtg actatgccaa acaatgaaca atttgacaaa    600
ttgtacattt gggggttca ccacccgggt acggacaagg accaaatctt cctgtatgca    660
caatcatcag gaagaatcac agtatctacc aaaagaagcc aacaagctgt aatcccgaat    720
atcggatcta gacccagaat aagggatatc cctagcagaa taagcatcta ttggacaata    780
gtaaaaccgg gagacatact tttgattaac agcacaggga atctaattgc tcctaggggt    840
tacttcaaaa tacgaagtgg gaaaagctca ataatgagat cagatgcacc cattggcaaa    900
tgcaagtctg aatgcatcac tccaaatgga agcattccca atgacaaacc attccaaaat    960
gtaaacagga tcacatacgg ggcctgtccc agatatgtta agcaaagcac tctgaaattg   1020
gcaacaggaa tgcgaaatgt accagagaga caaactagag gcatatttgg cgcaatagcg   1080
ggtttcatag aaaatggttg ggagggaatg gtggatggtt ggtacggctt caggcatcaa   1140
aattctgagg gaagaggaca agcagcagat ctcaaaagca ctcaagcagc aatcgatcaa   1200
atcaatggga agctgaatcg attgatcggg aaaaccaacg agaaattcca tcagattgaa   1260
aaagaattct cagaagtaga agggagaatt caggaccttg agaaatatgt tgaggacaca   1320
aaaatagatc tctggtcata caacgcggag cttcttgttg ccatggagaa ccaacataca   1380
attgatctaa ctgactcaga aatgaacaaa ctgtttgaaa aaacaaagaa gcaactgagg   1440
gaaaatgctg aggatatggg caatggttgt ttcaaaatat accacaaatg tgacaatgcc   1500
tgcataggat caatcagaaa tggaacttat gaccacgatg tatacaggga tgaagcatta   1560
aacaaccggt tccagatcaa gggagttgag ctgaagtcag ggtacaaaga ttggatccta   1620
tggatttcct ttgccatatc atcccttgta ctgttagttg ctttgttggg gttcatcatg   1680
tgggcctgcc aaaagggcaa cattaggtgc aacatttgca tttga                   1725
```

<210> SEQ ID NO 61
<211> LENGTH: 574
<212> TYPE: PRT
<213> ORGANISM: Artificial Sequence
<220> FEATURE:
<223> OTHER INFORMATION: PDI-H3 Switz-L431M-CysTm AA

<400> SEQUENCE: 61

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160
```

-continued

```
Ser Ser Cys Ile Arg Gly Ser Asn Ser Ser Phe Phe Ser Arg Leu Asn
                165                 170                 175

Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Met Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 62
<211> LENGTH: 4540
<212> TYPE: DNA
<213> ORGANISM: Artificial Sequence
<220> FEATURE:
<223> OTHER INFORMATION: Cloning vector 1190 from left to right T-DNA

<400> SEQUENCE: 62

```
tggcaggata tattgtggtg taaacaaatt gacgcttaga caacttaata acacattgcg     60
gacgttttta atgtactgaa ttaacgccga atcccgggct ggtatattta tatgttgtca    120
aataactcaa aaaccataaa agtttaagtt agcaagtgtg tacattttta cttgaacaaa    180
aatattcacc tactactgtt ataaatcatt attaaacatt agagtaaaga aatatggatg    240
ataagaacaa gagtagtgat attttgacaa caattttgtt gcaacatttg agaaaatttt    300
gttgttctct cttttcattg gtcaaaaaca atagagagag aaaaaggaag agggagaata    360
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
```

```
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccgcggat ggcgaaaaac   3060
gttgcgattt tcggcttatt gttttctctt cttgtgttgg ttccttctca gatcttcgcc   3120
tgcaggctcc tcagccaaaa cgacaccccc atctgtctat ccactggccc ctggatctgc   3180
tgcccaaact aactccatgg tgaccctggg atgcctggtc aagggctatt tccctgagcc   3240
agtgacagtg acctggaact ctggatccct gtccagcggt gtgcacacct tcccagctgt   3300
cctgcagtct gacctctaca ctctgagcag ctcagtgact gtcccctcca gcacctggcc   3360
cagcgagacc gtcacctgca acgttgccca cccggccagc agcaccaagg tggacaagaa   3420
aattgtgccc agggattgtg gttgtaagcc ttgcatatgt acagtcccag aagtatcatc   3480
tgtcttcatc ttccccccaa agcccaagga tgtgctcacc attactctga ctcctaaggt   3540
cacgtgtgtt gtggtagaca tcagcaagga tgatcccgag gtccagttca gctggtttgt   3600
agatgatgtg gaggtgcaca cagctcagac gcaaccccgg gaggagcagt tcaacagcac   3660
tttccgctca gtcagtgaac ttcccatcat gcaccaggac tggctcaatg gcaaggagcg   3720
atcgctcacc atcaccatca ccatcaccat caccattaaa ggcctatttt ctttagtttg   3780
aatttactgt tattcggtgt gcatttctat gtttggtgag cggttttctg tgctcagagt   3840
gtgtttattt tatgtaattt aatttctttg tgagctcctg tttagcaggt cgtcccttca   3900
gcaaggacac aaaaagattt taattttatt aaaaaaaaaa aaaaaaaaga ccgggaattc   3960
gatatcaagc ttatcgacct gcagatcgtt caaacatttg gcaataaagt ttcttaagat   4020
tgaatcctgt tgccggtctt gcgatgatta tcatataatt tctgttgaat tacgttaagc   4080
atgtaataat taacatgtaa tgcatgacgt tatttatgag atgggttttt atgattagag   4140
tcccgcaatt atacatttaa tacgcgatag aaaacaaaat atagcgcgca aactaggata   4200
aattatcgcg cgcggtgtca tctatgttac tagatctcta gagtctcaag cttggcgcgc   4260
ccacgtgact agtggcactg gccgtcgttt tacaacgtcg tgactgggaa aaccctggcg   4320
ttacccaact taatcgcctt gcagcacatc cccctttcgc cagctggcgt aatagcgaag   4380
aggcccgcac cgatcgccct tcccaacagt tgcgcagcct gaatggcgaa tgctagagca   4440
```

gcttgagctt ggatcagatt gtcgtttccc gccttcagtt taaactatca gtgtttgaca 4500
ggatatattg gcgggtaaac ctaagagaaa agagcgttta 4540

<210> SEQ ID NO 63
<211> LENGTH: 3105
<212> TYPE: DNA
<213> ORGANISM: Artificial Sequence
<220> FEATURE:
<223> OTHER INFORMATION: Construct 1314 from 2X35S prom to NOS term

<400> SEQUENCE: 63
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaatg gcgaaaaacg ttgcgatttt cggcttattg ttttctcttc ttgtgttggt 960
tccttctcag atcttcgctg acacattatg tataggttat catgcgaaca attcaacaga 1020
cactgtagac acagtactag aaaagaatgt aacagtaaca cactctgtta accttctaga 1080
agacaagcat aacgggaaac tatgcaaact aagaggggta gccccattgc atttgggtaa 1140
atgtaacatt gctggctgga tcctgggaaa tccagagtgt gaatcactct ccacagcaag 1200
ctcatggtcc tacattgtgg aaacacctag ttcagacaat ggaacgtgtt acccaggaga 1260
tttcatcgat tatgaggagc taagagagca attgagctca gtgtcatcat ttgaaaggtt 1320
tgagatattc cccaagacaa gttcatggcc caatcatgac tcgaacaaag gtgtaacggc 1380
agcatgtcct catgctggag caaaaagctt ctacaaaaat ttaatatggc tagttaaaaa 1440
aggaaattca tacccaaagc tcagcaaatc ctacattaat gataaaggga aagaagtcct 1500
cgtgctatgg ggcattcacc atccatctac tagtgctgac caacaaagtc tctatcagaa 1560
tgcagatgca tatgtttttg tggggtcatc aagatacagc aagaagttca agccggaaat 1620
agcaataaga cccaaagtga gggatcaaga agggagaatg aactattact ggacactagt 1680
agagccggga gacaaaataa cattcgaagc aactggaaat ctagtggtac cgagatatgc 1740
attcgcaatg gaaagaaatg ctggatctgg tattatcatt tcagatacac cagtccacga 1800
ttgcaataca acttgtcaaa cacccaaggg tgctataaac accagcctcc catttcagaa 1860
tatacatccg atcacaattg gaaaatgtcc aaaatatgta aaaagcacaa aattgagact 1920
ggccacagga ttgaggaata tcccgtctat tcaatctaga ggactatttg ggccattgc 1980

```
cggtttcatt gaagggggt ggacagggat ggtagatgga tggtacggtt atcaccatca   2040

aaatgagcag gggtcaggat atgcagccga cctgaagagc acacagaatg ccattgacga   2100

gattactaac aaagtaaatt ctgttattga aaagatgaat acacagttca cagcagtagg   2160

taaagagttc aaccacctgg aaaaaagaat agagaattta aataaaaaag ttgatgatgg   2220

tttcctggac atttggactt acaatgccga actgttggtt ctattggaaa atgaaagaac   2280

tttggactac cacgattcaa atgtgaagaa cttatatgaa aaggtaagaa gccagctaaa   2340

aaacaatgcc aaggaaattg gaaacggctg ctttgaattt taccacaaat gcgataacac   2400

gtgcatggaa agtgtcaaaa atgggactta tgactaccca aaatactcag aggaagcaaa   2460

attaaacaga gaagaaatag atggggtaaa gctggaatca acaaggattt accagatttt   2520

ggcgatctat tcaactgtcg ccagttcatt ggtactggta gtctccctgg gggcaatcag   2580

tttctggatg tgctctaatg ggtctctaca gtgtagaata tgtatttaaa ggcctatttt   2640

ctttagtttg aatttactgt tattcggtgt gcatttctat gtttggtgag cggttttctg   2700

tgctcagagt gtgtttattt tatgtaattt aatttctttg tgagctcctg tttagcaggt   2760

cgtcccttca gcaaggacac aaaaagattt taattttatt aaaaaaaaaa aaaaaaaaga   2820

ccgggaattc gatatcaagc ttatcgacct gcagatcgtt caaacatttg gcaataaagt   2880

ttcttaagat tgaatcctgt tgccggtctt gcgatgatta tcatataatt tctgttgaat   2940

tacgttaagc atgtaataat taacatgtaa tgcatgacgt tatttatgag atgggttttt   3000

atgattagag tcccgcaatt atacatttaa tacgcgatag aaaacaaaat atagcgcgca   3060

aactaggata aattatcgcg cgcggtgtca tctatgttac tagat                  3105
```

<210> SEQ ID NO 64
<211> LENGTH: 3105
<212> TYPE: DNA
<213> ORGANISM: Artificial Sequence
<220> FEATURE:
<223> OTHER INFORMATION: Construct 2980 from 2X35S prom to NOS term

<400> SEQUENCE: 64

```
gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780

acgtggggaa acccgaacca aaccttcttc taaactctct ctcatctctc ttaaagcaaa    840

cttctctctt gtctttcttg cgtgagcgat cttcaacgtt gtcagatcgt gcttcggcac    900
```

```
cagtacaatg gcgaaaaacg ttgcgatttt cggcttattg ttttctcttc ttgtgttggt    960
tccttctcag atcttcgcgg acacattatg tataggttat catgcgaaca attcaacaga   1020
cactgtagac acagtactag aaaagaatgt aacagtaaca cactctgtta accttctaga   1080
agacaagcat aacgggaaac tatgcaaact aagaggggta gccccattgc atttgggtaa   1140
atgtaacatt gctggctgga tcctgggaaa tccagagtgt gaatcactct ccacagcaag   1200
ctcatggtcc tacattgtgg aaacacctag ttcagacaat ggaacgtgtt acccaggaga   1260
tttcatcgat tatgaggagc taagagagca attgagctca gtgtcatcat ttgaaaggtt   1320
tgagatattc cccaagacaa gttcatggcc caatcatgac tcgaacaaag gtgtaacggc   1380
agcatgtcct catgctggag caaaaagctt ctacaaaaat ttaatatggc tagttaaaaa   1440
aggaaattca tacccaaagc tcagcaaatc ctacattaat gataaaggga aagaagtcct   1500
cgtgctatgg ggcattcacc atccatctac tagtgctgac caacaaagtc tctatcagaa   1560
tgcagatgca tatgtttttg tggggtcatc aagatacagc aagaagttca agccggaaat   1620
agcaataaga cccaaagtga gggatcaaga agggagaatg aactattact ggacactagt   1680
agagccggga gacaaaataa cattcgaagc aactggaaat ctagtggtac cgagatatgc   1740
attcgcaatg gaaagaaatg ctggatctgg tattatcatt tcagatacac cagtccacga   1800
ttgcaataca acttgtcaaa cacccaaggg tgctataaac accagcctcc catttcagaa   1860
tatacatccg atcacaattg gaaaatgtcc aaaatatgta aaaagcacaa aattgagact   1920
ggccacagga ttgaggaata tcccgtctat tcaatctaga ggactatttg gggccattgc   1980
cggtttcatt gaagggggt ggacagggat ggtagatgga tggtacggtt atcaccatca    2040
aaatgagcag gggtcaggat atgcagccga cctgaagagc acacagaatg ccattgacga   2100
gattactaac aaagtaaatt ctgttattga aaagatgaat acacaggaca cagcagtagg   2160
taaagagttc aaccacctgg aaaaaagaat agagaattta aataaaaaag ttgatgatgg   2220
tttcctggac atttggactt acaatgccga actgttggtt ctattggaaa atgaaagaac   2280
tttggactac cacgattcaa atgtgaagaa cttatatgaa aaggtaagaa gccagctaaa   2340
aaacaatgcc aaggaaattg gaaacggctg ctttgaattt taccacaaat gcgataacac   2400
gtgcatggaa agtgtcaaaa atgggactta tgactaccca aaatactcag aggaagcaaa   2460
attaaacaga gaagaaatag atggggtaaa gctggaatca acaaggattt accagatttt   2520
ggcgatctat tcaactgtcg ccagttcatt ggtactggta gtctccctgg gggcaatcag   2580
tttctggatg tgctctaatg ggtctctaca gtgtagaata tgtatttaaa ggcctatttt   2640
ctttagtttg aatttactgt tattcggtgt gcatttctat gtttggtgag cggttttctg   2700
tgctcagagt gtgtttattt tatgtaattt aatttctttg tgagctcctg tttagcaggt   2760
cgtcccttca gcaaggacac aaaaagattt taattttatt aaaaaaaaaa aaaaaaaaga   2820
ccgggaattc gatatcaagc ttatcgacct gcagatcgtt caaacatttg gcaataaagt   2880
ttcttaagat tgaatcctgt tgccggtctt gcgatgatta tcatataatt tctgttgaat   2940
tacgttaagc atgtaataat taacatgtaa tgcatgacgt tatttatgag atgggttttt   3000
atgattagag tcccgcaatt atacatttaa tacgcgatag aaaacaaaat atagcgcgca   3060
aactaggata aattatcgcg cgcggtgtca tctatgttac tagat                   3105
```

<210> SEQ ID NO 65
<211> LENGTH: 3105
<212> TYPE: DNA
<213> ORGANISM: Artificial Sequence
<220> FEATURE:
<223> OTHER INFORMATION: Construct 2995 from 2X35S prom to NOS term

<400> SEQUENCE: 65

```
gtcaacatgg tggagcacga cacacttgtc tactccaaaa atatcaaaga tacagtctca     60
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaatg gcgaaaaacg ttgcgatttt cggcttattg ttttctcttc ttgtgttggt    960
tccttctcag atcttcgcgg acacattatg tataggttat catgcgaaca attcaacaga   1020
cactgtagac acagtactag aaaagaatgt aacagtaaca cactctgtta accttctaga   1080
agacaagcat aacgggaaac tatgcaaact aagaggggta gccccattgc atttgggtaa   1140
atgtaacatt gctggctgga tcctgggaaa tccagagtgt gaatcactct ccacagcaag   1200
ctcatggtcc tacattgtgg aaacacctag ttcagacaat ggaacgtgtt acccaggaga   1260
tttcatcgat tatgaggagc taagagagca attgagctca gtgtcatcat ttgaaaggtt   1320
tgagatattc cccaagacaa gttcatggcc caatcatgac tcgaacaaag gtgtaacggc   1380
agcatgtcct catgctggag caaaaagctt ctacaaaaat ttaatatggc tagttaaaaa   1440
aggaaattca tacccaaagc tcagcaaatc ctacattaat gataaaggga aagaagtcct   1500
cgtgctatgg ggcattcacc atccatctac tagtgctgac caacaaagtc tctatcagaa   1560
tgcagatgca tatgtttttg tggggtcatc aagatacagc aagaagttca agccggaaat   1620
agcaataaga cccaaagtga gggatcaaga agggagaatg aactattact ggacactagt   1680
agagccggga gacaaaataa cattcgaagc aactggaaat ctagtggtac cgagatatgc   1740
attcgcaatg gaaagaaatg ctggatctgg tattatcatt tcagatacac cagtccacga   1800
ttgcaataca acttgtcaaa cacccaaggg tgctataaac accagcctcc catttcagaa   1860
tatacatccg atcacaattg gaaaatgtcc aaaatatgta aaaagcacaa aattgagact   1920
ggccacagga ttgaggaata tcccgtctat tcaatctaga ggactatttg gggccattgc   1980
cggtttcatt gaagggggggt ggacagggat ggtagatgga tggtacggtt atcaccatca   2040
aaatgagcag gggtcaggat atgcagccga cctgaagagc acacagaatg ccattgacga   2100
gattactaac aaagtaaatt ctgttattga aaagatgaat acacaggaca cagcagtagg   2160
taaagagttc aaccacctgg aaaaaagaat agagaattta aataaaaaag ttgatgatgg   2220
```

```
tttcctggac atttggactt acaatgccga actgttggtt ctaatggaaa atgaaagaac   2280

tttggactac cacgattcaa atgtgaagaa cttatatgaa aaggtaagaa gccagctaaa   2340

aaacaatgcc aaggaaattg gaaacggctg ctttgaattt taccacaaat gcgataacac   2400

gtgcatggaa agtgtcaaaa atgggactta tgactaccca aaatactcag aggaagcaaa   2460

attaaacaga gaagaaatag atggggtaaa gctggaatca acaaggattt accagatttt   2520

ggcgatctat tcaactgtcg ccagttcatt ggtactggta gtctccctgg gggcaatcag   2580

tttctggatg tgctctaatg ggtctctaca gtgtagaata tgtatttaaa ggcctatttt   2640

ctttagtttg aatttactgt tattcggtgt gcatttctat gtttggtgag cggttttctg   2700

tgctcagagt gtgtttattt tatgtaattt aatttctttg tgagctcctg tttagcaggt   2760

cgtcccttca gcaaggacac aaaaagattt taattttatt aaaaaaaaaa aaaaaaaaga   2820

ccgggaattc gatatcaagc ttatcgacct gcagatcgtt caaacatttg gcaataaagt   2880

ttcttaagat tgaatcctgt tgccggtctt gcgatgatta tcatataatt tctgttgaat   2940

tacgttaagc atgtaataat taacatgtaa tgcatgacgt tatttatgag atgggttttt   3000

atgattagag tcccgcaatt atacatttaa tacgcgatag aaaacaaaat atagcgcgca   3060

aactaggata aattatcgcg cgcggtgtca tctatgttac tagat                   3105
```

<210> SEQ ID NO 66
<211> LENGTH: 6360
<212> TYPE: DNA
<213> ORGANISM: Artificial Sequence
<220> FEATURE:
<223> OTHER INFORMATION: Cloning vector 3556 from left to right T-DNA

<400> SEQUENCE: 66

```
tggcaggata tattgtggtg taaacaaatt gacgcttaga caacttaata acacattgcg     60

gacgttttta atgtactgaa ttaacgccga atcccgggct ggtatattta tatgttgtca    120

aataactcaa aaaccataaa agtttaagtt agcaagtgtg tacattttta cttgaacaaa    180

aatattcacc tactactgtt ataaatcatt attaaacatt agagtaaaga aatatggatg    240

ataagaacaa gagtagtgat attttgacaa caattttgtt gcaacatttg agaaaatttt    300

gttgttctct cttttcattg gtcaaaaaca atagagagag aaaaaggaag agggagaata    360

aaaacataat gtgagtatga gagagaaagt tgtacaaaag ttgtaccaaa atagttgtac    420

aaatatcatt gaggaatttg acaaaagcta cacaaataag ggttaattgc tgtaaataaa    480

taaggatgac gcattagaga gatgtaccat tagagaattt ttggcaagtc attaaaaaga    540

aagaataaat tatttttaaa attaaaagtt gagtcatttg attaaacatg tgattattta    600

atgaattgat gaaagagttg gattaaagtt gtattagtaa ttagaatttg gtgtcaaatt    660

taatttgaca tttgatcttt tcctatatat tgccccatag agtcagttaa ctcattttta    720

tatttcatag atcaaataag agaaataacg gtatattaat ccctccaaaa aaaaaaaacg    780

gtatatttac taaaaaatct aagccacgta ggaggataac aggatccccg taggaggata    840

acatccaatc caaccaatca caacaatcct gatgagataa cccactttaa gcccacgcat    900

ctgtggcaca tctacattat ctaaatcaca cattcttcca cacatctgag ccacacaaaa    960

accaatccac atctttatca cccattctat aaaaaatcac actttgtgag tctacacttt   1020

gattcccttc aaacacatac aaagagaaga gactaattaa ttaattaatc atcttgagag   1080

aaaatggaac gagctataca aggaaacgac gctagggaac aagctaacag tgaacgttgg   1140

gatggaggat caggaggtac cacttctccc ttcaaacttc ctgacgaaag tccgagttgg   1200
```

```
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca cgcgtggcgc gccctggtat atttatatgt   2160
tgtcaaataa ctcaaaaacc ataaaagttt aagttagcaa gtgtgtacat ttttacttga   2220
acaaaaatat tcacctacta ctgttataaa tcattattaa acattagagt aaagaaatat   2280
ggatgataag aacaagagta gtgatatttt gacaacaatt ttgttgcaac atttgagaaa   2340
attttgttgt tctctctttt cattggtcaa aaacaataga gagagaaaaa ggaagaggga   2400
gaataaaaac ataatgtgag tatgagagag aaagttgtac aaaagttgta ccaaaatagt   2460
tgtacaaata tcattgagga atttgacaaa agctacacaa ataagggtta attgctgtaa   2520
ataaataagg atgacgcatt agagagatgt accattagag aatttttggc aagtcattaa   2580
aaagaaagaa taaattattt ttaaaattaa aagttgagtc atttgattaa acatgtgatt   2640
atttaatgaa ttgatgaaag agttggatta aagttgtatt agtaattaga atttggtgtc   2700
aaatttaatt tgacatttga tcttttccta tatattgccc catagagtca gttaactcat   2760
ttttatattt catagatcaa ataagagaaa taacggtata ttaatccctc caaaaaaaaa   2820
aaacggtata tttactaaaa aatctaagcc acgtaggagg ataacaggat ccccgtagga   2880
ggataacatc caatccaacc aatcacaaca atcctgatga gataacccac tttaagccca   2940
cgcatctgtg gcacatctac attatctaaa tcacacattc ttccacacat ctgagccaca   3000
caaaaaccaa tccacatctt tatcacccat tctataaaaa atcacacttt gtgagtctac   3060
actttgattc ccttcaaaca catacaaaga gaagagacta attaattaat taatcatctt   3120
gagagaaaat gagtcttcta accgaggtcg aaacgcctat cagaaacgaa tgggggtgca   3180
gatgcaacga ttcaagtgat cctcttgttg ttgccgcaag tataattggg attgtgcacc   3240
tgatattgtg gattattgat cgcctttttt ccaaaagcat ttatcgtatc tttaaacacg   3300
gtttaaaaag agggccttct acggaaggag taccagagtc tatgagggaa gaatatcgag   3360
aggaacagca gaatgctgtg gatgctgacg atggtcattt tgtcagcata gagctggagt   3420
aagagctcta agttaaaatg cttcttcgtc tcctatttat aatatggttt gttattgtta   3480
attttgttct tgtagaagag cttaattaat cgttgttgtt atgaaatact atttgtatga   3540
```

-continued gatgaactgg tgtaatgtaa ttcatttaca taagtggagt cagaatcaga atgtttcctc 3600
cataactaac tagacatgaa gacctgccgc gtacaattgt cttatatttg aacaactaaa 3660
attgaacatc ttttgccaca actttataag tggttaatat agctcaaata tatggtcaag 3720
ttcaatagat taataatgga aatatcagtt atcgaaattc attaacaatc aacttaacgt 3780
tattaactac taattttata tcatcccctt tgataaatga tagtacacca attaggaagg 3840
aactaggaga ttgtcgtttc ccgccttcag tttgcaagct gctctagccg tgtagccaat 3900
acgcaaaccg cctctccccg cgcgttggga attactagcg cgtgtcgaca agcttgcatg 3960
ccggtcaaca tggtggagca cgacacactt gtctactcca aaaatatcaa agatacagtc 4020
tcagaagacc aaagggcaat tgagactttt caacaaaggg taatatccgg aaacctcctc 4080
ggattccatt gcccagctat ctgtcacttt attgtgaaga tagtggaaaa ggaaggtggc 4140
tcctacaaat gccatcattg cgataaagga aaggccatcg ttgaagatgc ctctgccgac 4200
agtggtccca aagatggacc cccacccacg aggagcatcg tggaaaaaga agacgttcca 4260
accacgtctt caaagcaagt ggattgatgt gataacatgg tggagcacga cacacttgtc 4320
tactccaaaa atatcaaaga tacagtctca gaagaccaaa gggcaattga gacttttcaa 4380
caaagggtaa tatccggaaa cctcctcgga ttccattgcc cagctatctg tcactttatt 4440
gtgaagatag tggaaaagga aggtggctcc tacaaatgcc atcattgcga taaaggaaag 4500
gccatcgttg aagatgcctc tgccgacagt ggtcccaaag atggaccccc acccacgagg 4560
agcatcgtgg aaaaagaaga cgttccaacc acgtcttcaa agcaagtgga ttgatgtgat 4620
atctccactg acgtaaggga tgacgcacaa tcccactatc cttcgcaaga cccttcctct 4680
atataaggaa gttcatttca tttggagagg tattaaaatc ttaataggtt ttgataaaag 4740
cgaacgtggg gaaacccgaa ccaaaccttc ttctaaactc tctctcatct ctcttaaagc 4800
aaacttctct cttgtctttc ttgcgtgagc gatcttcaac gttgtcagat cgtgcttcgg 4860
caccgcggat ggcgaaaaac gttgcgattt tcggcttatt gttttctctt cttgtgttgg 4920
ttccttctca gatcttcgcc tgcaggctcc tcagccaaaa cgacaccccc atctgtctat 4980
ccactggccc ctggatctgc tgcccaaact aactccatgg tgaccctggg atgcctggtc 5040
aagggctatt tccctgagcc agtgacagtg acctggaact ctggatccct gtccagcggt 5100
gtgcacacct tcccagctgt cctgcagtct gacctctaca ctctgagcag ctcagtgact 5160
gtcccctcca gcacctggcc cagcgagacc gtcacctgca acgttgccca cccggccagc 5220
agcaccaagg tggacaagaa aattgtgccc agggattgtg gttgtaagcc ttgcatatgt 5280
acagtcccag aagtatcatc tgtcttcatc ttccccccaa agcccaagga tgtgctcacc 5340
attactctga ctcctaaggt cacgtgtgtt gtggtagaca tcagcaagga tgatcccgag 5400
gtccagttca gctggtttgt agatgatgtg gaggtgcaca cagctcagac gcaaccccgg 5460
gaggagcagt tcaacagcac tttccgctca gtcagtgaac ttcccatcat gcaccaggac 5520
tggctcaatg gcaaggagcg atcgctcacc atcaccatca ccatcaccat caccattaaa 5580
ggcctatttt ctttagtttg aatttactgt tattcggtgt gcatttctat gtttggtgag 5640
cggttttctg tgctcagagt gtgtttattt tatgtaattt aatttctttg tgagctcctg 5700
tttagcaggt cgtcccttca gcaaggacac aaaaagattt taattttatt aaaaaaaaaa 5760
aaaaaaaaga ccgggaattc gatatcaagc ttatcgacct gcagatcgtt caaacatttg 5820
gcaataaagt ttcttaagat tgaatcctgt tgccggtctt gcgatgatta tcatataatt 5880
tctgttgaat tacgttaagc atgtaataat taacatgtaa tgcatgacgt tatttatgag 5940

-continued

```
atgggttttt atgattagag tcccgcaatt atacatttaa tacgcgatag aaaacaaaat   6000

atagcgcgca aactaggata aattatcgcg cgcggtgtca tctatgttac tagatctcta   6060

gagtctcaag cttggcgcgc ccacgtgact agtggcactg gccgtcgttt tacaacgtcg   6120

tgactgggaa aaccctggcg ttacccaact taatcgcctt gcagcacatc ccccttttcgc   6180

cagctggcgt aatagcgaag aggcccgcac cgatcgccct tcccaacagt tgcgcagcct   6240

gaatggcgaa tgctagagca gcttgagctt ggatcagatt gtcgtttccc gccttcagtt   6300

taaactatca gtgtttgaca ggatatattg gcgggtaaac ctaagagaaa agagcgttta   6360
```

<210> SEQ ID NO 67
<211> LENGTH: 50
<212> TYPE: DNA
<213> ORGANISM: Artificial Sequence
<220> FEATURE:
<223> OTHER INFORMATION: Primer IF-H5ITMCT.s1-4r

<400> SEQUENCE: 67

```
actaaagaaa ataggccttt aaatgcaaat tctgcattgt aacgatccat                 50
```

<210> SEQ ID NO 68
<211> LENGTH: 1731
<212> TYPE: DNA
<213> ORGANISM: Artificial Sequence
<220> FEATURE:
<223> OTHER INFORMATION: PDI-H5 Indo DNA

<400> SEQUENCE: 68

```
atggcgaaaa acgttgcgat tttcggctta ttgttttctc ttcttgtgtt ggttccttct     60

cagatcttcg ccgatcagat ttgcattggt taccatgcaa acaattcaac agagcaggtt    120

gacacaatca tggaaaagaa cgttactgtt acacatgccc aagacatact ggaaaagaca    180

cacaacggga agctctgcga tctagatgga gtgaagcctc taattttaag agattgtagt    240

gtagctggat ggctcctcgg gaacccaatg tgtgacgaat tcatcaatgt accggaatgg    300

tcttacatag tggagaaggc caatccaacc aatgacctct gttacccagg gagtttcaac    360

gactatgaag aactgaaaca cctattgagc agaataaacc attttgagaa aattcaaatc    420

atccccaaaa gttcttggtc cgatcatgaa gcctcatcag gagttagctc agcatgtcca    480

tacctgggaa gtccctcctt ttttagaaat gtggtatggc ttatcaaaaa gaacagtaca    540

tacccaacaa taaagaaaag ctacaataat accaaccaag aggatctttt ggtactgtgg    600

ggaattcacc atcctaatga tgcggcagag cagacaaggc tatatcaaaa cccaaccacc    660

tatatttcca ttgggacatc aacactaaac cagagattgg taccaaaaat agctactaga    720

tccaaagtaa acgggcaaag tggaaggatg gagttcttct ggacaatttt aaaacctaat    780

gatgcaatca acttcgagag taatggaaat ttcattgctc cagaatatgc atacaaaatt    840

gtcaagaaag gggactcagc aattatgaaa agtgaattgg aatatggtaa ctgcaacacc    900

aagtgtcaaa ctccaatggg ggcgataaac tctagtatgc cattccacaa catacaccct    960

ctcaccatcg ggggaatgccc caaatatgtg aaatcaaaca gattagtcct tgcaacaggg   1020

ctcagaaata gccctcaaag agagagcaga agaaaaaaga gaggactatt tggagctata   1080

gcaggtttta tagagggagg atggcaggga atggtagatg gttggtatgg gtaccaccat   1140

agcaatgagc aggggagtgg gtacgctgca gacaaagaat ccactcaaaa ggcaatagat   1200

ggagtcacca ataaggtcaa ctcaatcatt gacaaaatga acactcagtt tgaggccgtt   1260
```

-continued

```
ggaagggaat ttaataactt agaaaggaga atagagaatt taaacaagaa gatggaagac   1320

gggtttctag atgtctggac ttataatgcc gaacttctgg ttctcatgga aaatgagaga   1380

actctagact ttcatgactc aaatgttaag aacctctacg acaaggtccg actacagctt   1440

agggataatg caaaggagct gggtaacggt tgtttcgagt tctatcacaa atgtgataat   1500

gaatgtatgg aaagtataag aaacggaacg tacaactatc cgcagtattc agaagaagca   1560

agattaaaaa gagaggaaat aagtggggta aaattggaat caataggaac ttaccaaata   1620

ctgtcaattt attcaacagt ggcgagttcc ctagcactgg caatcatgat ggctggtcta   1680

tctttatgga tgtgctccaa tggatcgtta caatgcagaa tttgcattta a            1731
```

```
<210> SEQ ID NO 69
<211> LENGTH: 576
<212> TYPE: PRT
<213> ORGANISM: Artificial Sequence
<220> FEATURE:
<223> OTHER INFORMATION: PDI-H5 Indo AA

<400> SEQUENCE: 69

Met Ala Lys Asn Val Ala Ile Phe Gly Leu Leu Phe Ser Leu Leu Val
1               5                   10                  15

Leu Val Pro Ser Gln Ile Phe Ala Asp Gln Ile Cys Ile Gly Tyr His
            20                  25                  30

Ala Asn Asn Ser Thr Glu Gln Val Asp Thr Ile Met Glu Lys Asn Val
        35                  40                  45

Thr Val Thr His Ala Gln Asp Ile Leu Glu Lys Thr His Asn Gly Lys
    50                  55                  60

Leu Cys Asp Leu Asp Gly Val Lys Pro Leu Ile Leu Arg Asp Cys Ser
65                  70                  75                  80

Val Ala Gly Trp Leu Leu Gly Asn Pro Met Cys Asp Glu Phe Ile Asn
                85                  90                  95

Val Pro Glu Trp Ser Tyr Ile Val Glu Lys Ala Asn Pro Thr Asn Asp
            100                 105                 110

Leu Cys Tyr Pro Gly Ser Phe Asn Asp Tyr Glu Glu Leu Lys His Leu
        115                 120                 125

Leu Ser Arg Ile Asn His Phe Glu Lys Ile Gln Ile Ile Pro Lys Ser
    130                 135                 140

Ser Trp Ser Asp His Glu Ala Ser Ser Gly Val Ser Ser Ala Cys Pro
145                 150                 155                 160

Tyr Leu Gly Ser Pro Ser Phe Phe Arg Asn Val Val Trp Leu Ile Lys
                165                 170                 175

Lys Asn Ser Thr Tyr Pro Thr Ile Lys Lys Ser Tyr Asn Asn Thr Asn
            180                 185                 190

Gln Glu Asp Leu Leu Val Leu Trp Gly Ile His His Pro Asn Asp Ala
        195                 200                 205

Ala Glu Gln Thr Arg Leu Tyr Gln Asn Pro Thr Thr Tyr Ile Ser Ile
    210                 215                 220

Gly Thr Ser Thr Leu Asn Gln Arg Leu Val Pro Lys Ile Ala Thr Arg
225                 230                 235                 240

Ser Lys Val Asn Gly Gln Ser Gly Arg Met Glu Phe Phe Trp Thr Ile
                245                 250                 255

Leu Lys Pro Asn Asp Ala Ile Asn Phe Glu Ser Asn Gly Asn Phe Ile
            260                 265                 270

Ala Pro Glu Tyr Ala Tyr Lys Ile Val Lys Lys Gly Asp Ser Ala Ile
        275                 280                 285
```

Met Lys Ser Glu Leu Glu Tyr Gly Asn Cys Asn Thr Lys Cys Gln Thr
    290                 295                 300

Pro Met Gly Ala Ile Asn Ser Ser Met Pro Phe His Asn Ile His Pro
305                 310                 315                 320

Leu Thr Ile Gly Glu Cys Pro Lys Tyr Val Lys Ser Asn Arg Leu Val
                325                 330                 335

Leu Ala Thr Gly Leu Arg Asn Ser Pro Gln Arg Glu Ser Arg Arg Lys
            340                 345                 350

Lys Arg Gly Leu Phe Gly Ala Ile Ala Gly Phe Ile Glu Gly Gly Trp
        355                 360                 365

Gln Gly Met Val Asp Gly Trp Tyr Gly Tyr His His Ser Asn Glu Gln
    370                 375                 380

Gly Ser Gly Tyr Ala Ala Asp Lys Glu Ser Thr Gln Lys Ala Ile Asp
385                 390                 395                 400

Gly Val Thr Asn Lys Val Asn Ser Ile Ile Asp Lys Met Asn Thr Gln
                405                 410                 415

Phe Glu Ala Val Gly Arg Glu Phe Asn Asn Leu Glu Arg Arg Ile Glu
            420                 425                 430

Asn Leu Asn Lys Lys Met Glu Asp Gly Phe Leu Asp Val Trp Thr Tyr
        435                 440                 445

Asn Ala Glu Leu Leu Val Leu Met Glu Asn Glu Arg Thr Leu Asp Phe
    450                 455                 460

His Asp Ser Asn Val Lys Asn Leu Tyr Asp Lys Val Arg Leu Gln Leu
465                 470                 475                 480

Arg Asp Asn Ala Lys Glu Leu Gly Asn Gly Cys Phe Glu Phe Tyr His
                485                 490                 495

Lys Cys Asp Asn Glu Cys Met Glu Ser Ile Arg Asn Gly Thr Tyr Asn
            500                 505                 510

Tyr Pro Gln Tyr Ser Glu Glu Ala Arg Leu Lys Arg Glu Glu Ile Ser
        515                 520                 525

Gly Val Lys Leu Glu Ser Ile Gly Thr Tyr Gln Ile Leu Ser Ile Tyr
    530                 535                 540

Ser Thr Val Ala Ser Ser Leu Ala Leu Ala Ile Met Met Ala Gly Leu
545                 550                 555                 560

Ser Leu Trp Met Cys Ser Asn Gly Ser Leu Gln Cys Arg Ile Cys Ile
                565                 570                 575

<210> SEQ ID NO 70
<211> LENGTH: 49
<212> TYPE: DNA
<213> ORGANISM: Artificial Sequence
<220> FEATURE:
<223> OTHER INFORMATION: Primer H5Ind(F393D).r

<400> SEQUENCE: 70
cttccaacgg cctcgtcctg agtgttcatt ttgtcaatga ttgagttga 49

<210> SEQ ID NO 71
<211> LENGTH: 49
<212> TYPE: DNA
<213> ORGANISM: Artificial Sequence
<220> FEATURE:
<223> OTHER INFORMATION: H5Ind(F393D).c

<400> SEQUENCE: 71
caaaatgaac actcaggacg aggccgttgg aagggaattt aataactta 49

<210> SEQ ID NO 72
<211> LENGTH: 1731
<212> TYPE: DNA
<213> ORGANISM: Artificial Sequence
<220> FEATURE:
<223> OTHER INFORMATION: PDI-H5 Indo-F393D DNA

<400> SEQUENCE: 72
atggcgaaaa acgttgcgat tttcggctta ttgttttctc ttcttgtgtt ggttccttct 60
cagatcttcg cggatcagat ttgcattggt taccatgcaa acaattcaac agagcaggtt 120
gacacaatca tggaaaagaa cgttactgtt acacatgccc aagacatact ggaaaagaca 180
cacaacggga agctctgcga tctagatgga gtgaagcctc taattttaag agattgtagt 240
gtagctggat ggctcctcgg gaacccaatg tgtgacgaat tcatcaatgt accggaatgg 300
tcttacatag tggagaaggc caatccaacc aatgacctct gttacccagg gagtttcaac 360
gactatgaag aactgaaaca cctattgagc agaataaacc attttgagaa aattcaaatc 420
atccccaaaa gttcttggtc cgatcatgaa gcctcatcag gagttagctc agcatgtcca 480
tacctgggaa gtccctcctt ttttagaaat gtggtatggc ttatcaaaaa gaacagtaca 540
tacccaacaa taaagaaaag ctacaataat accaaccaag aggatctttt ggtactgtgg 600
ggaattcacc atcctaatga tgcggcagag cagacaaggc tatatcaaaa cccaaccacc 660
tatatttcca ttgggacatc aacactaaac cagagattgg taccaaaaat agctactaga 720
tccaaagtaa acgggcaaag tggaaggatg gagttcttct ggacaatttt aaaacctaat 780
gatgcaatca acttcgagag taatggaaat ttcattgctc cagaatatgc atacaaaatt 840
gtcaagaaag ggactcagc aattatgaaa agtgaattgg aatatggtaa ctgcaacacc 900
aagtgtcaaa ctccaatggg ggcgataaac tctagtatgc cattccacaa catacaccct 960
ctcaccatcg ggaatgccc caaatatgtg aaatcaaaca gattagtcct tgcaacaggg 1020
ctcagaaata gccctcaaag agagagcaga agaaaaaaga gaggactatt tggagctata 1080
gcaggtttta tagagggagg atggcaggga atggtagatg gttggtatgg gtaccaccat 1140
agcaatgagc aggggagtgg gtacgctgca gacaaagaat ccactcaaaa ggcaatagat 1200
ggagtcacca ataaggtcaa ctcaatcatt gacaaaatga acactcagga cgaggccgtt 1260
ggaagggaat ttaataactt agaaaggaga atagagaatt taaacaagaa gatggaagac 1320
gggtttctag atgtctggac ttataatgcc gaacttctgg ttctcatgga aaatgagaga 1380
actctagact ttcatgactc aaatgttaag aacctctacg acaaggtccg actacagctt 1440
agggataatg caaaggagct gggtaacggt tgtttcgagt tctatcacaa atgtgataat 1500
gaatgtatgg aaagtataag aaacggaacg tacaactatc cgcagtattc agaagaagca 1560
agattaaaaa gagaggaaat aagtggggta aaattggaat caataggaac ttaccaaata 1620
ctgtcaattt attcaacagt ggcgagttcc ctagcactgg caatcatgat ggctggtcta 1680
tctttatgga tgtgctccaa tggatcgtta caatgcagaa tttgcattta a 1731

<210> SEQ ID NO 73
<211> LENGTH: 576
<212> TYPE: PRT
<213> ORGANISM: Artificial Sequence
<220> FEATURE:
<223> OTHER INFORMATION: PDI-H5 Indo-F393D AA

<400> SEQUENCE: 73

Met Ala Lys Asn Val Ala Ile Phe Gly Leu Leu Phe Ser Leu Leu Val

-continued

```
1               5                   10                  15

Leu Val Pro Ser Gln Ile Phe Ala Asp Gln Ile Cys Ile Gly Tyr His
            20                  25                  30

Ala Asn Asn Ser Thr Glu Gln Val Asp Thr Ile Met Glu Lys Asn Val
        35                  40                  45

Thr Val Thr His Ala Gln Asp Ile Leu Glu Lys Thr His Asn Gly Lys
    50                  55                  60

Leu Cys Asp Leu Asp Gly Val Lys Pro Leu Ile Leu Arg Asp Cys Ser
65                  70                  75                  80

Val Ala Gly Trp Leu Leu Gly Asn Pro Met Cys Asp Glu Phe Ile Asn
                85                  90                  95

Val Pro Glu Trp Ser Tyr Ile Val Glu Lys Ala Asn Pro Thr Asn Asp
            100                 105                 110

Leu Cys Tyr Pro Gly Ser Phe Asn Asp Tyr Glu Glu Leu Lys His Leu
        115                 120                 125

Leu Ser Arg Ile Asn His Phe Glu Lys Ile Gln Ile Ile Pro Lys Ser
    130                 135                 140

Ser Trp Ser Asp His Glu Ala Ser Ser Gly Val Ser Ser Ala Cys Pro
145                 150                 155                 160

Tyr Leu Gly Ser Pro Ser Phe Phe Arg Asn Val Val Trp Leu Ile Lys
                165                 170                 175

Lys Asn Ser Thr Tyr Pro Thr Ile Lys Lys Ser Tyr Asn Asn Thr Asn
            180                 185                 190

Gln Glu Asp Leu Leu Val Leu Trp Gly Ile His His Pro Asn Asp Ala
        195                 200                 205

Ala Glu Gln Thr Arg Leu Tyr Gln Asn Pro Thr Thr Tyr Ile Ser Ile
    210                 215                 220

Gly Thr Ser Thr Leu Asn Gln Arg Leu Val Pro Lys Ile Ala Thr Arg
225                 230                 235                 240

Ser Lys Val Asn Gly Gln Ser Gly Arg Met Glu Phe Phe Trp Thr Ile
                245                 250                 255

Leu Lys Pro Asn Asp Ala Ile Asn Phe Glu Ser Asn Gly Asn Phe Ile
            260                 265                 270

Ala Pro Glu Tyr Ala Tyr Lys Ile Val Lys Lys Gly Asp Ser Ala Ile
        275                 280                 285

Met Lys Ser Glu Leu Glu Tyr Gly Asn Cys Asn Thr Lys Cys Gln Thr
    290                 295                 300

Pro Met Gly Ala Ile Asn Ser Ser Met Pro Phe His Asn Ile His Pro
305                 310                 315                 320

Leu Thr Ile Gly Glu Cys Pro Lys Tyr Val Lys Ser Asn Arg Leu Val
                325                 330                 335

Leu Ala Thr Gly Leu Arg Asn Ser Pro Gln Arg Glu Ser Arg Arg Lys
            340                 345                 350

Lys Arg Gly Leu Phe Gly Ala Ile Ala Gly Phe Ile Glu Gly Gly Trp
        355                 360                 365

Gln Gly Met Val Asp Gly Trp Tyr Gly Tyr His His Ser Asn Glu Gln
    370                 375                 380

Gly Ser Gly Tyr Ala Ala Asp Lys Glu Ser Thr Gln Lys Ala Ile Asp
385                 390                 395                 400

Gly Val Thr Asn Lys Val Asn Ser Ile Ile Asp Lys Met Asn Thr Gln
                405                 410                 415

Asp Glu Ala Val Gly Arg Glu Phe Asn Asn Leu Glu Arg Arg Ile Glu
            420                 425                 430
```

```
Asn Leu Asn Lys Lys Met Glu Asp Gly Phe Leu Asp Val Trp Thr Tyr
        435                 440                 445

Asn Ala Glu Leu Leu Val Leu Met Glu Asn Glu Arg Thr Leu Asp Phe
    450                 455                 460

His Asp Ser Asn Val Lys Asn Leu Tyr Asp Lys Val Arg Leu Gln Leu
465                 470                 475                 480

Arg Asp Asn Ala Lys Glu Leu Gly Asn Gly Cys Phe Glu Phe Tyr His
                485                 490                 495

Lys Cys Asp Asn Glu Cys Met Glu Ser Ile Arg Asn Gly Thr Tyr Asn
            500                 505                 510

Tyr Pro Gln Tyr Ser Glu Glu Ala Arg Leu Lys Arg Glu Glu Ile Ser
        515                 520                 525

Gly Val Lys Leu Glu Ser Ile Gly Thr Tyr Gln Ile Leu Ser Ile Tyr
    530                 535                 540

Ser Thr Val Ala Ser Ser Leu Ala Leu Ala Ile Met Met Ala Gly Leu
545                 550                 555                 560

Ser Leu Trp Met Cys Ser Asn Gly Ser Leu Gln Cys Arg Ile Cys Ile
                565                 570                 575
```

<210> SEQ ID NO 74
<211> LENGTH: 51
<212> TYPE: DNA
<213> ORGANISM: Artificial Sequence
<220> FEATURE:
<223> OTHER INFORMATION: Primer IF-H5_Egy.r

<400> SEQUENCE: 74

```
actaaagaaa ataggccttt aaatgcaaat tctgcattgt agcgatccat t             51
```

<210> SEQ ID NO 75
<211> LENGTH: 1728
<212> TYPE: DNA
<213> ORGANISM: Artificial Sequence
<220> FEATURE:
<223> OTHER INFORMATION: PDI-H5 Egypt DNA

<400> SEQUENCE: 75

```
atggcgaaaa acgttgcgat tttcggctta ttgttttctc ttcttgtgtt ggttccttct     60

cagatcttcg cggatcagat ttgcattggt taccatgcaa acaactcgac agagcaggtt    120

gacacaataa tggaaaagaa tgtcactgtt acacacgccc aagacatact ggaaaagaca    180

cacaacggga aactctgcaa tctagatgga gtgaagcctc tcattttgag agattgtagt    240

gtagctggat ggctcctcgg gaacccaatg tgcgatgaat tcctcaatgt gccggaatgg    300

tcttacatag tggagaaaat caatccagcc aatgacctct gttatccagg gaatttcaac    360

gactatgaag aactgaaaca cctattgagc agaataaacc attttgagaa aattcagatc    420

attcccaaag attcttggtc agatcatgaa gcctcgggag tgagctcagc atgcccatac    480

caaggaagat cctccttttt tagaaatgtt gtatggctta ccaaaaagaa cgatgcatac    540

ccaacaataa agaaaagtta caataatact aaccaagaag atcttttggt actatggggg    600

attcaccatc caaatgatgc tgcagagcag acaaggcttt atcaaaaccc aactacctat    660

atctccgttg ggacatcaac actaaaccag agattggtac ccaaaatagc tactagatct    720

aaggtaaacg ggcaaagtgg aaggatggag ttcttttgga caattttaaa atcgaatgat    780

gcaataaact ttgagagcaa tggaaacttc attgctccag aaaatgcata caaaattgtc    840

aagaaaggag attcaacaat tatgaaaagt gagttggaat atagtaactg caacaccaag    900
```

```
tgtcagactc caataggggc gataaactcc agtatgccat tccacaacat ccaccctctc    960

accatcgggg aatgccccaa atatgtgaaa tcaaacagat tagtccttgc tactgggctc   1020

aggaatagcc ctcaaggaga gaaaagaaga aaaaagagag gactattcgg agccatagca   1080

ggctttatag agggaggatg gcagggaatg gtagatggtt ggtatgggta ccaccatagc   1140

aacgagcagg ggagtgggta cgctgcagac aaagaatcca ctcaaagggc tatagatgga   1200

gtcaccaata aggtcaattc gatcattgac aaaatgaaca ctcagtttga ggctgttgga   1260

agggaattta ataacttaga aaggagaata gaaaatttaa acaagaagat ggaagacgga   1320

ttcctagatg tctggactta taatgctgaa cttctggttc tcatggaaaa tgagagaact   1380

ctagactttc atgactcaaa tgtcaagaat ctttatgaca aggtccgact acagcttagg   1440

gataatgcaa aggagcttgg taacggttgt ttcgagttct atcacagatg tgataatgaa   1500

tgtatggaaa gtgtaagaaa cggaacgtat gactaccctc aatattcaga agaagcaaga   1560

ttaaaaagag aggaaataag tggagtaaaa ttggagtcaa taggaactta ccaaatactg   1620

tcaatttatt caacagtggc gagctcccta gcactggcaa tcatggtggc tggtctatct   1680

ttatggatgt gctccaatgg atcgctacaa tgcagaattt gcatttaa                1728
```

<210> SEQ ID NO 76
<211> LENGTH: 575
<212> TYPE: PRT
<213> ORGANISM: Artificial Sequence
<220> FEATURE:
<223> OTHER INFORMATION: PDI-H5 Egypt AA

<400> SEQUENCE: 76

```
Met Ala Lys Asn Val Ala Ile Phe Gly Leu Leu Phe Ser Leu Leu Val
1               5                   10                  15

Leu Val Pro Ser Gln Ile Phe Ala Asp Gln Ile Cys Ile Gly Tyr His
            20                  25                  30

Ala Asn Asn Ser Thr Glu Gln Val Asp Thr Ile Met Glu Lys Asn Val
        35                  40                  45

Thr Val Thr His Ala Gln Asp Ile Leu Glu Lys Thr His Asn Gly Lys
    50                  55                  60

Leu Cys Asn Leu Asp Gly Val Lys Pro Leu Ile Leu Arg Asp Cys Ser
65                  70                  75                  80

Val Ala Gly Trp Leu Leu Gly Asn Pro Met Cys Asp Glu Phe Leu Asn
                85                  90                  95

Val Pro Glu Trp Ser Tyr Ile Val Glu Lys Ile Asn Pro Ala Asn Asp
            100                 105                 110

Leu Cys Tyr Pro Gly Asn Phe Asn Asp Tyr Glu Glu Leu Lys His Leu
        115                 120                 125

Leu Ser Arg Ile Asn His Phe Glu Lys Ile Gln Ile Ile Pro Lys Asp
    130                 135                 140

Ser Trp Ser Asp His Glu Ala Ser Gly Val Ser Ser Ala Cys Pro Tyr
145                 150                 155                 160

Gln Gly Arg Ser Ser Phe Phe Arg Asn Val Val Trp Leu Thr Lys Lys
                165                 170                 175

Asn Asp Ala Tyr Pro Thr Ile Lys Lys Ser Tyr Asn Asn Thr Asn Gln
            180                 185                 190

Glu Asp Leu Leu Val Leu Trp Gly Ile His His Pro Asn Asp Ala Ala
        195                 200                 205

Glu Gln Thr Arg Leu Tyr Gln Asn Pro Thr Thr Tyr Ile Ser Val Gly
```

```
    210                 215                 220

Thr Ser Thr Leu Asn Gln Arg Leu Val Pro Lys Ile Ala Thr Arg Ser
225                 230                 235                 240

Lys Val Asn Gly Gln Ser Gly Arg Met Glu Phe Phe Trp Thr Ile Leu
                245                 250                 255

Lys Ser Asn Asp Ala Ile Asn Phe Glu Ser Asn Gly Asn Phe Ile Ala
            260                 265                 270

Pro Glu Asn Ala Tyr Lys Ile Val Lys Lys Gly Asp Ser Thr Ile Met
        275                 280                 285

Lys Ser Glu Leu Glu Tyr Ser Asn Cys Asn Thr Lys Cys Gln Thr Pro
    290                 295                 300

Ile Gly Ala Ile Asn Ser Ser Met Pro Phe His Asn Ile His Pro Leu
305                 310                 315                 320

Thr Ile Gly Glu Cys Pro Lys Tyr Val Lys Ser Asn Arg Leu Val Leu
                325                 330                 335

Ala Thr Gly Leu Arg Asn Ser Pro Gln Gly Glu Lys Arg Arg Lys Lys
            340                 345                 350

Arg Gly Leu Phe Gly Ala Ile Ala Gly Phe Ile Glu Gly Gly Trp Gln
        355                 360                 365

Gly Met Val Asp Gly Trp Tyr Gly Tyr His His Ser Asn Glu Gln Gly
    370                 375                 380

Ser Gly Tyr Ala Ala Asp Lys Glu Ser Thr Gln Arg Ala Ile Asp Gly
385                 390                 395                 400

Val Thr Asn Lys Val Asn Ser Ile Ile Asp Lys Met Asn Thr Gln Phe
                405                 410                 415

Glu Ala Val Gly Arg Glu Phe Asn Asn Leu Glu Arg Arg Ile Glu Asn
            420                 425                 430

Leu Asn Lys Lys Met Glu Asp Gly Phe Leu Asp Val Trp Thr Tyr Asn
        435                 440                 445

Ala Glu Leu Leu Val Leu Met Glu Asn Glu Arg Thr Leu Asp Phe His
    450                 455                 460

Asp Ser Asn Val Lys Asn Leu Tyr Asp Lys Val Arg Leu Gln Leu Arg
465                 470                 475                 480

Asp Asn Ala Lys Glu Leu Gly Asn Gly Cys Phe Glu Phe Tyr His Arg
                485                 490                 495

Cys Asp Asn Glu Cys Met Glu Ser Val Arg Asn Gly Thr Tyr Asp Tyr
            500                 505                 510

Pro Gln Tyr Ser Glu Glu Ala Arg Leu Lys Arg Glu Glu Ile Ser Gly
        515                 520                 525

Val Lys Leu Glu Ser Ile Gly Thr Tyr Gln Ile Leu Ser Ile Tyr Ser
    530                 535                 540

Thr Val Ala Ser Ser Leu Ala Leu Ala Ile Met Val Ala Gly Leu Ser
545                 550                 555                 560

Leu Trp Met Cys Ser Asn Gly Ser Leu Gln Cys Arg Ile Cys Ile
                565                 570                 575
```

<210> SEQ ID NO 77
<211> LENGTH: 49
<212> TYPE: DNA
<213> ORGANISM: Artificial Sequence
<220> FEATURE:
<223> OTHER INFORMATION: Primer H5Egy(F392D).r

<400> SEQUENCE: 77
cttccaacag cctcgtcctg agtgttcatt ttgtcaatga tcgaattga 49

<210> SEQ ID NO 78
<211> LENGTH: 49
<212> TYPE: DNA
<213> ORGANISM: Artificial Sequence
<220> FEATURE:
<223> OTHER INFORMATION: Primer H5Egy(F392D).c

<400> SEQUENCE: 78
caaaatgaac actcaggacg aggctgttgg aagggaattt aataactta 49

<210> SEQ ID NO 79
<211> LENGTH: 1728
<212> TYPE: DNA
<213> ORGANISM: Artificial Sequence
<220> FEATURE:
<223> OTHER INFORMATION: PDI-H5 Egypt-F392D DNA

<400> SEQUENCE: 79
atggcgaaaa acgttgcgat tttcggctta ttgttttctc ttcttgtgtt ggttccttct 60
cagatcttcg cggatcagat ttgcattggt taccatgcaa acaactcgac agagcaggtt 120
gacacaataa tggaaaagaa tgtcactgtt acacacgccc aagacatact ggaaaagaca 180
cacaacggga aactctgcaa tctagatgga gtgaagcctc tcattttgag agattgtagt 240
gtagctggat ggctcctcgg gaacccaatg tgcgatgaat tcctcaatgt gccggaatgg 300
tcttacatag tggagaaaat caatccagcc aatgacctct gttatccagg gaatttcaac 360
gactatgaag aactgaaaca cctattgagc agaataaacc attttgagaa aattcagatc 420
attcccaaag attcttggtc agatcatgaa gcctcgggag tgagctcagc atgcccatac 480
caaggaagat cctccttttt tagaaatgtt gtatggctta ccaaaaagaa cgatgcatac 540
ccaacaataa agaaaagtta caataatact aaccaagaag atcttttggt actatggggg 600
attcaccatc caaatgatgc tgcagagcag acaaggcttt atcaaaaccc aactacctat 660
atctccgttg ggacatcaac actaaaccag agattggtac ccaaaatagc tactagatct 720
aaggtaaacg ggcaaagtgg aaggatggag ttcttttgga caattttaaa atcgaatgat 780
gcaataaact ttgagagcaa tggaaacttc attgctccag aaaatgcata caaaattgtc 840
aagaaaggag attcaacaat tatgaaaagt gagttggaat atagtaactg caacaccaag 900
tgtcagactc caataggggc gataaactcc agtatgccat tccacaacat ccaccctctc 960
accatcgggg aatgccccaa atatgtgaaa tcaaacagat tagtccttgc tactgggctc 1020
aggaatagcc ctcaaggaga gaaaagaaga aaaaagagag gactattcgg agccatagca 1080
ggctttatag agggaggatg gcagggaatg gtagatggtt ggtatgggta ccaccatagc 1140
aacgagcagg ggagtgggta cgctgcagac aaagaatcca ctcaaagggc tatagatgga 1200
gtcaccaata aggtcaattc gatcattgac aaaatgaaca ctcaggacga ggctgttgga 1260
agggaattta ataacttaga aaggagaata gaaaatttaa acaagaagat ggaagacgga 1320
ttcctagatg tctggactta taatgctgaa cttctggttc tcatggaaaa tgagagaact 1380
ctagactttc atgactcaaa tgtcaagaat ctttatgaca aggtccgact acagcttagg 1440
gataatgcaa aggagcttgg taacggttgt ttcgagttct atcacagatg tgataatgaa 1500
tgtatggaaa gtgtaagaaa cggaacgtat gactaccctc aatattcaga agaagcaaga 1560
ttaaaaagag aggaaataag tggagtaaaa ttggagtcaa taggaactta ccaaatactg 1620
tcaatttatt caacagtggc gagctcccta gcactggcaa tcatggtggc tggtctatct 1680

-continued ttatggatgt gctccaatgg atcgctacaa tgcagaattt gcatttaa 1728

<210> SEQ ID NO 80
<211> LENGTH: 575
<212> TYPE: PRT
<213> ORGANISM: Artificial Sequence
<220> FEATURE:
<223> OTHER INFORMATION: PDI-H5 Egypt-F392D AA

<400> SEQUENCE: 80

```
Met Ala Lys Asn Val Ala Ile Phe Gly Leu Leu Phe Ser Leu Leu Val
1               5                   10                  15

Leu Val Pro Ser Gln Ile Phe Ala Asp Gln Ile Cys Ile Gly Tyr His
            20                  25                  30

Ala Asn Asn Ser Thr Glu Gln Val Asp Thr Ile Met Glu Lys Asn Val
        35                  40                  45

Thr Val Thr His Ala Gln Asp Ile Leu Glu Lys Thr His Asn Gly Lys
    50                  55                  60

Leu Cys Asn Leu Asp Gly Val Lys Pro Leu Ile Leu Arg Asp Cys Ser
65                  70                  75                  80

Val Ala Gly Trp Leu Leu Gly Asn Pro Met Cys Asp Glu Phe Leu Asn
                85                  90                  95

Val Pro Glu Trp Ser Tyr Ile Val Glu Lys Ile Asn Pro Ala Asn Asp
            100                 105                 110

Leu Cys Tyr Pro Gly Asn Phe Asn Asp Tyr Glu Glu Leu Lys His Leu
        115                 120                 125

Leu Ser Arg Ile Asn His Phe Glu Lys Ile Gln Ile Ile Pro Lys Asp
    130                 135                 140

Ser Trp Ser Asp His Glu Ala Ser Gly Val Ser Ser Ala Cys Pro Tyr
145                 150                 155                 160

Gln Gly Arg Ser Ser Phe Phe Arg Asn Val Val Trp Leu Thr Lys Lys
                165                 170                 175

Asn Asp Ala Tyr Pro Thr Ile Lys Lys Ser Tyr Asn Asn Thr Asn Gln
            180                 185                 190

Glu Asp Leu Leu Val Leu Trp Gly Ile His His Pro Asn Asp Ala Ala
        195                 200                 205

Glu Gln Thr Arg Leu Tyr Gln Asn Pro Thr Thr Tyr Ile Ser Val Gly
    210                 215                 220

Thr Ser Thr Leu Asn Gln Arg Leu Val Pro Lys Ile Ala Thr Arg Ser
225                 230                 235                 240

Lys Val Asn Gly Gln Ser Gly Arg Met Glu Phe Phe Trp Thr Ile Leu
                245                 250                 255

Lys Ser Asn Asp Ala Ile Asn Phe Glu Ser Asn Gly Asn Phe Ile Ala
            260                 265                 270

Pro Glu Asn Ala Tyr Lys Ile Val Lys Lys Gly Asp Ser Thr Ile Met
        275                 280                 285

Lys Ser Glu Leu Glu Tyr Ser Asn Cys Asn Thr Lys Cys Gln Thr Pro
    290                 295                 300

Ile Gly Ala Ile Asn Ser Ser Met Pro Phe His Asn Ile His Pro Leu
305                 310                 315                 320

Thr Ile Gly Glu Cys Pro Lys Tyr Val Lys Ser Asn Arg Leu Val Leu
                325                 330                 335

Ala Thr Gly Leu Arg Asn Ser Pro Gln Gly Glu Lys Arg Arg Lys Lys
            340                 345                 350

Arg Gly Leu Phe Gly Ala Ile Ala Gly Phe Ile Glu Gly Gly Trp Gln
```

```
        355                 360                 365

Gly Met Val Asp Gly Trp Tyr Gly Tyr His His Ser Asn Glu Gln Gly
    370                 375                 380

Ser Gly Tyr Ala Ala Asp Lys Glu Ser Thr Gln Arg Ala Ile Asp Gly
385                 390                 395                 400

Val Thr Asn Lys Val Asn Ser Ile Ile Asp Lys Met Asn Thr Gln Asp
                405                 410                 415

Glu Ala Val Gly Arg Glu Phe Asn Asn Leu Glu Arg Arg Ile Glu Asn
            420                 425                 430

Leu Asn Lys Lys Met Glu Asp Gly Phe Leu Asp Val Trp Thr Tyr Asn
        435                 440                 445

Ala Glu Leu Leu Val Leu Met Glu Asn Glu Arg Thr Leu Asp Phe His
    450                 455                 460

Asp Ser Asn Val Lys Asn Leu Tyr Asp Lys Val Arg Leu Gln Leu Arg
465                 470                 475                 480

Asp Asn Ala Lys Glu Leu Gly Asn Gly Cys Phe Glu Phe Tyr His Arg
                485                 490                 495

Cys Asp Asn Glu Cys Met Glu Ser Val Arg Asn Gly Thr Tyr Asp Tyr
            500                 505                 510

Pro Gln Tyr Ser Glu Glu Ala Arg Leu Lys Arg Glu Glu Ile Ser Gly
        515                 520                 525

Val Lys Leu Glu Ser Ile Gly Thr Tyr Gln Ile Leu Ser Ile Tyr Ser
    530                 535                 540

Thr Val Ala Ser Ser Leu Ala Leu Ala Ile Met Val Ala Gly Leu Ser
545                 550                 555                 560

Leu Trp Met Cys Ser Asn Gly Ser Leu Gln Cys Arg Ile Cys Ile
                565                 570                 575
```

<210> SEQ ID NO 81
<211> LENGTH: 1725
<212> TYPE: DNA
<213> ORGANISM: Artificial Sequence
<220> FEATURE:
<223> OTHER INFORMATION: PDI-H3 Switz-N382A DNA

<400> SEQUENCE: 81

```
atggcgaaaa acgttgcgat tttcggctta ttgttttctc ttcttgtgtt ggttccttct      60

cagatcttcg cgcaaaaact tcctggaaat gacaatagca cggcaacgct gtgccttggg     120

caccatgcag taccaaacgg aacgatagtg aaaacaatca cgaatgaccg aattgaagtt     180

actaatgcta ctgagctggt tcagaattcc tcaataggtg aaatatgcga cagtcctcat     240

cagatccttg atggagaaaa ctgcacacta atagatgctc tattgggaga ccctcagtgt     300

gatggctttc aaaataagaa atgggacctt tttgttgaac gaagcaaagc ctacagcaac     360

tgttaccctt atgatgtgcc ggattatgcc tcccttaggt cactagttgc ctcatccggc     420

acactggagt ttaacaatga aagcttcaat tgggctggag tcactcaaaa cggaacaagt     480

tcttcttgca taaggggatc taatagtagt ttctttagta gattaaattg gttgacccac     540

ttaaactcca aatacccagc attaaacgtg actatgccaa acaatgaaca atttgacaaa     600

ttgtacattt ggggggttca ccacccgggt acggacaagg accaaatctt cctgtatgca     660

caatcatcag gaagaatcac agtatctacc aaaagaagcc aacaagctgt aatcccgaat     720

atcggatcta gacccagaat aagggatatc cctagcagaa taagcatcta ttggacaata     780

gtaaaaccgg gagacatact tttgattaac agcacaggga atctaattgc tcctaggggt     840
```

```
tacttcaaaa tacgaagtgg gaaaagctca ataatgagat cagatgcacc cattggcaaa    900

tgcaagtctg aatgcatcac tccaaatgga agcattccca atgacaaacc attccaaaat    960

gtaaacagga tcacatacgg ggcctgtccc agatatgtta agcaaagcac tctgaaattg   1020

gcaacaggaa tgcgaaatgt accagagaga caaactagag gcatatttgg cgcaatagcg   1080

ggtttcatag aaaatggttg ggagggaatg gtggatggtt ggtacggctt caggcatcaa   1140

aattctgagg gaagaggaca agcagcagat ctcaaaagca ctcaagcagc aatcgatcaa   1200

atcaatggga agctggctcg attgatcggg aaaaccaacg agaaattcca tcagattgaa   1260

aaagaattct cagaagtaga agggagaatt caggaccttg agaaatatgt tgaggacaca   1320

aaaatagatc tctggtcata caacgcggag cttcttgttg ccctggagaa ccaacataca   1380

attgatctaa ctgactcaga aatgaacaaa ctgtttgaaa aaacaaagaa gcaactgagg   1440

gaaaatgctg aggatatggg caatggttgt ttcaaaatat accacaaatg tgacaatgcc   1500

tgcataggat caatcagaaa tggaacttat gaccacgatg tatacaggga tgaagcatta   1560

aacaaccggt tccagatcaa gggagttgag ctgaagtcag ggtacaaaga ttggatccta   1620

tggatttcct ttgccatatc atgttttttg ctttgtgttg ctttgttggg gttcatcatg   1680

tgggcctgcc aaaagggcaa cattaggtgc aacatttgca tttga                   1725
```

<210> SEQ ID NO 82
<211> LENGTH: 574
<212> TYPE: PRT
<213> ORGANISM: Artificial Sequence
<220> FEATURE:
<223> OTHER INFORMATION: PDI-H3 Switz-N382A AA

<400> SEQUENCE: 82

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160

Ser Ser Cys Ile Arg Gly Ser Asn Ser Ser Phe Phe Ser Arg Leu Asn
                165                 170                 175

Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205
```

```
Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Ala Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 83
<211> LENGTH: 1725
<212> TYPE: DNA
<213> ORGANISM: Artificial Sequence
<220> FEATURE:
<223> OTHER INFORMATION: PDI-H3 Switz-L384V DNA

<400> SEQUENCE: 83

```
atggcgaaaa acgttgcgat tttcggctta ttgttttctc ttcttgtgtt ggttccttct      60
cagatcttcg cgcaaaaact tcctggaaat gacaatagca cggcaacgct gtgccttggg     120
caccatgcag taccaaacgg aacgatagtg aaaacaatca cgaatgaccg aattgaagtt     180
actaatgcta ctgagctggt tcagaattcc tcaataggtg aaatatgcga cagtcctcat     240
cagatccttg atggagaaaa ctgcacacta atagatgctc tattgggaga ccctcagtgt     300
gatggctttc aaaataagaa atgggacctt tttgttgaac gaagcaaagc ctacagcaac     360
tgttaccctt atgatgtgcc ggattatgcc tcccttaggt cactagttgc ctcatccggc     420
acactggagt ttaacaatga aagcttcaat tgggctggag tcactcaaaa cggaacaagt     480
tcttcttgca taaggggatc taatagtagt ttctttagta gattaaattg gttgacccac     540
ttaaactcca aatacccagc attaaacgtg actatgccaa acaatgaaca atttgacaaa     600
ttgtacattt ggggggttca ccacccgggt acggacaagg accaaatctt cctgtatgca     660
caatcatcag gaagaatcac agtatctacc aaaagaagcc aacaagctgt aatcccgaat     720
atcggatcta gacccagaat aagggatatc cctagcagaa taagcatcta ttggacaata     780
gtaaaaccgg gagacatact tttgattaac agcacaggga atctaattgc tcctaggggt     840
tacttcaaaa tacgaagtgg gaaaagctca ataatgagat cagatgcacc cattggcaaa     900
tgcaagtctg aatgcatcac tccaaatgga agcattccca atgacaaacc attccaaaat     960
gtaaacagga tcacatacgg ggcctgtccc agatatgtta agcaaagcac tctgaaattg    1020
gcaacaggaa tgcgaaatgt accagagaga caaactagag gcatatttgg cgcaatagcg    1080
ggtttcatag aaaatggttg ggagggaatg gtggatggtt ggtacggctt caggcatcaa    1140
aattctgagg gaagaggaca agcagcagat ctcaaaagca ctcaagcagc aatcgatcaa    1200
atcaatggga agctgaatcg agtgatcggg aaaaccaacg agaaattcca tcagattgaa    1260
aaagaattct cagaagtaga agggagaatt caggaccttg agaaatatgt tgaggacaca    1320
aaaatagatc tctggtcata caacgcggag cttcttgttg ccctggagaa ccaacataca    1380
attgatctaa ctgactcaga aatgaacaaa ctgtttgaaa aaacaaagaa gcaactgagg    1440
gaaaatgctg aggatatggg caatggttgt ttcaaaatat accacaaatg tgacaatgcc    1500
tgcataggat caatcagaaa tggaacttat gaccacgatg tatacaggga tgaagcatta    1560
aacaaccggt tccagatcaa gggagttgag ctgaagtcag ggtacaaaga ttggatccta    1620
tggatttcct ttgccatatc atgtttttg ctttgtgttg ctttgttggg gttcatcatg     1680
tgggcctgcc aaaagggcaa cattaggtgc aacatttgca tttga                    1725
```

<210> SEQ ID NO 84
<211> LENGTH: 574
<212> TYPE: PRT
<213> ORGANISM: Artificial Sequence
<220> FEATURE:
<223> OTHER INFORMATION: PDI-H3 Switz-L384V AA

<400> SEQUENCE: 84

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60
```

```
Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Ala Gly Val Thr Gln Asn Gly Thr Ser
145                 150                 155                 160

Ser Ser Cys Ile Arg Gly Ser Asn Ser Ser Phe Phe Ser Arg Leu Asn
                165                 170                 175

Trp Leu Thr His Leu Asn Ser Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Arg Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Val Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480
```

```
Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570


<210> SEQ ID NO 85
<211> LENGTH: 1725
<212> TYPE: DNA
<213> ORGANISM: Artificial Sequence
<220> FEATURE:
<223> OTHER INFORMATION: PDI-H3 Penn-CysTm DNA

<400> SEQUENCE: 85

atggcgaaaa acgttgcgat tttcggctta ttgttttctc ttcttgtgtt ggttccttct      60

cagatcttcg cgcaaaaact tcctggaaat gacaatagca cggcaacgct gtgccttggg     120

caccatgcag taccaaacgg aacgatagtg aaaacaatca cgaatgaccg aattgaagtt     180

actaatgcta ctgagctggt tcagaattcc tcaataggtg aaatatgcga cagtcctcat     240

cagatccttg atggaaaaaa ctgcactcta atagatgctc tattgggaga ccctcagtgt     300

gatggctttc aaaataagag atgggacctt tttgttgaac gaagcaaagc ctacagcaac     360

tgttaccctt atgatgtgcc ggattatgcc tcccttaggt cactagttgc ctcatccggc     420

acactggagt ttaacgatga aagcttcaat tgggctggag tcactcaaaa cggaacaagt     480

tctgcttgca taaggggatc taatagtagt ttctttagta gattaaattg gttgacccac     540

tcaaacttca aatacccagc attgaacgtg actatgccaa acaatgaaca atttgacaaa     600

ttgtacattt gggggttca ccacccgggt acagacaagg accaaatctt cctgtacgct     660

caatcatcag gaagaatcac agtatctacc aaaagaagcc aacaagctgt aatcccgaat     720

atcggatcta gacccagaat aaggaatatc cctagcagaa taagcatcta ttggacaata     780

gtaaaaccgg gagacatact tttgattaac agcacaggga atctaattgc tcctaggggt     840

tacttcaaaa tacaaagtgg gaaaagctca ataatgagat cagatgcacc cattggcaaa     900

tgcaagtctg aatgcatcac tccaaatgga agcattccca atgacaaacc attccaaaat     960

gtaaacagga tcacatacgg ggcctgtccc agatatgtta agcaaagcac tctgaaattg    1020

gcaacaggaa tgcgaaatgt accagagaaa caaactagag gcatatttgg cgcaatagcg    1080

ggtttcatag aaaatggttg ggagggaatg aaggatggtt ggtacggttt caggcatcaa    1140

aattctgagg gaagaggaca agcagcagat ctcaaaagca ctcaagcagc aatcgatcaa    1200

atcaatggga agctgaatcg attgatcggg aaaaccaacg agaaattcca tcagattgaa    1260

aaagaattct cagaagtaga agggagaatt caggaccttg agaaatatgt tgaggacaca    1320

aaaatagatc tctggtcata caacgcggag cttcttgttg ccctggagaa ccaacataca    1380

attgatctaa ctgactcaga aatgaacaaa ctgtttgaaa aaacaaagaa gcaactgagg    1440

gaaaatgctg aggatatggg caatggttgt ttcaaaatat accacaaatg tgacaatgcc    1500

tgcataggat caatcagaaa tggaacttat gaccacgatg tatacaggga tgaagcttta    1560
```

aacaaccggt tccagatcaa gggagttgag ctgaagtcag ggtacaaaga ttggatccta 1620
tggatttcct ttgccatatc atcccttgta ctgttagttg ctttgttggg gttcatcatg 1680
tgggcctgcc aaaagggcaa cattaggtgc aacatttgca tttga 1725

<210> SEQ ID NO 86
<211> LENGTH: 574
<212> TYPE: PRT
<213> ORGANISM: Artificial Sequence
<220> FEATURE:
<223> OTHER INFORMATION: PDI-H3 Penn-CysTm AA

<400> SEQUENCE: 86

Met Ala Lys Asn Val Ala Ile Phe Gly Leu Leu Phe Ser Leu Leu Val
1 5 10 15

Leu Val Pro Ser Gln Ile Phe Ala Gln Lys Leu Pro Gly Asn Asp Asn
20 25 30

Ser Thr Ala Thr Leu Cys Leu Gly His His Ala Val Pro Asn Gly Thr
35 40 45

Ile Val Lys Thr Ile Thr Asn Asp Arg Ile Glu Val Thr Asn Ala Thr
50 55 60

Glu Leu Val Gln Asn Ser Ser Ile Gly Glu Ile Cys Asp Ser Pro His
65 70 75 80

Gln Ile Leu Asp Gly Lys Asn Cys Thr Leu Ile Asp Ala Leu Leu Gly
85 90 95

Asp Pro Gln Cys Asp Gly Phe Gln Asn Lys Arg Trp Asp Leu Phe Val
100 105 110

Glu Arg Ser Lys Ala Tyr Ser Asn Cys Tyr Pro Tyr Asp Val Pro Asp
115 120 125

Tyr Ala Ser Leu Arg Ser Leu Val Ala Ser Ser Gly Thr Leu Glu Phe
130 135 140

Asn Asp Glu Ser Phe Asn Trp Ala Gly Val Thr Gln Asn Gly Thr Ser
145 150 155 160

Ser Ala Cys Ile Arg Gly Ser Asn Ser Ser Phe Phe Ser Arg Leu Asn
165 170 175

Trp Leu Thr His Ser Asn Phe Lys Tyr Pro Ala Leu Asn Val Thr Met
180 185 190

Pro Asn Asn Glu Gln Phe Asp Lys Leu Tyr Ile Trp Gly Val His His
195 200 205

Pro Gly Thr Asp Lys Asp Gln Ile Phe Leu Tyr Ala Gln Ser Ser Gly
210 215 220

Arg Ile Thr Val Ser Thr Lys Arg Ser Gln Gln Ala Val Ile Pro Asn
225 230 235 240

Ile Gly Ser Arg Pro Arg Ile Arg Asn Ile Pro Ser Arg Ile Ser Ile
245 250 255

Tyr Trp Thr Ile Val Lys Pro Gly Asp Ile Leu Leu Ile Asn Ser Thr
260 265 270

Gly Asn Leu Ile Ala Pro Arg Gly Tyr Phe Lys Ile Gln Ser Gly Lys
275 280 285

Ser Ser Ile Met Arg Ser Asp Ala Pro Ile Gly Lys Cys Lys Ser Glu
290 295 300

Cys Ile Thr Pro Asn Gly Ser Ile Pro Asn Asp Lys Pro Phe Gln Asn
305 310 315 320

Val Asn Arg Ile Thr Tyr Gly Ala Cys Pro Arg Tyr Val Lys Gln Ser
325 330 335

```
Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Lys Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 87
<211> LENGTH: 1725
<212> TYPE: DNA
<213> ORGANISM: Artificial Sequence
<220> FEATURE:
<223> OTHER INFORMATION: PDI-H3 Penn-N382A-CysTm DNA

<400> SEQUENCE: 87

```
atggcgaaaa acgttgcgat tttcggctta ttgttttctc ttcttgtgtt ggttccttct      60

cagatcttcg cgcaaaaact tcctggaaat gacaatagca cggcaacgct gtgccttggg     120

caccatgcag taccaaacgg aacgatagtg aaaacaatca cgaatgaccg aattgaagtt     180

actaatgcta ctgagctggt tcagaattcc tcaataggtg aaatatgcga cagtcctcat     240

cagatccttg atggaaaaaa ctgcactcta atagatgctc tattgggaga ccctcagtgt     300

gatggctttc aaaataagag atgggacctt tttgttgaac gaagcaaagc ctacagcaac     360

tgttaccctt atgatgtgcc ggattatgcc tcccttaggt cactagttgc ctcatccggc     420

acactggagt ttaacgatga aagcttcaat tgggctggag tcactcaaaa cggaacaagt     480

tctgcttgca taaggggatc taatagtagt ttctttagta gattaaattg gttgacccac     540

tcaaacttca aatacccagc attgaacgtg actatgccaa acaatgaaca atttgacaaa     600

ttgtacattt ggggggttca ccacccgggt acagacaagg accaaatctt cctgtacgct     660

caatcatcag gaagaatcac agtatctacc aaaagaagcc aacaagctgt aatcccgaat     720
```

atcggatcta gacccagaat aaggaatatc cctagcagaa taagcatcta ttggacaata 780
gtaaaaccgg gagacatact tttgattaac agcacaggga atctaattgc tcctaggggt 840
tacttcaaaa tacaaagtgg gaaaagctca ataatgagat cagatgcacc cattggcaaa 900
tgcaagtctg aatgcatcac tccaaatgga agcattccca atgacaaacc attccaaaat 960
gtaaacagga tcacatacgg ggcctgtccc agatatgtta agcaaagcac tctgaaattg 1020
gcaacaggaa tgcgaaatgt accagagaaa caaactagag gcatatttgg cgcaatagcg 1080
ggtttcatag aaaatggttg ggagggaatg aaggatggtt ggtacggttt caggcatcaa 1140
aattctgagg gaagaggaca agcagcagat ctcaaaagca ctcaagcagc aatcgatcaa 1200
atcaatggga agctggctcg attgatcggg aaaaccaacg agaaattcca tcagattgaa 1260
aaagaattct cagaagtaga agggagaatt caggaccttg agaaatatgt tgaggacaca 1320
aaaatagatc tctggtcata caacgcggag cttcttgttg ccctggagaa ccaacataca 1380
attgatctaa ctgactcaga aatgaacaaa ctgtttgaaa aaacaaagaa gcaactgagg 1440
gaaaatgctg aggatatggg caatggttgt ttcaaaatat accacaaatg tgacaatgcc 1500
tgcataggat caatcagaaa tggaacttat gaccacgatg tatacaggga tgaagcttta 1560
aacaaccggt tccagatcaa gggagttgag ctgaagtcag ggtacaaaga ttggatccta 1620
tggatttcct ttgccatatc atcccttgta ctgttagttg ctttgttggg gttcatcatg 1680
tgggcctgcc aaaagggcaa cattaggtgc aacatttgca tttga 1725

<210> SEQ ID NO 88
<211> LENGTH: 574
<212> TYPE: PRT
<213> ORGANISM: Artificial Sequence
<220> FEATURE:
<223> OTHER INFORMATION: PDI-H3 Penn-N382A-CysTm AA

<400> SEQUENCE: 88

Met Ala Lys Asn Val Ala Ile Phe Gly Leu Leu Phe Ser Leu Leu Val
1 5 10 15

Leu Val Pro Ser Gln Ile Phe Ala Gln Lys Leu Pro Gly Asn Asp Asn
20 25 30

Ser Thr Ala Thr Leu Cys Leu Gly His His Ala Val Pro Asn Gly Thr
35 40 45

Ile Val Lys Thr Ile Thr Asn Asp Arg Ile Glu Val Thr Asn Ala Thr
50 55 60

Glu Leu Val Gln Asn Ser Ser Ile Gly Glu Ile Cys Asp Ser Pro His
65 70 75 80

Gln Ile Leu Asp Gly Lys Asn Cys Thr Leu Ile Asp Ala Leu Leu Gly
85 90 95

Asp Pro Gln Cys Asp Gly Phe Gln Asn Lys Arg Trp Asp Leu Phe Val
100 105 110

Glu Arg Ser Lys Ala Tyr Ser Asn Cys Tyr Pro Tyr Asp Val Pro Asp
115 120 125

Tyr Ala Ser Leu Arg Ser Leu Val Ala Ser Ser Gly Thr Leu Glu Phe
130 135 140

Asn Asp Glu Ser Phe Asn Trp Ala Gly Val Thr Gln Asn Gly Thr Ser
145 150 155 160

Ser Ala Cys Ile Arg Gly Ser Asn Ser Ser Phe Phe Ser Arg Leu Asn
165 170 175

Trp Leu Thr His Ser Asn Phe Lys Tyr Pro Ala Leu Asn Val Thr Met

```
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Gln Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Lys Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Ala Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 89
<211> LENGTH: 1725
<212> TYPE: DNA
<213> ORGANISM: Artificial Sequence
<220> FEATURE:
<223> OTHER INFORMATION: PDI-H3 Penn-L384V-CysTm DNA

<400> SEQUENCE: 89

```
atggcgaaaa acgttgcgat tttcggctta ttgttttctc ttcttgtgtt ggttccttct     60
cagatcttcg cgcaaaaact tcctggaaat gacaatagca cggcaacgct gtgccttggg    120
caccatgcag taccaaacgg aacgatagtg aaaacaatca cgaatgaccg aattgaagtt    180
actaatgcta ctgagctggt tcagaattcc tcaataggtg aaatatgcga cagtcctcat    240
cagatccttg atggaaaaaa ctgcactcta atagatgctc tattgggaga ccctcagtgt    300
gatggctttc aaaataagag atgggacctt tttgttgaac gaagcaaagc ctacagcaac    360
tgttaccctt atgatgtgcc ggattatgcc tcccttaggt cactagttgc ctcatccggc    420
acactggagt ttaacgatga aagcttcaat tgggctggag tcactcaaaa cggaacaagt    480
tctgcttgca taaggggatc taatagtagt ttctttagta gattaaattg gttgacccac    540
tcaaacttca aatacccagc attgaacgtg actatgccaa acaatgaaca atttgacaaa    600
ttgtacattt ggggggttca ccacccgggt acagacaagg accaaatctt cctgtacgct    660
caatcatcag gaagaatcac agtatctacc aaaagaagcc aacaagctgt aatcccgaat    720
atcggatcta gacccagaat aaggaatatc cctagcagaa taagcatcta ttggacaata    780
gtaaaaccgg gagacatact tttgattaac agcacaggga atctaattgc tcctaggggt    840
tacttcaaaa tacaaagtgg gaaaagctca ataatgagat cagatgcacc cattggcaaa    900
tgcaagtctg aatgcatcac tccaaatgga agcattccca atgacaaacc attccaaaat    960
gtaaacagga tcacatacgg ggcctgtccc agatatgtta agcaaagcac tctgaaattg   1020
gcaacaggaa tgcgaaatgt accagagaaa caaactagag gcatatttgg cgcaatagcg   1080
ggtttcatag aaaatggttg ggagggaatg aaggatggtt ggtacggttt caggcatcaa   1140
aattctgagg gaagaggaca agcagcagat ctcaaaagca ctcaagcagc aatcgatcaa   1200
atcaatggga agctgaatcg agtgatcggg aaaaccaacg agaaattcca tcagattgaa   1260
aaagaattct cagaagtaga agggagaatt caggaccttg agaaatatgt tgaggacaca   1320
aaaatagatc tctggtcata caacgcggag cttcttgttg ccctggagaa ccaacataca   1380
attgatctaa ctgactcaga aatgaacaaa ctgtttgaaa aaacaaagaa gcaactgagg   1440
gaaaatgctg aggatatggg caatggttgt ttcaaaatat accacaaatg tgacaatgcc   1500
tgcataggat caatcagaaa tggaacttat gaccacgatg tatacaggga tgaagcttta   1560
aacaaccggt tccagatcaa gggagttgag ctgaagtcag ggtacaaaga ttggatccta   1620
tggatttcct ttgccatatc atcccttgta ctgttagttg ctttgttggg gttcatcatg   1680
tgggcctgcc aaaagggcaa cattaggtgc aacatttgca tttga                   1725
```

<210> SEQ ID NO 90
<211> LENGTH: 574
<212> TYPE: PRT
<213> ORGANISM: Artificial Sequence
<220> FEATURE:
<223> OTHER INFORMATION: PDI-H3 Penn-L384V-CysTm AA

<400> SEQUENCE: 90

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30
```

-continued

```
Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Lys Asn Cys Thr Leu Ile Asp Ala Leu Leu Gly
                85                  90                  95

Asp Pro Gln Cys Asp Gly Phe Gln Asn Lys Arg Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asp Glu Ser Phe Asn Trp Ala Gly Val Thr Gln Asn Gly Thr Ser
145                 150                 155                 160

Ser Ala Cys Ile Arg Gly Ser Asn Ser Ser Phe Phe Ser Arg Leu Asn
                165                 170                 175

Trp Leu Thr His Ser Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Gln Ser Gly Lys
        275                 280                 285

Ser Ser Ile Met Arg Ser Asp Ala Pro Ile Gly Lys Cys Lys Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Lys Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Val Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
```

450 455 460

Asp Ser Glu Met Asn Lys Leu Phe Glu Lys Thr Lys Lys Gln Leu Arg
465 470 475 480

Glu Asn Ala Glu Asp Met Gly Asn Gly Cys Phe Lys Ile Tyr His Lys
485 490 495

Cys Asp Asn Ala Cys Ile Gly Ser Ile Arg Asn Gly Thr Tyr Asp His
500 505 510

Asp Val Tyr Arg Asp Glu Ala Leu Asn Asn Arg Phe Gln Ile Lys Gly
515 520 525

Val Glu Leu Lys Ser Gly Tyr Lys Asp Trp Ile Leu Trp Ile Ser Phe
530 535 540

Ala Ile Ser Ser Leu Val Leu Leu Val Ala Leu Leu Gly Phe Ile Met
545 550 555 560

Trp Ala Cys Gln Lys Gly Asn Ile Arg Cys Asn Ile Cys Ile
565 570

<210> SEQ ID NO 91
<211> LENGTH: 550
<212> TYPE: PRT
<213> ORGANISM: Alphainfluenza A virus

<400> SEQUENCE: 91

Gln Lys Ile Pro Gly Asn Asp Asn Ser Thr Ala Thr Leu Cys Leu Gly
1 5 10 15

His His Ala Val Pro Asn Gly Thr Ile Val Lys Thr Ile Thr Asn Asp
20 25 30

Arg Ile Glu Val Thr Asn Ala Thr Glu Leu Val Gln Asn Ser Ser Ile
35 40 45

Gly Glu Ile Cys Asp Ser Pro His Gln Ile Leu Asp Gly Glu Asn Cys
50 55 60

Thr Leu Ile Asp Ala Leu Leu Gly Asp Pro Gln Cys Asp Gly Phe Gln
65 70 75 80

Asn Lys Lys Trp Asp Leu Phe Val Glu Arg Ser Lys Ala Tyr Ser Asn
85 90 95

Cys Tyr Pro Tyr Asp Val Pro Asp Tyr Ala Ser Leu Arg Ser Leu Val
100 105 110

Ala Ser Ser Gly Thr Leu Glu Phe Asn Asn Glu Ser Phe Asn Trp Thr
115 120 125

Gly Val Thr Gln Asn Gly Thr Ser Ser Ala Cys Ile Arg Lys Ser Ser
130 135 140

Ser Ser Phe Phe Ser Arg Leu Asn Trp Leu Thr His Leu Asn Tyr Thr
145 150 155 160

Tyr Pro Ala Leu Asn Val Thr Val Pro Asn Asn Glu Gln Phe Asp Lys
165 170 175

Leu Tyr Ile Trp Gly Val His His Pro Gly Thr Asp Lys Asp Gln Ile
180 185 190

Phe Leu Tyr Ala Arg Ser Ser Gly Arg Ile Thr Val Ser Thr Lys Arg
195 200 205

Ser Gln Gln Ala Val Ile Pro Asn Ile Gly Ser Arg Pro Arg Ile Arg
210 215 220

Asp Ile Pro Ser Arg Ile Ser Ile Tyr Trp Thr Ile Val Lys Pro Gly
225 230 235 240

Asp Ile Leu Leu Ile Asn Ser Thr Gly Asn Leu Ile Ala Pro Arg Gly
245 250 255

```
Tyr Phe Lys Ile Arg Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys His Ser Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asn Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
    530                 535                 540

Arg Cys Asn Ile Cys Ile
545                 550


<210> SEQ ID NO 92
<211> LENGTH: 550
<212> TYPE: PRT
<213> ORGANISM: Alphainfluenza A virus

<400> SEQUENCE: 92

Gln Lys Ile Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Arg Ile Glu Val Thr Asn Ala Thr Glu Leu Val Gln Asn Ser Ser Ile
        35                  40                  45

Gly Glu Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80
```

-continued

```
Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Ile Arg Arg Ser Ser
    130                 135                 140

Ser Ser Phe Phe Ser Arg Leu Asn Trp Leu Thr His Leu Asn Tyr Thr
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Ser Ser Gly Arg Ile Thr Val Ser Thr Lys Arg
        195                 200                 205

Ser Gln Gln Ala Val Ile Pro Asn Ile Gly Ser Arg Pro Arg Ile Arg
    210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys His Ser Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asn Val Tyr Arg Asp Glu Ala Leu
                485                 490                 495
```

```
Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
    530                 535                 540

Arg Cys Asn Ile Cys Ile
545                 550


<210> SEQ ID NO 93
<211> LENGTH: 550
<212> TYPE: PRT
<213> ORGANISM: Alphainfluenza A virus

<400> SEQUENCE: 93

Gln Lys Ile Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Arg Ile Glu Val Thr Asn Ala Thr Glu Leu Val Gln Asn Ser Ser Ile
        35                  40                  45

Gly Glu Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Ile Arg Arg Ser Ser
    130                 135                 140

Ser Ser Phe Phe Ser Arg Leu Asn Trp Leu Thr His Leu Asn Tyr Thr
145                 150                 155                 160

Tyr Pro Ala Leu Asn Val Thr Met Pro Asn Lys Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Ser Ser Gly Arg Ile Thr Val Ser Thr Lys Arg
        195                 200                 205

Ser Gln Gln Ala Val Ile Pro Asn Ile Gly Ser Arg Pro Arg Ile Arg
    210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys His Ser Thr Leu Lys Leu Ala Thr Gly Met
305                 310                 315                 320
```

Arg Asn Val Pro Glu Lys Gln Thr Arg Gly Ile Phe Gly Ala Ile Ala
325 330 335

Gly Phe Ile Glu Asn Gly Trp Glu Gly Met Val Asp Gly Trp Tyr Gly
340 345 350

Phe Arg His Gln Asn Ser Glu Gly Arg Gly Gln Ala Ala Asp Leu Lys
355 360 365

Ser Thr Gln Ala Ala Ile Asp Gln Ile Asn Gly Lys Leu Asn Arg Leu
370 375 380

Ile Gly Lys Thr Asn Glu Lys Phe His Gln Ile Glu Lys Glu Phe Ser
385 390 395 400

Glu Val Glu Gly Arg Val Gln Asp Leu Glu Lys Tyr Val Glu Asp Thr
405 410 415

Lys Ile Asp Leu Trp Ser Tyr Asn Ala Glu Leu Leu Val Ala Leu Glu
420 425 430

Asn Gln His Thr Ile Asp Leu Thr Asp Ser Glu Met Asn Lys Leu Phe
435 440 445

Glu Lys Thr Lys Lys Gln Leu Arg Glu Asn Ala Glu Asp Met Gly Asn
450 455 460

Gly Cys Phe Lys Ile Tyr His Lys Cys Asp Asn Ala Cys Ile Gly Ser
465 470 475 480

Ile Arg Asn Glu Thr Tyr Asp His Asn Val Tyr Arg Asp Glu Ala Leu
485 490 495

Asn Asn Arg Phe Gln Ile Lys Gly Val Glu Leu Lys Ser Gly Tyr Lys
500 505 510

Asp Trp Ile Leu Trp Ile Ser Phe Ala Ile Ser Cys Phe Leu Leu Cys
515 520 525

Val Ala Leu Leu Gly Phe Ile Met Trp Ala Cys Gln Lys Gly Asn Ile
530 535 540

Arg Cys Asn Ile Cys Ile
545 550

<210> SEQ ID NO 94
<211> LENGTH: 550
<212> TYPE: PRT
<213> ORGANISM: Alphainfluenza A virus

<400> SEQUENCE: 94

Gln Lys Ile Pro Gly Asn Asp Asn Ser Thr Ala Thr Leu Cys Leu Gly
1 5 10 15

His His Ala Val Pro Asn Gly Thr Ile Val Lys Thr Ile Thr Asn Asp
20 25 30

Arg Ile Glu Val Thr Asn Ala Thr Glu Leu Val Gln Asn Ser Ser Ile
35 40 45

Gly Glu Ile Cys Asp Ser Pro His Gln Ile Leu Asp Gly Glu Asn Cys
50 55 60

Thr Leu Ile Asp Ala Leu Leu Gly Asp Pro Gln Cys Asp Gly Phe Gln
65 70 75 80

Asn Lys Lys Trp Asp Leu Phe Val Glu Arg Ser Lys Ala Tyr Ser Asn
85 90 95

Cys Tyr Pro Tyr Asp Val Pro Asp Tyr Ala Ser Leu Arg Ser Leu Val
100 105 110

Ala Ser Ser Gly Thr Leu Glu Phe Lys Asn Glu Ser Phe Asn Trp Thr
115 120 125

Gly Val Thr Gln Asn Gly Thr Ser Ser Ala Cys Ile Arg Arg Ser Ser

```
    130                 135                 140

Ser Ser Phe Phe Ser Arg Leu Asn Trp Leu Thr His Leu Asn Tyr Thr
145                 150                 155                 160

Tyr Pro Ala Leu Asn Val Thr Met Pro Asn Lys Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Ser Ser Gly Arg Ile Thr Val Ser Thr Lys Arg
        195                 200                 205

Ser Gln Gln Ala Val Ile Pro Asn Ile Gly Ser Arg Pro Arg Ile Arg
    210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys His Ser Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Val Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Glu Thr Tyr Asp His Asn Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
    530                 535                 540

Arg Cys Asn Ile Cys Ile
545                 550
```

<210> SEQ ID NO 95
<211> LENGTH: 550
<212> TYPE: PRT
<213> ORGANISM: Alphainfluenza A virus

<400> SEQUENCE: 95

```
Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Arg Ile Glu Val Thr Asn Ala Thr Glu Leu Val Gln Asn Ser Ser Ile
        35                  40                  45

Gly Glu Ile Cys Asp Ser Pro His Gln Ile Leu Asp Gly Lys Asn Cys
    50                  55                  60

Thr Leu Ile Asp Ala Leu Leu Gly Asp Pro Gln Cys Asp Gly Phe Gln
65                  70                  75                  80

Asn Lys Arg Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asp Glu Ser Phe Asn Trp Ala
        115                 120                 125

Gly Val Thr Gln Asn Gly Thr Ser Ser Ala Cys Ile Arg Gly Ser Asn
    130                 135                 140

Ser Ser Phe Phe Ser Arg Leu Asn Trp Leu Thr His Ser Asn Phe Lys
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Ser Ser Gly Arg Ile Thr Val Ser Thr Lys Arg
        195                 200                 205

Ser Gln Gln Ala Val Ile Pro Asn Ile Gly Ser Arg Pro Arg Ile Arg
    210                 215                 220

Asn Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Gln Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Ser Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Lys Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
```

370 375 380

Ile Gly Lys Thr Asn Glu Lys Phe His Gln Ile Glu Lys Glu Phe Ser
385 390 395 400

Glu Val Glu Gly Arg Ile Gln Asp Leu Glu Lys Tyr Val Glu Asp Thr
405 410 415

Lys Ile Asp Leu Trp Ser Tyr Asn Ala Glu Leu Leu Val Ala Leu Glu
420 425 430

Asn Gln His Thr Ile Asp Leu Thr Asp Ser Glu Met Asn Lys Leu Phe
435 440 445

Glu Lys Thr Lys Lys Gln Leu Arg Glu Asn Ala Glu Asp Met Gly Asn
450 455 460

Gly Cys Phe Lys Ile Tyr His Lys Cys Asp Asn Ala Cys Ile Gly Ser
465 470 475 480

Ile Arg Asn Gly Thr Tyr Asp His Asp Val Tyr Arg Asp Glu Ala Leu
485 490 495

Asn Asn Arg Phe Gln Ile Lys Gly Val Glu Leu Lys Ser Gly Tyr Lys
500 505 510

Asp Trp Ile Leu Trp Ile Ser Phe Ala Ile Ser Cys Phe Leu Leu Cys
515 520 525

Val Ala Leu Leu Gly Phe Ile Met Trp Ala Cys Gln Lys Gly Asn Ile
530 535 540

Arg Cys Asn Ile Cys Ile
545 550

<210> SEQ ID NO 96
<211> LENGTH: 550
<212> TYPE: PRT
<213> ORGANISM: Alphainfluenza A virus

<400> SEQUENCE: 96

Gln Lys Leu Pro Gly Asn Asp Asn Ser Thr Ala Thr Leu Cys Leu Gly
1 5 10 15

His His Ala Val Pro Asn Gly Thr Ile Val Lys Thr Ile Thr Asn Asp
20 25 30

Arg Ile Glu Val Thr Asn Ala Thr Glu Leu Val Gln Asn Ser Ser Ile
35 40 45

Gly Glu Ile Cys Asp Ser Pro His Gln Ile Leu Asp Gly Glu Asn Cys
50 55 60

Thr Leu Ile Asp Ala Leu Leu Gly Asp Pro Gln Cys Asp Gly Phe Gln
65 70 75 80

Asn Lys Lys Trp Asp Leu Phe Val Glu Arg Ser Lys Ala Tyr Ser Asn
85 90 95

Cys Tyr Pro Tyr Asp Val Pro Asp Tyr Ala Ser Leu Arg Ser Leu Val
100 105 110

Ala Ser Ser Gly Thr Leu Glu Phe Asn Asn Glu Ser Phe Asn Trp Ala
115 120 125

Gly Val Thr Gln Asn Gly Thr Ser Ser Ser Cys Ile Arg Gly Ser Asn
130 135 140

Ser Ser Phe Phe Ser Arg Leu Asn Trp Leu Thr His Leu Asn Ser Lys
145 150 155 160

Tyr Pro Ala Leu Asn Val Thr Met Pro Asn Asn Glu Gln Phe Asp Lys
165 170 175

Leu Tyr Ile Trp Gly Val His His Pro Gly Thr Asp Lys Asp Gln Ile
180 185 190

Phe Leu Tyr Ala Gln Ser Ser Gly Arg Ile Thr Val Ser Thr Lys Arg
195 200 205

Ser Gln Gln Ala Val Ile Pro Asn Ile Gly Ser Arg Pro Arg Ile Arg
210 215 220

Asp Ile Pro Ser Arg Ile Ser Ile Tyr Trp Thr Ile Val Lys Pro Gly
225 230 235 240

Asp Ile Leu Leu Ile Asn Ser Thr Gly Asn Leu Ile Ala Pro Arg Gly
245 250 255

Tyr Phe Lys Ile Arg Ser Gly Lys Ser Ser Ile Met Arg Ser Asp Ala
260 265 270

Pro Ile Gly Lys Cys Lys Ser Glu Cys Ile Thr Pro Asn Gly Ser Ile
275 280 285

Pro Asn Asp Lys Pro Phe Gln Asn Val Asn Arg Ile Thr Tyr Gly Ala
290 295 300

Cys Pro Arg Tyr Val Lys Gln Ser Thr Leu Lys Leu Ala Thr Gly Met
305 310 315 320

Arg Asn Val Pro Glu Arg Gln Thr Arg Gly Ile Phe Gly Ala Ile Ala
325 330 335

Gly Phe Ile Glu Asn Gly Trp Glu Gly Met Val Asp Gly Trp Tyr Gly
340 345 350

Phe Arg His Gln Asn Ser Glu Gly Arg Gly Gln Ala Ala Asp Leu Lys
355 360 365

Ser Thr Gln Ala Ala Ile Asp Gln Ile Asn Gly Lys Leu Asn Arg Leu
370 375 380

Ile Gly Lys Thr Asn Glu Lys Phe His Gln Ile Glu Lys Glu Phe Ser
385 390 395 400

Glu Val Glu Gly Arg Ile Gln Asp Leu Glu Lys Tyr Val Glu Asp Thr
405 410 415

Lys Ile Asp Leu Trp Ser Tyr Asn Ala Glu Leu Leu Val Ala Leu Glu
420 425 430

Asn Gln His Thr Ile Asp Leu Thr Asp Ser Glu Met Asn Lys Leu Phe
435 440 445

Glu Lys Thr Lys Lys Gln Leu Arg Glu Asn Ala Glu Asp Met Gly Asn
450 455 460

Gly Cys Phe Lys Ile Tyr His Lys Cys Asp Asn Ala Cys Ile Gly Ser
465 470 475 480

Ile Arg Asn Gly Thr Tyr Asp His Asp Val Tyr Arg Asp Glu Ala Leu
485 490 495

Asn Asn Arg Phe Gln Ile Lys Gly Val Glu Leu Lys Ser Gly Tyr Lys
500 505 510

Asp Trp Ile Leu Trp Ile Ser Phe Ala Ile Ser Cys Phe Leu Leu Cys
515 520 525

Val Ala Leu Leu Gly Phe Ile Met Trp Ala Cys Gln Lys Gly Asn Ile
530 535 540

Arg Cys Asn Ile Cys Ile
545 550

<210> SEQ ID NO 97
<211> LENGTH: 550
<212> TYPE: PRT
<213> ORGANISM: Alphainfluenza A virus

<400> SEQUENCE: 97

Gln Lys Leu Pro Gly Asn Asp Asn Ser Thr Ala Thr Leu Cys Leu Gly
1 5 10 15

-continued

```
His His Ala Val Pro Asn Gly Thr Ile Val Lys Thr Ile Thr Asn Asp
            20                  25                  30

Arg Ile Glu Val Thr Asn Ala Thr Glu Leu Val Gln Asn Ser Ser Ile
        35                  40                  45

Gly Glu Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Arg Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Ala
        115                 120                 125

Gly Val Thr Gln Asn Gly Thr Ser Ser Ser Cys Ile Arg Gly Ser Asn
    130                 135                 140

Ser Ser Phe Phe Ser Arg Leu Asn Trp Leu Thr His Leu Asn Ser Lys
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Lys Pro Ser Gly Arg Ile Thr Val Ser Thr Lys Arg
        195                 200                 205

Ser Gln Gln Ala Val Ile Pro Asn Ile Gly Ser Arg Pro Arg Ile Arg
    210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Arg Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430
```

-continued

```
Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
    530                 535                 540

Arg Cys Asn Ile Cys Ile
545                 550
```

<210> SEQ ID NO 98
<211> LENGTH: 5
<212> TYPE: PRT
<213> ORGANISM: Artificial Sequence
<220> FEATURE:
<223> OTHER INFORMATION: CysTM sequence (aa)

<400> SEQUENCE: 98

```
Ser Leu Val Leu Leu
1               5
```

<210> SEQ ID NO 99
<211> LENGTH: 5
<212> TYPE: PRT
<213> ORGANISM: Artificial Sequence
<220> FEATURE:
<223> OTHER INFORMATION: Native TMCT (aa)

<400> SEQUENCE: 99

```
Cys Phe Leu Leu Cys
1               5
```

<210> SEQ ID NO 100
<211> LENGTH: 15
<212> TYPE: DNA
<213> ORGANISM: Artificial equence
<220> FEATURE:
<223> OTHER INFORMATION: CysTM sequence (nt)

<400> SEQUENCE: 100
tcccttgtac tgtta 15

<210> SEQ ID NO 101
<211> LENGTH: 15
<212> TYPE: DNA
<213> ORGANISM: Artificial Sequence
<220> FEATURE:
<223> OTHER INFORMATION: Native TMCT (nt)

<400> SEQUENCE: 101
tgttttttgc tttgt 15

<210> SEQ ID NO 102
<211> LENGTH: 1701
<212> TYPE: DNA
<213> ORGANISM: Alphainfluenza A virus

<400> SEQUENCE: 102
atgaagacta tcattgcttt gagctacatt ctatgtctgg ttttcgctca aaaaattcct 60
ggaaatgaca atagcacggc aacgctgtgc cttgggcacc atgcagtacc aaacggaacg 120
atagtgaaaa caatcacgaa tgaccgaatt gaagttacta atgctactga gctggttcag 180
aattcctcaa taggtgaaat atgcgacagt cctcatcaga tccttgatgg agaaaactgc 240
acactaatag atgctctatt gggagaccct cagtgtgatg gctttcaaaa taagaaatgg 300 gaccttttg ttgaacgaag caaagcctac agcaactgtt acccttatga tgtgccggat 360
tatgcctccc ttaggtcact agttgcctca tccggcacac tggagtttaa caatgaaagc 420
ttcaattgga ctggagtcac tcaaaacgga acaagttctg cttgcataag gagatctagt 480
agtagtttct ttagtagatt aaattggttg acccacttaa actacacata cccagcattg 540
aacgtgacta tgccaaacaa tgaacaattt gacaaattgt acatttgggg ggttcaccac 600
ccgggtacgg acaaggacca aatcttcctg tatgctcaat catcaggaag aatcacagta 660
tctaccaaaa gaagccaaca agctgtaatc ccaaatatcg gatctagacc cagaataagg 720
gatatcccta gcagaataag catctattgg acaatagtaa aaccgggaga catacttttg 780
attaacagca cagggaatct aattgctcct aggggttact tcaaaatacg aagtgggaaa 840
agctcaataa tgagatcaga tgcacccatt ggcaaatgca agtctgaatg catcactcca 900
aatggaagca ttcccaatga caaaccattc caaaatgtaa acaggatcac atacggggcc 960
tgtcccagat atgttaagca tagcactctg aaattggcaa caggaatgcg aaatgtacca 1020
gagaaacaaa ctagaggcat atttggcgca atagcgggtt tcatagaaaa tggttgggag 1080
ggaatggtgg atggttggta cggtttcagg catcaaaatt ctgagggaag aggacaagca 1140
gcagatctca aaagcactca agcagcaatc gatcaaatca atgggaagct gaatcgattg 1200
atcgggaaaa ccaacgagaa attccatcag attgaaaaag aattctcaga agtagaagga 1260
agaattcagg accttgagaa atatgttgag gacactaaaa tagatctctg gtcatacaac 1320
gcggagcttc ttgttgccct ggagaaccaa catacaattg atctaactga ctcagaaatg 1380
aacaaactgt ttgaaaaaac aaagaagcaa ctgagggaaa atgctgagga tatgggcaat 1440
ggttgtttca aaatatacca caaatgtgac aatgcctgca taggatcaat aagaaatgga 1500
acttatgacc acaatgtgta cagggatgaa gcattaaaca accggttcca gatcaaggga 1560
gttgagctga agtcagggta caaagattgg atcctatgga tttcctttgc catatcatgt 1620
tttttgcttt gtgttgcttt gttggggttc atcatgtggg cctgccaaaa gggcaacatt 1680
aggtgcaaca tttgcatttg a 1701

<210> SEQ ID NO 103
<211> LENGTH: 3108
<212> TYPE: DNA
<213> ORGANISM: Artificial Sequence
<220> FEATURE:
<223> OTHER INFORMATION: Construct 2801 from 2X35S prom to NOS term

<400> SEQUENCE: 103
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240

-continued

```
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gaccccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaatg gcgaaaaacg ttgcgatttt cggcttattg ttttctcttc ttgtgttggt    960
tccttctcag atcttcgcgc aaaaacttcc tggaaatgac aatagcacgg caacgctgtg   1020
ccttgggcac catgcagtac caaacggaac gatagtgaaa acaatcacga atgaccgaat   1080
tgaagttact aatgctactg agctggttca gaattcctca ataggtgaaa tatgcgacag   1140
tcctcatcag atccttgatg gagaaaactg cacactaata gatgctctat tgggagaccc   1200
tcagtgtgat ggctttcaaa ataagaaatg ggaccttttt gttgaacgaa gcaaagccta   1260
cagcaactgt taccctttatg atgtgccgga ttatgcctcc cttaggtcac tagttgcctc   1320
atccggcaca ctggagttta acaatgaaag cttcaattgg gctggagtca ctcaaaacgg   1380
aacaagttct tcttgcataa ggggatctaa tagtagtttc tttagtagat taaattggtt   1440
gacccactta aactccaaat acccagcatt aaacgtgact atgccaaaca atgaacaatt   1500
tgacaaattg tacatttggg ggttcacca cccgggtacg gacaaggacc aaatcttcct   1560
gtatgcacaa tcatcaggaa gaatcacagt atctaccaaa agaagccaac aagctgtaat   1620
cccgaatatc ggatctagac ccagaataag ggatatccct agcagaataa gcatctattg   1680
gacaatagta aaaccgggag acatactttt gattaacagc acagggaatc taattgctcc   1740
taggggttac ttcaaaatac gaagtgggaa aagctcaata atgagatcag atgcacccat   1800
tggcaaatgc aagtctgaat gcatcactcc aaatggaagc attcccaatg acaaaccatt   1860
ccaaaatgta aacaggatca catacggggc ctgtcccaga tatgttaagc aaagcactct   1920
gaaattggca acaggaatgc gaaatgtacc agagagacaa actagaggca tatttggcgc   1980
aatagcgggt ttcatagaaa atggttggga gggaatggtg gatggttggt acggcttcag   2040
gcatcaaaat tctgagggaa gaggacaagc agcagatctc aaaagcactc aagcagcaat   2100
cgatcaaatc aatgggaagc tgaatcgatt gatcgggaaa accaacgaga aattccatca   2160
gattgaaaaa gaattctcag aagtagaagg gagaattcag gaccttgaga aatatgttga   2220
ggacacaaaa atagatctct ggtcatacaa cgcggagctt cttgttgccc tggagaacca   2280
acatacaatt gatctaactg actcagaaat gaacaaactg tttgaaaaaa caaagaagca   2340
actgagggaa aatgctgagg atatgggcaa tggttgtttc aaaatatacc acaaatgtga   2400
caatgcctgc ataggatcaa tcagaaatgg aacttatgac cacgatgtat acagggatga   2460
agcattaaac aaccggttcc agatcaaggg agttgagctg aagtcagggt acaaagattg   2520
gatcctatgg atttcctttg ccatatcatg ttttttgctt tgtgttgctt tgttggggtt   2580
catcatgtgg gcctgccaaa agggcaacat taggtgcaac atttgcattt gaaggcctat   2640
```

```
tttctttagt ttgaatttac tgttattcgg tgtgcatttc tatgtttggt gagcggtttt   2700
ctgtgctcag agtgtgttta ttttatgtaa tttaatttct ttgtgagctc ctgtttagca   2760
ggtcgtccct tcagcaagga cacaaaaaga ttttaatttt attaaaaaaa aaaaaaaaaa   2820
agaccgggaa ttcgatatca agcttatcga cctgcagatc gttcaaacat ttggcaataa   2880
agtttcttaa gattgaatcc tgttgccggt cttgcgatga ttatcatata atttctgttg   2940
aattacgtta agcatgtaat aattaacatg taatgcatga cgttatttat gagatgggtt   3000
tttatgatta gagtcccgca attatacatt taatacgcga tagaaaacaa aatatagcgc   3060
gcaaactagg ataaattatc gcgcgcggtg tcatctatgt tactagat               3108
```

<210> SEQ ID NO 104
<211> LENGTH: 3108
<212> TYPE: DNA
<213> ORGANISM: Artificial Sequence
<220> FEATURE:
<223> OTHER INFORMATION: Construct 3023 from 2X35S prom to NOS term

<400> SEQUENCE: 104

```
gtcaacatgg tggagcacga cacacttgtc tactccaaaa atatcaaaga tacagtctca     60
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaatg gcgaaaaacg ttgcgatttt cggcttattg ttttctcttc ttgtgttggt    960
tccttctcag atcttcgcgc aaaaacttcc tggaaatgac aatagcacgg caacgctgtg   1020
ccttgggcac catgcagtac caaacggaac gatagtgaaa acaatcacga atgaccgaat   1080
tgaagttact aatgctactg agctggttca gaattcctca ataggtgaaa tatgcgacag   1140
tcctcatcag atccttgatg gagaaaactg cacactaata gatgctctat tgggagaccc   1200
tcagtgtgat ggctttcaaa ataagaaatg ggaccttttt gttgaacgaa gcaaagccta   1260
cagcaactgt taccctlatg atgtgccgga ttatgcctcc cttaggtcac tagttgcctc   1320
atccggcaca ctggagttta acaatgaaag cttcaattgg gctggagtca ctcaaaacgg   1380
aacaagttct tcttgcataa ggggatctaa tagtagtttc tttagtagat taaattggtt   1440
gacccactta aactccaaat acccagcatt aaacgtgact atgccaaaca atgaacaatt   1500
tgacaaattg tacatttggg gggttcacca cccgggtacg gacaaggacc aaatcttcct   1560
```

```
gtatgcacaa tcatcaggaa gaatcacagt atctaccaaa agaagccaac aagctgtaat   1620

cccgaatatc ggatctagac ccagaataag ggatatccct agcagaataa gcatctattg   1680

gacaatagta aaaccgggag acatactttt gattaacagc acagggaatc taattgctcc   1740

taggggttac ttcaaaatac gaagtgggaa aagctcaata atgagatcag atgcacccat   1800

tggcaaatgc aagtctgaat gcatcactcc aaatggaagc attcccaatg acaaaccatt   1860

ccaaaatgta aacaggatca catacggggc ctgtcccaga tatgttaagc aaagcactct   1920

gaaattggca acaggaatgc gaaatgtacc agagagacaa actagaggca tatttggcgc   1980

aatagcgggt ttcatagaaa atggttggga gggaatggtg gatggttggt acggcttcag   2040

gcatcaaaat tctgagggaa gaggacaagc agcagatctc aaaagcactc aagcagcaat   2100

cgatcaaatc aatgggaagc tggctcgatt gatcgggaaa accaacgaga aattccatca   2160

gattgaaaaa gaattctcag aagtagaagg gagaattcag gaccttgaga aatatgttga   2220

ggacacaaaa atagatctct ggtcatacaa cgcggagctt cttgttgccc tggagaacca   2280

acatacaatt gatctaactg actcagaaat gaacaaactg tttgaaaaaa caaagaagca   2340

actgagggaa aatgctgagg atatgggcaa tggttgtttc aaaatatacc acaaatgtga   2400

caatgcctgc ataggatcaa tcagaaatgg aacttatgac cacgatgtat acagggatga   2460

agcattaaac aaccggttcc agatcaaggg agttgagctg aagtcagggt acaaagattg   2520

gatcctatgg atttcctttg ccatatcatg ttttttgctt tgtgttgctt tgttggggtt   2580

catcatgtgg gcctgccaaa agggcaacat taggtgcaac atttgcattt gaaggcctat   2640

tttctttagt ttgaatttac tgttattcgg tgtgcatttc tatgtttggt gagcggtttt   2700

ctgtgctcag agtgtgttta ttttatgtaa tttaatttct ttgtgagctc ctgtttagca   2760

ggtcgtccct tcagcaagga cacaaaaaga ttttaatttt attaaaaaaa aaaaaaaaaa   2820

agaccgggaa ttcgatatca agcttatcga cctgcagatc gttcaaacat ttggcaataa   2880

agtttcttaa gattgaatcc tgttgccggt cttgcgatga ttatcatata atttctgttg   2940

aattacgtta agcatgtaat aattaacatg taatgcatga cgttatttat gagatgggtt   3000

tttatgatta gagtcccgca attatacatt taatacgcga tagaaaacaa aatatagcgc   3060

gcaaactagg ataaattatc gcgcgcggtg tcatctatgt tactagat               3108
```

<210> SEQ ID NO 105
<211> LENGTH: 3108
<212> TYPE: DNA
<213> ORGANISM: Artificial Sequence
<220> FEATURE:
<223> OTHER INFORMATION: Construct 2811 from 2X35S prom to NOS term

<400> SEQUENCE: 105

```
gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540
```

-continued

```
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaatg gcgaaaaacg ttgcgatttt cggcttattg ttttctcttc ttgtgttggt    960
tccttctcag atcttcgcgc aaaaacttcc tggaaatgac aatagcacgg caacgctgtg   1020
ccttgggcac catgcagtac caaacggaac gatagtgaaa acaatcacga atgaccgaat   1080
tgaagttact aatgctactg agctggttca gaattcctca ataggtgaaa tatgcgacag   1140
tcctcatcag atccttgatg gagaaaactg cacactaata gatgctctat tgggagaccc   1200
tcagtgtgat ggctttcaaa ataagaaatg ggaccttttt gttgaacgaa gcaaagccta   1260
cagcaactgt taccctt atg atgtgccgga ttatgcctcc cttaggtcac tagttgcctc   1320
atccggcaca ctggagttta acaatgaaag cttcaattgg gctggagtca ctcaaaacgg   1380
aacaagttct tcttgcataa ggggatctaa tagtagtttc tttagtagat taaattggtt   1440
gacccactta aactccaaat acccagcatt aaacgtgact atgccaaaca atgaacaatt   1500
tgacaaattg tacatttggg gggttcacca cccgggtacg gacaaggacc aaatcttcct   1560
gtatgcacaa tcatcaggaa gaatcacagt atctaccaaa agaagccaac aagctgtaat   1620
cccgaatatc ggatctagac ccagaataag ggatatccct agcagaataa gcatctattg   1680
gacaatagta aaaccgggag acatactttt gattaacagc acagggaatc taattgctcc   1740
taggggttac ttcaaaatac gaagtgggaa aagctcaata atgagatcag atgcacccat   1800
tggcaaatgc aagtctgaat gcatcactcc aaatggaagc attcccaatg acaaaccatt   1860
ccaaaatgta aacaggatca catacggggc ctgtcccaga tatgttaagc aaagcactct   1920
gaaattggca acaggaatgc gaaatgtacc agagagacaa actagaggca tatttggcgc   1980
aatagcgggt ttcatagaaa atggttggga gggaatggtg gatggttggt acggcttcag   2040
gcatcaaaat tctgagggaa gaggacaagc agcagatctc aaaagcactc aagcagcaat   2100
cgatcaaatc aatgggaagc tgaatcgatt gatcgggaaa accaacgaga aattccatca   2160
gattgaaaaa gaattctcag aagtagaagg gagaattcag gaccttgaga aatatgttga   2220
ggacacaaaa atagatctct ggtcatacaa cgcggagctt cttgttgccc tggagaacca   2280
acatacaatt gatctaactg actcagaaat gaacaaactg tttgaaaaaa caaagaagca   2340
actgagggaa aatgctgagg atatgggcaa tggttgtttc aaaatatacc acaaatgtga   2400
caatgcctgc ataggatcaa tcagaaatgg aacttatgac cacgatgtat acagggatga   2460
agcattaaac aaccggttcc agatcaaggg agttgagctg aagtcagggt acaaagattg   2520
gatcctatgg atttcctttg ccatatcatc ccttgtactg ttagttgctt tgttggggtt   2580
catcatgtgg gcctgccaaa agggcaacat taggtgcaac atttgcattt gaaggcctat   2640
tttctttagt ttgaatttac tgttattcgg tgtgcatttc tatgtttggt gagcggtttt   2700
ctgtgctcag agtgtgttta ttttatgtaa tttaatttct ttgtgagctc ctgtttagca   2760
ggtcgtccct tcagcaagga cacaaaaaga ttttaatttt attaaaaaaa aaaaaaaaaa   2820
agaccgggaa ttcgatatca agcttatcga cctgcagatc gttcaaacat ttggcaataa   2880
```

-continued

```
agtttcttaa gattgaatcc tgttgccggt cttgcgatga ttatcatata atttctgttg   2940

aattacgtta agcatgtaat aattaacatg taatgcatga cgttatttat gagatgggtt   3000

tttatgatta gagtcccgca attatacatt taatacgcga tagaaaacaa aatatagcgc   3060

gcaaactagg ataaattatc gcgcgcggtg tcatctatgt tactagat                3108
```

INFLUENZA VIRUS HEMAGGLUTININ MUTANTS

FIELD OF INVENTION

The present invention relates to producing mutant viral proteins in plants. More specifically, the present invention relates to producing and increasing influenza virus-like particle production in plants.

BACKGROUND OF THE INVENTION

Influenza viruses are enveloped, single-stranded-RNA viruses of the Orthomyxoviridae family. Influenza viruses are highly contagious and can cause mild to serious illness across all age groups.

Vaccination remains the most effective method to prevent influenza infection. Conventionally, vaccination is accomplished using live attenuated or whole inactivated forms of the virus, which elicit an immune response when administered to a patient. To eliminate the potential risk of live attenuated and whole inactivated viruses re-acquiring the competency to replicate and become infectious, vaccines comprising recombinant viral proteins have also been used to elicit protective immunity to influenza infection.

However, the use of recombinant viral proteins as the immunogenic component of vaccines is subject to a number of limitations. Firstly, in the absence of the full complement of viral proteins and genetic components required for optimal expression and proper protein folding, the yield of recombinant viral proteins in standard in vitro expression systems may be insufficient for the purpose of vaccine production. Second, recombinant viral protein vaccines may exhibit poor immunogenicity, owing to improper folding, poor antigen presentation, and/or the generation of a primarily humoral immune response that is ineffective in conferring long-lasting, protective immunity.

There are four types of influenza virus: A, B, C and D, of which influenza A and B are the causative organism for seasonal disease epidemics in humans.

Influenza A viruses are further divided based on the expression of hemagglutinin (HA) and neuraminidase (NA) glycoprotein subtypes on the surface of the virus. There are 18 different HA subtypes (H1-H18).

HA is a trimeric lectin that facilitates binding of the influenza virus particle to sialic acid-containing proteins on the surface of target cells and mediates release of the viral genome into the target cell. HA proteins comprise two structural elements: the head, which is the primary target of seroprotective antibodies; and the stalk. HA is translated as a single polypeptide, HA0 (assembled as trimers), that must be cleaved by a serine endoprotease between the HA1 (~40 kDa) and HA2 (~20 kDa) subdomains. After cleavage, the two disulfide-bonded protein domains adopt the requisite conformation necessary for viral infectivity. HA1 forms the globular head domain containing the receptor-binding site (RBS), and is the least conserved segment of influenza virus. HA2 is a single-pass integral membrane protein with fusion peptide (FP), soluble ectodomain (SE), transmembrane (TM), and cytoplasmic tail (CT) with respective lengths of approximately 25, 160, 25, and 10 residues. HA2 together with the N and C terminal HA1 residues forms a stalk domain, which includes the transmembrane region, and is relatively conserved.

Various mutations in influenza virus proteins, particularly influenza HA, have been investigated.

For example, Castelán-Vega et al. (*Adv Appl Bioinform Chem.* 2014:7:37-44) used a stability prediction algorithm to compare 7,479 full-length amino acid sequences of HA from the influenza A (H1N1)pdm09 virus and identified that D104N, A259T, S124N, and E172K mutations resulted in a predicted enhancement of influenza HA stability. In contrast, S206T, K285E, and E47K mutations had a predicted destabilizing effect on HA.

In comparing the sequences of the original influenza A (H1N1)pdm [A/California/7/2009] and a later-emerging influenza strain [A/Brisbane/10/2010], Cotter et al. (*PLoS Pathog.* 2014;10(1):e1003831) identified that a E47K mutation in the stalk region of A/California/7/2009 HA stabilized the trimer structure, lowered the pH for membrane fusion, and increased the thermal and acid stability of the virus. Cotter et al. additionally observed that A/California/7/2009 E47K mutant HA was more infectious in ferrets than its wildtype counterpart.

Antanasijevic et al. (*J Biol Chem.* 2014:289(32):22237-45) investigated the structure-function properties of H5 HA stem loop region by site directed mutagenesis at 14 different positions. A/Vietnam/1203/04 (H5N1) mutants were expressed in HEK 293T cells and Antanasijevic reported that most mutations in the stem loop region did not disrupt expression, proteolytic processing, viral assembly, or receptor binding. However, Antanasijevic observed that HA1-D26K, HA1-M102L, HA2-V52A and HA2-155A mutants (based on H3 numbering) exhibited significantly reduced levels of total HA, suggesting reduced expression and/or assembly of HA into viral particles. HA1-D26K, HA2-T49A and HA2-M102L mutants also exhibited lower hemagglutination titers as compared to wildtype virus. Antanasijevic additionally observed that all single mutants exhibited decreased entry into A549 lung cells, with the most pronounced impairment shown in HA1-D26K and HA2-155A mutants. Antanasijivec further demonstrated that the HA2-L99A mutant was more sensitive to A549 lung cell inhibition by C179 neutralizing antibody as compared to wildtype virus, suggesting that the mutation enhances antibody binding and/or the mode of neutralizing action. In contrast, HA1-128A, HA1-M31A, HA1-M31L, HA2-145A, and HA2-155V mutants were rendered less sensitive to entry inhibition by C179 neutralizing antibody.

WO2013/177444 and its companion publication Lu et al. (*Proc Natl Acad Sci USA.* 2014:111(1):125-30) reported a method for the production of properly folded HA stem domain from A/California/05/2009 (H1N1) using an *Escherichia coli*-based cell-free protein expression system and a simple refolding protocol. For inducing the trimerization of HA stem domain, either a chloramphenicol acetyl transferase (CAT) or foldon domain was fused to the C terminus of the HA. To mitigate newly exposed hydrophobicity and/or intermolecular ion pairing causing aggregation of expressed HA stem protein, five groups of mutations were evaluated: M1 (169T+172E+174T+C77T); M2 (169T+172E+174T+C77T+F164D); M3 (169T+172E+174T+C77T+F164D+L174D); M4 (F164D); and M5 (F164D+L174D). Lu observed that the M5 (F164D+L174D) mutations appeared to be the most influential mutations for improving HA stem protein solubility. Additional deletions (H38 to C43 and C49 to N61) and a C77T mutation were made to M5 mutants to avoid the formation of undesirable disulfide bonds, reduce surface hydrophobicity and pI, and avoid regions with disordered structure.

U.S. application Ser. No. 13/838,796 and its companion publication by Holtz et al. (*BMC Biotechnology.* 2014:14:111) teach the improved stability and maintained potency of recombinant HA by the mutation of cysteine residues in the carboxy terminal region of the HA protein including the transmembrane (TM) and cytosolic domain (CT). Specifically, Holtz et al. demonstrate C539A, C546A, C549A, C524S and C528A mutations in recombinant Perth/16/2009 HA (H3N2). Mutation of all five cysteine residues, or different subsets thereof, resulted in HA yields, purities, particle size, hemagglutination activity, and thermostability comparable to recombinant wildtype HA protein. In contrast, C64S and C76S mutations resulted in significantly reduced HA expression, indicating the critical role of these residues in proper HA folding. By using a single radial immune-diffusion assay (SRID), Holtz et al. also show that the five cysteine residue mutations improve potency of recombinant HA as compared to wildtype protein, by preventing disulfide cross-linking in the TM and CT domains. The mutant HA proteins maintain potency for at least 12 months at 25° C., whereas wildtype HA protein exhibited less than 40% potency after only 50 days post purification.

WO2015/020913 teaches the mutation of specific residues at one or more positions selected from the group of 403, 406, 411, 422, 429, 432, 433, and 435 of influenza A/Puerto Rico/8/1934 (H1N1) to tyrosine. These mutations facilitate the formation of di-tyrosine cross-links that stabilize or "lock" the stalk domain of influenza HA in its native trimeric conformation.

WO2013/079473 discloses a modified influenza HA lacking a globular head domain. The polypeptide taught in WO2013/079473 comprises an HA1 domain where amino acids 53 to 620 (with reference to A/Brisbane/59/2007 [H1N1] numbering) are deleted and replaced with covalently linked sequence of 0 to 10 amino acids, and an HA2 domain, wherein the C-terminal amino acid of the HA1 domain is an amino acid other than arginine or lysine, and wherein one or more amino acids at position 406, 409, 413 and 416 are mutated to an amino acid selected from the group consisting of: serine, threonine, asparagine, glutamine, arginine, histidine, lysine, aspartic acid, glutamic acid, and glycine.

WO2014/191435 similarly teaches a modified influenza HA comprising an HA1 domain having a deleted segment replaced with a covalently linked sequence of 0 to 50 amino acids, and an HA2 domain, wherein the HA is resistant to cleavage at the junction between HA1 and HA2 and wherein one or more amino acids at positions 337, 340, 352, 353, 402, 406, 409, 413 and/or 416 have been mutated.

Virus-like particles (VLPs) are potential candidates for inclusion in immunogenic compositions. VLPs closely resemble mature virions, but they do not contain viral genomic material. Therefore, VLPs are non-replicative in nature, which make them safe for administration as a vaccine. In addition, VLPs can be engineered to express viral glycoproteins on the surface of the VLP, which is their most native physiological configuration. Moreover, since VLPs resemble intact virions and are multivalent particulate structures, VLPs may be more effective in inducing neutralizing antibodies to the glycoprotein than soluble envelope protein antigens.

VLPs have been produced in plants (see for example WO2009/076778; WO2009/009876; WO 2009/076778; WO 2010/003225; WO 2010/003235; WO2010/006452; WO2011/03522; WO 2010/148511; and WO2014153674 which are incorporated herein by reference).

WO2009/076778 teaches a method of producing influenza VLPs in plants comprising introducing a nucleic acid having a regulatory region active in the plant operatively linked to a nucleotide sequence encoding an influenza HA from a type A or type B influenza.

WO2009/009876 teaches a method of producing influenza HA VLPs in plants, wherein influenza HA self-assembles into VLPs in plant cells and bud from plant cell membranes.

WO2010/003225 discloses a method of producing influenza HA VLPs in plants comprising introducing a nucleic acid having a regulatory region active in the plant, operatively linked to a nucleotide sequence encoding an influenza HA from A/California/04/09 (H1N1).

WO2010/006452 teaches the production of VLPs comprising modified influenza HA proteins, wherein glycosylation sites at positions 154, 165, 286, or combinations thereof (with reference to A/Vietnam/1194/04 [H5N1] numbering), have been abolished by mutating the residues at said positions to amino acids other than asparagine. WO2010/006452 further teaches that amino acids at positions 156, 167, 288, or combinations thereof, may be mutated to residues other than serine or threonine to similarly abolish the N-linked glycosylation signal triad "N-X-S/T". By selectively deleting glycosylation sites located in the globular head of the HA protein, WO2010/006452 demonstrates that the resulting HA protein has increased antigenicity and broader cross-reactivity.

WO2011/035422 teaches a method of preparing plant-derived VLPs comprising: obtaining a plant or plant matter comprising apoplast-localized VLPs; producing a protoplast/spheroplast fraction and an apoplast fraction; and recovering the apoplast fraction comprising the plant-derived VLPs.

WO2010/148511 discloses a method for producing influenza VLPs in plants, wherein the VLPs comprise chimeric HA proteins. The chimeric HA proteins comprise a stem domain cluster having an F'1, F'2 and F subdomain: a head domain cluster having an RB, E1 and E2 subdomain; and a transmembrane domain cluster having a transmembrane domain and a C-terminal tail domain, wherein at least one subdomain is derived from a first influenza strain and the other subdomains are derived from one or more second influenza strain.

WO2014/153674 teaches a method of producing influenza VLPs in a plant, wherein the VLPs comprise modified influenza HA having a modified proteolytic loop. The modified proteolytic loop comprises the removal of the proteolytic cleavage site between HA1 and HA2 domains of the HA0 precursor. The HA protein is thus stabilized and increased protein yields are achieved as compared to native HA protein.

SUMMARY OF THE INVENTION

The present invention relates to the production of modified influenza viral proteins in plants. More specifically, the present invention relates to producing and increasing influenza virus-like particle (VLP) production in plants, wherein the VLPs comprise the modified influenza viral proteins for example a modified hemagglutinin (HA) protein.

It is an object of the invention to provide an improved method to increase influenza VLP production in plants.

According to the present invention, there is provided:

A. A nucleic acid comprising a nucleotide sequence encoding a modified influenza H3 hemagglutinin (HA) protein, the HA protein comprising an amino acid sequence comprising at least one substitution when compared to a corresponding wildtype amino acid sequence, said at least one substitution being at one or more than one amino acids corresponding to amino acids at position 382, 384, 392 or 431 of A/Hong Kong/4801/14 HA.

The HA protein may comprise an amino acid sequence with a substitution to a non-asparagine at the amino acid corresponding to the amino acid at position 382 of A/Hong Kong/4801/14 HA. The HA protein may comprise an amino acid sequence with a substitution to an alanine or a conserved substitution of alanine at the amino acid corresponding to the amino acid at position 382 of A/Hong Kong/4801/14 HA.

The HA protein may comprise an amino acid sequence with a substitution to a non-leucine at the amino acid corresponding to the amino acid at position 384 of A/Hong Kong/4801/14 HA. The HA protein may comprise an amino acid sequence with a substitution to a valine or a conserved substitution of valine at the amino acid corresponding to the amino acid at position 384 of A/Hong Kong/4801/14 HA.

The HA protein may comprise an amino acid sequence with a substitution to a non-phenylalanine at the amino acid corresponding to the amino acid at position 392 of A/Hong Kong/4801/14 HA. The HA protein may comprise an amino acid sequence with a substitution to an aspartic acid or a conserved substitution of aspartic acid at the amino acid corresponding to the amino acid at position 392 of A/Hong Kong/4801/14 HA.

The HA protein may comprise an amino acid sequence with a substitution to a non-leucine at the amino acid corresponding to the amino acid at position 431 of A/Hong Kong/4801/14 HA. The HA protein may comprise an amino acid sequence with a substitution to a methionine or a conserved substitution of methionine at the amino acid corresponding to the amino acid at position 431 of A/Hong Kong/4801/14 HA.

It is further provided:

B. A nucleic acid comprising, a nucleotide sequence encoding a modified influenza H3 hemagglutinin (HA) protein, the HA protein comprising an amino acid sequence comprising at least one substitution when compared to a corresponding wildtype amino acid sequence, said at least one substitution being at one or more than one amino acid corresponding to amino acids at positions 382, 384, 392, 431, 524, 525, 526 or 528 of A/Hong Kong/4801/14 HA.

The HA protein may further comprise an amino acid sequence with a first substitution to a non-asparagine at the amino acid corresponding to amino acid at position 382 of A/Hong Kong/4801/14 HA, a second substitution to a non-cysteine at the amino acid corresponding to amino acid at position 524 of A/Hong Kong/4801/14 HA and a third substitution to a non-cysteine at the amino acid corresponding to amino acid at position 528 of A/Hong Kong/4801/14 HA. The HA protein may further comprise an amino acid sequence with a first substitution to an alanine or a conserved substitution of alanine at the amino acid corresponding to amino acid at position 382 of A/Hong Kong/4801/14 HA, a second substitution to a serine or a conserved substitution of serine at the amino acid corresponding to amino acid at position 524 of A/Hong Kong/4801/14 HA and a third substitution to a leucine or a conserved substitution of leucine at the amino acid corresponding to amino acid at position 528 of A/Hong Kong/4801/14 HA.

The HA protein may further comprise an amino acid sequence with a first substitution to a non-leucine at the amino acid corresponding to amino acid at position 384 of A/Hong Kong/4801/14 HA, a second substitution to a non-cysteine at the amino acid corresponding to amino acid at position 524 of A/Hong Kong/4801/14 HA and a third substitution to a non-cysteine at the amino acid corresponding to amino acid at position 528 of A/Hong Kong/4801/14 HA. The HA protein may further comprise an amino acid sequence with a first substitution to a valine or a conserved substitution of valine at the amino acid corresponding to amino acid at position 384 of A/Hong Kong/4801/14 HA, a second substitution to a serine or a conserved substitution of serine at the amino acid corresponding to amino acid at position 524 of A/Hong Kong/4801/14 HA and a third substitution to a leucine or a conserved substitution of leucine at the amino acid corresponding to amino acid at position 528 of A/Hong Kong/4801/14 HA.

The HA protein may further comprise an amino acid sequence with a first substitution to a non-phenylalanine at the amino acid corresponding to amino acid at position 392 of A/Hong Kong/4801/14 HA, a second substitution to a non-cysteine at the amino acid corresponding to amino acid at position 524 of A/Hong Kong/4801/14 HA and a third substitution to a non-cysteine at the amino acid corresponding to amino acid at position 528 of A/Hong Kong/4801/14 HA. The HA protein may further comprise an amino acid sequence with a first substitution to an aspartic acid or a conserved substitution of aspartic acid at the amino acid corresponding to amino acid at position 392 of A/Hong Kong/4801/14 HA, a second substitution to a serine or a conserved substitution of serine at the amino acid corresponding to amino acid at position 524 of A/Hong Kong/4801/14 HA and a third substitution to a leucine or a conserved substitution of leucine at the amino acid corresponding to amino acid at position 528 of A/Hong Kong/4801/14 HA.

The HA protein may further comprise an amino acid sequence with a first substitution to non-leucine at the amino acid corresponding to amino acid at position 431 of A/Hong Kong/4801/14 HA, a second substitution to a non-cysteine at the amino acid corresponding to amino acid at position 524 of A/Hong Kong/4801/14 HA and a third substitution to a non-cysteine at the amino acid corresponding to amino acid at position 528 of A/Hong Kong/4801/14 HA. The HA protein may further comprise an amino acid sequence with a first substitution to a methionine or a conserved substitution of methionine at the amino acid corresponding to amino acid at position 431 of A/Hong Kong/4801/14 HA, a second substitution to a serine or a conserved substitution of serine at the amino acid corresponding to amino acid at position 524 of A/Hong Kong/4801/14 HA and a third substitution to a leucine or a conserved substitution of leucine at the amino acid corresponding to amino acid at position 528 of A/Hong Kong/4801/14 HA.

The HA protein may further comprise an amino acid sequence with a first substitution to a non-asparagine at the amino acid corresponding to amino acid at position 382 of A/Hong Kong/4801/14 HA, a second substitution to a non-leucine at the amino acid corresponding to amino acid at position 384 of A/Hong Kong/4801/14 HA, a third substitution to a non-cysteine at the amino acid corresponding to amino acid at position 524 of A/Hong Kong/4801/14 HA and a fourth substitution to a non-cysteine at the amino acid corresponding to amino acid at position 528 of A/Hong Kong/4801/14 HA. The HA protein may further comprise an amino acid sequence with a first substitution to an alanine or a conserved substitution of alanine at the amino acid corresponding to amino acid at position 382 of A/Hong Kong/4801/14 HA, a second substitution to a valine or a conserved substitution of valine at the amino acid corresponding to amino acid at position 384 of A/Hong Kong/4801/14 HA, a third substitution to a serine or a conserved substitution of serine at the amino acid corresponding to amino acid at position 524 of A/Hong Kong/4801/14 HA and a fourth substitution to a leucine or a conserved substitution of leucine at the amino acid corresponding to amino acid at position 528 of A/Hong Kong/4801/14 HA.

The HA protein may further comprise an amino acid sequence with a substitution at amino acids corresponding to amino acids at positions 525, 526 or 525 and 526 of A/Hong Kong/4801/14 HA, wherein the substitution of the amino acid at position 525 is to a non-phenylalanine and the substitution of the amino acid at position 526 is to a non-leucine. The HA protein may further comprise an amino acid sequence with a substitution at amino acids corresponding to amino acids at positions 525, 526 or 525 and 526 of A/Hong Kong/4801/14 HA, wherein the substitution of the amino acid at position 525 is to a leucine or a conserved substitution of leucine and the substitution of the amino acid at position 526 is to a valine or a conserved substitution of valine.

Further provided are HA protein encoded by the recombinant nucleic acids as described under A or B and virus-like particle (VLP) comprising the HA protein encoded by the recombinant nucleic acids as described under A or B.

Therefore it is further provided a modified HA protein comprising an amino acid sequence comprising at least one substitution when compared to a corresponding wildtype amino acid sequence, said at least one substitution being at one or more than one amino acids corresponding to amino acids at position 382, 384, 392 or 431 of A/Hong Kong/4801/14 HA.

In another aspect it is provided a modified influenza H3 hemagglutinin (HA) protein, the HA protein comprising an amino acid sequence comprising at least one substitution when compared to a corresponding wildtype amino acid sequence, said at least one substitution being at one or more than one amino acid corresponding to amino acids at positions 382, 384, 392, 431, 524, 525, 526 or 528 of A/Hong Kong/4801/14 HA.

Furthermore a method of producing an influenza virus like particle (VLP) in a plant, portion of a plant, or a plant cell, is provided, the method comprising:

a) introducing the recombinant nucleic acid as described under A or B into the plant, portion of the plant, or plant cell: and
b) incubating the plant, portion of the plant, or plant cell under conditions that permit expression of the HA protein encoded by the recombinant nucleic acid, thereby producing the VLP. The method may further comprises a step c) of harvesting the plant, portion of the plant, or plant cell, and purifying the VLP.

It is further provided a method of producing an influenza virus like particle (VLP) in a plant, portion of a plant, or a plant cell, comprising:

a) providing a plant, portion of a plant, or plant cell comprising the recombinant nucleic acid as described under A or B; and
b) incubating the plant, portion of the plant, or plant cell under conditions that permit expression of the HA protein encoded by the recombinant nucleic acid, thereby producing the VLP. The method may further comprises a step c) of harvesting the plant, portion of the plant, or plant cell, and purifying the VLP.

Furthermore, it is provided a method of increasing yield of production of an influenza virus like particle (VLP) in a plant, portion of a plant, or a plant cell, comprising: a) introducing the recombinant nucleic acid of A or B into the plant, portion of the plant, or plant cell: or providing a plant, portion of a plant, or plant cell comprising the recombinant nucleic acid of A or B; and b) incubating the plant, portion of the plant, or plant cell under conditions that permit expression of the HA protein encoded by the recombinant nucleic acid, thereby producing the VLP at a higher yield compared to plant, portion of the plant, or plant cell expressing an unmodified influenza HA protein. The method may further comprises a step c) of harvesting the plant, portion of the plant, or plant cell, and purifying the VLP.

The methods may further comprise introducing a second nucleic acid encoding a proton channel protein: wherein the plant, portion of the plant, or plant cell is incubated under conditions that permit expression of the proton channel protein encoded by the second nucleic acid. The proton channel protein may be an influenza A subtype M2 protein.

It is further provided a VLP produced by the method as described herewith.

The VLP may comprise one or more than one lipid derived from the plant, portion of the plant, or plant cell, plant-specific N-glycans, modified N-glycans or a combination thereof.

In addition a method of producing an antibody or antibody fragment is provided, the method comprising administering the VLP as described to a subject, or a host animal, thereby producing the antibody or the antibody fragment. Antibodies or the antibody fragments produced by the method are also provided.

Furthermore it is provided a plant, portion of the plant, or plant cell comprising the recombinant nucleic acid of A or B or HA protein encoded by the recombinant nucleic acid of A or B. The HA protein may form VLP. Accordingly, a plant, portion of the plant, or plant cell comprising VLP comprising HA protein encoded by the recombinant nucleic acid of A or B are also provided.

In addition, it is provided a composition for inducing an immune response comprising, an effective dose of the VLP as described herewith, and a pharmaceutically acceptable carrier, adjuvant, vehicle or excipient. A method for inducing immunity to an influenza infection in a subject, the method comprising administering the VLP as described is also provided. The VLP may be administered to the subject orally, intranasally, intramuscularly, intraperitoneally, intravenously or subcutaneously.

Furthermore, it is provided a modified influenza hemagglutinin (HA) protein comprising an amino acid sequence having from about 30% to about 100%, sequence identity or sequence similarity with a sequence of the sequences of SEQ ID NO: 21, SEQ ID NO: 25, SEQ ID NO: 27, SEQ ID NO: 31, SEQ ID NO: 33, SEQ ID NO: 35, SEQ ID NO: 37, SEQ ID NO: 39, SEQ ID NO: 43, SEQ ID NO: 47, SEQ ID NO: 49, SEQ ID NO: 53, SEQ ID NO: 57, SEQ ID NO: 59, SEQ ID NO: 61, SEQ ID NO: 82, SEQ ID NO: 84, SEQ ID NO: 86, SEQ ID NO: 88, SEQ ID NO: 90, SEQ ID NO: 98, provided that the influenza HA protein comprises at least on substitution as described herewith and is able to form VLPs, induces an immune response when administered to a subject, induces hemagglutination or a combination thereof.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows a sequence alignment of the amino acid sequences of hemagglutinin (HA) of A/Bangkok/3007/15 (H3N2) (SEQ ID NO: 91); A/Hongkong/4801/14 (H3N2)

(SEQ ID NO: 92); A/Minnesota/40/15 (H3N2) (SEQ ID NO: 93); A/South Australia/1/16 (H3N2) (SEQ ID NO: 94); A/Pennsylvania/09/15 (H3N2) (SEQ ID NO:95); A/Switzerland/9715293/13 (H3N2)(SEQ ID NO: 96); A/Mississippi/16/16 (H3N2) (SEQ ID NO: 97); Outlined residues align with amino acids N382, L384, F392, L431 of HA from influenza H3 strains (H3N2) for example A/Hongkong/4801/14 (H3N2) (SEQ ID NO: 92).

Figure 2:
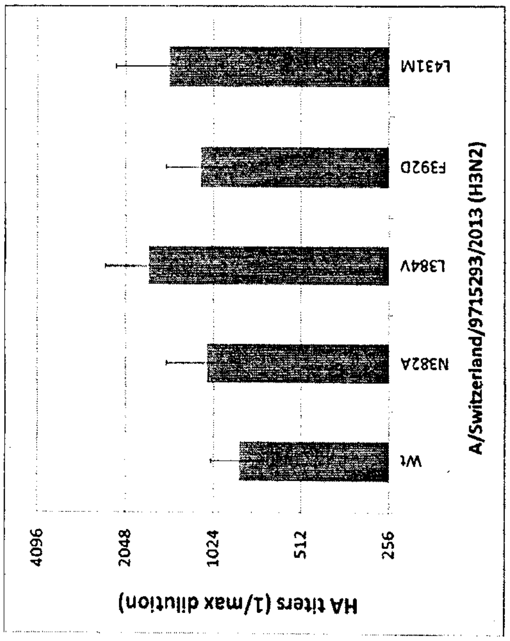

FIG. 2 shows the hemagglutination titers of wildtype A/Switzerland/9715293/13 H3, N382A A/Switzerland/9715293/13 mutant H3, L384V A/Switzerland/9715293/13 mutant H3, F392D A/Switzerland/9715293/13 mutant H3 and L431M A/Switzerland/9715293/13 mutant H3.

Figure 3:
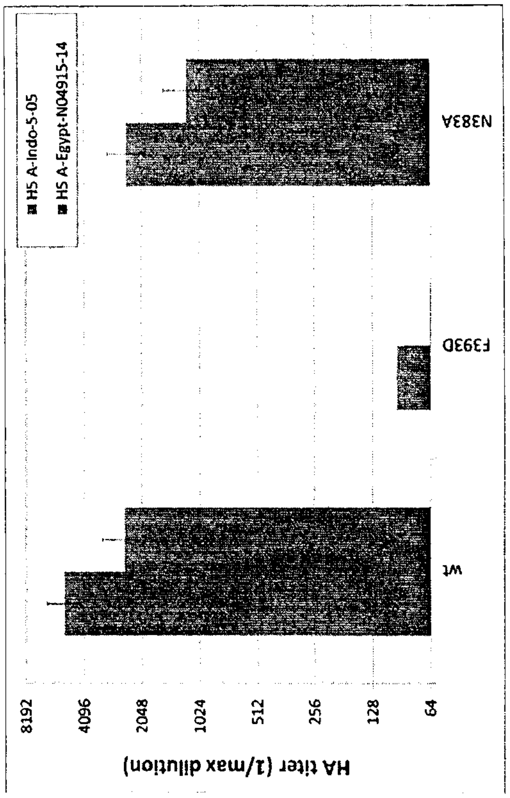

FIG. 3 shows the hemagglutination titers of wildtype A/Indonesia/5/2005 H5, wildtype A/Egypt/N04915/2014 H5, F393D A/Indonesia/5/2005 mutant H5, F393D A/Egypt/N04915/2014 mutant H5, N383A A/Indonesia/5/2005 mutant H5, and N383A A/Egypt/N04915/2014 mutant H5. The numbering is in accordance with A/Indonesia/5/2005.

FIG. 4A shows a schematic representation of vector 3045 (H3 A-Swi-9715293-13 (F392D)). FIG. 4B shows a schematic representation of vector 3022 (H3 A-Swi-9715293-13 (L431M)). FIG. 4C shows a schematic representation of vector 3023 (H3 A-Swi-9715293-13 (N382A)). FIG. 4D shows a schematic representation of vector 3034 (H3 A-Swi-9715293-13 (L384V)).

FIG. 5A shows a schematic representation of vector 3556 (Vector for In-Fusion cloning into CPMV 160-based expression cassette in addition to M2 helper protein under the control of alfalfa plastocyanin promoter and terminator). FIG. 5B shows a schematic representation of vector 1190 (Vector for In-Fusion cloning into CPMV 160-based expression cassette).

Figure 6B:
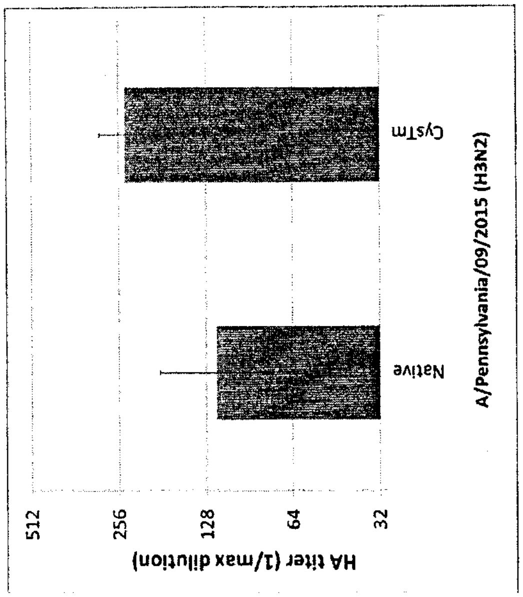
Figure 6A:
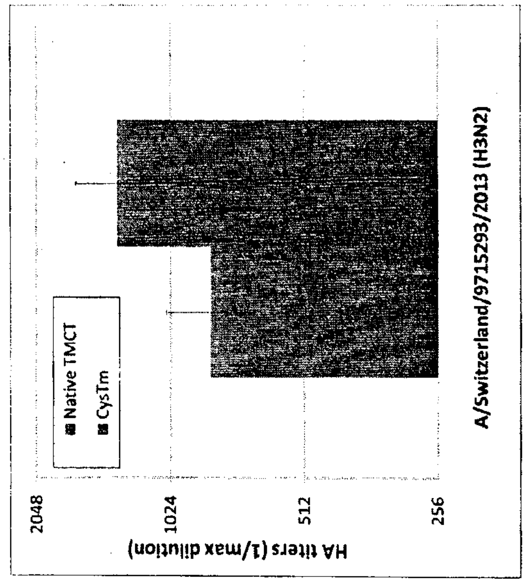

FIG. 6A shows the hemagglutination titers of wildtype A/Switzerland/9715293/13 H3 and CysTM A/Switzerland/9715293/13 mutant H3.

FIG. 6B shows the hemagglutination titers of wildtype A/Pennsylvania/09/2015 H3, and CysTM A/Pennsylvania/09/2015 mutant H3.

Figure 7C:
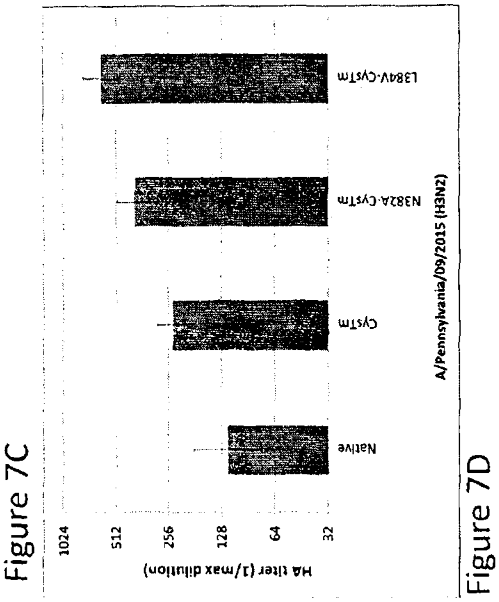
Figure 7D:
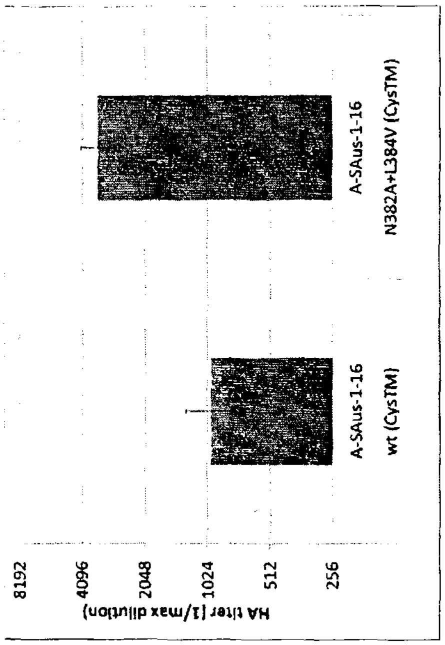
Figure 7A:
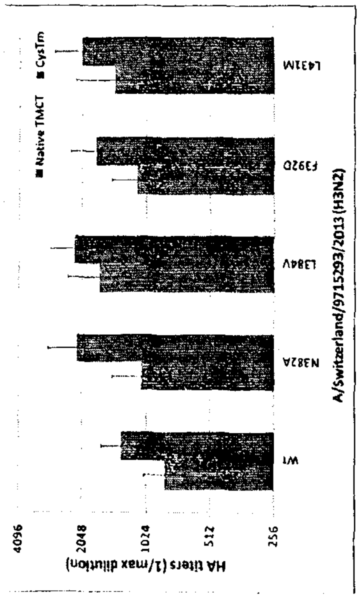
Figure 7B:
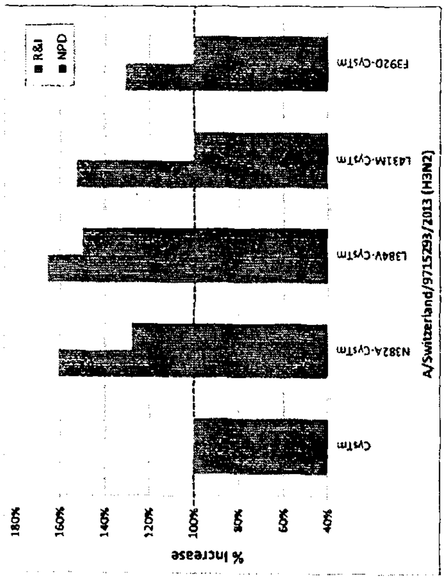
Figure 7E:
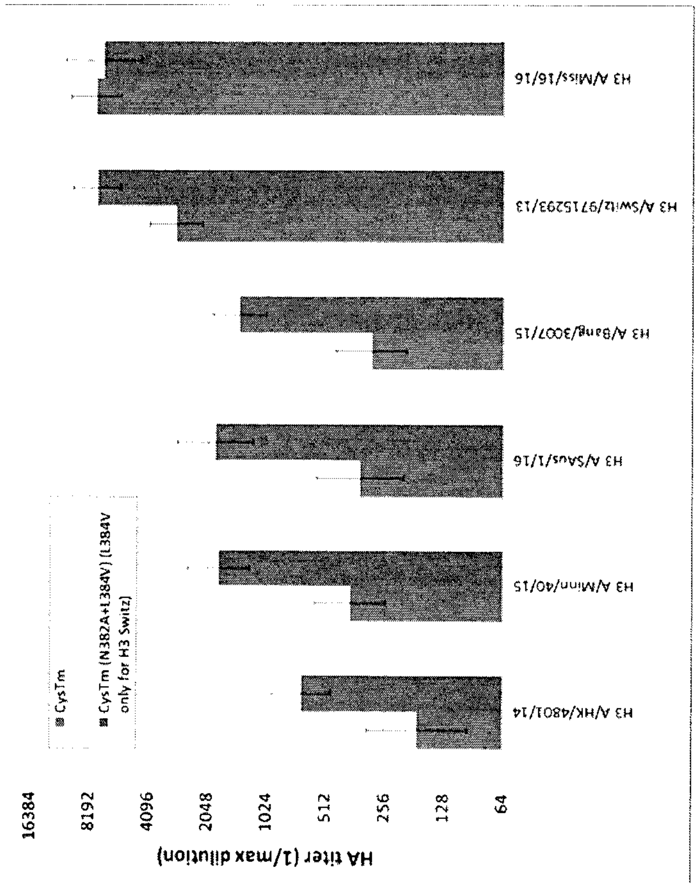

FIG. 7A shows the hemagglutination titers of wildtype A/Switzerland/9715293/13 H3, N382A A/Switzerland/9715293/13 mutant H3, L384V A/Switzerland/9715293/13 mutant H3, F392D A/Switzerland/9715293/13 mutant H3, L431M A/Switzerland/9715293/13 mutant H3, A/Switzerland/9715293/13 H3 with CysTM modification, N382A+CysTM A/Switzerland/9715293/13 mutant H3, L384V+CysTM A/Switzerland/9715293/13 mutant H3, F392D+CysTM A/Switzerland/9715293/13 mutant H3 and L431M+CysTM A/Switzerland/9715293/13 mutant H3. FIG. 7B shows the post-density gradient VLP yields of CysTM A/Switzerland/9715293/13 mutant H3, N382A+CysTM A/Switzerland/9715293/13 mutant H3, L384V+CysTM A/Switzerland/9715293/13 mutant H3, F392D+CysTM A/Switzerland/9715293/13 mutant H3, and L431M+CysTM A/Switzerland/9715293/13 mutant H3 expressed as percentages relative to CysTM A/Switzerland/9715293/13 mutant H3. FIG. 7C shows the hemagglutination titers of wildtype A/Pennsylvania/09/2015 H3, CysTM A/Pennsylvania/09/2015 mutant H3, N382A+CysTM A/Pennsylvania/09/2015 mutant H3, and L384V+CysTM A/Pennsylvania/09/2015 mutant H3. FIG. 7D shows the hemagglutination titers of CysTM A/S. Australia/1/16 mutant H3 and N382A+L384V+CysTM A/S. Australia/1/16 mutant H3. FIG. 7E shows the hemagglutination titers of CysTM A/Hong Kong/4801/14 mutant H3 and N382A+L384V+CysTM A/Hong Kong/4801/14 mutant H3; CysTM A/Minnesota/40/15 mutant H3 and N382A+L384V+CysTM A/Minnesota/40/15 mutant H3; CysTM A/S. Australia/1/16 mutant H3 and N382A+L384V+CysTM A/S. Australia/1/16 mutant H3; CysTM A/Bangkok/3007/15 mutant H3 and N382A+L384V+CysTM A/Bangkok/3007/15 mutant H3; CysTM A/Switzerland/9715293/13 mutant H3, and L384V+CysTM A/Switzerland/9715293/13 mutant H3; CysTM A/Mississippi/16/16 mutant H3 and N382A+L384V+CysTM A/Mississippi/16/16 mutant H3.

FIG. 8A shows a schematic representation of vector 3340 (H3 A-HK-4801-14). FIG. 8B shows a schematic representation of vector 3341 (H3 A-HK-4801-14). FIG. 8C shows a schematic representation of vector 3375 (H3 A-HK-4801-14 (N382A+L384V)). FIG. 8D shows a schematic representation of vector 3914 (H3 A-Minn-40-15). FIG. 8E shows a schematic representation of vector 3915 (H3 A-Minn-40-15 (N382A+L384V)). FIG. 8F shows a schematic representation of vector 3924 (H3 A-SAus-1-16). FIG. 8G shows a schematic representation of vector 3925 (H3 A-SAus-1-16 (N382A+L384V)). FIG. 8H shows a schematic representation of vector 3904 (H3 A-Bang-3007-15). FIG. 8I shows a schematic representation of vector 3905 (H3 A-Bang-3007-15 (N382A+L384V)). FIG. 8J shows a schematic representation of vector 2801 (H3 A-Swi-9715293-13). FIG. 8K shows a schematic representation of vector 2811 (H3 A-Swi-9715293-13). FIG. 8L shows a schematic representation of vector 3063 (H3 A-Swi-9715293-13 (N382A)). FIG. 8M shows a schematic representation of vector 3074 (H3 A-Swi-9715293-13 (L384V)). FIG. 8N shows a schematic representation of vector 3085 (H3 A-Swi-9715293-13 (F392D)). FIG. 8O shows a schematic representation of vector 3062 (H3 A-Swi-9715293-13 (L431M)). FIG. 8P shows a schematic representation of vector 3312 (H3 A-Penn-09-15). FIG. 8Q shows a schematic representation of vector 3313 (H3 A-Penn-09-15). FIG. 8R shows a schematic representation of vector 3314 (H3 A-Penn-09-15 (N382A)). FIG. 8S shows a schematic representation of vector 3315 (H3 A-Penn-09-15 (L384V)).

FIG. 9A shows a schematic representation of vector 2295 (H5 A-Indo-5-05). FIG. 9B shows a schematic representation of vector 3680 (H5 A-Indo-5-05 (F393D)). FIG. 9C shows a schematic representation of vector 3645 (H5 A-Egypt-N04915-14). FIG. 9D shows a schematic representation of vector 3690 (H5 A-Egypt-N04915-14 (F392D)).

DETAILED DESCRIPTION

The following description is of a preferred embodiment.

As used herein, the terms “comprising”, “having”, “including”, “containing”, and grammatical variations thereof, are inclusive or open-ended and do not exclude additional, un-recited elements and/or method steps. The term “consisting essentially of” when used herein in connection with a product, use or method, denotes that additional elements and/or method steps may be present, but that these additions do not materially affect the manner in which the recited method or use functions. The term “consisting of” when used herein in connection with a product, use or method, excludes the presence of additional elements and/or method steps. A product, use or method described herein as comprising certain elements and/or steps may also, in certain embodiments, consist essentially of those elements and/or steps, and in other embodiments consist of those elements and/or steps, whether or not these embodiments are specifically referred to. In addition, the use of the singular includes the plural, and “or” means “and/or” unless otherwise stated. Unless otherwise defined herein, all technical and scientific terms used herein have the same meaning as commonly understood by one of ordinary skill in the art. As used herein, the term “about” refers to an approximately +/−10% variation from a given value. It is to be understood that such a variation is always included in any given value provided herein, whether or not it is specifically referred to. The use of the word “a” or “an” when used herein in conjunction with the term “comprising” may mean “one,” but it is also consistent with the meaning of “one or more,” “at least one” and “one or more than one.”

The term “plant”, “portion of a plant”, “plant portion”, “plant matter”, “plant biomass”, “plant material”, plant extract”, or “plant leaves”, as used herein, may comprise an entire plant, tissue, cells, or any fraction thereof, intracellular plant components, extracellular plant components, liquid or solid extracts of plants, or a combination thereof, that are capable of providing the transcriptional, translational, and post-translational machinery for expression of one or more than one nucleic acids described herein, and/or from which an expressed protein or VLP may be extracted and purified. Plants may include, but are not limited to, herbaceous plants. Furthermore, plants may include, but are not limited to, agricultural crops including for example canola, *Brassica* spp., maize, *Nicotiana* spp., (tobacco) for example, *Nicotiana benthamiana. Nicotiana rustica. Nicotiana, tabacum. Nicotiana alata. Arabidopsis thaliana*, alfalfa, potato, sweet potato (*Ipomoea batatus*), *ginseng*, pea, oat, rice, soybean, wheat, barley, sunflower, cotton, corn, rye (*Secale cereale*), *sorghum* (*Sorghum bicolor. Sorghum vulgare*), safflower (Carthamus tinctorius).

The term “plant portion”, as used herein, refers to any part of the plant including but not limited to leaves, stem, root, flowers, fruits, a plant cell obtained from leaves, stem, root, flowers, fruits, a plant extract obtained from leaves, stem, root, flowers, fruits, or a combination thereof. The term “plant extract”, as used herein, refers to a plant-derived product that is obtained following treating a plant, a portion of a plant, a plant cell, or a combination thereof, physically (for example by freezing followed by extraction in a suitable buffer), mechanically (for example by grinding or homogenizing the plant or portion of the plant followed by extraction in a suitable buffer), enzymatically (for example using cell wall degrading enzymes), chemically (for example using one or more chelators or buffers), or a combination thereof. A plant extract may be further processed to remove undesired plant components for example cell wall debris. A plant extract may be obtained to assist in the recovery of one or more components from the plant, portion of the plant or plant cell, for example a protein (including protein complexes, protein surprastructures and/or VLPs), a nucleic acid, a lipid, a carbohydrate, or a combination thereof from the plant, portion of the plant, or plant cell. If the plant extract comprises proteins, then it may be referred to as a protein extract. A protein extract may be a crude plant extract, a partially purified plant or protein extract, or a purified product, that comprises one or more proteins, protein complexes, protein suprastructures, and/or VLPs, from the plant tissue. If desired a protein extract, or a plant extract, may be partially purified using techniques known to one of skill in the art, for example, the extract may be subjected to salt or pH precipitation, centrifugation, gradient density centrifugation, filtration, chromatography, for example, size exclusion chromatography, ion exchange chromatography, affinity chromatography, or a combination thereof. A protein extract may also be purified, using techniques that are known to one of skill in the art.

The term “construct”, “vector” or “expression vector”, as used herein, refers to a recombinant nucleic acid for transferring exogenous nucleic acid sequences into host cells (e.g. plant cells) and directing expression of the exogenous nucleic acid sequences in the host cells. “Expression cassette” refers to a nucleotide sequence comprising a nucleic acid of interest under the control of, and operably (or operatively) linked to, an appropriate promoter or other regulatory elements for transcription of the nucleic acid of interest in a host cell. As one of skill in the art would appreciate, the expression cassette may comprise a termination (terminator) sequence that is any sequence that is active the plant host. For example the termination sequence may be derived from the RNA-2 genome segment of a bipartite RNA virus, e.g. a comovirus, the termination sequence may be a NOS terminator, or terminator sequence may be obtained from the 3'UTR of the alfalfa plastocyanin gene.

The constructs of the present disclosure may further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO: U.S. Pat. No. 4,962,028; which is incorporated herein by reference), the promoter used in regulating plastocyanin expression.

By “regulatory region” “regulatory element” or “promoter” it is meant a portion of nucleic acid typically, but not always, upstream of the protein coding region of a gene, which may be comprised of either DNA or RNA, or both DNA and RNA. When a regulatory region is active, and in operative association, or operatively linked, with a nucleotide sequence of interest, this may result in expression of the nucleotide sequence of interest. A regulatory element may be capable of mediating organ specificity, or controlling developmental or temporal gene activation. A “regulatory region” includes promoter elements, core promoter elements exhibiting a basal promoter activity, elements that are inducible in response to an external stimulus, elements that mediate promoter activity such as negative regulatory elements or transcriptional enhancers. “Regulatory region”, as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term “regulatory element” or “regulatory region” typically refers to a sequence of DNA, usually, but not always, upstream (5) to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358). Examples, of potential inducible promoters include, but not limited to, tetracycline-inducible promoter (Gatz, C., 1997, Ann. Rev. Plant Physiol. Plant Mol. Biol. 48, 89-108), steroid inducible promoter (Aoyama, T. and Chua, N. H., 1997, Plant J. 2, 397-404) and ethanol-inducible promoter (Salter, M. G., et al, 1998, Plant Journal 16, 127-132: Caddick, M. X., et al, 1998, Nature Biotech. 16, 177-180) cytokinin inducible IB6 and CKII genes (Brandstatter, I. and Kieber, J. J., 1998, Plant Cell 10, 1009-1019; Kakimoto, T., 1996, Science 274, 982-985) and the auxin inducible element, DR5 (Ulmasov, T., et al., 1997, Plant Cell 9, 1963-1971).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812; which is incorporated herein by reference), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004), the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The expression constructs as described above may be present in a vector. The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

The term "native", "native protein" or "native domain", as used herein, refers to a protein or domain having a primary amino acid sequence identical to wildtype. Native proteins or domains may be encoded by nucleotide sequences having 100% sequence similarity to the wildtype sequence. A native amino acid sequence may also be encoded by a human codon (hCod) optimized nucleotide sequence or a nucleotide sequence comprising an increased GC content when compared to the wild type nucleotide sequence provided that the amino acid sequence encoded by the hCod-nucleotide sequence exhibits 100% sequence identity with the native amino acid sequence.

By a nucleotide sequence that is "human codon optimized" or a "hCod" nucleotide sequence, it is meant the selection of appropriate DNA nucleotides for the synthesis of an oligonucleotide sequence or fragment thereof that approaches the codon usage generally found within an oligonucleotide sequence of a human nucleotide sequence. By "increased GC content" it is meant the selection of appropriate DNA nucleotides for the synthesis of an oligonucleotide sequence or fragment thereof in order to approach codon usage that, when compared to the corresponding native oligonucleotide sequence, comprises an increase of GC content, for example, from about 1 to about 30%, or any amount therebetween, over the length of the coding portion of the oligonucleotide sequence. For example, from about 1, 2, 4, 6, 8, 10, 12, 14, 16, 18, 20, 22, 24, 26, 28, 30%, or any amount therebetween, over the length of the coding portion of the oligonucleotide sequence. As described below, a human codon optimized nucleotide sequence, or a nucleotide sequence comprising an increased GC contact (when compared to the wild type nucleotide sequence) exhibits increased expression within a plant, portion of a plant, or a plant cell, when compared to expression of the non-human optimized (or lower GC content) nucleotide sequence.

Modified influenza hemagglutinin (HA) proteins (also termed modified HA protein, modified influenza HA protein, modified HA, modified influenza HA, mutant HA, influenza mutant HA, influenza HA variants or HA variants) and methods of producing modified influenza HA proteins in plants are described herein. The modified influenza HA proteins disclosed herewith comprise modifications or mutations that have been found to result in improved HA characteristics as compared to the wildtype HA or unmodified HA proteins. For example, the modified influenza HA protein may have an amino acid sequence with at least one substitution of an amino acid when compared to a corresponding wildtype amino acid sequence.

Examples of improved characteristics of the modified HA protein include, increased HA protein yield when expressed in plant cells as compared to the wildtype or unmodified HA of the same strain or subtype of influenza that does not comprise the modification(s) or mutation(s); improved hemagglutination titer of the modified HA protein when compared to the wildtype or unmodified HA protein: improved integrity, stability, or both integrity and stability, of virus like particles (VLPs) that are comprised of the modified HA proteins as compared to the integrity, stability or both of VLPs comprising wildtype HA that does not comprise the modification(s) or mutation(s); increased VLP yield when expressed in plant cells as compared to the wildtype level of VLP production that does not comprise the modification(s) or mutation(s); and a combination thereof.

Influenza Subtypes and Strain

The term "influenza virus subtype" as used herein refers to influenza A virus variants that are characterized by various combinations of the hemagglutinin (H or HA) and neuramidase (N) viral surface proteins. According to the present specification, influenza virus subtypes and hemagglutinin (HA) from such virus subtypes may be referred to by their H number, such as, for example, "HA of the H3 subtype", "H3 HA" or "H3 influenza". The term "subtype" specifically includes all individual "strains" within each subtype, which usually result from mutations and may show different pathogenic profiles. Such strains may also be referred to as various "isolates" of a viral subtype. Accordingly, as used herein, the terms "strains" and "isolates" may be used interchangeably.

Traditionally, different strains of influenza have been categorized based upon, e.g., the ability of influenza to agglutinate red blood cells (RBCs or erythrocytes). Antibodies specific for particular influenza strains may bind to the virus and, thus, prevent such agglutination. Assays determining strain types based on such inhibition are typically known as hemagglutinin inhibition assays (HI assays or HAI assays) and are standard and well known methods in the art to characterize influenza strains.

However, HA proteins from different virus strains also show significant sequence similarity at both the nucleic acid and amino acid levels. This level of similarity varies when strains of different subtypes are compared, with some strains clearly displaying higher levels of similarity than others (Air, Proc. Natl. Acad. Sci. USA, 1981, 78:7643). The levels of amino acid similarity vary between virus strains of one subtype and virus strains of other subtypes (Air, Proc. Natl. Acad. Sci. USA, 1981, 78:7643). This variation is sufficient to establish discrete subtypes and the evolutionary lineage of the different strains, but the DNA and amino acid sequences of different strains are still readily aligned using conventional bioinformatics techniques (Air, Proc. Natl. Acad. Sci. USA, 1981, 78:7643; Suzuki and Nei, Mol. Biol. Evol. 2002, 19:501).

Multiple nucleotide sequences, or corresponding polypeptide sequences of hemagglutinin (HA), may be aligned to determine a "consensus" or "consensus sequence" of a subtype (see FIG. 1).

Based on sequence similarities, influenza virus subtypes can further be classified by reference to their phylogenetic group. Phylogenetic analysis (Fouchier et al., J Virol. 2005 March; 79(5):2814-22) has demonstrated a subdivision of HAs that falls into two main groups (Air, Proc. Natl. Acad. Sci. USA, 1981, 78:7643): inter alia the H1, H2, H5 and H9 subtypes in phylogenetic group 1 and inter alia the H3, H4 and H7 subtypes in phylogenetic group 2.

New influenza HA proteins, HA modifications, HA protein variants and mutants are created by introducing changes to the amino acid sequence of HA protein that results in an improved characteristic of the HA as described above. Isolation of nucleic acids encoding such HA molecules is routine, as is modification of the nucleic acid to introduce changes in the amino acid sequence, e.g., by site-directed mutagenesis.

Modified influenza HA proteins and methods of producing modified influenza HA proteins in plants are described herein. It has been observed that the modification for example by substitution of specific amino acids in HA proteins for example HA from subtype H3 results in improved characteristics of the modified HA protein when compared to the wildtype HA protein or unmodified HA protein.

The one or more than one modification, mutation or substitution of the HA protein as described herein are not located in the globular head domain of the HA protein, are not located in known epitopic regions of the HA protein nor do these modifications, mutations or substitutions add or remove glycosylation sites within the HA protein.

The HA protein, mutant HA protein or modified HA protein as described herein is modified and comprises one or more than one mutation, modification, or substitution in its amino acid sequence at any one or more amino acid that correspond to one or more than one mutation, or modification, at any one or more amino acid that corresponds with positions 382, 384, 392, 431, 524, 525, 526, 527 or 528 of the amino acid sequence of A/Hong Kong/4801/14 (SEQ ID NO: 92; see FIG. 1).

By "correspond to an amino acid" or "corresponding to an amino acid", it is meant that an amino acid corresponds to an amino acids in a sequence alignment with an influenza reference strain as described below.

The amino acid residue number or residue position of HA is in accordance with the numbering of the HA of an influenza reference strain. For example in the case of influenza H3, the reference strain may be A/Hong Kong/4801/14 [SEQ ID NO: 92 see FIG. 1]. The corresponding amino acid positions may be determined by aligning the sequences of the HA (for example H3 HA) with the sequence of HA of their respective reference strain. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Current Protocols in Molecular Biology (Ausubel et al., eds. 1995 supplement)). An amino acid sequence alignment of several influenza A HA domains, which are not to be considered limiting, is shown in FIG. 1.

When referring to modifications, mutants or variants, the wild type amino acid residue (also referred to as simply 'amino acid') is followed by the residue number and the new or substituted amino acid. For example, substitution of Asparagine (N, Asn) for Alanine (A, Ala) in residue or amino acid at position 382 is denominated N382A (see Table 1). 382 (N382A)

The modified HA, HA mutants or variants for example modified H3 HA are designated in the same manner by using the single letter amino acid code for the wildtype residue followed by its position and the single letter amino acid code of the replacement residue. Multiple mutants are indicated by component single mutants separated by slashes (/) or pluses (+). Mutations or modifications in the transmembrane (TM) domain or region are indicated as (CysTM). Thus for example the H3 HA mutant N382A+L384V (CysTM) is a mutant in which Alanine (A, Ala) replaces Asparagine (N, Asp) at residue position 382 and Valine (V, Val) replaces Leucine (L, Leu) at residue position 384 and the H3 HA mutant has further mutations in the transmembrane domain.

TABLE 1

Positions of modification in HA and the corresponding amino acid/residue position in reference strains of influenza H3 and H5. The exemplified modification is shown in brackets.

| Position of Modification in HA (exemplification) | H3 HA[1] | H5 HA[2] |
|---|---|---|
| 382 (N382A) | N382 | N383 |
| 384 (L384V) | L384 | I385 |
| 392 (F392D) | F392 | F393 |
| 431(L431M) | L431 | M432 |
| 524 (C524S) | C524 | S526 |
| 525 (F525L) | F525 | L527 |
| 526 (L526V) | L526 | A528 |
| 527 | L527 | L529 |
| 528 (C528L) | C528 | A530 |

[1]A/Hong Kong/4801/14
[2]A/Indonesia /05/05

The modified influenza hemagglutinin (HA) protein may comprise an amino acid sequence having at least one amino acid substitution when compared to a corresponding wild-type amino acid sequence.

By "amino acid substitution" or "substitution" it is meant the replacement of an amino acid in the amino acid sequence of a protein with a different amino acid. The terms amino acid, amino acid residue or residue are used interchangeably in the disclosure. One or more amino acids may be replaced with one or more amino acids that are different than the original or wildtype amino acid at this position, without changing the overall length of the amino acid sequence of the protein. The substitution or replacement may be experimentally induced by altering the codon sequence in a nucleotide sequence encoding the protein to the codon sequence of a different amino acid compared to the original or wildtype amino acid. The resulting protein is a modified protein, for example a modified influenza HA protein. The modified influenza HA protein does not occur naturally.

The modified HA includes non-naturally occurring HA protein, having at least one modification to naturally occurring HA and having improved characteristics compared to naturally occurring HA protein from which the amino acid sequence of the modified HA is derived. Modified HA proteins have an amino acid sequence, not found in nature, which is derived by replacement of one or more amino acid residues of an HA protein with one or more different amino acids.

Accordingly, modified HA, mutant HA or recombinant HA refers to an HA in which the DNA sequence encoding the naturally-occurring HA is modified to produce a modified or mutant DNA sequence which encodes the modification, mutation or substitution of one or more amino acids in the HA amino acid sequence.

Some of the residues identified for modification, mutation or substitution correspond to conserved residues whereas others are not. In the case of residues which are not conserved, the replacement of one or more amino acids is limited to substitutions which produce a modified HA which has an amino acid sequence that does not correspond to one found in nature. In the case of conserved residues, such modification, substitution or replacements should also not result in a naturally-occurring HA sequences.

Conservative Substitutions

As described herein, residues in HA proteins may be identified and modified, substituted or mutated to produce modified HA protein or HA protein variants. The substitutions or mutations at specific positions are not limited to the amino acid substitutions described herewith or as given in the examples. For example, the HA variants may contain conserved or conservative substitutions of describes amino acid substitutions.

As used herein, the term "conserved substitution" or "conservative substitution" and grammatical variations thereof, refers to the presence of an amino acid residue in the sequence of the HA protein that is different from, but is in the same class of amino acid as the described substitution or described residue (i.e., a nonpolar residue replacing a nonpolar residue, an aromatic residue replacing an aromatic residue, a polar-uncharged residue replacing a polar-uncharged residue, a charged residue replacing a charged residue). In addition, conservative substitutions can encompass a residue having an interfacial hydropathy value of the same sign and generally of similar magnitude as the residue that is replacing the wildtype residue.

As used herein, the term "nonpolar residue" refers to glycine (G, Gly), alanine (A, Ala), valine (V, Val), leucine (L, Leu), isoleucine (I, Ile), and proline (P, Pro); the term "aromatic residue" refers to phenylalanine (F, Phe), tyrosine (Y, Tyr), and tryptophan (W, Trp); the term "polar uncharged residue" refers to serine (S, Ser), threonine (T, Thr), cysteine (C, Cys), methionine (M, Met), asparagine (N, Asn) and glutamine (Q, Gln); the term "charged residue" refers to the negatively charged amino acids aspartic acid (D, Asp) and glutamic acid (E, Glu), as well as the positively charged amino acids lysine (K, Lys), arginine (R, Arg), and histidine (H, His). Other classification of amino acids may be as follows:

- amino acids with hydrophobic side chain (aliphatic): Alanine (A, Ala), Isoleucine (I, Ile), Leucine (L, Leu), Methionine (M, Met) and Valine (V, Val);
- amino acids with hydrophobic side chain (aromatic): Phenylalanine (F, Phe), Tryptophan (W, Trp), Tyrosine (Y, Tyr);
- amino acids with polar neutral side chain: Asparagine (N, Asn), Cysteine (C, Cys), Glutamine (Q, Gln), Serine (S, Ser) and Threonine (T, Thr);
- amino acids with electrically charged side chains (acidic): Aspartic acid (D, Asp), Glutamic acid (E, Glu);
- amino acids with electrically charged side chains (basic): Arginine (R, Arg); Histidine (H, His); Lysine (K, Lys), Glycine G, Gly) and Proline (P, Pro).

Conservative amino acid substitutions are likely to have a similar effect on the activity of the resultant HA protein variant or modified HA protein, as the original substitution or modification. Further information about conservative substitutions can be found, for instance, in Ben Bassat et al. (J. Bacteriol, 169:751-757, 1987), O'Regan et al. (Gene, 77:237-251, 1989), Sahin-Toth et al. (Protein ScL, 3:240-247, 1994), Hochuli et al (Bio/Technology, 6:1321-1325, 1988) and in widely used textbooks of genetics and molecular biology.

The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., Proc. Natl. Acad. Sci. USA, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows exemplary conservative amino acid substitutions: Table 2.

TABLE 2

Exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

istics of the H3 HA protein. As described herewith and as shown in the Examples, only modifications or combinations of modifications at specific positions improved the characteristics of the H3 HA protein. Modifications at 13 positions or combinations of positions had negative effects on the characteristics of the H3 HA protein (data not shown).

Examples of improved characteristics of the H3 HA mutant or modified H3 HA protein include, increased HA protein yield or accumulation when expressed in plant cells as compared to the wildtype or unmodified HA of the same strain or subtype of influenza that does not comprise the modification(s) or mutation(s); improved hemagglutination titer of the modified or mutated HA protein when compared to the wildtype or unmodified HA protein: improved integrity, stability, or both integrity and stability, of VLPs that are comprised of the modified HA proteins as compared to the integrity, stability or both of VLPs comprising wildtype HA that does not comprise the mutation(s); increased VLP yield when expressed in plant cells as compared to the wildtype level of VLP production that does not comprise the modification(s) or mutation(s); and a combination thereof.

The nucleotide sequence encoding the modified HA protein may be optimized for human codon usage, for increased GC content, or a combination thereof. The modified HA protein may be expressed in a plant, portion of a plant, or plant cell.

A. H3 HA Modifications I

Modified influenza H3 HA proteins and methods of producing modified influenza H3 HA proteins in plants are described herein. It has been observed that the modification of specific amino acids in HA proteins from subtype H3 results in improved characteristics of the modified H3 HA protein when compared to the wildtype H3 HA protein or unmodified H3 HA protein.

A total of 33 single, double and/or triple modifications to residues that are not part of the HA transmembrane (TM) and cytosolic domain (CT) and/or modifications to residues that are part of the transmembrane (TM) and cytosolic domain (CT) of HA were tested to improve the character- The modified H3 HA protein or mutant H3 HA protein as described herein is modified and comprises one or more than one mutation, or modification, at any one or more residues in sequence alignment with positions 382, 384, 392 and/or 431 of reference strain A/Hong Kong/4801/14 (SEQ ID NO: 92; see FIG. 1). It is therefore provided influenza H3 HA polypeptides, proteins, and/or protein complexes such as for example virus-like particle (VLP) that comprise modifications or mutations at one or more of amino acid positions 382, 384, 392 and 431, where such amino acid numbering is based upon the sequence of A/Hong Kong/4801/14 as shown in FIG. 1 (SEQ ID NO: 92), or at amino acid positions that correspond to such amino acid positions, for example as determined by alignment of an HA amino acid sequence to SEQ ID NO: 92. Non-limiting examples of influenza H3 HA amino acid sequences that comprise one or more of such mutations include SEQ ID NOs: 91, 92, 93, 94, 95, 96 and 97.

The modified H3 HA protein described herewith includes H3 HA protein with amino acid sequences that have about 70, 75, 80, 85, 87, 90, 91, 92, 93 94, 95, 96, 97, 98, 99, 100% or any amount therebetween, sequence identity, or sequence similarity, with the amino acid sequence encoding HA from H3 (SEQ ID NO: 91-97), wherein the amino acid sequence has one or more than one mutation, or modification, at any one or more residues in sequence alignment with positions 382, 384, 392 and 431 of A/Hong Kong/4801/14 HA (SEQ ID NO:92).

Furthermore, the H3 HA protein may be encoded by a nucleotide sequences that has about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 (SEQ ID NO: 91-97), wherein the H3 HA protein has one or more than one mutation, or modification, at any one or more residues in sequence alignment with positions 382, 384, 392 and 431 of A/Hong Kong/4801/14 (SEQ ID NO: 92) HA and wherein the nucleotide sequence encodes a hemagglutinin protein that when expressed forms a VLP.

Non-limiting examples of strains from which the H3 HA might be derived are A/Bangkok/3007/15 (H3N2) (SEQ ID NO: 91); A/Hongkong/4801/14 (H3N2) (SEQ ID NO: 92); A/Minnesota/40/15 (H3N2) (SEQ ID NO: 93); A/South Australia/1/16 (H3N2) (SEQ ID NO: 94); A/Pennsylvania/09/15 (H3N2) (SEQ ID NO: 95); A/Switzerland/9715293/13 (H3N2) (SEQ ID NO: 96) and A/Mississippi/16/16 (H3N2) (SEQ ID NO: 97).

Modification at Position 382

In one aspect it is provided a H3 HA that may have modified residue at position 382 (numbering in accordance with A/Hong Kong/4801/14 HA numbering, SEQ ID NO: 92).

Antanasijevic et al. (*J Biol Chem.* 2014:289(32):22237-45) investigated the structure-function properties of H5 HA stem loop region by site directed mutagenesis at 14 different positions. Mutated positions $Thr^{41}$, $Gln^{42}$, $Ile^{45}$, $Asn^{53}$, and $Leu^{99}$ of HA2 are highly conserved and were designed to assay the importance of these residues to HA function. Antanasijevic observed that conserved mutations at positions HA1-128V, HA2-T41A, HA2-T49A, HA2-N53A, and HA2-D57E disrupted entry of the virus. In case of the mutational effect on entry inhibition by the small molecule MBX2329, substitutions to HA2-$Ile^{45}$, HA2-$Val^{52}$, HA2-$Asn^{53}$ and HA2-$Ser^{54}$ of the outer face and HA2-$Leu^{99}$ of the inner face had the largest effects. These residues are highly conserved in the Group 1 HA (e.g. H1 and H5). Position 53 in the HA of H5 of Antanasijevic corresponds to position 380 in H1 HA and position 382 in H3 HA of the current disclosure.

It was unexpectedly found that modification of the conserved residue at position 380 in H1 HA from an Asparagine to Alanine lead to an approximate 80% decrease in hemagglutination titer of the modified H1 HA when compared to wildtype H1 HA (data not shown). The equivalent modification in HA from H5 also lead to a decrease in hemagglutination titer (see FIG. 3, Table 7). However, modification of equivalent position in HA from H3 (N382A) from an Asparagine to Alanine lead to an approximate 130% increase in hemagglutination titer when compared to wildtype H3 HA (see FIG. 2, Table 5).

Accordingly, the residue at position 382 of H3 HA may be modified to be a non-Asparagine. For example the residue at position 382 may be modified to be a hydrophobic amino acid for example Alanine or a conserved substitution of Alanine for example Serine (S, Ser), Glycine (G, Gly), Threonine (T, Thr), Cysteine (C, Cys) or Valine (V, Val).

For example the modified H3 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H3 A/Hong Kong/4801/14 (SEQ ID NO: 92), wherein the amino acid sequence has an Alanine (A, Ala) or a conserved substitution of Alanine (A, Ala) at position 382, and wherein the sequence does not occur naturally. The conserved substitution of Alanine may for example be Serine (S, Ser), Glycine (G, Gly), Threonine (T, Thr), Cysteine (C, Cys) or Valine (V, Val).

The present specification also provides a nucleic acid comprising a nucleotide sequence encoding a modified H3 HA with a substitution at positions 382, as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 A/Hong Kong/4801/14 (SEQ ID NO: 102), wherein the nucleotide sequence encodes a modified H3 HA protein that has an Alanine (A, Ala) or a conserved substitution of Alanine (A, Ala) at position 382, and wherein the sequence does not occur naturally. The conserved substitution may for example be Serine (S, Ser), Glycine (G, Gly), Threonine (T, Thr), Cysteine (C, Cys) or Valine (V, Val).

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 102, wherein the nucleotide sequence encodes a modified H3 HA protein that has an Alanine (A, Ala) or a conserved substitution of Alanine (A, Ala) at position 382, and wherein the sequence does not occur naturally. The conserved substitution may for example be Serine (S, Ser), Glycine (G, Gly), Threonine (T, Thr), Cysteine (C, Cys) or Valine (V, Val).

In addition to residue at position 382, residues at positions 384, 524, 525, 526, 527, 528 or any combination thereof may be modified in the H3 HA.

Furthermore, it is provided a method of producing VLPs that comprise a modified H3 HA with a substitution at least at position 382 and optionally at position 384, 524, 525, 526, 527, 528 or any combination thereof in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H3 HA with a substitution at least at position 382 and optionally substitutions at positions 384, 524, 525, 526, 527, 528 or any combination thereof in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H3 HA with a substitution at least at position 382 and optionally substitutions at positions 384, 524, 525, 526, 527, 528 or any combination thereof. The VLP may be produced by the method as provided by the present specification. The VLP comprising the modified H3 HA show improved characteristics when compared to VLPs that comprise the unmodified H3 HA protein.

Modification at Position 384

In another aspect it is provided a H3 HA that may have a modified residue at position 384 (A/Hong Kong/4801/14 HA numbering, SEQ ID NO: 92).

As shown for example in FIG. 2 and Table 5 having the residue at position 384 modified from Leucine to Valine lead to an approximately 200% increase in hemagglutination titer as compared to wildtype H3 HA.

Accordingly, the residue at position 384 of H3 HA may be modified to be a non-Leucine. For example the residue at position 384 may be modified to be a for example Valine or a conserved substitution of Valine that is not Leucine for example Isoleucine, Methionine, Alanine, or Threonine.

For example the modified H3 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H3 A/Hong Kong/4801/14 (SEQ ID NO: 92), wherein the amino acid sequence has an Valine (V, Val) or a conserved substitution of Valine that is not Leucine at position 384, wherein the sequence does not occur naturally and wherein the HA protein when expressed form VLP. The conserved substitution of Valine may for example be Isoleucine, Methionine, Alanine, or Threonine.

The present specification also provides a nucleic acid comprising a nucleotide sequence encoding a modified H3 HA with a substitution at positions 384 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 A/Hong Kong/4801/14 (SEQ ID NO: 102), wherein the nucleotide sequence encodes a modified H3 HA protein that has a Valine (V, Val) or a conserved substitution of Valine (V, Val) that is not Leucine at position 384, wherein the sequence does not occur naturally and wherein the nucleotide sequence encodes HA protein that when expressed form VLP. The conserved substitution of Valine may for example be Isoleucine, Methionine, Alanine, or Threonine.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 102, wherein the nucleotide sequence encodes a modified H3 HA protein that has a Valine (V, Val) or a conserved substitution of Valine (V, Val) that is not Leucine at position 384, wherein the sequence does not occur naturally and wherein the nucleotide sequence encodes HA protein that when expressed form VLP. The conserved substitution of Valine may for example be Isoleucine, Methionine, Alanine, or Threonine.

In addition to residue at position 384, residues at positions 382, 524, 525, 526, 527, 528 or any combination thereof may be modified in the H3 HA.

Furthermore, it is provided a method of producing VLPs that comprise a modified H3 HA with a substitution at least at positions 384 and optionally substitutions at positions 382, 524, 525, 526, 527, 528 or any combination thereof in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H3 HA with a substitution at least at 384 and optionally substitutions at positions 382, 524, 525, 526, 527, 528 or any combination thereof, as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H3 HA with a substitution at least at position 384 and optionally substitutions at positions 382, 524, 525, 526, 527, 528 or any combination thereof. The VLP may be produced by the method as provided by the present specification. The VLP comprising the modified H3 HA show improved characteristics when compared to VLPs that comprise the unmodified H3 HA protein.

Modification at Position 392

In another aspect it is provided a H3 HA that may have modified residue at position 392 (H3 A/Hong Kong/4801/14 HA numbering, SEQ ID NO: 92).

As shown for example in FIG. 2 and Table 5 having the residue at position 392 modified from Phenylalanine to Aspartic Acid lead to an approximately 140% increase in hemagglutination titer as compared to wildtype H3 HA.

Accordingly, the residue at position 392 of H3 HA may be modified to be a non-Phenylalanine. For example the residue at position 392 may be modified to be for example Aspartic Acid or a conserved substitution of Aspartic Acid for example Glutamic acid, Asparagine, Glutamine, or Serine.

For example the modified H3 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H3 A/Hong Kong/4801/14 (SEQ ID NO: 92), wherein the amino acid sequence has an Aspartic Acid or a conserved substitution of Aspartic Acid for example Glutamic acid, Asparagine, Glutamine, or Serine at position 392, wherein the sequence does not occur naturally and wherein the HA protein when expressed form VLP. The conserved substitution of Aspartic Acid may for example be Glutamic acid, Asparagine, Glutamine, or Serine.

The present specification also provides a nucleic acid comprising a nucleotide sequence encoding a modified H3 HA with a substitution at positions 392 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 A/Hong Kong/4801/14 (SEQ ID NO: 102), wherein the nucleotide sequence encodes a modified H3 HA protein that has an Aspartic Acid or a conserved substitution of Aspartic Acid at position 392, wherein the sequence does not occur naturally and wherein the nucleotide sequence encodes HA protein that when expressed form VLP. The conserved substitution of Aspartic Acid may for example be Glutamic acid, Asparagine, Glutamine, or Serine.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 102, wherein the nucleotide sequence encodes a modified H3 HA protein that has an Aspartic Acid or a conserved substitution of Aspartic Acid at position 392, wherein the sequence does not occur naturally and wherein the nucleotide sequence encodes HA protein that when expressed form VLP. The conserved substitution of Aspartic Acid may for example be Glutamic acid, Asparagine, Glutamine, or Serine.

Furthermore, it is provided a method of producing VLPs that comprise a modified H3 HA with a substitution at least at positions 392 as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H3 HA with a substitution at least at 392, as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H3 HA with a substitution at least at position 392. The VLP may be produced by the method as provided by the present specification. The VLP comprising the modified H3 HA show improved characteristics when compared to VLPs that comprise the unmodified H3 HA protein.

Modification at Position 431

In another aspect it is provided a H3 HA that may have modified residue at position 431 (H3 A/Hong Kong/4801/14 HA numbering, SEQ ID NO: 92).

As shown for example in FIG. 2 and Table 5 having the residue at position 431 modified from Leucine to Methionine lead to an approximately 170% increase in hemagglutination titer as compared to wildtype H3 HA.

Accordingly, the residue at position 431 of H3 HA may be modified to be a non-Leucine. For example the residue at position 431 may be modified to be for example Methionine or a conserved substitution of Methionine for example Leucine, Isoleucine, Glutamine, Valine or Phenylalanine.

For example the modified H3 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H3 A/Hong Kong/4801/14 (SEQ ID NO: 92), wherein the amino acid sequence has Methionine or a conserved substitution of Methionine at position 431, wherein the sequence does not occur naturally and wherein the HA protein that when expressed form VLP. The conserved substitution of Methionine may for example be Leucine, Isoleucine, Glutamine, Valine or Phenylalanine.

The present specification also provides a nucleic acid comprising a nucleotide sequence encoding a modified H3 HA with a substitution at positions 431 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 A/Hong Kong/4801/14 (SEQ ID NO: 102), wherein the nucleotide sequence encodes a modified H3 HA protein that has Methionine or a conserved substitution of Methionine at position 431, wherein the sequence does not occur naturally and wherein the nucleotide sequence encodes HA protein that when expressed form VLP. The conserved substitution of Methionine may for example be Leucine, Isoleucine, Glutamine, Valine or Phenylalanine.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 102, wherein the nucleotide sequence encodes a modified H3 HA protein that has Methionine or a conserved substitution of Methionine at position 431, wherein the sequence does not occur naturally and wherein the nucleotide sequence encodes HA protein that when expressed form VLP. The conserved substitution of Aspartic Acid may for example be Leucine, Isoleucine, Glutamine, Valine or Phenylalanine.

Furthermore, it is provided a method of producing VLPs that comprise a modified H3 HA with a substitution at least at positions 431 as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H3 HA with a substitution at least at 431, as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H3 HA with a substitution at least at position 431. The VLP may be produced by the method as provided by the present specification. The VLP comprising the modified H3 HA show improved characteristics when compared to VLPs that comprise the unmodified H3 HA protein.

B. H3 HA Modifications II

Modification at Position 382, 384, 392, 431 and/or 524-528 ("CysTM")

Modified influenza H3 HA proteins and methods of producing modified influenza H3 HA proteins in plants are described herein. It has been observed that the modification of specific amino acids in HA proteins from subtype H3 results in improved characteristics of the modified H3 HA protein when compared to the wildtype H3 HA protein or unmodified H3 HA protein.

In one aspect, cysteine residues at position 524 and/or 528 (H3 A/Hong Kong/4801/14 numbering, SEQ ID NO: 92) or residues equivalent to these positions as determined by alignment may be substituted for non-cysteine residues at these positions. Furthermore, residues at position 525, 526 and/or 527 (H3 A/Hong Kong/4801/14 HA numbering) may also be modified. These modification or substitution may be referred to as the "CysTM modification", "CysTM", "CysTM mutation", "CysTM substitution" or "CysTM replacement" or grammatically equivalent expressions.

U.S. application Ser. No. 13/838,796 and its companion publication by Holtz et al. (*BMC Biotechnology*. 2014:14:111) teach the improved stability and maintained potency of recombinant HA by the mutation of cysteine residues in the carboxy terminal region of the HA protein including the transmembrane (TM) and cytosolic domain (CT). Specifically, Holtz et al. demonstrate C539A, C546A, C549A, C524S and C528A mutations in recombinant Perth/16/2009 HA (H3N2). Mutation of all five cysteine residues, or different subsets thereof, resulted in HA yields, purities, particle size, hemagglutination activity, and thermostability comparable to recombinant wildtype HA protein. In contrast, mutations of a pair of conserved cysteine residues in the ectodomain known to form a disulfide bond (C64S and C76S) resulted in significantly reduced HA expression, indicating the critical role of these residues in proper HA folding. By using a single radial immune-diffusion assay (SRID), Holtz et al. also show that the five cysteine residue mutations improve potency of recombinant HA as compared to wildtype protein, by preventing disulfide cross-linking in the TM and CT domains. The mutant HA proteins maintain potency for at least 12 months at 25° C., whereas wildtype HA protein exhibited less than 40% potency after only 50 days post purification.

Xu et al. (Virus Genes (2013) 47:20-26) showed that mutant H3 HAs with mutations of one or two of the TM cysteines (C540/544) could be expressed properly in cells, however the mutant exhibited lower thermal resistance and enhanced fusion activity in comparison with wildtype H3 HA proteins.

A total of 33 single, double or triple modifications in combination with modifications to the transmembrane (TM) as described herein ("CysTM modification") were tested to improve the characteristics of the H3 HA protein. As described herewith and as shown in the Examples, only modifications or combinations of modifications at certain positions improved the characteristics of the H3 HA protein. Modifications at 13 positions or combinations of positions had negative effects on the characteristics of the H3 HA protein (data not shown).

Examples of improved characteristics of the H3 HA mutant protein include, increased HA protein yield when expressed in plant cells as compared to the wildtype or unmodified HA of the same strain or subtype of influenza that does not comprise the modification(s) or mutation(s); improved hemagglutination titer of the modified or mutated HA protein when compared to the wildtype or unmodified HA protein: improved integrity, stability, or both integrity and stability, of VLPs that are comprised of the modified HA proteins as compared to the integrity, stability or both of VLPs comprising wildtype HA that does not comprise the mutation(s); increased VLP yield when expressed in plant cells as compared to the wildtype level of VLP production that does not comprise the modification(s) or mutation(s); and a combination thereof.

In one aspect, it is provided a modified H3 HA having cysteine residues at position 524 and/or 528 (A/Hong Kong/4801/14 numbering) or residues equivalent to these positions as determined by alignment substituted for non-cysteine residues at these positions. For example a cysteine residues at position 524 may be substituted with a Serine (S, Ser) or a conserved substitution of Serine or a cysteine at position 528 may be substituted by a Leucine (L, Leu) or a conserved substitution of Leucine.

Furthermore, the sequence between the two cysteines at position 524 and 528 (A/Hong Kong/4801/14 numbering, SEQ ID NO: 92) may also be modified. For example in the sequence "$C_{524}X_{525}X_{526}X_{527}C_{528}$", C524 (position 524) may be substituted with a Serine (S, Ser) or a conserved substitution of Serine; if $X_{525}$ (position 525) is not Leucine, the residue $X_{525}$ may be replaced with Leucine (L, Leu) or a conserved substitution of Leucine; if $X_{526}$ (position 526) is not Valine, $X_{526}$ may be replaced Valine (V, Val) or a conserved substitution of Valine; if $X_{527}$ (position 527) is not Leucine, the residue at position $X_{527}$ may be replaced with Leucine (L, Leu) or a conserved substitution of Leucine and $C_{528}$ (position 528) may be substituted with a Leucine (L, Leu) or a conserved substitution of Leucine. For example, in one embodiment the sequence "CFLLC" at position 524 to 528 may be replaced with the sequence "SLVLL" (SEQ ID NO: 98).

HA proteins from other strains than H3 influenza that have cysteine residues at position 524 and/or 528 or residues equivalent to these positions as determined by alignment may also be modified as described herewith. For example HA proteins from influenza B strains that have cysteine residues at positions that are equivalent to position 524 and/or 528 of H3 HA may be modified to non-cysteine residues as described herewith.

In addition to the mutation of the transmembrane domain as described herein, the modified H3 HA proteins may further comprise one or more than one substitutions of amino acids at positions 382, 384, 392, and/or 431, which resulted in an improved characteristic of the modified HA3 protein, or VLP produced using the modified HA protein. It is to be understood that the improved characteristic is not limited to substituting the specific amino acid at the specified sites, as one of skill in the art would understand that amino acids with similar properties may be substituted for the amino acids at the identified positions.

Accordingly, the modified H3 HA protein or mutant H3 HA protein as described herein may comprise one or more than one mutation, or modification, at any one or more residues in sequence alignment with positions 382, 384, 392, 431, 524, 525, 526, 527 or 528 of reference strain H3 A/Hong Kong/4801/14 (SEQ ID NO: 92: see FIG. 1). It is therefore provided influenza H3 HA polypeptides, proteins, and/or protein complexes such as for example virus-like particle (VLP) that comprise modifications or mutations at one or more of amino acid positions 382, 384, 392, 431, 524, 525, 526, 527 or 528, where such amino acid numbering is based upon the sequence of H3 A/Hong Kong/4801/14 as shown in FIG. 1 (SEQ ID NO: 92), or at amino acid positions that correspond to such amino acid positions, for example as determined by alignment of an HA amino acid sequence to SEQ ID NO: 92. Non-limiting examples of influenza H3 HA amino acid sequences that comprise one or more of such mutations include SEQ ID NOs: 91, 92, 93, 94, 95, 96 and 97.

The modified H3 HA protein described herewith includes H3 HA protein with amino acid sequences that have about 70, 75, 80, 85, 87, 90, 91, 92, 93 94, 95, 96, 97, 98, 99, 100% or any amount therebetween, sequence identity, or sequence similarity, with the amino acid sequence encoding HA from H3 (SEQ ID NO: 91-97), wherein the amino acid sequence has one or more than one mutation, or modification, at any one or more residues in sequence alignment with positions 382, 384, 392, 431, 524, 525, 526, 527 or 528 of A/Hong Kong/4801/14 HA (SEQ ID NO: 92).

Furthermore, the H3 HA protein may be encoded by a nucleotide sequences that has about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 (SEQ ID NO: 91-97 sequences of H3 strains), wherein the H3 HA protein has one or more than one mutation, or modification, at any one or more residues in sequence alignment with positions 382, 384, 392, 431, 524, 525, 526, 527 or 528 of H3 A/Hong Kong/4801/14 HA (SEQ ID NO: 92) and wherein the nucleotide sequence encodes a hemagglutinin protein that when expressed forms a VLP.

Non-limiting examples of strains from which the H3 HA might be derived are A/Bangkok/3007/15 (H3N2) (SEQ ID NO: 91); A/Hongkong/4801/14 (H3N2) (SEQ ID NO: 92); A/Minnesota/40/15 (H3N2) (SEQ ID NO: 93); A/South Australia/1/16 (H3N2) (SEQ ID NO: 94); A/Pennsylvania/09/15 (H3N2) (SEQ ID NO: 95); A/Switzerland/9715293/13 (H3N2) (SEQ ID NO: 96) and A/Mississippi/16/16 (H3N2) (SEQ ID NO: 97).

Modification at position 524-528 (CysTM) and 382

In another aspect it is provided a H3 HA that may have a modified residue at position 382, and may have been modified to have cysteine residue at positions 524 and/or 528 (H3 A/Hongkong/4801/14 numbering, SEQ ID NO: 92). Furthermore, residues at position 525, 526 and/or 527 (H3 A/Hongkong/4801/14 numbering) may also be modified.

As shown for example in FIGS. 7A, 7B and 7C, an H3 HA having cysteine residues at positions 524 and 528 modified to be non-cysteine and having residue at position 382 modified from Asparagine to Alanine lead to an approximately 260% increase in hemagglutination titer as compared to wildtype H3 HA.

Accordingly, it is provided a modified H3 HA protein that comprise one or more than one modification at position 524, 525, 526, 527 or 528 and a modification at position 382. In a non-limiting example the modified H3 HA has modifications at least at positions 382, 524 and 528.

The residue at position 382 of H3 HA may be modified to be a non-Asparagine. For example the residue at position 382 may be modified to be a hydrophobic amino acid for example Alanine or a conserved substitution of Alanine for example Serine (S, Ser), Glycine (G, Gly), Threonine (T, Thr), Cysteine (C, Cys) or Valine (V, Val). The residue at position 524 may be modified to a non-cysteine, a Serine or a conserved substitution of Serine (S, Ser) and the residue at position 528 may be modified to a non-cysteine, Leucine (L, Leu) or a conserved substitution of Leucine.

For example the modified H3 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H3 A/Hongkong/4801/14 (SEQ ID NO: 92), wherein the amino acid sequence has an Alanine (A, Ala) or a conserved substitution of Alanine (A, Ala) at position 382, no cysteine residue at positions 524 and 528, wherein the sequence does not occur naturally and wherein the HA when expressed form VLP. The conserved substitution of Alanine may for example be Serine (S, Ser), Glycine (G, Gly), Threonine (T, Thr), Cysteine (C, Cys) or Valine (V, Val). The non-cysteine at position 524 may be a Serine (S, Ser) or a conserved substitution of Serine and the non-cysteine at position 528 may be Leucine (L, Leu) or a conserved substitution of Leucine. The conserved substitution of Serine (Se, Ser) may for example be Threonine (T, Thr), Alanine (A, Ala), Asparagine (N, Asn), Aspartic Acid (D, Asp), Glutamine (Q, Gln), Glycine (G, Gly), Glutamic acid (E, Glu) or Lysine (L, Lys). The conserved substitution of Leucine may for example be Isoleucine (I, Ile), Valine (V, Val), Methionine (M, Met), Phenylalanine (F, Phe), or Valine (V, Val).

The present specification also provides a nucleic acid comprising a nucleotide sequence encoding a modified H3 HA with a substitution at positions 382, 524 and 528 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 A/Hongkong/4801/14 (SEQ ID NO: 102), wherein the nucleotide sequence encodes a modified H3 HA protein that has an Alanine (A, Ala) or a conserved substitution of Alanine (A, Ala) at position 382, no cysteine residue at positions 524 and 528, wherein the sequence does not occur naturally and wherein the HA when expressed form VLP. The conserved substitution for Alanine may for example be Serine (S, Ser), Glycine (G, Gly), Threonine (T, Thr), Cysteine (C, Cys) or Valine (V, Val). The non-cysteine at position 524 may be a Serine (S, Ser) or a conserved substitution of Serine and the non-cysteine at position 528 may be Leucine (L, Leu) or a conserved substitution of Leucine. The conserved substitution of Serine (Se, Ser) may for example be Threonine (T, Thr), Alanine (A, Ala), Asparagine (N, Asn), Aspartic Acid (D, Asp), Glutamine (Q, Gln), Glycine (G, Gly), Glutamic acid (E, Glu) or Lysine (L, Lys). The conserved substitution of Leucine may for example be Isoleucine (I, Ile), Valine (V, Val), Methionine (M, Met), Phenylalanine (F, Phe), or Valine (V, Val).

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 102, wherein the nucleotide sequence encodes a modified H3 HA protein that has an Alanine (A, Ala) or a conserved substitution of Alanine (A, Ala) at position 382, no cysteine residue at positions 524 and 528, wherein the sequence does not occur naturally and wherein the HA when expressed form VLP. The conserved substitution of Alanine may for example be Serine (S, Ser), Glycine (G, Gly), Threonine (T, Thr), Cysteine (C, Cys) or Valine (V, Val).

In addition to residues at position 382, 524 and 528, the modified H3 HA may have further residues modified. For example one or more than one residues at position 384, 525, 526 and 527 may be modified. In a non-limiting example the modified H3 HA may have substituted residues at position 382, 524, 528 and one or more substitutions at positions 384, 525, 526, 527 or a combination thereof.

Furthermore, it is provided a method of producing VLPs that comprise a modified H3 HA with a substitution at least at positions 382, 524 and 528 and optionally substitutions at positions 384, 525, 526, 527 above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H3 HA with a substitution at least at position 382, 524 and 528 and optionally substitutions at positions 384, 525, 526, 527, as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H3 HA with a substitution at least at position 382, 524 and 528 and optionally substitutions at positions 384, 525, 526, 527. The VLP may be produced by the method as provided by the present specification. The VLP comprising the modified H3 HA show improved characteristics when compared to VLPs that comprise the unmodified H3 HA protein.

Modification at Position 524-528 (CysTM) and 384

In another aspect it is provided a H3 HA that may have modified residue at position 384, and may be modified to have no cysteine residue at positions 524 and 528 (H3 A/Hongkong/4801/14 numbering, SEQ ID NO: 92). Furthermore, residues at position 525, 526 and/or 527 (H3 A/Hongkong/4801/14 numbering) may also be modified.

As shown for example in FIGS. 7A, 7B and 7C, an H3 HA having cysteine residues at positions 524 and 528 modified to be non-cysteine residues and having residue at position 384 modified from Leucine to Valine, lead to an approximately 270% increase in hemagglutination titer as compared to wildtype H3 HA.

Accordingly, it is provided a modified H3 HA protein that comprise one or more than one modification at position 524, 525, 526, 527 or 528 and a modification at position 384. In a non-limiting example the modified H3 HA has modifications at least at positions 384, 524 and 528.

The residue at position 384 of H3 HA may be modified to be a non-Leucine. For example the residue at position 384 may be modified to another hydrophobic amino acid for example Valine or a conserved substitution of Valine for example Isoleucine, Leucine, Methionine, Alanine or Threonine.

For example the modified H3 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H3 A/Hongkong/4801/14 (SEQ ID NO: 92), wherein the amino acid sequence has a Valine or a conserved substitution of Valine at position 384, no cysteine residue at positions 524 and 528, wherein the sequence does not occur naturally and wherein the HA when expressed form VLP. The conserved substitution of Valine may for example be Isoleucine, Leucine, Methionine, Alanine or Threonine.

The present specification also provides a nucleic acid comprising a nucleotide sequence encoding a modified H3 HA with a substitution at positions 384, 524 and 528 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 A/Hongkong/4801/14 (SEQ ID NO: 102), wherein the nucleotide sequence encodes a modified H3 HA protein that has a Valine or a conserved substitution of Valine at position 384, no cysteine residue at positions 524 and 528 and wherein the sequence does not occur naturally. The conserved substitution may for example be Isoleucine, Leucine, Methionine, Alanine or Threonine.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 102, wherein the nucleotide sequence encodes a modified H3 HA protein that has a Valine or a conserved substitution of Valine at position 384, no cysteine residue at positions 524 and 528, wherein the sequence does not occur naturally and wherein the HA when expressed form VLP. The conserved substitution of Valine may for example be Isoleucine, Leucine, Methionine, Alanine or Threonine.

In addition to residues at position 384, 524 and 528, the modified H3 HA may have further residues modified. For example one or more than one residues at position 382, 525, 526 and 527 may be modified. In a non-limiting example the modified H3 HA may have substituted residues at position 384, 524, 528 and one or more substitutions at positions 382, 525, 526, 527 or a combination thereof.

Furthermore, it is provided a method of producing VLPs that comprise a modified H3 HA with a substitution at least at positions 384, 524 and 528 and optionally substitutions at positions 382, 525, 526, 527 above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H3 HA with a substitution at least at position 384, 524 and 528 and optionally substitutions at positions 382, 525, 526, 527, as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H3 HA with a substitution at least at position 384, 524 and 528 and optionally substitutions at positions 382, 525, 526, 527. The VLP may be produced by the method as provided by the present specification. The VLP comprising the modified H3 HA show improved characteristics when compared to VLPs that comprise the unmodified H3 HA protein.

Modification at Position 524-528 (CysTM) and 392

In another aspect it is provided a H3 HA that may have modified residue at position 392, and may have no cysteine residue at positions 524 and 528 (H3 A/Hongkong/4801/14 numbering, SEQ ID NO: 92). Furthermore, residues at position 525, 526 and/or 527 (H3 A/Hongkong/4801/14 numbering) may also be modified.

As shown for example in FIGS. 7A and 7B, an H3 HA having cysteine residues at positions 524 and 528 modified to be no cysteine and having residue at position 392 modified from Phenylalanine to Aspartic Acid, lead to an 200% to 270% increase in hemagglutination titer as compared to wildtype H3 HA.

Accordingly, it is provided a modified H3 HA protein that comprise one or more than one modification at position 524, 525, 526, 527 or 528 and a modification at position 392. In a non-limiting example the modified H3 HA has modifications at least at positions 392, 524 and 528.

The residue at position 392 of H3 HA may be modified to be a non-Phenylalanine. For example the residue at position 392 may be modified to a charged amino acid for example Aspartic Acid or a conserved substitution of Aspartic Acid for example Glutamine, Asparagine, Glutamic Acid or Serine.

For example the modified H3 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H3 A/Hongkong/4801/14 (SEQ ID NO: 92), wherein the amino acid sequence has a Aspartic Acid or a conserved substitution of Aspartic Acid at position 392, no cysteine residue at positions 524 and 528, wherein the sequence does not occur naturally and wherein the HA when expressed form VLP. The conserved substitution of Aspartic Acid may for example be Glutamine, Asparagine, Glutamic Acid or Serine. The non-cysteine at position 524 may be a Serine (S, Ser) or a conserved substitution of Serine and the non-cysteine at position 528 may be Leucine (L, Leu) or a conserved substitution of Leucine. The conserved substitution of Serine (Se, Ser) may for example be Threonine (T, Thr), Alanine (A, Ala), Asparagine (N, Asn), Aspartic Acid (D, Asp), Glutamine (Q, Gln), Glycine (G, Gly), Glutamic acid (E, Glu) or Lysine (L, Lys). The conserved substitution of Leucine may for example be Isoleucine (I, Ile), Valine (V, Val), Methionine (M, Met), Phenylalanine (F, Phe), or Valine (V, Val).

The present specification also provides a nucleic acid comprising a nucleotide sequence encoding a modified H3 HA with a substitution at positions 392, 524 and 528 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 A/Hongkong/4801/14 (SEQ ID NO: 102), wherein the nucleotide sequence encodes a modified H3 HA protein that has Aspartic Acid or a conserved substitution of Aspartic Acid at position 392, no cysteine residue at positions 524 and 528, wherein the sequence does not occur naturally and wherein the HA when expressed form VLP. The conserved substitution may for example be Glutamine, Asparagine, Glutamic Acid or Serine.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 102, wherein the nucleotide sequence encodes a modified H3 HA protein that has Aspartic Acid or a conserved substitution of Aspartic Acid at position 392, no cysteine residue at positions 524 and 528, wherein the sequence does not occur naturally and wherein the HA when expressed form VLP. The conserved substitution may for example be Glutamine, Asparagine, Glutamic Acid or Serine.

In addition to residues at positions 392, 524 and 528, the modified H3 HA may have further residues modified. For example one or more than one residues at position 525, 526 and 527 may be modified. In a non-limiting example the modified H3 HA may have substituted residues at position 392, 524, 528 and one or more substitutions at positions 525, 526, 527 or a combination thereof.

Furthermore, it is provided a method of producing VLPs that comprise a modified H3 HA with a substitution at least at positions 392, 524 and 528 and optionally substitutions at positions 525, 526, 527 above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H3 HA with a substitution at least at position 392, 524 and 528 and optionally substitutions at positions 525, 526, 527, as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H3 HA with a substitution at least at position 392, 524 and 528 and optionally substitutions at positions 525, 526, 527. The VLP may be produced by the method as provided by the present specification. The VLP comprising the modified H3 HA show improved characteristics when compared to VLPs that comprise the unmodified H3 HA protein.

Modification at Position 524-528 (CysTM) and 431

In another aspect it is provided a H3 HA that may have a modified residue at position 431, and may have no cysteine residue at positions 524 and 528 (H3 A/Hongkong/4801/14 numbering, SEQ ID NO: 92). Furthermore, residues at position 525, 526 and/or 527 (H3 A/Hongkong/4801/14 numbering) may also be modified.

As shown for example in FIGS. 7A and 7B, an H3 HA having cysteine residues at positions 524 and 528 modified to be no cysteine and having residue at position 431 modified from Leucine to Methionine, lead to an approximately 250% increase in hemagglutination titer as compared to wildtype H3 HA.

Accordingly, it is provided a modified H3 HA protein that comprise one or more than one modification at position 524, 525, 526, 527 or 528 and a modification at position 431. In a non-limiting example the modified H3 HA has modifications at least at positions 431, 524 and 528.

The residue at position 431 of H3 HA may be modified to be a non-Leucine. For example the residue at position 431 may be modified be Methionine or a conserved substitution of Methionine for example Leucine, Isoleucine, Glutamine, Valine, or Phenylalanine.

For example the modified H3 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H3 A/Hongkong/4801/14 (SEQ ID NO: 92), wherein the amino acid sequence has a Methionine or a conserved substitution of Methionine at position 431, no cysteine residue at positions 524 and 528, wherein the sequence does not occur naturally and wherein the HA when expressed form VLP. The conserved substitution of Methionine may for example be example Leucine, Isoleucine, Glutamine, Valine, or Phenylalanine. The non-cysteine at position 524 may be a Serine (S, Ser) or a conserved substitution of Serine and the non-cysteine at position 528 may be Leucine (L, Leu) or a conserved substitution of Leucine. The conserved substitution of Serine (Se, Ser) may for example be Threonine (T, Thr), Alanine (A, Ala), Asparagine (N, Asn), Aspartic Acid (D, Asp), Glutamine (Q, Gln), Glycine (G, Gly), Glutamic acid (E, Glu) or Lysine (L, Lys). The conserved substitution of Leucine may for example be Isoleucine (I, Ile), Valine (V, Val), Methionine (M, Met), Phenylalanine (F, Phe), or Valine (V, Val).

The present specification also provides a nucleic acid comprising a nucleotide sequence encoding a modified H3 HA with a substitution at positions 431, 524 and 528 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 A/Hongkong/4801/14 (SEQ ID NO: 102), wherein the nucleotide sequence encodes a modified H3 HA protein that has Methionine or a conserved substitution of Methionine at position 431, no cysteine residue at positions 524 and 528, wherein the sequence does not occur naturally and wherein the HA when expressed form VLP. The conserved substitution may for example be Leucine, Isoleucine, Glutamine, Valine, or Phenylalanine.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 102, wherein the nucleotide sequence encodes a modified H3 HA protein that has Methionine or a conserved substitution of Methionine at position 431, no cysteine residue at positions 524 and 528, wherein the sequence does not occur naturally and wherein the HA when expressed form VLP. The conserved substitution may for example be Leucine, Isoleucine, Glutamine, Valine, or Phenylalanine.

In addition to residues at positions 431, 524 and 528, the modified H3 HA may have further residues modified. For example one or more than one residues at position 525, 526 and 527 may be modified. In a non-limiting example the modified H3 HA may have substituted residues at position 431, 524, 528 and one or more substitutions at positions 525, 526, 527 or a combination thereof.

Furthermore, it is provided a method of producing VLPs that comprise a modified H3 HA with a substitution at least at positions 431, 524 and 528 and optionally substitutions at positions 525, 526, 527 above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H3 HA with a substitution at least at position 431, 524 and 528 and optionally substitutions at positions 525, 526, 527, as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H3 HA with a substitution at least at position 431, 524 and 528 and optionally substitutions at positions 525, 526, 527. The VLP may be produced by the method as provided by the present specification. The VLP comprising the modified H3 HA show improved characteristics when compared to VLPs that comprise the unmodified H3 HA protein.

Modification at Position 524-528 (CysTM), 382 and 384

In another aspect it is provided a H3 HA that may have modified residues at position 382 and 384, and may have no cysteine residue at positions 524 and 528 (H3 A/Hongkong/4801/14 numbering, SEQ ID NO: 92). Furthermore, residues at position 525, 526 and/or 527 (H3 A/Hongkong/4801/14 numbering) may also be modified.

As shown for example in FIG. 7E, an H3 HA having cysteine residues at positions 524 and 528 modified to be non-cysteine and having residue at position 382 modified from Asparagine to Alanine and residue at position 384 modified from Leucine to Valine, lead to an approximately 400% to 500% increase in hemagglutination titer as compared to wildtype H3 HA.

Accordingly, it is provided a modified H3 HA protein that comprise one or more than one modification at position 524, 525, 526, 527 or 528 and a modification at position 382 and 384. In a non-limiting example the modified H3 HA has modifications at least at positions 382, 384, 524 and 528.

The residue at position 382 of H3 HA may be modified to be a non-Asparagine. For example the residue at position 382 may be modified to be a hydrophobic amino acid for example Alanine or a conserved substitution of Alanine for example Serine (S, Ser), Glycine (G, Gly), Threonine (T, Thr), Cysteine (C, Cys) or Valine (V, Val). The residue at position 384 of H3 HA may be modified to be a non-Leucine. For example the residue at position 384 may be modified to another hydrophobic amino acid for example Valine or a conserved substitution of Valine for example Isoleucine, Leucine, Methionine, Alanine or Threonine.

For example the modified H3 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H3 A/Hongkong/4801/14 (SEQ ID NO: 92), wherein the amino acid sequence has an Alanine (A, Ala) or a conserved substitution of Alanine (A, Ala) at position 382, a Valine or a conserved substitution of Valine at position 384, no cysteine residue at positions 524 and 528 and wherein the sequence does not occur naturally and wherein the HA when expressed form VLP. The conserved substitution of Alanine may for example be Serine (S, Ser), Glycine (G, Gly), Threonine (T, Thr), Cysteine (C, Cys) or Valine (V, Val). The conserved substitution of Valine may for example be Isoleucine (I, Ile), Leucine (L, Leu), Methionine (M, Met), Alanine A, Ala) or Threonine (T, Thr). The non-cysteine at position 524 may be a Serine (S, Ser) or a conserved substitution of Serine and the non-cysteine at position 528 may be Leucine (L, Leu) or a conserved substitution of Leucine. The conserved substitution of Serine (Se, Ser) may for example be Threonine (T, Thr), Alanine (A, Ala), Asparagine (N, Asn), Aspartic Acid (D, Asp), Glutamine (Q, Gln), Glycine (G, Gly), Glutamic acid (E, Glu) or Lysine (L, Lys). The conserved substitution of Leucine may for example be Isoleucine (I, Ile), Valine (V, Val), Methionine (M, Met), Phenylalanine (F, Phe), or Valine (V, Val).

The present specification also provides a nucleic acid comprising a nucleotide sequence encoding a modified H3 HA with a substitution at positions 382, 384, 524 and 528 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H3 A/Hongkong/4801/14 (SEQ ID NO: 102), wherein the nucleotide sequence encodes a modified H3 HA protein that has an Alanine (A, Ala) or a conserved substitution of Alanine (A, Ala) at position 382, a Valine or a conserved substitution of Valine at position 384, no cysteine residue at positions 524 and 528 and wherein the sequence does not occur naturally and wherein the HA when expressed form VLP. The conserved substitution of Alanine may for example be Serine (S, Ser), Glycine (G, Gly), Threonine (T, Thr), Cysteine (C, Cys) or Valine (V, Val). The conserved substitution of Valine may for example be Isoleucine (I, Ile), Leucine (L, Leu), Methionine (M, Met), Alanine A, Ala) or Threonine (T, Thr). The non-cysteine at position 524 may be a Serine (S, Ser) or a conserved substitution of Serine and the non-cysteine at position 528 may be Leucine (L, Leu) or a conserved substitution of Leucine. The conserved substitution of Serine (Se, Ser) may for example be Threonine (T, Thr), Alanine (A, Ala), Asparagine (N, Asn), Aspartic Acid (D, Asp), Glutamine (Q, Gln), Glycine (G, Gly), Glutamic acid (E, Glu) or Lysine (L, Lys). The conserved substitution of Leucine may for example be Isoleucine (I, Ile), Valine (V, Val), Methionine (M, Met), Phenylalanine (F, Phe), or Valine (V, Val).

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 102, wherein the nucleotide sequence encodes a modified H3 HA protein that has an Alanine (A, Ala) or a conserved substitution of Alanine (A, Ala) at position 382, a Valine or a conserved substitution of Valine at position 384, no cysteine residue at positions 524 and 528 and wherein the sequence does not occur naturally and wherein the HA when expressed form VLP. The conserved substitution of Alanine may for example be Serine (S, Ser), Glycine (G, Gly), Threonine (T, Thr), Cysteine (C, Cys) or Valine (V, Val). The conserved substitution of Valine may for example be Isoleucine (I, Ile), Leucine (L, Leu), Methionine (M, Met), Alanine A, Ala) or Threonine (T, Thr). The non-cysteine at position 524 may be a Serine (S, Ser) or a conserved substitution of Serine and the non-cysteine at position 528 may be Leucine (L, Leu) or a conserved substitution of Leucine. The conserved substitution of Serine (Se, Ser) may for example be Threonine (T, Thr), Alanine (A, Ala), Asparagine (N, Asn), Aspartic Acid (D, Asp), Glutamine (Q, Gln), Glycine (G, Gly), Glutamic acid (E, Glu) or Lysine (L, Lys). The conserved substitution of Leucine may for example be Isoleucine (I, Ile), Valine (V, Val), Methionine (M, Met), Phenylalanine (F, Phe), or Valine (V, Val).

In addition to residues at position 382, 384, 524 and 528, the modified H3 HA may have further residues modified. For example one or more than one residues at positions 525, 526 and 527 may be modified. In a non-limiting example the modified H3 HA may have substituted residues at positions 382, 384, 524, 528 and one or more substitutions at positions 525, 526, 527 or a combination thereof.

Furthermore, it is provided a method of producing VLPs that comprise a modified H3 HA with a substitution at least at positions 382, 384, 524 and 528 and optionally substitutions at positions 525, 526, 527 above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H3 HA with a substitution at least at position 382, 384, 524 and 528 and optionally substitutions at positions 525, 526, 527, as described above in a plant. The method involves introducing a nucleic acid encoding a modified H3 HA operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H3 HA with a substitution at least at position 382, 384, 524 and 528 and optionally substitutions at positions 525, 526, 527. The VLP may be produced by the method as provided by the present specification. The VLP comprising the modified H3 HA show improved characteristics when compared to VLPs that comprise the unmodified H3 HA protein.

Also provided herein are methods of increasing production or yield of VLPs comprising mutant influenza HAs in plants. For example, a method may involve introducing a nucleic acid encoding a mutant influenza HA, as described herein, into the plant, portion of the plant, or plant cell. The nucleic acid encoding the mutant influenza HA may be optimized for human codon usage, increased GC content, or a combination thereof. One or more than one mutant influenza HA protein may be expressed in a plant, portion of the plant, or plant cell, in order to produce a VLP comprising one or more than one mutant influenza HA protein. Alternatively, the method may comprise providing a plant, portion of the plant, or plant cell that comprises the nucleic acid encoding the mutant influenza HA protein in order to produce a VLP comprising the one or more than one mutant influenza HA protein.

The methods of producing a VLP comprising a mutant influenza HA may further comprise a step of introducing a second nucleic acid sequence into the plant, portion of the plant, or plant cell, wherein the second nucleic acid encodes a proton channel protein that is co-expressed with the mutant influenza HA. For example, the proton channel protein may be an influenza A subtype M2 protein, such as A/New Caledonia/20/99 M2. The co-expression of the proton channel protein may lead to an increased accumulation of mutant influenza HA protein and/or VLP comprising the mutant influenza HA protein as for example described in WO 2013/044390 which is incorporated herein by reference.

Furthermore, the mutant influenza HA might further comprise a modified proteolytic loop or cleavage site as described in WO 2013/044390 and WO 2014/153674 and which are incorporated herein by reference.

By "co-expression", it is meant the introduction and expression of two or more nucleotide sequences, each of the two or more nucleotide sequences encoding a protein of interest, or a fragment of a protein of interest within a plant, portion of a plant or a plant cell. The two or more nucleotide sequences may be introduced into the plant, portion of the plant or the plant cell within one vector, so that each of the two or more nucleotide sequences is under the control of a separate regulatory region (e.g. comprising a dual construct). Alternatively, the two or more nucleotide sequences may be introduced into the plant, portion of the plant or the plant cell within separate vectors (e.g. comprising single constructs), and each vector comprising appropriate regulatory regions for the expression of the corresponding nucleic acid. For example, two nucleotide sequences, each on a separate vector and introduced into separate *Agrobacterium tumefaciens* hosts, may be co-expressed by mixing suspensions of each *A. tumefaciens* host in a desired volume (for example, an equal volume, or the ratios of each *A. tumefaciens* host may be altered) before vacuum infiltration. In this manner, co-infiltration of multiple *A. tumefaciens* suspensions permits co-expression of multiple transgenes.

The nucleic acid encoding a mutant influenza HA as described herein may further comprise sequences that enhance expression of the mutant influenza HA in a plant, portion of the plant, or plant cell. Sequences that enhance expression may include, a cowpea mosaic virus (CPMV) enhancer element in operative association with the nucleic acid encoding the mutant influenza HA protein.

The nucleic acid comprising a nucleotide sequence encoding a modified influenza hemagglutinin (HA) protein, as described herein may further comprise sequences that enhance expression of the HA protein in the plant, portion of the plant, or plant cell. Sequences that enhance expression may include, a CPMV enhancer element, or a plant-derived expression enhancer, in operative association with the nucleic acid encoding the modified influenza hemagglutinin (HA) protein. The sequence encoding the modified influenza hemagglutinin (HA) may also be optimized for human codon usage, increased GC content, or a combination thereof.

The term "CPMV enhancer element", as used herein, refers to a nucleotide sequence encoding the 5'UTR regulating the Cowpea Mosaic Virus (CPMV) RNA2 polypeptide or a modified CPMV sequence as is known in the art. For example, a CPMV enhancer element or a CPMV expression enhancer, includes a nucleotide sequence as described in WO2015/14367; WO2015/103704; WO2007/135480; WO2009/087391; Sainsbury F., and Lomonossoff G. P., (2008, Plant Physiol. 148: pp. 1212-1218), each of which is incorporated herein by reference. A CPMV enhancer sequence can enhance expression of a downstream heterologous open reading frame (ORF) to which they are attached. The CPMV expression enhancer may include CPMV HT, CPMVX (where X=160, 155, 150, 114), for example CPMV 160, CPMVX+(where X=160, 155, 150, 114), for example CPMV 160+, CPMV-HT+, CPMV HT+ [WT115], or CPMV HT+(WO2015/143567; WO2015/103704 which are incorporated herein by reference). The CPMV expression enhancer may be used within a plant expression system comprising a regulatory region that is operatively linked with the CPMV expression enhancer sequence and a nucleotide sequence of interest.

The term "CPMV enhancer element", as used herein, refers to a nucleotide sequence encoding the 5'UTR regulating the Cowpea Mosaic Virus (CPMV) RNA2 polypeptide or a modified CPMV sequence as is known in the art. For example, a CPMV enhancer element or a CPMV expression enhancer, includes a nucleotide sequence as described in WO2015/14367; WO2015/103704; WO2007/135480; WO2009/087391; Sainsbury F., and Lomonossoff G. P., (2008, Plant Physiol. 148: pp. 1212-1218), each of which is incorporated herein by reference. A CPMV enhancer sequence can enhance expression of a downstream heterologous open reading frame (ORF) to which they are attached. The CPMV expression enhancer may include CPMV HT, CPMVX, CPMVX+, CPMV-HT+, CPMV HT+ [WT115], or CPMV HT+(WO2015/14367; WO2015/103704 which are incorporated herein by reference). The CPMV expression enhancer may be used within a plant expression system comprising a regulatory region that is operatively linked with the CPMV expression enhancer sequence and a nucleotide sequence of interest.

The term "S'UTR" or "5' untranslated region" or "5' leader sequence" refers to regions of an mRNA that are not translated. The 5'UTR typically begins at the transcription start site and ends just before the translation initiation site or start codon of the coding region. The 5' UTR may modulate the stability and/or translation of an mRNA transcript.

The term "plant-derived expression enhancer", as used herein, refers to a nucleotide sequence obtained from a plant, the nucleotide sequence encoding a 5'UTR. Examples of a plant derived expression enhancer are described in U.S. Provisional Patent Application No. 62/643,053 (Filed Mar. 14, 2018; which is incorporated herein by reference) or in Diamos A. G. et al. (2016, Front Plt Sci. 7:1-15; which is incorporated herein by reference). The plant-derived expression enhancer may be selected from nbMT78, nbATL75, nbDJ46, nbCHP79, nbEN42, atHSP69, atGRP62, atPK65, atRP46, nb30S72, nbGT61, nbPV55, nbPPI43, nbPM64, and nbH2A86 as described in U.S. 62/643,053). The plant derived expression enhancer may be used within a plant expression system comprising a regulatory region that is operatively linked with the plant-derived expression enhancer sequence and a nucleotide sequence of interest.

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

When one or more than one mutant influenza HA protein is expressed in a plant, portion of the plant, or plant cell, the one or more than one mutant influenza HA proteins self-assemble into VLPs. The plant, portion of the plant, or plant cell, may be harvested under suitable extraction and purification conditions to maintain the integrity of the VLP, and the VLP comprising the one or more than one mutant influenza HA may be purified.

The present invention also provides the use of a mutant influenza HA, or VLP comprising the mutant influenza HA, as described herein, for inducing immunity to an influenza infection in a subject. Also disclosed herein is an antibody or antibody fragment, prepared by administering the mutant influenza HA or VLP comprising the mutant influenza HA, to a subject or a host animal. Further provided is a composition comprising an effective dose of a mutant influenza HA or VLP comprising the mutant influenza HA, as described herein, and a pharmaceutically acceptable carrier, adjuvant, vehicle, or excipient, for inducing an immune response in a subject. Also provided is a vaccine for inducing an immune response in a subject, wherein the vaccine comprises an effective dose of the mutant influenza HA.

Also provided herein are methods for inducing immunity to an influenza infection in a subject comprising of administering the mutant influenza HA or VLP comprising the mutant influenza HA, to a subject orally, intranasally, intramuscularly, intraperitoneally, intravenously, or subcutaneously.

The term "influenza virus", as used herein, refers to an enveloped viral strain of the family Orthomyxoviridae that is characterized as having a negative sense single-stranded RNA genome. The influenza virus genome comprises eight gene segments coding for 12-14 proteins depending on the strain.

There are four types of influenza virus: A, B, C and D, of which influenza A or B are the causative organism for seasonal disease epidemics in humans. Influenza A is further classified based on the expression of HA and neuraminidase (NA) glycoprotein subtypes.

The term "hemagglutinin" or "HA", as used herein, refers to a trimeric lectin that facilitates binding of the influenza virus particle to sialic acid-containing proteins on the surface of target cells and mediates release of the viral genome into the target cell. There are 18 different HA subtypes (H1-H18). HA proteins comprise two structural elements: the head, which is the primary target of seroprotective antibodies; and the stalk. HA is translated as a single polypeptide, HA0 (assembled as trimers), that must be cleaved by a serine endoprotease between the HA1 (~40 kDa) and HA2 (~20 kDa) subdomains. After cleavage, the two disulfide-bonded protein domains adopt the requisite conformation necessary for viral infectivity.

Influenza A HA proteins or modified influenza A HA proteins as disclosed herein, include any known HA proteins derived from any known influenza A strain, but also modifications to known influenza A strains that develop over time. For example, influenza HA may be derived from A/Hong Kong/4801/14 (H3N2), A/Minnesota/40/15 (H3N2), A/South Australia/1/16 (H3N2), A/Bangkok/3007/15 (H3N2), A/Switzerland/9715293/13 (H3N2), A/Mississippi/16/16 (H3N2), or A/Pennsylvania/09/2015 (H3N2). Influenza A HA may include HA derived from strains, wherein the HA has about 30-100%, or any amount therebetween, amino acid sequence identity to any HA derived from the influenza A strains listed above, provided that the influenza HA protein comprises at least one substitution as described herewith and is able to form VLPs, induces an immune response when administered to a subject, induces hemagglutination or a combination thereof.

For example, influenza HA proteins may have 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100%, or any amount therebetween, amino acid sequence identity (sequence similarity, percent identity, percent similarity) to any HA derived from the influenza A strains listed above and comprises at least one substitution as described herewith and is able to form VLPs, induces an immune response when administered to a subject, induces hemagglutination or a combination thereof. An amino acid sequence alignment of several influenza A HA domains, which are not to be considered limiting, is shown in FIG. 1.

The terms "percent similarity", "sequence similarity", "percent identity", or "sequence identity", when referring to a particular sequence, are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Natl. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

The term "virus-like particle", VLP, "virus like particles", or "VLPs", as used herein, refers to influenza particles that comprise one or more than one influenza HA protein, and that self-assemble into non-replicating, non-infectious viral capsid structures lacking all parts of the influenza genome.

Influenza HA Protein Production in Plants

Influenza A HA protein includes any HA protein comprising an amino acid sequence having from about 30 to about 100%, from about 40 to about 100%, from about 50 to about 100%, from about 60 to about 100%, from about 70 to about 100%, from about 80 to about 100%, from about 85 to about 100%, from about 90 to about 100%, from 95 to about 100%, or from about 97 to about 100% from about 98 to about 100%, or any amount therebetween, sequence identity or sequence similarity with influenza A HA sequence from a A/Hong Kong/4801/14 (H3N2, SEQ ID NO: 92), A/Minnesota/40/15 (H3N2, SEQ ID NO: 93), A/South Australia/1/16 (H3N2, SEQ ID NO: 94), A/Bangkok/3007/15 (H3N2, SEQ ID NO: 91), A/Switzerland/9715293/13 (H3N2, SEQ ID NO: 96), A/Mississippi/16/16 (H3N2, SEQ ID NO: 97), and A/Pennsylvania/09/2015 (H3N2, SEQ ID NO: 95), provided that the influenza HA protein comprises at least one substitution as described herewith and is able to form VLPs, induces an immune response when administered to a subject, induces hemagglutination or a combination thereof.

Furthermore the modified influenza HA protein includes any HA protein comprising an amino acid sequence having from about 30% to about 100%, from about 40% to about 100%, from about 50% to about 100%, from about 60% to about 100%, from about 70% to about 100%, from about 80% to about 100%, from about 85% to about 100%, from about 90% to about 100%, from 95% to about 100%, or from about 97% to about 100% from about 98% to about 100%, or any amount therebetween, sequence identity or sequence similarity with a sequence of the sequences of SEQ ID NO: 25, SEQ ID NO: 30, SEQ ID NO: 35, SEQ ID NO: 39, SEQ ID NO: 43, SEQ ID NO: 47, SEQ ID NO: 49, SEQ ID NO: 53, SEQ ID NO: 57, SEQ ID NO: 59, SEQ ID NO: 61, SEQ ID NO: 82, SEQ ID NO: 84, SEQ ID NO: 86, SEQ ID NO: 88, SEQ ID NO: 90, provided that the influenza HA protein comprises at least one substitution as described herewith and is able to form VLPs, induces an immune response when administered to a subject, induces hemagglutination or a combination thereof.

As described herein, one or more than one specific mutation or modification in influenza HA results in increased accumulation of HA protein and increased VLP production in plants, as compared to wildtype influenza HA.

Examples of mutant influenza A HA proteins having enhanced influenza HA and/or VLP production in plants include, but are not limited to the following:

CysTM A/Hong Kong/4801/14 Mutant H3 (Construct #3341, SEQ ID NO: 21), N382A+L384V+CysTM A/Hong Kong/4801/14 Mutant H3 (Construct #3375, SEQ ID NO: 25); CysTM A/Minnesota/40/15 Mutant H3 (Construct #3914, SEQ ID NO:27); N382A+L384V+CysTM A/Minnesota/40/15 Mutant H3 (Construct #3915, SEQ ID NO:30); CysTM A/S. Australia/1/16 Mutant H3 (Construct #3924, SEQ ID NO: 33); N382A+L384V+CysTM A/S. Australia/1/16 Mutant H3 (Construct #3925, SEQ ID NO: 35); N382A+L384V+CysTM A/Bangkok/3007/15 Mutant H3 (Construct #3905, SEQ ID NO: 39); N382A A/Switzerland/9715293/13 Mutant H3 (Construct #3023, SEQ ID NO: 82); L384V A/Switzerland/9715293/13 Mutant H3 (Construct #3034, SEQ ID NO: 84); F392D A/Switzerland/9715293/13 Mutant H3 (Construct #3045, SEQ ID NO: 43; L431M A/Switzerland/9715293/13 Mutant H3 (Construct #3022, SEQ ID NO: 47); CysTM A/Switzerland/9715293/13 Mutant H3 (Construct #2811, SEQ ID NO: 49); N382A+CysTM A/Switzerland/9715293/13 Mutant H3 (Construct #3063, SEQ ID NO:53); L384V+CysTM A/Switzerland/9715293/13 Mutant H3 (Construct #3074, SEQ ID NO:57); F392D+CysTM A/Switzerland/9715293/13 Mutant H3 (Construct #3085, SEQ ID NO: 59); and L431M+ CysTM A/Switzerland/9715293/13 Mutant H3 (Construct #3062, SEQ ID NO: 61), CysTM A/Pennsylvania/09/2015 mutant H3 (Construct #3313, SEQ ID NO: 86), N382A+CysTM A/Pennsylvania/09/2015 mutant H3 (Construct #3314, SEQ ID NO: 88), and L384V+ CysTM A/Pennsylvania/09/2015 mutant H3 (Construct #3315, SEQ ID NO: 90).

Induction of Immunity Against Influenza Infection

An "immune response" generally refers to a response of the adaptive immune system of a subject. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity may be of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-influenza HA antibody titres may be quantified using an ELISA assay: isotypes of antigen-specific or cross reactive antibodies may also be measured using anti-isotype antibodies (e.g. anti-IgG, IgA, IgE or IgM). Methods and techniques for performing such assays are well-known in the art.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be quantified in a number of ways, including: enumeration of lysis plaques (plaque assay) following crystal violent fixation/coloration of cells; microscopic observation of cell lysis in in vitro culture; and 2) ELISA and spectrophotometric detection of influenza virus.

The term "epitope" or "epitopes", as used herein, refers to a structural part of an antigen to which an antibody specifically binds.

Immune responses elicited in response to administration of plant-produced wildtype influenza HA proteins or VLPs, or mutant influenza HA proteins or VLPs may for example be observed in Balb/C mice. Serum samples from blood collected from animals may be analyzed by ELISA for H3-specific total IgG and IgA antibodies. Mice immunized with either plant-produced wildtype influenza HA or mutant influenza HA proteins may exhibit HA-specific IgG antibody titers in sera for each treatment group.

Plant Expression

The constructs of the present invention may be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, *Fundamentals of Gene Transfer in Plants*. In *Plant Metabolism,* 2d Ed. DT. Dennis, DH Turpin, DD Lefebrvre, DB Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991*, Gene* 100: 247-250), Scheid et al. (1991*, Mol. Gen. Genet.* 228: 104-112), Guerche et al. (1987*, Plant Science* 52: 111-116), Neuhause et al. (1987*, Theor. Appl Genet.* 75: 30-36), Klein et al. (2987*, Nature* 327: 70-73); Freeman et al. (1984*, Plant Cell Physiol.* 29: 1353), Howell et al. (1985*, Science* 227: 1229-1231), DeBlock et al. (1989*, Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002*, J Virol Meth,* 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009, *Methods in molecular biology*, Vol 483, pages 41-50; Liu and Lomonossoff, 2002, *Journal of Virological Methods,* 105:343-348; which is incorporated herein by reference). Alternatively, a vacuum-based transient expression method, as described by Kapila et al. (1997, *Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy R R D ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al. (Cell Culture and Somatic Cell Genetics of Plants, Vol I, II and III, Laboratory Procedures and Their Applications, Academic Press, 1984), and Weissbach and Weissbach (Methods for Plant Molecular Biology, Academic Press, 1989). The method of obtaining transformed and regenerated plants is not critical to the present invention.

If plants, plant portions or plant cells are to be transformed or co-transformed by two or more nucleic acid constructs, the nucleic acid construct may be introduced into the *Agrobacterium* in a single transfection event so that the nucleic acids are pooled, and the bacterial cells transfected. Alternatively, the constructs may be introduced serially. In this case, a first construct is introduced into the *Agrobacterium* as described, the cells are grown under selective conditions (e.g. in the presence of an antibiotic) where only the singly transformed bacteria can grow. Following this first selection step, a second nucleic acid construct is introduced into the *Agrobacterium* as described, and the cells are grown under doubly-selective conditions, where only the doubly-transformed bacteria can grow. The doubly-transformed bacteria may then be used to transform a plant, portion of the plant or plant cell as described herein, or may be subjected to a further transformation step to accommodate a third nucleic acid construct.

Alternatively, if plants, plant portions, or plant cells are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various Agrobacteria populations comprising the desired constructs may be varied.

TABLE 3

SEQ ID NOs and Description of Sequences

| SEQ ID NO: | Description of Sequence |
|---|---|
| SEQ ID NO: 1 | PDI - H3 HK DNA |
| SEQ ID NO: 2 | PDI - H3 HK AA |
| SEQ ID NO: 3 | PDI - H3 Minn DNA |
| SEQ ID NO: 4 | PDI - H3 Minn AA |
| SEQ ID NO: 5 | PDI - H3 SAus DNA |
| SEQ ID NO: 6 | PDI - H3 SAus AA |
| SEQ ID NO: 7 | PDI - H3 Bang DNA |
| SEQ ID NO: 8 | PDI - H3 Bang AA |
| SEQ ID NO: 9 | PDI - H3 Switz DNA |
| SEQ ID NO: 10 | PDI - H3 Switz AA |
| SEQ ID NO: 11 | PDI - H3 Miss DNA |
| SEQ ID NO: 12 | PDI - H3 Miss AA |
| SEQ ID NO: 13 | PDI - H3 Penn DNA |
| SEQ ID NO: 14 | PDI - H3 Penn AA |
| SEQ ID NO: 15 | IF - CPMV(fl5'UTR)_SpPDI.c |
| SEQ ID NO: 16 | IF - H1cTMCT.S1 - 4r |
| SEQ ID NO: 17 | IF - H3A - Ala.r |
| SEQ ID NO: 18 | H3_Swi_SL VLL.r |
| SEQ ID NO: 19 | H3_Swi_SL VLL.c |
| SEQ ID NO: 20 | PDI - H3 HK - CysTm DNA |
| SEQ ID NO: 21 | PDI - H3 HK - CysTm AA |
| SEQ ID NO: 22 | H3_HK480114(N382A + L384V).r |
| SEQ ID NO: 23 | H3_HK480114(N382A + L384V).c |
| SEQ ID NO: 24 | PDI - H3 HK - N382A + L384V - CysTm DNA |
| SEQ ID NO: 25 | PDI - H3 HK - N382A + L384V - CysTm AA |
| SEQ ID NO: 26 | PDI - H3 Minn - CysTm DNA |
| SEQ ID NO: 27 | PDI - H3 Minn - CysTm AA |
| SEQ ID NO: 28 | H3Minn(N382A + L384V).r |
| SEQ ID NO: 29 | H3Minn(N382A + L384V).c |
| SEQ ID NO: 30 | PDI - H3 Minn - N382A + L384V - CysTm DNA |
| SEQ ID NO: 31 | PDI - H3 Minn - N382A + L384V - CysTm AA |
| SEQ ID NO: 32 | PDI - H3 SAus - CysTm DNA |
| SEQ ID NO: 33 | PDI - H3 SAus - CysTm AA |
| SEQ ID NO: 34 | PDI - H3 SAus - N382A + L384V - CysTm DNA |
| SEQ ID NO: 35 | PDI - H3 SAus - N382A + L384V - CysTm AA |
| SEQ ID NO: 36 | PDI - H3 Bang - CysTm DNA |
| SEQ ID NO: 37 | PDI - H3 Bang - CysTm AA |
| SEQ ID NO: 38 | PDI - H3 Bang - N382A + L384V - CysTm DNA |
| SEQ ID NO: 39 | PDI - H3 Bang - N382A + L384V - CysTm AA |
| SEQ ID NO: 40 | H3_Swi(F392D).r |
| SEQ ID NO: 41 | H3_Swi(F392D).c |
| SEQ ID NO: 42 | PDI - H3 Switz - F392D DNA |
| SEQ ID NO: 43 | PDI - H3 Switz - F392D AA |
| SEQ ID NO: 44 | H3_Swi(L431M).r |
| SEQ ID NO: 45 | H3_Swi(L431M).c |
| SEQ ID NO: 46 | PDI - H3 Switz - L431M DNA |
| SEQ ID NO: 47 | PDI - H3 Switz - L431M AA |
| SEQ ID NO: 48 | PDI - H3 Switz - CysTm DNA |
| SEQ ID NO: 49 | PDI - H3 Switz - CysTm AA |
| SEQ ID NO: 50 | H3_Swi(N382A).r |
| SEQ ID NO: 51 | H3_Swi(N382A).c AA |
| SEQ ID NO: 52 | PDI - H3 Switz - N382A - CysTm DNA |
| SEQ ID NO: 53 | PDI - H3 Switz - N382A - CysTm AA |
| SEQ ID NO: 54 | H3_Swi(L384V).r |
| SEQ ID NO: 55 | H3_Swi(L384V).c |
| SEQ ID NO: 56 | PDI - H3 Switz - L384V - CysTm DNA |
| SEQ ID NO: 57 | PDI - H3 Switz - L384V - CysTm AA |
| SEQ ID NO: 58 | PDI - H3 Switz - F392D - CysTm DNA |

TABLE 3-continued

SEQ ID NOs and Description of Sequences

| SEQ ID NO: | Description of Sequence |
|---|---|
| SEQ ID NO: 59 | PDI - H3 Switz - F392D - CysTm AA |
| SEQ ID NO: 60 | PDI - H3 Switz - L431M - CysTm DNA |
| SEQ ID NO: 61 | PDI - H3 Switz - L431M - CysTm AA |
| SEQ ID NO: 62 | Cloning vector 1190 from left to right T - DNA |
| SEQ ID NO: 63 | Construct 1314 from 2X35S prom to NOS term |
| SEQ ID NO: 64 | Construct 2980 from 2X35S prom to NOS term |
| SEQ ID NO: 65 | Construct 2995 from 2X35S prom to NOS term |
| SEQ ID NO: 66 | Cloning vector 3556 from left to right T - DNA |
| SEQ ID NO: 67 | IF - H5ITMCT.s1 - 4r |
| SEQ ID NO: 68 | PDI - H5 Indo DNA |
| SEQ ID NO: 69 | PDI - H5 Indo AA |
| SEQ ID NO: 70 | H5Ind(F393D).r |
| SEQ ID NO: 71 | H5Ind(F393D).c |
| SEQ ID NO: 72 | PDI - H5 Indo - F393D DNA |
| SEQ ID NO: 73 | PDI - H5 Indo - F393D AA |
| SEQ ID NO: 74 | IF - H5_Egy.r |
| SEQ ID NO: 75 | PDI - H5 Egypt DNA |
| SEQ ID NO: 76 | PDI - H5 Egypt AA |
| SEQ ID NO: 77 | H5Egy(F392D).r |
| SEQ ID NO: 78 | H5Egy(F392D).c |
| SEQ ID NO: 79 | PDI - H5 Egypt - F392D DNA |
| SEQ ID NO: 80 | PDI - H5 Egypt - F392D AA |
| SEQ ID NO: 81 | PDI - H3 Switz - N382A DNA |
| SEQ ID NO: 82 | PDI - H3 Switz - N382A AA |
| SEQ ID NO: 83 | PDI - H3 Switz - L384V DNA |
| SEQ ID NO: 84 | PDI - H3 Switz - L384V AA |
| SEQ ID NO: 85 | PDI - H3 Penn - CysTm DNA |
| SEQ ID NO: 86 | PDI - H3 Penn - CysTm AA |
| SEQ ID NO: 87 | PDI - H3 Penn - N382A - CysTm DNA |
| SEQ ID NO: 88 | PDI - H3 Penn - N382A - CysTm AA |
| SEQ ID NO: 89 | PDI - H3 Penn - L384V - CysTm DNA |
| SEQ ID NO: 90 | PDI - H3 Penn - L384V - CysTm AA |
| SEQ ID NO: 91 | A/Bangkok/3007/15 (H3N2) (aa) |
| SEQ ID NO: 92 | A/Hongkong/4801/14 (H3N2) (aa) |
| SEQ ID NO: 93 | A/Minnesota/40/15 (H3N2) (aa) |
| SEQ ID NO: 94 | A/South Australia/1/16 (H3N2) (aa) |
| SEQ ID NO: 95 | A/Pennsylvania/09/15 (H3N2) (aa) |
| SEQ ID NO: 96 | A/Switzerland/9715293/13 (H3N2) (aa) |
| SEQ ID NO: 97 | A/Mississippi/16/16 (H3N2) (aa) |
| SEQ ID NO: 98 | CysTM mutation (aa) |
| SEQ ID NO: 99 | wt CysTM (aa) |
| SEQ ID NO: 100 | CysTM mutation (nt) |
| SEQ ID NO: 101 | wt CysTM (nt) |
| SEQ ID NO: 102 | A/Hong Kong/4801/14 (nt) |
| SEQ ID NO: 103 | Construct No. 2801 (nt) |
| SEQ ID NO: 104 | Construct No. 3023 (nt) |
| SEQ ID NO: 105 | Construct No. 2811 (nt) |

The present invention will be further illustrated in the following examples.

Example 1: Influenza HA Constructs

The influenza HA constructs were produced using techniques well known within the art. For example wildtype H3 A-Switzerland/9715293/13 HA, N382A A/Switzerland/9715293/13 H3 HA and CysTM A-Switzerland-9715293-13 were cloned as described below. Other H3 HA mutants were obtained using similar techniques and the HA sequences primers, templates and products are described in Example 3 (Influenza HA and VLP Production in Plants) and Table 4.

A summary of the wildtype and mutated HA proteins, primers, templates and products is provided in Table 4 below. For Influenza H3 constructs other than H3 A/Switzerland/9715293/13 HA proteins which were cloned into the 1190 cloning vector without M2, the cloning vector used integrates an influenza M2 ion channel gene under the control of Alfalfa Plastocyanin promoter and terminator in addition to the 2X35S promoter/CPMV 160+CPMV 3'UTR/NOS-based expression cassette. Plasmid number 3556 (SEQ ID NO: 66; FIG. 5A) was digested with SacII and StuI restriction enzymes and used for the In-Fusion reaction.

Modification of H3 HA

2X35S/CPMV 160/PDISP-HA0 H3 A-Switzerland-9715293-13/NOS (Construct Number 2801)

A sequence encoding mature HA0 from influenza HA from H3 A/Switzerland/9715293/13 fused to alfalfa PDI secretion signal peptide (PDISP) was cloned into 2X35S/CPMV 160/NOS expression system using the following PCR-based method. A fragment containing the PDISP-H3 A/Switzerland/9715293/13 coding sequence was amplified using primers IF-CPMV(fl5'UTR)_SpPDI.c (SEQ ID NO: 15) and IF-H3A-Ala.r (SEQ ID NO: 17), using PDISP-H1 A/Switzerland/9715293/13 gene sequence (SEQ ID NO: 9) as template. The PCR product was cloned in 2X35S/CPMV 160/NOS expression system using In-Fusion cloning system (Clontech, Mountain View, CA). Construct number 1190 (FIG. 5B) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 62. The resulting construct was given number 2801 (SEQ ID NO: 103). The amino acid sequence of mature HA0 from influenza HA from A/Switzerland/9715293/13 fused to alfalfa PDI secretion signal peptide (PDISP) is presented in SEQ ID NO: 10. A representation of plasmid 2801 is presented in FIG. 8J.

2X35S/CPMV 160/PDISP-HA0 H3 A-Switzerland-9715293-13 (N382A)/NOS (Construct Number 3023)

A sequence encoding mature HA0 from influenza HA from A/Switzerland/9715293/13 (N382A) fused to alfalfa PDI secretion signal peptide (PDISP) was cloned into 2X35S/CPMV 160/NOS expression system using the following PCR-based method. In a first round of PCR, a fragment containing the PDISP-H3 A/Switzerland/9715293/13 with the mutated N382A amino acid was amplified using primers IF-CPMV(fl5'UTR)_SpPDI.c (SEQ ID NO: 15) and H3_Swi(N382A).r (SEQ ID NO: 50), using PDISP-H3 A/Switzerland/9715293/13 gene sequence (SEQ ID NO: 9) as template. A second fragment containing the N382A mutation with the remaining of the H3 A/Switzerland/9715293/13 was amplified using H3_Swi(N382A).c (SEQ ID NO: 51) and IF-H3A-Ala.r (SEQ ID NO: 17), using PDISP-H3 A/Switzerland/9715293/13 gene sequence (SEQ ID NO: 9) as template. The PCR products from both amplifications were then mixed and used as template for a second round of amplification using IF-CPMV(fl5'

UTR)_SpPDI.c (SEQ ID NO: 15) and IF-H3A-Ala.r (SEQ ID NO: 17) as primers. The final PCR product was cloned in 2X35S/CPMV 160/NOS expression system using In-Fusion cloning system (Clontech, Mountain View, CA). Construct number 1190 (FIG. 5B) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 62. The resulting construct was given number 3023 (SEQ ID NO: 104). The amino acid sequence of mutated PDISP-H3 A-Switzerland-9715293-13 (N382A) is presented in SEQ ID NO: 82. A representation of plasmid 3023 is presented in FIG. 4C.

2X35S/CPMV 160/PDISP-HA0 H3 A-Switzerland-9715293-13 (CysTM)/NOS (Construct Number 2811)

A sequence encoding mature HA0 from influenza HA from A/Switzerland/9715293/13 (CysTM) fused to alfalfa PDI secretion signal peptide (PDISP) was cloned into 2X35S/CPMV 160/NOS expression system using the following PCR-based method. In a first round of PCR, a fragment containing the PDISP-H3 A/Switzerland/9715293/13 with the mutated CysTM amino acids was amplified using primers IF-CPMV(fl5'UTR)_SpPDI.c (SEQ ID NO: 15) and H3_Swi_SLVLL.r (SEQ ID NO: 18), using PDISP-H3 A/Switzerland/9715293/13 gene sequence (SEQ ID NO: 9) as template. A second fragment containing the CysTm mutations with the remaining of the H3 A/Switzerland/9715293/13 was amplified using H3_Swi_SLVLL.c (SEQ ID NO: 19) and IF-H3A-Ala.r (SEQ ID NO: 17), using PDISP-H3 A/Switzerland/9715293/13 gene sequence (SEQ ID NO: 9) as template. The PCR products from both amplifications were then mixed and used as template for a second round of amplification using IF-CPMV(fl5'UTR)_SpPDI.c (SEQ ID NO: 15) and IF-H3A-Ala.r (SEQ ID NO: 17) as primers. The final PCR product was cloned in 2X35S/CPMV 160/NOS expression system using In-Fusion cloning system (Clontech, Mountain View, CA). Construct number 1190 (FIG. 5B) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 62. The resulting construct was given number 2811 (SEQ ID NO: 105). The amino acid sequence of mutated PDISP-H3 A-Switzerland-9715293-13 (CysTM) is presented in SEQ ID NO: 49. A representation of plasmid 2811 is presented in FIG. 8K.

Example 2: Methods

*Agrobacterium tumefaciens* Transfection

*Agrobacterium tumefaciens* strain AGL1 was transfected by electroporation with the wildtype influenza HA or mutant influenza HA expression vectors using the methods described by D'Aoust et al., 2008 (*Plant Biotech. J.* 6:930-40). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

*N. benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

Agrobacteria transfected with each wildtype influenza HA or mutant influenza HA expression vector were grown in a YEB medium supplemented with 10 mM 2-(N-morpholino)ethanesulfonic acid (MES), 20 μM acetosyringone, 50 μg/ml kanamycin and 25 μg/ml of carbenicillin pH 5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 6 or 9 day incubation period until harvest.

Leaf Harvest and Total Protein Extraction

Proteins were extracted from fresh biomass cut into ~1 $cm^2$ pieces by an overnight enzymatic extraction at room temperature using an orbital shaker. The slurry was then filtered through a large pore nylon filter to remove coarse undigested vegetal tissue.

To obtain the "Full Process yields", the slurry was centrifuged to remove protoplasts and intracellular contaminants. The supernatant was clarified by depth-filtration. The clarified fraction was then loaded over a cation exchange column with a step-elution step with increasing concentrations of NaCl. The purified VLPs were concentrated by TFF, diafiltered against a formulation buffer and passed through a filter. Protein content of purified VLP was analysed by BCA assay and activity was analysed by a hemagglutination assay. Relative yields were obtained by comparing the protein yields from the new construct to the native construct (or to CysTM for H3 strains) used as control.

To obtain the "Post-Density Gradient Yields", the slurry was centrifuged to remove protoplasts and intracellular contaminants. The supernatant was centrifuged further to remove additional debris. The supernatant was the clarified by depth-filtration using glass fiber filter. The clarified fraction was then loaded on a discontinuous iodixanol density gradient. Separation density gradient centrifugation was performed as follows: 38 ml tubes containing discontinuous iodixanol density gradient in Tris buffer (successive layers of 35%, 30%, 25%, 20%, 15, 10% and 5%) were prepared and overlaid with clarified extract. The gradients were centrifuged at 120 000 g for 2 hours (4° C.). After centrifugation, the first 5 mL collected from the bottom to the top were discarded while the next 5 mL were collected for protein content analysis (BCA), activity measurement (hemagglutination assay) and intensity measurement of the HA0 band on a reduced SDS-PAGE (densitometry). Relative yields were obtained by comparing the HA0 band intensity from the new construct to the native construct (or CysTM for H3 strains) used as control.

Hemagglutination Assay

Hemagglutination assay was based on a method described by Nayak and Reichl (2004). Briefly, serial double dilutions of the test samples (100 μL) were made in V-bottomed 96-well microtiter plates containing 100 μL PBS, leaving 100 μL of diluted sample per well. One hundred microliters of 0.5% guinea pig red blood cells suspension (Bio Link Inc., Syracuse, NY) were added to each well, and plates were incubated for 2 h at room temperature. The reciprocal of the highest dilution showing complete hemagglutination was recorded as HA activity. In parallel, a recombinant HA standard (A/Vietnam/1203/2004 H5N1) (Protein Science Corporation, Meriden, CT) was diluted in PBS and run as a control on each plate.

Protein Analysis and Immunoblotting

Immunoblotting was performed with a first incubation with a primary mAb, diluted 1/500 in 2% skim milk in TBS-Tween 20 0.1%. Peroxydase-conjugated goat anti-mouse (Jackson Immunoresearch, cat #115-035-146) diluted 1/10000 was used as secondary antibody for chemiluminescence detection in 2% skim milk in TBS-Tween 20 0.1% Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

Example 3: Influenza HA and VLP Production in Plants

Modification of H3 HA I

The influenza HA constructs were produced using techniques well known within the art (see Example 1). A summary of the wildtype and mutated HA proteins, primers, templates and products is provided in Table 4 below. The sequences used are provided in Example 4 and in the sequence listing.

N382A A/Switzerland/9715293/13 Mutant H3

N382A A/Switzerland/9715293/13 Mutant H3 (Construct #3023) was constructed by mutating the asparagine at position 382 of wildtype/Switzerland/9715293/13 H3 to alanine. As shown in FIG. 2, purified extracts from *N. benthamiana* plants agroinfiltrated with Construct #3023 exhibited an approximate 30% increase in hemagglutination titer as compared to extracts from *N. benthamiana* plants agroinfiltrated with wildtype A/Switzerland/9715293/13 H3 (Construct #2801).

L384V A/Switzerland/9715293/13 Mutant H3

L384V A/Switzerland/9715293/13 Mutant H3 (Construct #3034) was constructed by mutating the leucine at position 384 of wildtype/Switzerland/9715293/13 H3 to valine. As shown in FIG. 2, purified extracts from *N. benthamiana* plants agroinfiltrated with Construct #3034 exhibited an approximate 100% increase in hemagglutination titer as compared to extracts from *N. benthamiana* plants agroinfiltrated with wildtype A/Switzerland/9715293/13 H3 (Construct #2801).

F392D A/Switzerland/9715293/13 Mutant H3

F392D A/Switzerland/9715293/13 Mutant H3 was constructed by mutating the phenylalanine at position 392 of wildtype A/Switzerland/9715293/13 H3 to aspartic acid (Construct #3045). As shown in FIG. 2, purified extracts from *N. benthamiana* plants agroinfiltrated with Construct #3045 exhibited an approximate 40% increase in hemagglutination titer as compared to extracts from *N. benthamiana* plants agroinfiltrated with wildtype A/Switzerland/9715293/13 H3 (Construct #2801).

L431M A/Switzerland/9715293/13 Mutant H3

L431M A/Switzerland/9715293/13 Mutant H3 was constructed by mutating the leucine at position 431 of wildtype A/Switzerland/9715293/13 H3 to methionine (Construct #3022). As shown in FIG. 2, purified extracts from *N. benthamiana* plants agroinfiltrated with Construct #3022 exhibited an approximate 70% increase in hemagglutination titer as compared to extracts from *N. benthamiana* plants agroinfiltrated with wildtype A/Switzerland/9715293/13 H3 (Construct #2811).

The one or more than one mutations described herein specifically increase influenza HA protein production and VLP yield in plants. It was observed that mutations at other positions significantly reduced, or had no significant effect, on influenza HA protein accumulation or VLP production in plant cells.

The increased hemagglutination titers achieved with the influenza HA proteins comprising the one or more than one mutation described herein was also observed to be specific to influenza H3 HAs. Similar enhancements were not observed in plants agroinfiltrated with constructs encoding mutant influenza HAs derived from non-H3 strains.

For example, F393D A/Indonesia/5/2005 Mutant H5 was constructed by mutating the phenylalanine at position 393 of wildtype A/Indonesia/5/2005 H5 to aspartic acid (Construct #3680). As shown in FIG. 3, purified extracts from *N. benthamiana* plants agroinfiltrated with Construct #3680 exhibited an approximate 98% reduction in hemagglutination titer as compared to extracts from *N. benthamiana* plants agroinfiltrated with wildtype A/Indonesia/5/2005 H5 (Construct #2295).

Similarly, purified extracts from *N. benthamiana* plants agroinfiltrated with F392D A/Egypt/N04915/2014 Mutant H5 (Construct #3690), exhibited an approximate 99% reduction in hemagglutination titer as compared to extracts from *N. benthamiana* plants agroinfiltrated with wildtype A/Egypt/N04915/2014 H5 (Construct #3645) (see FIG. 3, Table 7).

Modification of H3 HA II

CysTM A/Switzerland/9715293/13 Mutant H3

CysTM A/Switzerland/9715293/13 Mutant H3 (Construct #2811) was constructed by replacing the "CFLLC" sequence at positions 524-528 (SEQ ID NO: 99) of wildtype A/Switzerland/9715293/13 H3 to "SLVLL" (SEQ ID NO: 98). As shown in FIG. 6A, purified extracts from *N. benthamiana* plants agroinfiltrated with Construct #2811 exhibited an approximate 60% increase in hemagglutination titer as compared to extracts from *N. benthamiana* plants agroinfiltrated with wildtype A/Switzerland/9715293/13 H3 (Construct #2801).

CysTM A/Pennsylvania/09/2015 Mutant H3

CysTM A/Pennsylvania/09/2015 Mutant H3 (Construct #3313) was constructed by replacing the "CFLLC" sequence at positions 524-528 (SEQ ID NO: 99) of wildtype A/Pennsylvania/09/2015 H3 to "SLVLL" (SEQ ID NO: 98). As shown in FIG. 7C, purified extracts from *N. benthamiana* plants agroinfiltrated with Construct #3313 exhibited an approximate 100% increase in hemagglutination titer as compared to extracts from *N. benthamiana* plants agroinfiltrated with wildtype A/Pennsylvania/09/2015 H3 (Construct #3312).

N382A+CysTM A/Switzerland/9715293/13 Mutant H3

N382A+CysTM A/Switzerland/9715293/13 Mutant H3 (Construct #3063) was constructed by mutating the asparagine at position 382 of wildtype A/Switzerland/9715293/13 H3 to alanine and replacing the "CFLLC" sequence at positions 524-528 (SEQ ID NO: 99) to "SLVLL" (SEQ ID NO: 98). As shown in FIG. 7A, purified extracts from *N. benthamiana* plants agroinfiltrated with Construct #3063 exhibited an approximate 160% increase in hemagglutination titer as compared to extracts from *N. benthamiana* plants agroinfiltrated with wildtype A/Switzerland/9715293/13 H3 (Construct #2801). As further shown in FIG. 7B, *N. benthamiana* plants agroinfiltrated with Construct #3063 exhibited an approximate 30% increase in VLP yield following Iodixanol gradient purification, in comparison to plants infiltrated with CysTM A/Switzerland/9715293/13 Mutant H3 (Construct #2811).

N382A+CysTM A/Pennsylvania/09/2015 Mutant H3

N382A+CysTM A/Pennsylvania/09/2015 Mutant H3 (Construct #3314) was constructed by mutating the asparagine at position 382 of wildtype A/Pennsylvania/09/2015 H3 to alanine and replacing the "CFLLC" sequence at positions 524-528 (SEQ ID NO: 99) to "SLVLL" (SEQ ID NO: 98). As shown in FIG. 7C, purified extracts from *N. benthamiana* plants agroinfiltrated with Construct #3314 exhibited an approximate 300% increase in hemagglutination titer as compared to extracts from *N. benthamiana* plants agroinfiltrated with wildtype A/Pennsylvania/09/2015 H3 (Construct #3312).

L384V+CysTM A/Switzerland/9715293/13 Mutant H3

L384V+CysTM A/Switzerland/9715293/13 Mutant H3 (Construct #3074) was constructed by mutating the leucine at position 384 of wildtype A/Switzerland/9715293/13 H3 to valine and replacing the "CFLLC" sequence at positions 524-528 (SEQ ID NO: 99) to "SLVLL" (SEQ ID NO: 98). As shown in FIG. 7C, purified extracts from *N. benthamiana* plants agroinfiltrated with Construct #3074 exhibited an approximate 380% increase in hemagglutination titer as compared to extracts from *N. benthamiana* plants agroinfiltrated with wildtype A/Switzerland/9715293/13 H3 (Construct #2801). Furthermore, as shown in FIG. 7B, *N. benthamiana* plants agroinfiltrated with Construct #3074 exhibited an approximate 50% increase in VLP yield following sucrose gradient purification, in comparison to plants infiltrated with CysTM A/Switzerland/9715293/13 Mutant H3 (Construct #2811).

L384V+CysTM A/Pennsylvania/09/2015 Mutant H3

L384V+CysTM A/Pennsylvania/09/2015 Mutant H3 (Construct #3315) was constructed by mutating the leucine at position 384 of wildtype A/Pennsylvania/09/2015 H3 to valine and replacing the "CFLLC" sequence at positions 524-528 (SEQ ID NO: 99) to "SLVLL" (SEQ ID NO: 98). As shown in FIG. 7C, purified extracts from *N. benthamiana* plants agroinfiltrated with Construct #3315 exhibited an approximate 380% increase in hemagglutination titer as compared to extracts from *N. benthamiana* plants agroinfiltrated with wildtype A/Pennsylvania/09/2015 H3 (Construct #3312).

F392D+CysTM A/Switzerland/9715293/13 Mutant H3

F392D+CysTM A/Switzerland/9715293/13 Mutant H3 (Construct #3085) was constructed by mutating the phenylalanine at position 392 of wildtype/Switzerland/9715293/13 H3 to aspartic acid and replacing the "CFLLC" sequence at positions 524-528 (SEQ ID NO: 99) to "SLVLL" (SEQ ID NO: 98). As shown in FIG. 7A, purified extracts from *N. benthamiana* plants agroinfiltrated with Construct #3085 exhibited an approximate 170% increase in hemagglutination titer as compared to extracts from *N. benthamiana* plants agroinfiltrated with wildtype A/Switzerland/9715293/13 H3 (Construct #2801).

L431M+CysTM A/Switzerland/9715293/13 Mutant H3

L431M+CysTM A/Switzerland/9715293/13 Mutant H3 (Construct #3062) was constructed by mutating the leucine at position 431 of wildtype/Switzerland/9715293/13 H3 to methionine and replacing the "CFLLC" sequence at positions 524-528 (SEQ ID NO: 99) to "SLVLL" (SEQ ID NO: 98). As shown in FIG. 7A, purified extracts from *N. benthamiana* plants agroinfiltrated with Construct #3062 exhibited an approximate 150% increase in hemagglutination titer as compared to extracts from *N. benthamiana* plants agroinfiltrated with wildtype A/Switzerland/9715293/13 H3 (Construct #2801).

N382A+L384V+CysTM A/Hong Kong 4801/14 Mutant H3

N382A+L384V+CysTM A/Hong Kong/4801/14 Mutant H3 (Construct #3375) was constructed by mutating the asparagine at position 382 of wildtype A/Hong Kong/4801/14 to an alanine residue, the leucine at position 384 to a valine residue, and the "CFLLC" sequence at positions 524-528 (SEQ ID NO: 99) to "SLVLL" (SEQ ID NO: 98). As shown in FIG. 7E, purified extracts from *N. benthamiana* plants agroinfiltrated with Construct #3375 exhibited an approximate 300% increase in hemagglutination titer as compared to extracts from *N. benthamiana* plants agroinfiltrated with CysTM A/Hong Kong/4801/14 Mutant H3 (Construct #3341).

N382A+L384V+CysTM A/Minnesota/40/15 Mutant H3

N382A+L384V+CysTM A/Minnesota/40/15 Mutant H3 (Construct #3915) was constructed by mutating the asparagine at position 382 of wildtype A/Minnesota/40/15 to an alanine residue, the leucine at position 384 to a valine residue, and the "CFLLC" sequence at positions 524-528 (SEQ ID NO: 99) to "SLVLL" (SEQ ID NO: 98). As shown in FIG. 7E, purified extracts from *N. benthamiana* plants agroinfiltrated with Construct #3915 exhibited an approximate 400% increase in hemagglutination titer as compared to extracts from *N. benthamiana* plants agroinfiltrated with CysTM A/Minnesota/40/15 Mutant H3 (Construct #3914).

N382A+L384V+CysTM A/S. Australia/1/16 Mutant H3

N382A+L384V+CysTM A/S. Australia/1/16 Mutant H3 (Construct #3925) was constructed by mutating the asparagine at position 382 of wildtype A/S. Australia/1/16 to an alanine residue, the leucine at position 384 to a valine residue, and the "CFLLC" sequence at positions 524-528 (SEQ ID NO: 99) to "SLVLL" (SEQ ID NO: 98). As shown in FIGS. 7D and 7E, purified extracts from *N. benthamiana* plants agroinfiltrated with Construct #3925 exhibited an approximate 400% increase in hemagglutination titer as compared to extracts from *N. benthamiana* plants agroinfiltrated with CysTM A/S. Australia/1/16 Mutant H3 (Construct #3924).

N382A+L384V+CysTM A/Bangkok/3007/15 Mutant H3

N382A+L384V+CysTM A/Bangkok/3007/15 Mutant H3 (Construct #3905) was constructed by mutating the asparagine at position 382 of wildtype A/Bangkok/3007/15 to an alanine residue, the leucine at position 384 to a valine residue, and the "CFLLC" sequence at positions 524-528 (SEQ ID NO: 99) to "SLVLL" (SEQ ID NO: 98). As shown in FIG. 7E, purified extracts from *N. benthamiana* plants agroinfiltrated with Construct #3905 exhibited an approximate 400% increase in hemagglutination titer as compared to extracts from *N. benthamiana* plants agroinfiltrated with CysTM A/Bangkok/3007/15 Mutant H3 (Construct #3904).

The one or more than one mutations described herein specifically increase influenza HA protein production and VLP yield in plants. It was observed that mutations at other positions significantly reduced, or had no significant effect, on influenza HA protein accumulation or VLP production in plant cells.

The increased hemagglutination titers achieved with the influenza HA proteins comprising the one or more than one mutation described herein was also observed to be specific to influenza H3 HAs. Similar enhancements were not observed in plants agroinfiltrated with constructs encoding mutant influenza HAs derived from non-H3 strains.

For example, F393D A/Indonesia/5/2005 Mutant H5 was constructed by mutating the phenylalanine at position 393 of wildtype A/Indonesia/5/2005 H5 to aspartic acid (Construct #3680). As shown in FIG. 3, purified extracts from *N. benthamiana* plants agroinfiltrated with Construct #3680 exhibited an approximate 98% reduction in hemagglutination titer as compared to extracts from *N. benthamiana* plants agroinfiltrated with wildtype A/Indonesia/5/2005 H5 (Construct #2295).

Similarly, purified extracts from *N. benthamiana* plants agroinfiltrated with F392D A/Egypt/N04915/2014 Mutant H5 (Construct #3690), exhibited an approximate 99% reduction in hemagglutination titer as compared to extracts from *N. benthamiana* plants agroinfiltrated with wildtype A/Egypt/N04915/2014 H5 (Construct #3690) (see FIG. 3).

TABLE 4

Examples of constructs that have been prepared as described herein. Sequences are provided in Example 4 and the sequence listing.

| Construct Name | TMCT | Construct # | FIG. | Primer 1 | Primer 2 |
|---|---|---|---|---|---|
| H3 A-HK-4801-14 | — | 3340 | 8A | SEQ ID NO: 15 | SEQ ID NO: 17 |
| H3 A-HK-4801-14 | CysTm | 3341 | 8B | SEQ ID NO: 15 | SEQ ID NO: 18 |
| H3 A-HK-4801-14 (N382A + L384V) | CysTm | 3375 | 8C | SEQ ID NO: 15 | SEQ ID NO: 22 |
| H3 A-Minn-40-15 | CysTM | 3914 | 8D | SEQ ID NO: 15 | SEQ ID NO: 18 |
| H3 A-Minn-40-15 (N382A + L384V) | CysTM | 3915 | 8E | SEQ ID NO: 15 | SEQ ID NO: 28 |
| H3 A-SAus-1-16 | CysTM | 3924 | 8F | SEQ ID NO: 15 | SEQ ID NO: 18 |
| H3 A-SAus-1-16 (N382A + L384V) | CysTM | 3925 | 8G | SEQ ID NO: 15 | SEQ ID NO: 28 |
| H3 A-Bang-3007-15 | CysTM | 3904 | 8H | SEQ ID NO: 15 | SEQ ID NO: 18 |
| H3 A-Bang-3007-15 (N382A + L384V) | CysTM | 3905 | 8I | SEQ ID NO: 15 | SEQ ID NO: 22 |
| H3 A-Swi-9715293-13 | Wt | 2801 | 8J | SEQ ID NO: 15 | SEQ ID NO: 17 |
| H3 A-Swi-9715293-13 (F392D) | Wt | 3045 | 4A | SEQ ID NO: 15 | SEQ ID NO: 40 |
| H3 A-Swi-9715293-13 (L431M) | Wt | 3022 | 4B | SEQ ID NO: 15 | SEQ ID NO: 44 |
| H3 A-Swi-9715293-13 | CysTM | 2811 | 8K | SEQ ID NO: 15 | SEQ ID NO: 18 |
| H3 A-Swi-9715293-13 (N382A) | CysTM | 3063 | 8L | SEQ ID NO: 15 | SEQ ID NO: 50 |
| H3 A-Swi-9715293-13 (L384V) | CysTM | 3074 | 8M | SEQ ID NO: 15 | SEQ ID NO: 54 |
| H3 A-Swi-9715293-13 (F392D) | CysTM | 3085 | 8N | SEQ ID NO: 15 | SEQ ID NO: 40 |
| H3 A-Swi-9715293-13 (L431M) | CysTM | 3062 | 8O | SEQ ID NO: 15 | SEQ ID NO: 44 |
| H5 A-Indo-5-05 | Wt | 2295 | 9A | SEQ ID NO: 15 | SEQ ID NO: 67 |
| H5 A-Indo-5-05 (F393D) | Wt | 3680 | 9B | SEQ ID NO: 15 | SEQ ID NO: 70 |
| H5 A-Egypt-N04915-14 | Wt | 3645 | 9C | SEQ ID NO: 15 | SEQ ID NO: 74 |
| H5 A-Egypt-N04915-14 (F392D) | Wt | 3690 | 9D | SEQ ID NO: 15 | SEQ ID NO: 77 |
| H3 A-Swi-9715293-13 (N382A) | Wt | 3023 | 4C | SEQ ID NO: 15 | SEQ ID NO: 50 |
| H3 A-Swi-9715293-13 (L384V) | Wt | 3034 | 4D | SEQ ID NO: 15 | SEQ ID NO: 54 |
| H3 A-Penn-09-15 | Wt | 3312 | 8P | SEQ ID NO: 15 | SEQ ID NO: 17 |
| H3 A-Penn-09-15 | CysTM | 3313 | 8Q | SEQ ID NO: 15 | SEQ ID NO: 18 |
| H3 A-Penn-09-15 (N382A) | CysTM | 3314 | 8R | SEQ ID NO: 15 | SEQ ID NO: 50 |
| H3 A-Penn-09-15 (L384V) | CysTM | 3315 | 8S | SEQ ID NO: 15 | SEQ ID NO: 54 |

| Construct Name | Primer 3 | Primer 4 | Template for PCR | Resulting Gene | Resulting Protein |
|---|---|---|---|---|---|
| H3 A-HK-4801-14 | — | — | SEQ ID NO: 1 | SEQ ID NO: 1 | SEQ ID NO: 2 |
| H3 A-HK-4801-14 | SEQ ID NO: 19 | SEQ ID NO: 17 | SEQ ID NO: 1 | SEQ ID NO: 20 | SEQ ID NO: 21 |
| H3 A-HK-4801-14 (N382A + L384V) | SEQ ID NO: 23 | SEQ ID NO: 17 | SEQ ID NO: 20 | SEQ ID NO: 24 | SEQ ID NO: 25 |
| H3 A-Minn-40-15 | SEQ ID NO: 19 | SEQ ID NO: 17 | SEQ ID NO: 3 | SEQ ID NO: 26 | SEQ ID NO: 27 |
| H3 A-Minn-40-15 (N382A + L384V) | SEQ ID NO: 29 | SEQ ID NO: 17 | SEQ ID NO: 26 | SEQ ID NO: 30 | SEQ ID NO: 31 |
| H3 A-SAus-1-16 | SEQ ID NO: 19 | SEQ ID NO: 17 | SEQ ID NO: 5 | SEQ ID NO: 32 | SEQ ID NO: 33 |
| H3 A-SAus-1-16 (N382A + L384V) | SEQ ID NO: 29 | SEQ ID NO: 17 | SEQ ID NO: 32 | SEQ ID NO: 34 | SEQ ID NO: 35 |
| H3 A-Bang-3007-15 | SEQ ID NO: 19 | SEQ ID NO: 17 | SEQ ID NO: 7 | SEQ ID NO: 36 | SEQ ID NO: 37 |
| H3 A-Bang-3007-15 (N382A + L384V) | SEQ ID NO: 23 | SEQ ID NO: 17 | SEQ ID NO: 36 | SEQ ID NO: 38 | SEQ ID NO: 39 |
| H3 A-Swi-9715293-13 | — | — | SEQ ID NO: 9 | SEQ ID NO: 9 | SEQ ID NO: 10 |
| H3 A-Swi-9715293-13 (F392D) | SEQ ID NO: 41 | SEQ ID NO: 17 | SEQ ID NO: 9 | SEQ ID NO: 42 | SEQ ID NO: 43 |
| H3 A-Swi-9715293-13 (L431M) | SEQ ID NO: 45 | SEQ ID NO: 17 | SEQ ID NO: 9 | SEQ ID NO: 46 | SEQ ID NO: 47 |
| H3 A-Swi-9715293-13 | SEQ ID NO: 19 | SEQ ID NO: 17 | SEQ ID NO: 9 | SEQ ID NO: 48 | SEQ ID NO: 49 |
| H3 A-Swi-9715293-13 (N382A) | SEQ ID NO: 51 | SEQ ID NO: 17 | SEQ ID NO: 48 | SEQ ID NO: 52 | SEQ ID NO: 53 |
| H3 A-Swi-9715293-13 (L384V) | SEQ ID NO: 55 | SEQ ID NO: 17 | SEQ ID NO: 48 | SEQ ID NO: 56 | SEQ ID NO: 57 |
| H3 A-Swi-9715293-13 (F392D) | SEQ ID NO: 41 | SEQ ID NO: 17 | SEQ ID NO: 48 | SEQ ID NO: 58 | SEQ ID NO: 59 |
| H3 A-Swi-9715293-13 (L431M) | SEQ ID NO: 45 | SEQ ID NO: 17 | SEQ ID NO: 48 | SEQ ID NO: 60 | SEQ ID NO: 61 |
| H5 A-Indo-5-05 | — | — | SEQ ID NO: 68 | SEQ ID NO: 68 | SEQ ID NO: 69 |
| H5 A-Indo-5-05 (F393D) | SEQ ID NO: 71 | SEQ ID NO: 67 | SEQ ID NO: 68 | SEQ ID NO: 72 | SEQ ID NO: 73 |
| H5 A-Egypt-N04915-14 | — | — | SEQ ID NO: 75 | SEQ ID NO: 75 | SEQ ID NO: 76 |
| H5 A-Egypt-N04915-14 (F392D) | SEQ ID NO: 78 | SEQ ID NO: 74 | SEQ ID NO: 75 | SEQ ID NO: 79 | SEQ ID NO: 80 |
| H3 A-Swi-9715293-13 (N382A) | SEQ ID NO: 51 | SEQ ID NO: 17 | SEQ ID NO: 9 | SEQ ID NO: 81 | SEQ ID NO: 82 |
| H3 A-Swi-9715293-13 (L384V) | SEQ ID NO: 55 | SEQ ID NO: 17 | SEQ ID NO: 9 | SEQ ID NO: 83 | SEQ ID NO: 84 |
| H3 A-Penn-09-15 | — | — | SEQ ID NO: 13 | SEQ ID NO: 13 | SEQ ID NO: 14 |
| H3 A-Penn-09-15 | SEQ ID NO: 19 | SEQ ID NO: 17 | SEQ ID NO: 85 | SEQ ID NO: 86 | SEQ ID NO: 86 |
| H3 A-Penn-09-15 (N382A) | SEQ ID NO: 51 | SEQ ID NO: 17 | SEQ ID NO: 87 | SEQ ID NO: 88 | SEQ ID NO: 88 |
| H3 A-Penn-09-15 (L384V) | SEQ ID NO: 55 | SEQ ID NO: 17 | SEQ ID NO: 89 | SEQ ID NO: 89 | SEQ ID NO: 90 |

Example 3: Hemagglutination Titer, Post-Density Gradient Yields and Full Process Yields A Summary of the measured Hemagglutination Titer is given in Tables 5 and 6A. Hemagglutination Titer were measured as described in Example 2. The relative hemagglutination titer were obtained by comparing the hemagglutination titer of the mutated or modified HA protein to either wildtype HA (Table 5) or the CysTM mutant HA protein (Table 6A).

A Summary of the measured Post-Density Gradient Yields is given in Tables A 5B and C5B. Post-Density Gradient Yields were measured as described in Example 2. Relative yields were obtained by comparing the HA0 band intensity from the mutated or modified HA protein to either the HA0 band intensity of wildtype HA (Table A 5B) or the HA0 band intensity of CysTM mutant HA protein (Table 6B).

A Summary of the measured Full Process Yield is given in Table 6C. Full Process Yield were obtained as described above in Example 2. Relative yields were obtained by comparing the protein yield from the mutated or modified HA protein to either the protein yield of wildtype HA or the protein yield of CysTM mutant HA protein (Table 6C).

TABLE 5

Summary of relative Hemagglutination Titer for H3. Numbering is in accordance with H3 A/Hongkong/4801/14.

| | WT | N382A | L384V | F392D | L431M |
|---|---|---|---|---|---|
| H3 A/ Switzerland/ 9715293/13 | 100% | 130% | 200% | 140% | 170% |

TABLE 6A

Summary of relative Hemagglutination Titer for H3. Numbering is in accordance with H3 A/Hongkong/4801/14.

| | WT | CysTM | N382A + CysTM | L384V + CysTM | F392D + CysTM | L431M + CysTM | N382A + L384V + CysTM |
|---|---|---|---|---|---|---|---|
| H3 A/Hongkong/4801/14 | | 100% | | | | | 400% |
| H3 A/Minnesota/40/15 | | 100% | | | | | 500% |
| H3 A/S.Aus/1/16 | | 100% | | | | | 300-500% |
| H3 A/Bangkok/3007/15 | | 100% | | | | | 500% |
| H3 A/Switzerland/9715293/13 | 100% | 160% | 260% | 270% | 200-270% | 250% | 480% |
| H3 A/Mississippi/16/16 | | 100% | | | | | 100% |

TABLE 6B

Summary of Post-Density Gradient Yields for H3 (expressed in %). Numbering is in accordance with H3 A/Hongkong/4801/14.

| | WT | CysTM | N382A + CysTM | L384V + CysTM | N392D + CysTM | L431M + CysTM |
|---|---|---|---|---|---|---|
| H3 A/Switzerland/9715293/13 | 93% | 100% | 129% | 150% | 100% | 100% |

TABLE 6C

Summary of relative Full Process Yield for H3. Numbering is in accordance with H3 A/Hongkong/4801/14.

| | WT | CysTM | N382A + CysTM | L384V + CysTM | N382A + L384V + CysTM |
|---|---|---|---|---|---|
| H3 A/ Hongkong/4801/14/ | | 100% | 135% | 135% | 150% |
| H3 A/Minnesota/40/15 | | 100% | | | 280% |
| H3 A/S.Aus/1/16 | | 100% | | | 395% |
| H3 A/Switzerland/ 9715293/13 | 100% | 196% | | | |
| H3 A/Mississippi/16/16 | | 100% | | | 152% |

TABLE 7

| Summary of relative Hemagglutination Titer for H5. Numbering in accordance with H5 A/Indonesia/5/2005 | WT | N382A | F393D |
|---|---|---|---|
| H5 A/Indonesia/5/2005 | 100% | 50% | 2% |
| H5 A/Egypt/N04915/2014 | 100% | 50% | 1% |

Example 4: Sequences

The following sequences were used (also see Table 4):

PDI-H3 HK DNA (SEQ ID NO: 1)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCATCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGACTGGAGTCACTCAAAACGGAACAAGTTCT

GCTTGCATAAGGAGATCTAGTAGTAGTTTCTTTAGTAGATTAAATTGGTTGACCCACTTAAACTACACA

TACCCAGCATTGAACGTGACTATGCCAAACAATGAACAATTTGACAAATTGTACATTTGGGGGGTTCAC

CACCCGGGTACGGACAAGGACCAAATCTTCCTGTATGCTCAATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGTGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGAAGAATTCAGGACCTTGAGAAATATGTT

GAGGACACTAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATAAGA

AATGGAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGGTGCAACATTTGCATTTGA

PDI-H3 HK AA (SEQ ID NO: 2)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWTGVTQNGTSSACIRRSSSSFFSRLNWLTHLNYTYPALNVTMPNNEQFDKLYIWGVH

HPGTDKDQIFLYAQSSGRITVSTKRSQQAVIPNIGSRPRIRDIPSRISIYWTIVKPGDILLINSTGNLI

-continued

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLNRLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHNVYRDEALNNRFQIKGVELKSGYKDWILWISFAISCFLLC

VALLGFIMWACQKGNIRCNICI

PDI-H3 Minn DNA (SEQ ID NO: 3)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCACCATGCAGTACCAAAC

GGAACGATAGTGAAAACAATCACAAATGACCGAATTGAAGTTACTAATGCTACTGAGTTGGTTCAGAAT

TCCTCAATAGGTGAAATATGCGACAGTCCTCATCAGATCCTTGATGGAGAGAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGACTGGAGTCACTCAAAACGGAACAAGTTCT

GCTTGCATAAGGAGATCTAGTAGTAGTTTCTTTAGTAGATTAAATTGGTTGACCCACTTAAACTACACA

TATCCAGCATTGAACGTGACTATGCCAAACAAGGAACAATTTGACAAATTGTACATTTGGGGGGTTCAC

CACCCGGGTACGGACAAGGACCAAATCTTCCTGTATGCTCAATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGGTTGATCGGGAAAACCAACGAG

AAATTCCATCAGATTGAAAAAGAATTCTCAGAAGTAGAAGGAAGAGTTCAAGACCTTGAGAAATATGTT

GAGGACACTAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGAAATGGTTGTTTCAAAATATACCACAAATGTGACAATGCCTGCATAGGATCAATAAGA

AATGAAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGATGCAACATTTGCATTTGA

PDI-H3 Minn AA (SEQ ID NO: 4)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWTGVTQNGTSSACIRRSSSSFFSRLNWLTHLNYTYPALNVTMPNKEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLNRLIGKTNE

KFHQIEKEFSEVEGRVQDLEKYVEDTKIDLWSYNAELLVALENQHTIDLTDSEMNKLFEKTKKQLRENA

EDMGNGCFKIYHKCDNACIGSIRNETYDHNVYRDEALNNRFQIKGVELKSGYKDWILWISFAISCFLLC

VALLGFIMWACQKGNIRCNICI

-continued

PDI-H3 SAus DNA (SEQ ID NO: 5)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCACCATGCAGTACCAAAC

GGAACGATAGTGAAAACAATCACAAATGACCGAATTGAAGTTACTAATGCTACTGAGTTGGTTCAGAAT

TCCTCAATAGGTGAAATATGCGACAGTCCTCATCAGATCCTTGATGGAGAGAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAAAAATGAAAGCTTCAATTGGACTGGAGTCACTCAAAACGGAACAAGTTCT

GCTTGCATAAGGAGATCTAGTAGTAGTTTCTTTAGTAGATTAAATTGGTTGACCCACTTAAACTACACA

TATCCAGCATTGAACGTGACTATGCCAAACAAGGAACAATTTGACAAATTGTACATTTGGGGGGTTCAC

CACCCGGGTACGGACAAGGACCAAATCTTCCTGTATGCTCAATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGGTTGATCGGGAAAACCAACGAG

AAATTCCATCAGATTGAAAAAGAATTCTCAGAAGTAGAAGGAAGAGTTCAAGACCTTGAGAAATATGTT

GAGGACACTAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGAAATGGTTGTTTCAAAATATACCACAAATGTGACAATGCCTGCATAGGATCAATAAGA

AATGAAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGATGCAACATTTGCATTTGA

PDI-H3 SAus AA (SEQ ID NO: 6)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLEVERSKAYSNCYPYDVPDYASLRSLVAS

SGTLEFKNESFNWTGVTQNGTSSACIRRSSSSFFSRLNWLTHLNYTYPALNVTMPNKEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLNRLIGKTNE

KFHQIEKEFSEVEGRVQDLEKYVEDTKIDLWSYNAELLVALENQHTIDLTDSEMNKLFEKTKKQLRENA

EDMGNGCFKIYHKCDNACIGSIRNETYDHNVYRDEALNNRFQIKGVELKSGYKDWILWISFAISCFLLC

VALLGFIMWACQKGNIRCNICI

PDI-H3 Bang DNA (SEQ ID NO: 7)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCACCATGCAGTACCAAAC

GGAACGATAGTGAAAACAATCACAAATGACCGAATTGAAGTTACTAATGCTACTGAGCTGGTTCAGAAT

-continued

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGACTGGAGTCACTCAAAACGGAACAAGTTCT

GCTTGCATAAGGAAATCTAGTAGTAGTTTCTTTAGTAGATTAAATTGGTTGACCCACTTAAACTACACA

TACCCAGCATTGAACGTGACTGTGCCAAACAATGAACAATTTGACAAATTGTACATTTGGGGGGTTCAC

CACCCGGGTACGGACAAGGACCAAATCTTCCTGTATGCTCGATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGAAGAATTCAGGACCTTGAGAAATATGTT

GAGGACACTAAAATAGATCTCTGGTCATACAACGCGGAGCTTCTTGTTGCCCTGGAGAATCAACATACA

ATTGATCTAACTGACTCAGAAATGAACAAACTGTTTGAAAAAACAAAGAAGCAACTGAGGGAAAATGCT

GAGGATATGGGAAATGGTTGTTTCAAAATATACCACAAATGTGACAATGCCTGCATAGGATCAATAAGA

AATGGAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGGTGCAACATTTGCATTTGA

PDI-H3 Bang AA (SEQ ID NO: 8)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWTGVTQNGTSSACIRKSSSSFFSRLNWLTHLNYTYPALNVTVPNNEQFDKLYIWGVH

HPGTDKDQIFLYARSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLNRLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHNVYRDEALNNRFQIKGVELKSGYKDWILWISFAISCFLLC

VALLGFIMWACQKGNIRCNICI

PDI-H3 Switz DNA (SEQ ID NO: 9)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

-continued

TACCCAGCATTAAACGTGACTATGCCAAACAATGAACAATTTGACAAATTGTACATTTGGGGGGTTCAC
CACCCGGGTACGGACAAGGACCAAATCTTCCTGTATGCACAATCATCAGGAAGAATCACAGTATCTACC
AAAAGAAGCCAACAAGCTGTAATCCCGAATATCGGATCTAGACCCAGAATAAGGGATATCCCTAGCAGA
ATAAGCATCTATTGGACAATAGTAAAACCGGGAGACATACTTTTGATTAACAGCACAGGGAATCTAATT
GCTCCTAGGGGTTACTTCAAAATACGAAGTGGGAAAAGCTCAATAATGAGATCAGATGCACCCATTGGC
AAATGCAAGTCTGAATGCATCACTCCAAATGGAAGCATTCCCAATGACAAACCATTCCAAAATGTAAAC
AGGATCACATACGGGGCCTGTCCCAGATATGTTAAGCAAAGCACTCTGAAATTGGCAACAGGAATGCGA
AATGTACCAGAGAGACAAACTAGAGGCATATTTGGCGCAATAGCGGGTTTCATAGAAAATGGTTGGGAG
GGAATGGTGGATGGTTGGTACGGCTTCAGGCATCAAAATTCTGAGGGAAGAGGACAAGCAGCAGATCTC
AAAAGCACTCAAGCAGCAATCGATCAAATCAATGGGAAGCTGAATCGATTGATCGGGAAAACCAACGAG
AAATTCCATCAGATTGAAAAAGAATTCTCAGAAGTAGAAGGGAGAATTCAGGACCTTGAGAAATATGTT
GAGGACACAAAAATAGATCTCTGGTCATACAACGCGGAGCTTCTTGTTGCCCTGGAGAACCAACATACA
ATTGATCTAACTGACTCAGAAATGAACAAACTGTTTGAAAAAACAAAGAAGCAACTGAGGGAAAATGCT
GAGGATATGGGCAATGGTTGTTTCAAAATATACCACAAATGTGACAATGCCTGCATAGGATCAATCAGA
AATGGAACTTATGACCACGATGTATACAGGGATGAAGCATTAAACAACCGGTTCCAGATCAAGGGAGTT
GAGCTGAAGTCAGGGTACAAAGATTGGATCCTATGGATTTCCTTTGCCATATCATGTTTTTTGCTTTGT
GTTGCTTTGTTGGGGTTCATCATGTGGGCCTGCCAAAAGGGCAACATTAGGTGCAACATTTGCATTTGA

PDI-H3 Switz AA (SEQ ID NO: 10)

MAKNVAIFGLLFSLLVLVPSQIFAQKLPGNDNSTATLCLGHHAVPNGTIVKTITNDRIEVTNATELVQN
SSIGEICDSPHQILDGENCTLIDALLGDPQCDGFQNKKWDLFVERSKAYSNCYPYDVPDYASLRSLVAS
SGTLEFNNESFNWAGVTQNGTSSSCIRGSNSSFFSRLNWLTHLNSKYPALNVTMPNNEQFDKLYIWGVH
HPGTDKDQIFLYAQSSGRITVSTKRSQQAVIPNIGSRPRIRDIPSRISIYWTIVKPGDILLINSTGNLI
APRGYFKIRSGKSSIMRSDAPIGKCKSECITPNGSIPNDKPFQNVNRITYGACPRYVKQSTLKLATGMR
NVPERQTRGIFGAIAGFIENGWEGMVDGWYGFRHQNSEGRGQAADLKSTQAAIDQINGKLNRLIGKTNE
KFHQIEKEFSEVEGRIQDLEKYVEDTKIDLWSYNAELLVALENQHTIDLTDSEMNKLFEKTKKQLRENA
EDMGNGCFKIYHKCDNACIGSIRNGTYDHDVYRDEALNNRFQIKGVELKSGYKDWILWISFAISCFLLC
VALLGFIMWACQKGNIRCNICI

PDI-H3 Miss DNA (SEQ ID NO: 11)

ATGGCGAAAAACGTTGCGATTTTCGGCTTATTGTTTTCTCTTCTTGTGTTGGTTCCTTCTCAGATCTTC
GCGCAAAAACTTCCTGGAAATGACAATAGCACGGCAACGCTGTGCCTTGGGCACCATGCAGTACCAAAC
GGAACGATAGTGAAAACAATCACGAATGACCGAATTGAAGTTACTAATGCTACTGAGCTGGTTCAGAAT
TCCTCAATAGGTGAAATATGCGACAGTCCTCATCAGATCCTTGATGGAGAAAACTGCACACTAATAGAT
GCTCTATTGGGAGACCCTCAGTGTGATGGCTTTCAAAATAAGAAATGGGACCTTTTTGTTGAACGAAGC
AGAGCCTACAGCAACTGTTACCCTTATGATGTGCCGGATTATGCCTCCCTTAGGTCACTAGTTGCCTCA
TCCGGCACACTGGAGTTTAACAATGAAAGCTTCAATTGGGCTGGAGTCACTCAAAACGGAACAAGTTCT
TCTTGCATAAGGGGATCTAATAGTAGTTTCTTTAGTAGATTAAATTGGTTGACCCACTTAAACTCCAAA
TACCCAGCATTAAACGTGACTATGCCAAACAATGAACAATTTGACAAATTGTACATTTGGGGGGTTCAC
CACCCGGGTACGGACAAGGACCAAATCTTCCTGTATGCAAAACCATCAGGAAGAATCACAGTATCTACC
AAAAGAAGCCAACAAGCTGTAATCCCGAATATCGGATCTAGACCCAGAATAAGGGATATCCCTAGCAGA
ATAAGCATCTATTGGACAATAGTAAAACCGGGAGACATACTTTTGATTAACAGCACAGGGAATCTAATT

-continued

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAACACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGGTGCAACATTTGCATTTGA

PDI-H3 Miss AA (SEQ ID NO: 12)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGFQNKKWDLFVERSRAYSNCYPYDVPDYASLRSLVAS

SGTLEENNESFNWAGVTQNGTSSSCIRGSNSSFFSRLNWLTHLNSKYPALNVTMPNNEQFDKLYIWGVH

HPGTDKDQIFLYAKPSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQNTLKLATGMR

NVPERQTRGIFGAIAGFIENGWEGMVDGWYGFRHQNSEGRGQAADLKSTQAAIDQINGKLNRLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISCFLLC

VALLGFIMWACQKGNIRCNICI

PDI-H3 Penn DNA (SEQ ID NO: 13)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAAAAAACTGCACTCTAATAGAT

GCTCTATTGGGAGACCCTCAGTGTGATGGCTTTCAAAATAAGAGATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACGATGAAAGCTTCAATTGGGCTGGAGTCACTCAAAACGGAACAAGTTCT

GCTTGCATAAGGGGATCTAATAGTAGTTTCTTTAGTAGATTAAATTGGTTGACCCACTCAAACTTCAAA

TACCCAGCATTGAACGTGACTATGCCAAACAATGAACAATTTGACAAATTGTACATTTGGGGGGTTCAC

CACCCGGGTACAGACAAGGACCAAATCTTCCTGTACGCTCAATCATCAGGAAGAATCACAGTATCTACC

AAAAGAAGCCAACAAGCTGTAATCCCGAATATCGGATCTAGACCCAGAATAAGGAATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACAAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGAAGGATGGTTGGTACGGTTTCAGGCATCAAAATTCTGAGGGAAGAGGACAAGCAGCAGATCTC

-continued

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCTTTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGGTGCAACATTTGCATTTGA

PDI-H3 Penn AA (SEQ ID NO: 14)

MAKNVAIFGLLFSLLVLVPSQIFAQKLPGNDNSTATLCLGHHAVPNGTIVKTITNDRIEVTNATELVQN

SSIGEICDSPHQILDGKNCTLIDALLGDPQCDGFQNKRWDLFVERSKAYSNCYPYDVPDYASLRSLVAS

SGTLEENDESFNWAGVTQNGTSSACIRGSNSSFFSRLNWLTHSNFKYPALNVTMPNNEQFDKLYIWGVH

HPGTDKDQIFLYAQSSGRITVSTKRSQQAVIPNIGSRPRIRNIPSRISIYWTIVKPGDILLINSTGNLI

APRGYFKIQSGKSSIMRSDAPIGKCKSECITPNGSIPNDKPFQNVNRITYGACPRYVKQSTLKLATGMR

NVPEKQTRGIFGAIAGFIENGWEGMKDGWYGFRHQNSEGRGQAADLKSTQAAIDQINGKLNRLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISCFLLC

VALLGFIMWACQKGNIRCNICI

IF-CPMV(fL5'UTR)_SpPDI.c (SEQ ID NO: 15)

TCGTGCTTCGGCACCAGTACAATGGCGAAAAACGTTGCGATTTTCGGCT

IF-H1cTMCT.S1-4r (SEQ ID NO: 16)

ACTAAAGAAAATAGGCCTTTAAATACATATTCTACACTGTAGAGAC

IF-H3A-Ala.r (SEQ ID NO: 17)

ACTAAAGAAAATAGGCCTTCAAATGCAAATGTTGCACCTAATGTTGCCCTTTTGG

H3_Swi_SLVLL.r (SEQ ID NO: 18)

AGCAACTAACAGTACAAGGGATGATATGGCAAAGGAAATCCATAGGATCCA

H3_Swi_SLVLL.c (SEQ ID NO: 19)

TCCTTTGCCATATCATCCCTTGTACTGTTAGTTGCTTTGTTGGGGTTCATCAT

PDI-H3 HK-CysTm DNA (SEQ ID NO: 20)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCATCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGACTGGAGTCACTCAAAACGGAACAAGTTCT

GCTTGCATAAGGAGATCTAGTAGTAGTTTCTTTAGTAGATTAAATTGGTTGACCCACTTAAACTACACA

TACCCAGCATTGAACGTGACTATGCCAAACAATGAACAATTTGACAAATTGTACATTTGGGGGGTTCAC

CACCCGGGTACGGACAAGGACCAAATCTTCCTGTATGCTCAATCATCAGGAAGAATCACAGTATCTACC

AAAAGAAGCCAACAAGCTGTAATCCCAAATATCGGATCTAGACCCAGAATAAGGGATATCCCTAGCAGA

-continued

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGTGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGAAGAATTCAGGACCTTGAGAAATATGTT

GAGGACACTAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATAAGA

AATGGAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 HK-CysTm AA (SEQ ID NO: 21)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWTGVTQNGTSSACIRRSSSSFFSRLNWLTHLNYTYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLNRLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHNVYRDEALNNRFQIKGVELKSGYKDWILWISFAISSLVLL

VALLGFIMWACQKGNIRCNICI*

H3_HK480114(N382A + L384V).r (SEQ ID NO: 22)

TTGGTTTTCCCGATCACTCGAGCCAGCTTCCCATTGATTTGATCGATT

H3_HK480114(N382A + L384V).c (SEQ ID NO: 23)

GGGAAGCTGGCTCGAGTGATCGGGAAAACCAACGAGAAATTCCATCAG

PDI-H3 HK-N382A + L384V - CysTm DNA (SEQ ID NO: 24)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCATCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGACTGGAGTCACTCAAAACGGAACAAGTTCT

GCTTGCATAAGGAGATCTAGTAGTAGTTTCTTTAGTAGATTAAATTGGTTGACCCACTTAAACTACACA

TACCCAGCATTGAACGTGACTATGCCAAACAATGAACAATTTGACAAATTGTACATTTGGGGGGTTCAC

CACCCGGGTACGGACAAGGACCAAATCTTCCTGTATGCTCAATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

-continued

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGTGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGGCTCGAGTGATCGGGAAAACCAACGAG

AAATTCCATCAGATTGAAAAAGAATTCTCAGAAGTAGAAGGAAGAATTCAGGACCTTGAGAAATATGTT

GAGGACACTAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATAAGA

AATGGAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 HK-N382A + L384V - CysTm AA (SEQ ID NO: 25)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWTGVTQNGTSSACIRRSSSSFFSRLNWLTHLNYTYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLARVIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHNVYRDEALNNRFQIKGVELKSGYKDWILWISFAISSLVLL

VALLGFIMWACQKGNIRCNICI*

PDI-H3 Minn-CysTm DNA (SEQ ID NO: 26)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCACCATGCAGTACCAAAC

GGAACGATAGTGAAAACAATCACAAATGACCGAATTGAAGTTACTAATGCTACTGAGTTGGTTCAGAAT

TCCTCAATAGGTGAAATATGCGACAGTCCTCATCAGATCCTTGATGGAGAGAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGACTGGAGTCACTCAAAACGGAACAAGTTCT

GCTTGCATAAGGAGATCTAGTAGTAGTTTCTTTAGTAGATTAAATTGGTTGACCCACTTAAACTACACA

TATCCAGCATTGAACGTGACTATGCCAAACAAGGAACAATTTGACAAATTGTACATTTGGGGGGTTCAC

CACCCGGGTACGGACAAGGACCAAATCTTCCTGTATGCTCAATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGCGCAATAGCGGGTTTCATAGAAAATGGTTGGGAG

-continued

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGGTTGATCGGGAAAACCAACGAG

AAATTCCATCAGATTGAAAAAGAATTCTCAGAAGTAGAAGGAAGAGTTCAAGACCTTGAGAAATATGTT

GAGGACACTAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGAAATGGTTGTTTCAAAATATACCACAAATGTGACAATGCCTGCATAGGATCAATAAGA

AATGAAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGATGCAACATTTGCATTTGA

PDI-H3 Minn-CysTm AA (SEQ ID NO: 27)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESENWTGVTQNGTSSACIRRSSSSFFSRLNWLTHLNYTYPALNVTMPNKEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLNRLIGKTNE

KFHQIEKEFSEVEGRVQDLEKYVEDTKIDLWSYNAELLVALENQHTIDLTDSEMNKLFEKTKKQLRENA

EDMGNGCFKIYHKCDNACIGSIRNETYDHNVYRDEALNNRFQIKGVELKSGYKDWILWISFAISSLVLL

VALLGFIMWACQKGNIRCNICI*

H3Minn(N382A + L384V).r (SEQ ID NO: 28)

GTTGGTTTTCCCGATCACCCGAGCCAGCTTCCCATTGATTTGATCGATTGCTGCTTGAGT

H3Minn(N382A + L384V).c (SEQ ID NO: 29)

AATCAATGGGAAGCTGGCTCGGGTGATCGGGAAAACCAACGAGAAATTCCATCAGA

PDI-H3 Minn-N382A + L384V - CysTm DNA (SEQ ID NO: 30)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCACCATGCAGTACCAAAC

GGAACGATAGTGAAAACAATCACAAATGACCGAATTGAAGTTACTAATGCTACTGAGTTGGTTCAGAAT

TCCTCAATAGGTGAAATATGCGACAGTCCTCATCAGATCCTTGATGGAGAGAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGACTGGAGTCACTCAAAACGGAACAAGTTCT

GCTTGCATAAGGAGATCTAGTAGTAGTTTCTTTAGTAGATTAAATTGGTTGACCCACTTAAACTACACA

TATCCAGCATTGAACGTGACTATGCCAAACAAGGAACAATTTGACAAATTGTACATTTGGGGGGTTCAC

CACCCGGGTACGGACAAGGACCAAATCTTCCTGTATGCTCAATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

-continued

AAAAGCACTCAAGCAGCAATCGATCAAATCAATGGGAAGCTGGCTCGGGTGATCGGGAAAACCAACGAG

AAATTCCATCAGATTGAAAAAGAATTCTCAGAAGTAGAAGGAAGAGTTCAAGACCTTGAGAAATATGTT

GAGGACACTAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGAAATGGTTGTTTCAAAATATACCACAAATGTGACAATGCCTGCATAGGATCAATAAGA

AATGAAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGATGCAACATTTGCATTTGA

PDI-H3 Minn-N382A + L384V - CysTm AA (SEQ ID NO: 31)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWTGVTQNGTSSACIRRSSSFFSRLNWLTHLNYTYPALNVTMPNKEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLARVIGKTNE

KFHQIEKEFSEVEGRVQDLEKYVEDTKIDLWSYNAELLVALENQHTIDLTDSEMNKLFEKTKKQLRENA

EDMGNGCFKIYHKCDNACIGSIRNETYDHNVYRDEALNNRFQIKGVELKSGYKDWILWISFAISSLVLL

VALLGFIMWACQKGNIRCNICI*

PDI-H3 SAus-CysTm DNA (SEQ ID NO: 32)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCACCATGCAGTACCAAAC

GGAACGATAGTGAAAACAATCACAAATGACCGAATTGAAGTTACTAATGCTACTGAGTTGGTTCAGAAT

TCCTCAATAGGTGAAATATGCGACAGTCCTCATCAGATCCTTGATGGAGAGAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAAAAATGAAAGCTTCAATTGGACTGGAGTCACTCAAAACGGAACAAGTTCT

GCTTGCATAAGGAGATCTAGTAGTAGTTTCTTTAGTAGATTAAATTGGTTGACCCACTTAAACTACACA

TATCCAGCATTGAACGTGACTATGCCAAACAAGGAACAATTTGACAAATTGTACATTTGGGGGGTTCAC

CACCCGGGTACGGACAAGGACCAAATCTTCCTGTATGCTCAATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGGTTGATCGGGAAAACCAACGAG

AAATTCCATCAGATTGAAAAAGAATTCTCAGAAGTAGAAGGAAGAGTTCAAGACCTTGAGAAATATGTT

GAGGACACTAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

-continued

GAGGATATGGGAAATGGTTGTTTCAAAATATACCACAAATGTGACAATGCCTGCATAGGATCAATAAGA

AATGAAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGATGCAACATTTGCATTTGA

PDI-H3 SAus-CysTm AA (SEQ ID NO: 33)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFKNESFNWTGVTQNGTSSACIRRSSSFFSRLNWLTHLNYTYPALNVTMPNKEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLNRLIGKTNE

KFHQIEKEFSEVEGRVQDLEKYVEDTKIDLWSYNAELLVALENQHTIDLTDSEMNKLFEKTKKQLRENA

EDMGNGCFKIYHKCDNACIGSIRNETYDHNVYRDEALNNRFQIKGVELKSGYKDWILWISFAISSLVLL

VALLGFIMWACQKGNIRCNICI*

PDI-H3 SAus-N382A + L384V - CysTm DNA (SEQ ID NO: 34)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCACCATGCAGTACCAAAC

GGAACGATAGTGAAAACAATCACAAATGACCGAATTGAAGTTACTAATGCTACTGAGTTGGTTCAGAAT

TCCTCAATAGGTGAAATATGCGACAGTCCTCATCAGATCCTTGATGGAGAGAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAAAAATGAAAGCTTCAATTGGACTGGAGTCACTCAAAACGGAACAAGTTCT

GCTTGCATAAGGAGATCTAGTAGTAGTTTCTTTAGTAGATTAAATTGGTTGACCCACTTAAACTACACA

TATCCAGCATTGAACGTGACTATGCCAAACAAGGAACAATTTGACAAATTGTACATTTGGGGGGTTCAC

CACCCGGGTACGGACAAGGACCAAATCTTCCTGTATGCTCAATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGGCTCGGGTGATCGGGAAAACCAACGAG

AAATTCCATCAGATTGAAAAAGAATTCTCAGAAGTAGAAGGAAGAGTTCAAGACCTTGAGAAATATGTT

GAGGACACTAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGAAATGGTTGTTTCAAAATATACCACAAATGTGACAATGCCTGCATAGGATCAATAAGA

AATGAAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGATGCAACATTTGCATTTGA

-continued

PDI-H3 SAus-N382A + L384V - CysTm AA (SEQ ID NO: 35)

MAKNVAIFGLLESLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFKNESFNWTGVTQNGTSSACIRRSSSSFFSRLNWLTHLNYTYPALNVTMPNKEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLARVIGKTNE

KFHQIEKEFSEVEGRVQDLEKYVEDTKIDLWSYNAELLVALENQHTIDLTDSEMNKLFEKTKKQLRENA

EDMGNGCFKIYHKCDNACIGSIRNETYDHNVYRDEALNNRFQIKGVELKSGYKDWILWISFAISSLVLL

VALLGFIMWACQKGNIRCNICI*

PDI-H3 Bang-CysTm DNA (SEQ ID NO: 36)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCACCATGCAGTACCAAAC

GGAACGATAGTGAAAACAATCACAAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGACTGGAGTCACTCAAAACGGAACAAGTTCT

GCTTGCATAAGGAAATCTAGTAGTAGTTTCTTTAGTAGATTAAATTGGTTGACCCACTTAAACTACACA

TACCCAGCATTGAACGTGACTGTGCCAAACAATGAACAATTTGACAAATTGTACATTTGGGGGGTTCAC

CACCCGGGTACGGACAAGGACCAAATCTTCCTGTATGCTCGATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGAAGAATTCAGGACCTTGAGAAATATGTT

GAGGACACTAAAATAGATCTCTGGTCATACAACGCGGAGCTTCTTGTTGCCCTGGAGAATCAACATACA

ATTGATCTAACTGACTCAGAAATGAACAAACTGTTTGAAAAAACAAAGAAGCAACTGAGGGAAAATGCT

GAGGATATGGGAAATGGTTGTTTCAAAATATACCACAAATGTGACAATGCCTGCATAGGATCAATAAGA

AATGGAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Bang-CysTm AA (SEQ ID NO: 37)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWTGVTQNGTSSACIRKSSSSFFSRLNWLTHLNYTYPALNVTVPNNEQFDKLYIWGVH

-continued

HPGTDKDQIFLYARSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLNRLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHNVYRDEALNNRFQIKGVELKSGYKDWILWISFAISSLVLL

VALLGFIMWACQKGNIRCNICI*

PDI-H3 Bang-N382A + L384V - CysTm DNA (SEQ ID NO: 38)

ATGGCGAAAAACGTTGCGATTTTCGGCTTATTGTTTTCTCTTCTTGTGTTGGTTCCTTCTCAGATCTTC

GCGCAAAAAATTCCTGGAAATGACAATAGCACGGCAACGCTGTGCCTTGGGCACCATGCAGTACCAAAC

GGAACGATAGTGAAAACAATCACAAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGACTGGAGTCACTCAAAACGGAACAAGTTCT

GCTTGCATAAGGAAATCTAGTAGTAGTTTCTTTAGTAGATTAAATTGGTTGACCCACTTAAACTACACA

TACCCAGCATTGAACGTGACTGTGCCAAACAATGAACAATTTGACAAATTGTACATTTGGGGGGTTCAC

CACCCGGGTACGGACAAGGACCAAATCTTCCTGTATGCTCGATCATCAGGAAGAATCACAGTATCTACC

AAAAGAAGCCAACAAGCTGTAATCCCAAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCATAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGGTGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGGCTCGAGTGATCGGGAAAACCAACGAG

AAATTCCATCAGATTGAAAAAGAATTCTCAGAAGTAGAAGGAAGAATTCAGGACCTTGAGAAATATGTT

GAGGACACTAAAATAGATCTCTGGTCATACAACGCGGAGCTTCTTGTTGCCCTGGAGAATCAACATACA

ATTGATCTAACTGACTCAGAAATGAACAAACTGTTTGAAAAAACAAAGAAGCAACTGAGGGAAAATGCT

GAGGATATGGGAAATGGTTGTTTCAAAATATACCACAAATGTGACAATGCCTGCATAGGATCAATAAGA

AATGGAACTTATGACCACAATGTGTACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Bang-N382A + L384V - CysTm AA (SEQ ID NO: 39)

MAKNVAIFGLLFSLLVLVPSQIFAQKIPGNDNSTATLCLGHHAVPNGTIVKTITNDRIEVTNATELVQN

SSIGEICDSPHQILDGENCTLIDALLGDPQCDGFQNKKWDLEVERSKAYSNCYPYDVPDYASLRSLVAS

SGTLEFNNESFNWTGVTQNGTSSACIRKSSSSFFSRLNWLTHLNYTYPALNVTVPNNEQFDKLYIWGVH

HPGTDKDQIFLYARSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKHSTLKLATGMR

NVPEKQTRGIFGAIAGFIENGWEGMVDGWYGFRHQNSEGRGQAADLKSTQAAIDQINGKLARVIGKTNE

-continued

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHNVYRDEALNNRFQIKGVELKSGYKDWILWISFAISSLVLL

VALLGFIMWACQKGNIRCNICI*

H3_Swi(F392D).r (SEQ ID NO: 40)

TTTTCAATCTGATGGTCTTTCTCGTTGGTTTTCCCGATCAATCGATTCAGCTTC

H3_Swi(F392D).c (SEQ ID NO: 41)

TCGGGAAAACCAACGAGAAAGACCATCAGATTGAAAAAGAATTCTCAG

PDI-H3 Switz-F392D DNA (SEQ ID NO: 42)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

TACCCAGCATTAAACGTGACTATGCCAAACAATGAACAATTTGACAAATTGTACATTTGGGGGGTTCAC

CACCCGGGTACGGACAAGGACCAAATCTTCCTGTATGCACAATCATCAGGAAGAATCACAGTATCTACC

AAAAGAAGCCAACAAGCTGTAATCCCGAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAAGACCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGGTGCAACATTTGCATTTGA

PDI-H3 Switz-F392D AA (SEQ ID NO: 43)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESENWAGVTQNGTSSSCIRGSNSSFFSRLNWLTHLNSKYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQSTLKLATGMR

NVPERQTRGIFGAIAGFIENGWEGMVDGWYGFRHQNSEGRGQAADLKSTQAAIDQINGKLNRLIGKTNE

-continued

KDHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISCFLLC

VALLGFIMWACQKGNIRCNICI*

H3_Swi(L431M).r (SEQ ID NO: 44)

TTGTATGTTGGTTCTCCATGGCAACAAGAAGCTCCGCGTTGTATGACCAG

H3_Swi(L431M).c (SEQ ID NO: 45)

GGAGCTTCTTGTTGCCATGGAGAACCAACATACAATTGATCTAACTGACTCAGA

PDI-H3 Switz-L431M DNA (SEQ ID NO: 46)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

TACCCAGCATTAAACGTGACTATGCCAAACAATGAACAATTTGACAAATTGTACATTTGGGGGGTTCAC

CACCCGGGTACGGACAAGGACCAAATCTTCCTGTATGCACAATCATCAGGAAGAATCACAGTATCTACC

AAAAGAAGCCAACAAGCTGTAATCCCGAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCATGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGGTGCAACATTTGCATTTGA

PDI-H3 Switz-L431M AA (SEQ ID NO: 47)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGEQNKKWDLFVERSKAYSNCYPYDVPDYASLRSLVAS

SGTLEFNNESFNWAGVTQNGTSSSCIRGSNSSFFSRLNWLTHLNSKYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQSTLKLATGMR

NVPERQTRGIFGAIAGFIENGWEGMVDGWYGFRHQNSEGRGQAADLKSTQAAIDQINGKLNRLIGKTNE

KFHQIEKEFSEVEGRIQDLEKYVEDTKIDLWSYNAELLVAMENQHTIDLTDSEMNKLFEKTKKQLRENA

-continued

EDMGNGCFKIYHKCDNACIGSIRNGTYDHDVYRDEALNNRFQIKGVELKSGYKDWILWISFAISCFLLC

VALLGFIMWACQKGNIRCNICI

PDI-H3 Switz-CysTm DNA (SEQ ID NO: 48)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

TACCCAGCATTAAACGTGACTATGCCAAACAATGAACAATTTGACAAATTGTACATTTGGGGGGTTCAC

CACCCGGGTACGGACAAGGACCAAATCTTCCTGTATGCACAATCATCAGGAAGAATCACAGTATCTACC

AAAAGAAGCCAACAAGCTGTAATCCCGAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Switz-CysTm AA (SEQ ID NO: 49)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWAGVTQNGTSSSCIRGSNSSFFSRLNWLTHLNSKYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQSTLKLATGMR

NVPERQTRGIFGAIAGFIENGWEGMVDGWYGFRHQNSEGRGQAADLKSTQAAIDQINGKLNRLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISSLVLL

VALLGFIMWACQKGNIRCNICI*

-continued

H3_Swi(N382A).r (SEQ ID NO: 50)

TTTCCCGATCAATCGAGCCAGCTTCCCATTGATTTGATCGATTGCTGC

H3_Swi(N382A).c (SEQ ID NO: 51)

TCAAATCAATGGGAAGCTGGCTCGATTGATCGGGAAAACCAACGAGAAATTCCA

PDI-H3 Switz-N382A - CysTm DNA (SEQ ID NO: 52)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

TACCCAGCATTAAACGTGACTATGCCAAACAATGAACAATTTGACAAATTGTACATTTGGGGGGTTCAC

CACCCGGGTACGGACAAGGACCAAATCTTCCTGTATGCACAATCATCAGGAAGAATCACAGTATCTACC

AAAAGAAGCCAACAAGCTGTAATCCCGAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGGCTCGATTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Switz-N382A - CysTm AA (SEQ ID NO: 53)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESENWAGVTQNGTSSSCIRGSNSSFFSRLNWLTHLNSKYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQSTLKLATGMR

NVPERQTRGIFGAIAGFIENGWEGMVDGWYGFRHQNSEGRGQAADLKSTQAAIDQINGKLARLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISSLVLL

VALLGFIMWACQKGNIRCNICI*

-continued

H3_Swi(L384V).r (SEQ ID NO: 54)

TTGGTTTTCCCGATCACTCGATTCAGCTTCCCATTGATTTGATCGATT

H3_Swi(L384V).c (SEQ ID NO: 55)

GGGAAGCTGAATCGAGTGATCGGGAAAACCAACGAGAAATTCCATCAG

PDI-H3 Switz-L384V - CysTm DNA (SEQ ID NO: 56)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

TACCCAGCATTAAACGTGACTATGCCAAACAATGAACAATTTGACAAATTGTACATTTGGGGGGTTCAC

CACCCGGGTACGGACAAGGACCAAATCTTCCTGTATGCACAATCATCAGGAAGAATCACAGTATCTACC

AAAAGAAGCCAACAAGCTGTAATCCCGAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGAATCGAGTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Switz-L384V - CysTm AA (SEQ ID NO: 57)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGFQNKKWDLEVERSKAYSNCYPYDVPDYASLRSLVAS

SGTLEFNNESFNWAGVTQNGTSSSCIRGSNSSFFSRLNWLTHLNSKYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQSTLKLATGMR

NVPERQTRGIFGAIAGFIENGWEGMVDGWYGFRHQNSEGRGQAADLKSTQAAIDQINGKLNRVIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISSLVLL

VALLGFIMWACQKGNIRCNICI*

-continued

PDI-H3 Switz-F392D - CysTm DNA (SEQ ID NO: 58)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

TACCCAGCATTAAACGTGACTATGCCAAACAATGAACAATTTGACAAATTGTACATTTGGGGGGTTCAC

CACCCGGGTACGGACAAGGACCAAATCTTCCTGTATGCACAATCATCAGGAAGAATCACAGTATCTACC

AAAAGAAGCCAACAAGCTGTAATCCCGAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAAGACCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Switz-F392D - CysTm AA (SEQ ID NO: 59)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWAGVTQNGTSSSCIRGSNSSFFSRLNWLTHLNSKYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQSTLKLATGMR

NVPERQTRGIFGAIAGFIENGWEGMVDGWYGFRHQNSEGRGQAADLKSTQAAIDQINGKLNRLIGKTNE

KDHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISSLVLL

VALLGFIMWACQKGNIRCNICI*

PDI-H3 Switz-L431M - CysTm DNA (SEQ ID NO: 60)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

-continued

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

TACCCAGCATTAAACGTGACTATGCCAAACAATGAACAATTTGACAAATTGTACATTTGGGGGGTTCAC

CACCCGGGTACGGACAAGGACCAAATCTTCCTGTATGCACAATCATCAGGAAGAATCACAGTATCTACC

AAAAGAAGCCAACAAGCTGTAATCCCGAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCATGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Switz-L431M - CysTm AA (SEQ ID NO: 61)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESENWAGVTQNGTSSSCIRGSNSSFFSRLNWLTHLNSKYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQSTLKLATGMR

NVPERQTRGIFGAIAGFIENGWEGMVDGWYGFRHQNSEGRGQAADLKSTQAAIDQINGKLNRLIGKTNE

KFHQIEKEFSEVEGRIQDLEKYVEDTKIDLWSYNAELLVAMENQHTIDLTDSEMNKLFEKTKKQLRENA

EDMGNGCFKIYHKCDNACIGSIRNGTYDHDVYRDEALNNRFQIKGVELKSGYKDWILWISFAISSLVLL

VALLGFIMWACQKGNIRCNICI*

Cloning vector 1190 from left to right T-DNA (SEQ ID NO: 62)

TGGCAGGATATATTGTGGTGTAAACAAATTGACGCTTAGACAACTTAATAACACATTGCGGACGTTTTT

AATGTACTGAATTAACGCCGAATCCCGGGCTGGTATATTTATATGTTGTCAAATAACTCAAAAACCATA

AAAGTTTAAGTTAGCAAGTGTGTACATTTTTACTTGAACAAAAATATTCACCTACTACTGTTATAAATC

ATTATTAAACATTAGAGTAAAGAAATATGGATGATAAGAACAAGAGTAGTGATATTTTGACAACAATTT

TGTTGCAACATTTGAGAAAATTTTGTTGTTCTCTCTTTTCATTGGTCAAAAACAATAGAGAGAGAAAAA

GGAAGAGGGAGAATAAAAACATAATGTGAGTATGAGAGAGAAAGTTGTACAAAAGTTGTACCAAAATAG

TTGTACAAATATCATTGAGGAATTTGACAAAAGCTACACAAATAAGGGTTAATTGCTGTAAATAAATAA

GGATGACGCATTAGAGAGATGTACCATTAGAGAATTTTTGGCAAGTCATTAAAAAGAAAGAATAAATTA

-continued

TTTTTAAAATTAAAAGTTGAGTCATTTGATTAAACATGTGATTATTTAATGAATTGATGAAAGAGTTGG

ATTAAAGTTGTATTAGTAATTAGAATTTGGTGTCAAATTTAATTTGACATTTGATCTTTTCCTATATAT

TGCCCCATAGAGTCAGTTAACTCATTTTTATATTTCATAGATCAAATAAGAGAAATAACGGTATATTAA

TCCCTCCAAAAAAAAAAAACGGTATATTTACTAAAAAATCTAAGCCACGTAGGAGGATAACAGGATCCC

CGTAGGAGGATAACATCCAATCCAACCAATCACAACAATCCTGATGAGATAACCCACTTTAAGCCCACG

CATCTGTGGCACATCTACATTATCTAAATCACACATTCTTCCACACATCTGAGCCACACAAAAACCAAT

CCACATCTTTATCACCCATTCTATAAAAAATCACACTTTGTGAGTCTACACTTTGATTCCCTTCAAACA

CATACAAAGAGAAGAGACTAATTAATTAATTAATCATCTTGAGAGAAAATGGAACGAGCTATACAAGGA

AACGACGCTAGGGAACAAGCTAACAGTGAACGTTGGGATGGAGGATCAGGAGGTACCACTTCTCCCTTC

AAACTTCCTGACGAAAGTCCGAGTTGGACTGAGTGGCGGCTACATAACGATGAGACGAATTCGAATCAA

GATAATCCCCTTGGTTTCAAGGAAAGCTGGGGTTTCGGGAAAGTTGTATTTAAGAGATATCTCAGATAC

GACAGGACGGAAGCTTCACTGCACAGAGTCCTTGGATCTTGGACGGGAGATTCGGTTAACTATGCAGCA

TCTCGATTTTTCGGTTTCGACCAGATCGGATGTACCTATAGTATTCGGTTTCGAGGAGTTAGTATCACC

GTTTCTGGAGGGTCGCGAACTCTTCAGCATCTCTGTGAGATGGCAATTCGGTCTAAGCAAGAACTGCTA

CAGCTTGCCCCAATCGAAGTGGAAAGTAATGTATCAAGAGGATGCCCTGAAGGTACTCAAACCTTCGAA

AAAGAAAGCGAGTAAGTTAAAATGCTTCTTCGTCTCCTATTTATAATATGGTTTGTTATTGTTAATTTT

GTTCTTGTAGAAGAGCTTAATTAATCGTTGTTGTTATGAAATACTATTTGTATGAGATGAACTGGTGTA

ATGTAATTCATTTACATAAGTGGAGTCAGAATCAGAATGTTTCCTCCATAACTAACTAGACATGAAGAC

CTGCCGCGTACAATTGTCTTATATTTGAACAACTAAAATTGAACATCTTTTGCCACAACTTTATAAGTG

GTTAATATAGCTCAAATATATGGTCAAGTTCAATAGATTAATAATGGAAATATCAGTTATCGAAATTCA

TTAACAATCAACTTAACGTTATTAACTACTAATTTTATATCATCCCCTTTGATAAATGATAGTACACCA

ATTAGGAAGGAGCATGCTCGCCTAGGAGATTGTCGTTTCCCGCCTTCAGTTTGCAAGCTGCTCTAGCCG

TGTAGCCAATACGCAAACCGCCTCTCCCCGCGCGTTGGGAATTACTAGCGCGTGTCGACAAGCTTGCAT

GCCGGTCAACATGGTGGAGCACGACACACTTGTCTACTCCAAAAATATCAAAGATACAGTCTCAGAAGA

CCAAAGGGCAATTGAGACTTTTCAACAAAGGGTAATATCCGGAAACCTCCTCGGATTCCATTGCCCAGC

TATCTGTCACTTTATTGTGAAGATAGTGGAAAAGGAAGGTGGCTCCTACAAATGCCATCATTGCGATAA

AGGAAAGGCCATCGTTGAAGATGCCTCTGCCGACAGTGGTCCCAAAGATGGACCCCCACCCACGAGGAG

CATCGTGGAAAAAGAAGACGTTCCAACCACGTCTTCAAAGCAAGTGGATTGATGTGATAACATGGTGGA

GCACGACACACTTGTCTACTCCAAAAATATCAAAGATACAGTCTCAGAAGACCAAAGGGCAATTGAGAC

TTTTCAACAAAGGGTAATATCCGGAAACCTCCTCGGATTCCATTGCCCAGCTATCTGTCACTTTATTGT

GAAGATAGTGGAAAAGGAAGGTGGCTCCTACAAATGCCATCATTGCGATAAAGGAAAGGCCATCGTTGA

AGATGCCTCTGCCGACAGTGGTCCCAAAGATGGACCCCCACCCACGAGGAGCATCGTGGAAAAAGAAGA

CGTTCCAACCACGTCTTCAAAGCAAGTGGATTGATGTGATATCTCCACTGACGTAAGGGATGACGCACA

ATCCCACTATCCTTCGCAAGACCCTTCCTCTATATAAGGAAGTTCATTTCATTTGGAGAGGTATTAAAA

TCTTAATAGGTTTTGATAAAAGCGAACGTGGGGAAACCCGAACCAAACCTTCTTCTAAACTCTCTCTCA

TCTCTCTTAAAGCAAACTTCTCTCTTGTCTTTCTTGCGTGAGCGATCTTCAACGTTGTCAGATCGTGCT

TCGGCACCGCGGATGGCGAAAAACGTTGCGATTTTCGGCTTATTGTTTTCTCTTCTTGTGTTGGTTCCT

TCTCAGATCTTCGCCTGCAGGCTCCTCAGCCAAAACGACACCCCCATCTGTCTATCCACTGGCCCCTGG

ATCTGCTGCCCAAACTAACTCCATGGTGACCCTGGGATGCCTGGTCAAGGGCTATTTCCCTGAGCCAGT

GACAGTGACCTGGAACTCTGGATCCCTGTCCAGCGGTGTGCACACCTTCCCAGCTGTCCTGCAGTCTGA

-continued

CCTCTACACTCTGAGCAGCTCAGTGACTGTCCCCTCCAGCACCTGGCCCAGCGAGACCGTCACCTGCAA

CGTTGCCCACCCGGCCAGCAGCACCAAGGTGGACAAGAAAATTGTGCCCAGGGATTGTGGTTGTAAGCC

TTGCATATGTACAGTCCCAGAAGTATCATCTGTCTTCATCTTCCCCCCAAAGCCCAAGGATGTGCTCAC

CATTACTCTGACTCCTAAGGTCACGTGTGTTGTGGTAGACATCAGCAAGGATGATCCCGAGGTCCAGTT

CAGCTGGTTTGTAGATGATGTGGAGGTGCACACAGCTCAGACGCAACCCCGGGAGGAGCAGTTCAACAG

CACTTTCCGCTCAGTCAGTGAACTTCCCATCATGCACCAGGACTGGCTCAATGGCAAGGAGCGATCGCT

CACCATCACCATCACCATCACCATCACCATTAAAGGCCTATTTTCTTTAGTTTGAATTTACTGTTATTC

GGTGTGCATTTCTATGTTTGGTGAGCGGTTTTCTGTGCTCAGAGTGTGTTTATTTTATGTAATTTAATT

TCTTTGTGAGCTCCTGTTTAGCAGGTCGTCCCTTCAGCAAGGACACAAAAAGATTTTAATTTTATTAAA

AAAAAAAAAAAAAAAGACCGGGAATTCGATATCAAGCTTATCGACCTGCAGATCGTTCAAACATTTGGC

AATAAAGTTTCTTAAGATTGAATCCTGTTGCCGGTCTTGCGATGATTATCATATAATTTCTGTTGAATT

ACGTTAAGCATGTAATAATTAACATGTAATGCATGACGTTATTTATGAGATGGGTTTTTATGATTAGAG

TCCCGCAATTATACATTTAATACGCGATAGAAAACAAAATATAGCGCGCAAACTAGGATAAATTATCGC

GCGCGGTGTCATCTATGTTACTAGATCTCTAGAGTCTCAAGCTTGGCGCGCCCACGTGACTAGTGGCAC

TGGCCGTCGTTTTACAACGTCGTGACTGGGAAAACCCTGGCGTTACCCAACTTAATCGCCTTGCAGCAC

ATCCCCCTTTCGCCAGCTGGCGTAATAGCGAAGAGGCCCGCACCGATCGCCCTTCCCAACAGTTGCGCA

GCCTGAATGGCGAATGCTAGAGCAGCTTGAGCTTGGATCAGATTGTCGTTTCCCGCCTTCAGTTTAAAC

TATCAGTGTTTGACAGGATATATTGGCGGGTAAACCTAAGAGAAAAGAGCGTTTA

Construct 1314 from 2X35S prom to NOS term (SEQ ID NO: 63)

GTCAACATGGTGGAGCACGACACACTTGTCTACTCCAAAAATATCAAAGATACAGTCTCAGAAGACCAA

AGGGCAATTGAGACTTTTCAACAAAGGGTAATATCCGGAAACCTCCTCGGATTCCATTGCCCAGCTATC

TGTCACTTTATTGTGAAGATAGTGGAAAAGGAAGGTGGCTCCTACAAATGCCATCATTGCGATAAAGGA

AAGGCCATCGTTGAAGATGCCTCTGCCGACAGTGGTCCCAAAGATGGACCCCCACCCACGAGGAGCATC

GTGGAAAAAGAAGACGTTCCAACCACGTCTTCAAAGCAAGTGGATTGATGTGATAACATGGTGGAGCAC

GACACACTTGTCTACTCCAAAAATATCAAAGATACAGTCTCAGAAGACCAAAGGGCAATTGAGACTTTT

CAACAAAGGGTAATATCCGGAAACCTCCTCGGATTCCATTGCCCAGCTATCTGTCACTTTATTGTGAAG

ATAGTGGAAAAGGAAGGTGGCTCCTACAAATGCCATCATTGCGATAAAGGAAAGGCCATCGTTGAAGAT

GCCTCTGCCGACAGTGGTCCCAAAGATGGACCCCCACCCACGAGGAGCATCGTGGAAAAAGAAGACGTT

CCAACCACGTCTTCAAAGCAAGTGGATTGATGTGATATCTCCACTGACGTAAGGGATGACGCACAATCC

CACTATCCTTCGCAAGACCCTTCCTCTATATAAGGAAGTTCATTTCATTTGGAGAGGTATTAAAATCTT

AATAGGTTTTGATAAAAGCGAACGTGGGGAAACCCGAACCAAACCTTCTTCTAAACTCTCTCTCATCTC

TCTTAAAGCAAACTTCTCTCTTGTCTTTCTTGCGTGAGCGATCTTCAACGTTGTCAGATCGTGCTTCGG

CACCAGTACAATGGCGAAAAACGTTGCGATTTTCGGCTTATTGTTTTCTCTTCTTGTGTTGGTTCCTTC

TCAGATCTTCGCTGACACATTATGTATAGGTTATCATGCGAACAATTCAACAGACACTGTAGACACAGT

ACTAGAAAAGAATGTAACAGTAACACACTCTGTTAACCTTCTAGAAGACAAGCATAACGGGAAACTATG

CAAACTAAGAGGGGTAGCCCCATTGCATTTGGGTAAATGTAACATTGCTGGCTGGATCCTGGGAAATCC

AGAGTGTGAATCACTCTCCACAGCAAGCTCATGGTCCTACATTGTGGAAACACCTAGTTCAGACAATGG

AACGTGTTACCCAGGAGATTTCATCGATTATGAGGAGCTAAGAGAGCAATTGAGCTCAGTGTCATCATT

TGAAAGGTTTGAGATATTCCCCAAGACAAGTTCATGGCCCAATCATGACTCGAACAAAGGTGTAACGGC

AGCATGTCCTCATGCTGGAGCAAAAAGCTTCTACAAAAAATTTAATATGGCTAGTTAAAAAAGGAAATTC

ATACCCAAAGCTCAGCAAATCCTACATTAATGATAAAGGGAAAGAAGTCCTCGTGCTATGGGGCATTCA

-continued

```
CCATCCATCTACTAGTGCTGACCAACAAAGTCTCTATCAGAATGCAGATGCATATGTTTTTGTGGGGTC

ATCAAGATACAGCAAGAAGTTCAAGCCGGAAATAGCAATAAGACCCAAAGTGAGGGATCAAGAAGGGAG

AATGAACTATTACTGGACACTAGTAGAGCCGGGAGACAAAATAACATTCGAAGCAACTGGAAATCTAGT

GGTACCGAGATATGCATTCGCAATGGAAAGAAATGCTGGATCTGGTATTATCATTTCAGATACACCAGT

CCACGATTGCAATACAACTTGTCAAACACCCAAGGGTGCTATAAACACCAGCCTCCCATTTCAGAATAT

ACATCCGATCACAATTGGAAAATGTCCAAAATATGTAAAAAGCACAAAATTGAGACTGGCCACAGGATT

GAGGAATATCCCGTCTATTCAATCTAGAGGACTATTTGGGGCCATTGCCGGTTTCATTGAAGGGGGGTG

GACAGGGATGGTAGATGGATGGTACGGTTATCACCATCAAAATGAGCAGGGGTCAGGATATGCAGCCGA

CCTGAAGAGCACACAGAATGCCATTGACGAGATTACTAACAAAGTAAATTCTGTTATTGAAAAGATGAA

TACACAGTTCACAGCAGTAGGTAAAGAGTTCAACCACCTGGAAAAAAGAATAGAGAATTTAAATAAAAA

AGTTGATGATGGTTTCCTGGACATTTGGACTTACAATGCCGAACTGTTGGTTCTATTGGAAAATGAAAG

AACTTTGGACTACCACGATTCAAATGTGAAGAACTTATATGAAAAGGTAAGAAGCCAGCTAAAAAACAA

TGCCAAGGAAATTGGAAACGGCTGCTTTGAATTTTACCACAAATGCGATAACACGTGCATGGAAAGTGT

CAAAAATGGGACTTATGACTACCCAAAATACTCAGAGGAAGCAAAATTAAACAGAGAAGAAATAGATGG

GGTAAAGCTGGAATCAACAAGGATTTACCAGATTTTGGCGATCTATTCAACTGTCGCCAGTTCATTGGT

ACTGGTAGTCTCCCTGGGGGCAATCAGTTTCTGGATGTGCTCTAATGGGTCTCTACAGTGTAGAATATG

TATTTAAAGGCCTATTTTCTTTAGTTTGAATTTACTGTTATTCGGTGTGCATTTCTATGTTTGGTGAGC

GGTTTTCTGTGCTCAGAGTGTGTTTATTTTATGTAATTTAATTTCTTTGTGAGCTCCTGTTTAGCAGGT

CGTCCCTTCAGCAAGGACACAAAAAGATTTTAATTTTATTAAAAAAAAAAAAAAAAAAGACCGGGAATT

CGATATCAAGCTTATCGACCTGCAGATCGTTCAAACATTTGGCAATAAAGTTTCTTAAGATTGAATCCT

GTTGCCGGTCTTGCGATGATTATCATATAATTTCTGTTGAATTACGTTAAGCATGTAATAATTAACATG

TAATGCATGACGTTATTTATGAGATGGGTTTTTATGATTAGAGTCCCGCAATTATACATTTAATACGCG

ATAGAAAACAAAATATAGCGCGCAAACTAGGATAAATTATCGCGCGCGGTGTCATCTATGTTACTAGAT
Construct 2980 from 2X35S prom to NOS term
                                                             (SEQ ID NO: 64)
GTCAACATGGTGGAGCACGACACACTTGTCTACTCCAAAAATATCAAAGATACAGTCTCAGAAGACCAA

AGGGCAATTGAGACTTTTCAACAAAGGGTAATATCCGGAAACCTCCTCGGATTCCATTGCCCAGCTATC

TGTCACTTTATTGTGAAGATAGTGGAAAAGGAAGGTGGCTCCTACAAATGCCATCATTGCGATAAAGGA

AAGGCCATCGTTGAAGATGCCTCTGCCGACAGTGGTCCCAAAGATGGACCCCCACCCACGAGGAGCATC

GTGGAAAAAGAAGACGTTCCAACCACGTCTTCAAAGCAAGTGGATTGATGTGATAACATGGTGGAGCAC

GACACACTTGTCTACTCCAAAAATATCAAAGATACAGTCTCAGAAGACCAAAGGGCAATTGAGACTTTT

CAACAAAGGGTAATATCCGGAAACCTCCTCGGATTCCATTGCCCAGCTATCTGTCACTTTATTGTGAAG

ATAGTGGAAAAGGAAGGTGGCTCCTACAAATGCCATCATTGCGATAAAGGAAAGGCCATCGTTGAAGAT

GCCTCTGCCGACAGTGGTCCCAAAGATGGACCCCCACCCACGAGGAGCATCGTGGAAAAAGAAGACGTT

CCAACCACGTCTTCAAAGCAAGTGGATTGATGTGATATCTCCACTGACGTAAGGGATGACGCACAATCC

CACTATCCTTCGCAAGACCCTTCCTCTATATAAGGAAGTTCATTTCATTTGGAGAGGTATTAAAATCTT

AATAGGTTTTGATAAAAGCGAACGTGGGGAAACCCGAACCAAACCTTCTTCTAAACTCTCTCTCATCTC

TCTTAAAGCAAACTTCTCTCTTGTCTTTCTTGCGTGAGCGATCTTCAACGTTGTCAGATCGTGCTTCGG

CACCAGTACAATGGCGAAAAACGTTGCGATTTTCGGCTTATTGTTTTCTCTTCTTGTGTTGGTTCCTTC

TCAGATCTTCGCGGACACATTATGTATAGGTTATCATGCGAACAATTCAACAGACACTGTAGACACAGT

ACTAGAAAAGAATGTAACAGTAACACACTCTGTTAACCTTCTAGAAGACAAGCATAACGGGAAACTATG
```

-continued

CAAACTAAGAGGGGTAGCCCCATTGCATTTGGGTAAATGTAACATTGCTGGCTGGATCCTGGGAAATCC

AGAGTGTGAATCACTCTCCACAGCAAGCTCATGGTCCTACATTGTGGAAACACCTAGTTCAGACAATGG

AACGTGTTACCCAGGAGATTTCATCGATTATGAGGAGCTAAGAGAGCAATTGAGCTCAGTGTCATCATT

TGAAAGGTTTGAGATATTCCCCAAGACAAGTTCATGGCCCAATCATGACTCGAACAAAGGTGTAACGGC

AGCATGTCCTCATGCTGGAGCAAAAAGCTTCTACAAAAATTTAATATGGCTAGTTAAAAAAGGAAATTC

ATACCCAAAGCTCAGCAAATCCTACATTAATGATAAAGGGAAAGAAGTCCTCGTGCTATGGGGCATTCA

CCATCCATCTACTAGTGCTGACCAACAAAGTCTCTATCAGAATGCAGATGCATATGTTTTTGTGGGGTC

ATCAAGATACAGCAAGAAGTTCAAGCCGGAAATAGCAATAAGACCCAAAGTGAGGGATCAAGAAGGGAG

AATGAACTATTACTGGACACTAGTAGAGCCGGGAGACAAAATAACATTCGAAGCAACTGGAAATCTAGT

GGTACCGAGATATGCATTCGCAATGGAAAGAAATGCTGGATCTGGTATTATCATTTCAGATACACCAGT

CCACGATTGCAATACAACTTGTCAAACACCCAAGGGTGCTATAAACACCAGCCTCCCATTTCAGAATAT

ACATCCGATCACAATTGGAAAATGTCCAAAATATGTAAAAAGCACAAAATTGAGACTGGCCACAGGATT

GAGGAATATCCCGTCTATTCAATCTAGAGGACTATTTGGGGCCATTGCCGGTTTCATTGAAGGGGGGTG

GACAGGGATGGTAGATGGATGGTACGGTTATCACCATCAAAATGAGCAGGGGTCAGGATATGCAGCCGA

CCTGAAGAGCACACAGAATGCCATTGACGAGATTACTAACAAAGTAAATTCTGTTATTGAAAAGATGAA

TACACAGGACACAGCAGTAGGTAAAGAGTTCAACCACCTGGAAAAAAGAATAGAGAATTTAAATAAAAA

AGTTGATGATGGTTTCCTGGACATTTGGACTTACAATGCCGAACTGTTGGTTCTATTGGAAAATGAAAG

AACTTTGGACTACCACGATTCAAATGTGAAGAACTTATATGAAAAGGTAAGAAGCCAGCTAAAAAACAA

TGCCAAGGAAATTGGAAACGGCTGCTTTGAATTTTACCACAAATGCGATAACACGTGCATGGAAAGTGT

CAAAAATGGGACTTATGACTACCCAAAATACTCAGAGGAAGCAAAATTAAACAGAGAAGAAATAGATGG

GGTAAAGCTGGAATCAACAAGGATTTACCAGATTTTGGCGATCTATTCAACTGTCGCCAGTTCATTGGT

ACTGGTAGTCTCCCTGGGGGCAATCAGTTTCTGGATGTGCTCTAATGGGTCTCTACAGTGTAGAATATG

TATTTAAAGGCCTATTTTCTTTAGTTTGAATTTACTGTTATTCGGTGTGCATTTCTATGTTTGGTGAGC

GGTTTTCTGTGCTCAGAGTGTGTTTATTTTATGTAATTTAATTTCTTTGTGAGCTCCTGTTTAGCAGGT

CGTCCCTTCAGCAAGGACACAAAAAGATTTTAATTTTATTAAAAAAAAAAAAAAAAAAGACCGGGAATT

CGATATCAAGCTTATCGACCTGCAGATCGTTCAAACATTTGGCAATAAAGTTTCTTAAGATTGAATCCT

GTTGCCGGTCTTGCGATGATTATCATATAATTTCTGTTGAATTACGTTAAGCATGTAATAATTAACATG

TAATGCATGACGTTATTTATGAGATGGGTTTTTATGATTAGAGTCCCGCAATTATACATTTAATACGCG

ATAGAAAACAAAATATAGCGCGCAAACTAGGATAAATTATCGCGCGCGGTGTCATCTATGTTACTAGAT

Construct 2995 from 2X35S prom to NOS term (SEQ ID NO: 65)

GTCAACATGGTGGAGCACGACACACTTGTCTACTCCAAAAATATCAAAGATACAGTCTCAGAAGACCAA

AGGGCAATTGAGACTTTTCAACAAAGGGTAATATCCGGAAACCTCCTCGGATTCCATTGCCCAGCTATC

TGTCACTTTATTGTGAAGATAGTGGAAAAGGAAGGTGGCTCCTACAAATGCCATCATTGCGATAAAGGA

AAGGCCATCGTTGAAGATGCCTCTGCCGACAGTGGTCCCAAAGATGGACCCCCACCCACGAGGAGCATC

GTGGAAAAAGAAGACGTTCCAACCACGTCTTCAAAGCAAGTGGATTGATGTGATAACATGGTGGAGCAC

GACACACTTGTCTACTCCAAAAATATCAAAGATACAGTCTCAGAAGACCAAAGGGCAATTGAGACTTTT

CAACAAAGGGTAATATCCGGAAACCTCCTCGGATTCCATTGCCCAGCTATCTGTCACTTTATTGTGAAG

ATAGTGGAAAAGGAAGGTGGCTCCTACAAATGCCATCATTGCGATAAAGGAAAGGCCATCGTTGAAGAT

GCCTCTGCCGACAGTGGTCCCAAAGATGGACCCCCACCCACGAGGAGCATCGTGGAAAAAGAAGACGTT

CCAACCACGTCTTCAAAGCAAGTGGATTGATGTGATATCTCCACTGACGTAAGGGATGACGCACAATCC

CACTATCCTTCGCAAGACCCTTCCTCTATATAAGGAAGTTCATTTCATTTGGAGAGGTATTAAAATCTT

-continued

AATAGGTTTTGATAAAAGCGAACGTGGGGAAACCCGAACCAAACCTTCTTCTAAACTCTCTCTCATCTC

TCTTAAAGCAAACTTCTCTCTTGTCTTTCTTGCGTGAGCGATCTTCAACGTTGTCAGATCGTGCTTCGG

CACCAGTACAATGGCGAAAAACGTTGCGATTTTCGGCTTATTGTTTTCTCTTCTTGTGTTGGTTCCTTC

TCAGATCTTCGCGGACACATTATGTATAGGTTATCATGCGAACAATTCAACAGACACTGTAGACACAGT

ACTAGAAAAGAATGTAACAGTAACACACTCTGTTAACCTTCTAGAAGACAAGCATAACGGGAAACTATG

CAAACTAAGAGGGGTAGCCCCATTGCATTTGGGTAAATGTAACATTGCTGGCTGGATCCTGGGAAATCC

AGAGTGTGAATCACTCTCCACAGCAAGCTCATGGTCCTACATTGTGGAAACACCTAGTTCAGACAATGG

AACGTGTTACCCAGGAGATTTCATCGATTATGAGGAGCTAAGAGAGCAATTGAGCTCAGTGTCATCATT

TGAAAGGTTTGAGATATTCCCCAAGACAAGTTCATGGCCCAATCATGACTCGAACAAAGGTGTAACGGC

AGCATGTCCTCATGCTGGAGCAAAAAGCTTCTACAAAAAATTTAATATGGCTAGTTAAAAAAGGAAATTC

ATACCCAAAGCTCAGCAAATCCTACATTAATGATAAAGGGAAAGAAGTCCTCGTGCTATGGGGCATTCA

CCATCCATCTACTAGTGCTGACCAACAAAGTCTCTATCAGAATGCAGATGCATATGTTTTTGTGGGGTC

ATCAAGATACAGCAAGAAGTTCAAGCCGGAAATAGCAATAAGACCCAAAGTGAGGGATCAAGAAGGGAG

AATGAACTATTACTGGACACTAGTAGAGCCGGGAGACAAAATAACATTCGAAGCAACTGGAAATCTAGT

GGTACCGAGATATGCATTCGCAATGGAAAGAAATGCTGGATCTGGTATTATCATTTCAGATACACCAGT

CCACGATTGCAATACAACTTGTCAAACACCCAAGGGTGCTATAAACACCAGCCTCCCATTTCAGAATAT

ACATCCGATCACAATTGGAAAATGTCCAAAATATGTAAAAAGCACAAAATTGAGACTGGCCACAGGATT

GAGGAATATCCCGTCTATTCAATCTAGAGGACTATTTGGGGCCATTGCCGGTTTCATTGAAGGGGGGTG

GACAGGGATGGTAGATGGATGGTACGGTTATCACCATCAAAATGAGCAGGGGTCAGGATATGCAGCCGA

CCTGAAGAGCACACAGAATGCCATTGACGAGATTACTAACAAAGTAAATTCTGTTATTGAAAAGATGAA

TACACAGGACACAGCAGTAGGTAAAGAGTTCAACCACCTGGAAAAAAGAATAGAGAATTTAAATAAAAA

AGTTGATGATGGTTTCCTGGACATTTGGACTTACAATGCCGAACTGTTGGTTCTAATGGAAAATGAAAG

AACTTTGGACTACCACGATTCAAATGTGAAGAACTTATATGAAAAGGTAAGAAGCCAGCTAAAAAACAA

TGCCAAGGAAATTGGAAACGGCTGCTTTGAATTTTACCACAAATGCGATAACACGTGCATGGAAAGTGT

CAAAAATGGGACTTATGACTACCCAAAATACTCAGAGGAAGCAAAATTAAACAGAGAAGAAATAGATGG

GGTAAAGCTGGAATCAACAAGGATTTACCAGATTTTGGCGATCTATTCAACTGTCGCCAGTTCATTGGT

ACTGGTAGTCTCCCTGGGGGCAATCAGTTTCTGGATGTGCTCTAATGGGTCTCTACAGTGTAGAATATG

TATTTAAAGGCCTATTTTCTTTAGTTTGAATTTACTGTTATTCGGTGTGCATTTCTATGTTTGGTGAGC

GGTTTTCTGTGCTCAGAGTGTGTTTATTTTATGTAATTTAATTTCTTTGTGAGCTCCTGTTTAGCAGGT

CGTCCCTTCAGCAAGGACACAAAAAGATTTTAATTTTATTAAAAAAAAAAAAAAAAAAGACCGGGAATT

CGATATCAAGCTTATCGACCTGCAGATCGTTCAAACATTTGGCAATAAAGTTTCTTAAGATTGAATCCT

GTTGCCGGTCTTGCGATGATTATCATATAATTTCTGTTGAATTACGTTAAGCATGTAATAATTAACATG

TAATGCATGACGTTATTTATGAGATGGGTTTTTATGATTAGAGTCCCGCAATTATACATTTAATACGCG

ATAGAAAACAAAATATAGCGCGCAAACTAGGATAAATTATCGCGCGCGGTGTCATCTATGTTACTAGAT

Cloning vector 3556 from left to right T-DNA (SEQ ID NO: 66)

TGGCAGGATATATTGTGGTGTAAACAAATTGACGCTTAGACAACTTAATAACACATTGCGGACGTTTTT

AATGTACTGAATTAACGCCGAATCCCGGGCTGGTATATTTATATGTTGTCAAATAACTCAAAAACCATA

AAAGTTTAAGTTAGCAAGTGTGTACATTTTTACTTGAACAAAAATATTCACCTACTACTGTTATAAATC

ATTATTAAACATTAGAGTAAAGAAATATGGATGATAAGAACAAGAGTAGTGATATTTTGACAACAATTT

TGTTGCAACATTTGAGAAAATTTTGTTGTTCTCTCTTTTCATTGGTCAAAAACAATAGAGAGAGAAAAA

-continued

GGAAGAGGGAGAATAAAAACATAATGTGAGTATGAGAGAGAAAGTTGTACAAAAGTTGTACCAAAATAG

TTGTACAAATATCATTGAGGAATTTGACAAAAGCTACACAAATAAGGGTTAATTGCTGTAAATAAATAA

GGATGACGCATTAGAGAGATGTACCATTAGAGAATTTTTGGCAAGTCATTAAAAAGAAAGAATAAATTA

TTTTTAAAATTAAAAGTTGAGTCATTTGATTAAACATGTGATTATTTAATGAATTGATGAAAGAGTTGG

ATTAAAGTTGTATTAGTAATTAGAATTTGGTGTCAAATTTAATTTGACATTTGATCTTTTCCTATATAT

TGCCCCATAGAGTCAGTTAACTCATTTTTATATTTCATAGATCAAATAAGAGAAATAACGGTATATTAA

TCCCTCCAAAAAAAAAAAACGGTATATTTACTAAAAAATCTAAGCCACGTAGGAGGATAACAGGATCCC

CGTAGGAGGATAACATCCAATCCAACCAATCACAACAATCCTGATGAGATAACCCACTTTAAGCCCACG

CATCTGTGGCACATCTACATTATCTAAATCACACATTCTTCCACACATCTGAGCCACACAAAAACCAAT

CCACATCTTTATCACCCATTCTATAAAAAATCACACTTTGTGAGTCTACACTTTGATTCCCTTCAAACA

CATACAAAGAGAAGAGACTAATTAATTAATTAATCATCTTGAGAGAAAATGGAACGAGCTATACAAGGA

AACGACGCTAGGGAACAAGCTAACAGTGAACGTTGGGATGGAGGATCAGGAGGTACCACTTCTCCCTTC

AAACTTCCTGACGAAAGTCCGAGTTGGACTGAGTGGCGGCTACATAACGATGAGACGAATTCGAATCAA

GATAATCCCCTTGGTTTCAAGGAAAGCTGGGGTTTCGGGAAAGTTGTATTTAAGAGATATCTCAGATAC

GACAGGACGGAAGCTTCACTGCACAGAGTCCTTGGATCTTGGACGGGAGATTCGGTTAACTATGCAGCA

TCTCGATTTTTCGGTTTCGACCAGATCGGATGTACCTATAGTATTCGGTTTCGAGGAGTTAGTATCACC

GTTTCTGGAGGGTCGCGAACTCTTCAGCATCTCTGTGAGATGGCAATTCGGTCTAAGCAAGAACTGCTA

CAGCTTGCCCCAATCGAAGTGGAAAGTAATGTATCAAGAGGATGCCCTGAAGGTACTCAAACCTTCGAA

AAAGAAAGCGAGTAAGTTAAAATGCTTCTTCGTCTCCTATTTATAATATGGTTTGTTATTGTTAATTTT

GTTCTTGTAGAAGAGCTTAATTAATCGTTGTTGTTATGAAATACTATTTGTATGAGATGAACTGGTGTA

ATGTAATTCATTTACATAAGTGGAGTCAGAATCAGAATGTTTCCTCCATAACTAACTAGACATGAAGAC

CTGCCGCGTACAATTGTCTTATATTTGAACAACTAAAATTGAACATCTTTTGCCACAACTTTATAAGTG

GTTAATATAGCTCAAATATATGGTCAAGTTCAATAGATTAATAATGGAAATATCAGTTATCGAAATTCA

TTAACAATCAACTTAACGTTATTAACTACTAATTTTATATCATCCCCTTTGATAAATGATAGTACACCA

ATTAGGAAGGAGCATGCTCGCCTAGGAGATTGTCGTTTCCCGCCTTCAGTTTGCAAGCTGCTCTAGCCG

TGTAGCCAATACGCAAACCGCCTCTCCCCGCGCGTTGGGAATTACTAGCGCGTGTCGACACGCGTGGCG

CGCCCTGGTATATTTATATGTTGTCAAATAACTCAAAAACCATAAAAGTTTAAGTTAGCAAGTGTGTAC

ATTTTTACTTGAACAAAAATATTCACCTACTACTGTTATAAATCATTATTAAACATTAGAGTAAAGAAA

TATGGATGATAAGAACAAGAGTAGTGATATTTTGACAACAATTTTGTTGCAACATTTGAGAAAATTTTG

TTGTTCTCTCTTTTCATTGGTCAAAAACAATAGAGAGAGAAAAAGGAAGAGGGAGAATAAAAACATAAT

GTGAGTATGAGAGAGAAAGTTGTACAAAAGTTGTACCAAAATAGTTGTACAAATATCATTGAGGAATTT

GACAAAAGCTACACAAATAAGGGTTAATTGCTGTAAATAAATAAGGATGACGCATTAGAGAGATGTACC

ATTAGAGAATTTTTGGCAAGTCATTAAAAAGAAAGAATAAATTATTTTTAAAATTAAAAGTTGAGTCAT

TTGATTAAACATGTGATTATTTAATGAATTGATGAAAGAGTTGGATTAAAGTTGTATTAGTAATTAGAA

TTTGGTGTCAAATTTAATTTGACATTTGATCTTTTCCTATATATTGCCCCATAGAGTCAGTTAACTCAT

TTTTATATTTCATAGATCAAATAAGAGAAATAACGGTATATTAATCCCTCCAAAAAAAAAAAACGGTAT

ATTTACTAAAAAATCTAAGCCACGTAGGAGGATAACAGGATCCCCGTAGGAGGATAACATCCAATCCAA

CCAATCACAACAATCCTGATGAGATAACCCACTTTAAGCCCACGCATCTGTGGCACATCTACATTATCT

AAATCACACATTCTTCCACACATCTGAGCCACACAAAAACCAATCCACATCTTTATCACCCATTCTATA

AAAAATCACACTTTGTGAGTCTACACTTTGATTCCCTTCAAACACATACAAAGAGAAGAGACTAATTAA

TTAATTAATCATCTTGAGAGAAAATGAGTCTTCTAACCGAGGTCGAAACGCCTATCAGAAACGAATGGG

-continued

GGTGCAGATGCAACGATTCAAGTGATCCTCTTGTTGTTGCCGCAAGTATAATTGGGATTGTGCACCTGA

TATTGTGGATTATTGATCGCCTTTTTTCCAAAAGCATTTATCGTATCTTTAAACACGGTTTAAAAAGAG

GGCCTTCTACGGAAGGAGTACCAGAGTCTATGAGGGAAGAATATCGAGAGGAACAGCAGAATGCTGTGG

ATGCTGACGATGGTCATTTTGTCAGCATAGAGCTGGAGTAAGAGCTCTAAGTTAAAATGCTTCTTCGTC

TCCTATTTATAATATGGTTTGTTATTGTTAATTTTGTTCTTGTAGAAGAGCTTAATTAATCGTTGTTGT

TATGAAATACTATTTGTATGAGATGAACTGGTGTAATGTAATTCATTTACATAAGTGGAGTCAGAATCA

GAATGTTTCCTCCATAACTAACTAGACATGAAGACCTGCCGCGTACAATTGTCTTATATTTGAACAACT

AAAATTGAACATCTTTTGCCACAACTTTATAAGTGGTTAATATAGCTCAAATATATGGTCAAGTTCAAT

AGATTAATAATGGAAATATCAGTTATCGAAATTCATTAACAATCAACTTAACGTTATTAACTACTAATT

TTATATCATCCCCTTTGATAAATGATAGTACACCAATTAGGAAGGAACTAGGAGATTGTCGTTTCCCGC

CTTCAGTTTGCAAGCTGCTCTAGCCGTGTAGCCAATACGCAAACCGCCTCTCCCCGCGCGTTGGGAATT

ACTAGCGCGTGTCGACAAGCTTGCATGCCGGTCAACATGGTGGAGCACGACACACTTGTCTACTCCAAA

AATATCAAAGATACAGTCTCAGAAGACCAAAGGGCAATTGAGACTTTTCAACAAAGGGTAATATCCGGA

AACCTCCTCGGATTCCATTGCCCAGCTATCTGTCACTTTATTGTGAAGATAGTGGAAAAGGAAGGTGGC

TCCTACAAATGCCATCATTGCGATAAAGGAAAGGCCATCGTTGAAGATGCCTCTGCCGACAGTGGTCCC

AAAGATGGACCCCCACCCACGAGGAGCATCGTGGAAAAAGAAGACGTTCCAACCACGTCTTCAAAGCAA

GTGGATTGATGTGATAACATGGTGGAGCACGACACACTTGTCTACTCCAAAAATATCAAAGATACAGTC

TCAGAAGACCAAAGGGCAATTGAGACTTTTCAACAAAGGGTAATATCCGGAAACCTCCTCGGATTCCAT

TGCCCAGCTATCTGTCACTTTATTGTGAAGATAGTGGAAAAGGAAGGTGGCTCCTACAAATGCCATCAT

TGCGATAAAGGAAAGGCCATCGTTGAAGATGCCTCTGCCGACAGTGGTCCCAAAGATGGACCCCCACCC

ACGAGGAGCATCGTGGAAAAAGAAGACGTTCCAACCACGTCTTCAAAGCAAGTGGATTGATGTGATATC

TCCACTGACGTAAGGGATGACGCACAATCCCACTATCCTTCGCAAGACCCTTCCTCTATATAAGGAAGT

TCATTTCATTTGGAGAGGTATTAAAATCTTAATAGGTTTTGATAAAAGCGAACGTGGGGAAACCCGAAC

CAAACCTTCTTCTAAACTCTCTCTCATCTCTCTTAAAGCAAACTTCTCTCTTGTCTTTCTTGCGTGAGC

GATCTTCAACGTTGTCAGATCGTGCTTCGGCACCGCGGATGGCGAAAAACGTTGCGATTTTCGGCTTAT

TGTTTTCTCTTCTTGTGTTGGTTCCTTCTCAGATCTTCGCCTGCAGGCTCCTCAGCCAAAACGACACCC

CCATCTGTCTATCCACTGGCCCCTGGATCTGCTGCCCAAACTAACTCCATGGTGACCCTGGGATGCCTG

GTCAAGGGCTATTTCCCTGAGCCAGTGACAGTGACCTGGAACTCTGGATCCCTGTCCAGCGGTGTGCAC

ACCTTCCCAGCTGTCCTGCAGTCTGACCTCTACACTCTGAGCAGCTCAGTGACTGTCCCCTCCAGCACC

TGGCCCAGCGAGACCGTCACCTGCAACGTTGCCCACCCGGCCAGCAGCACCAAGGTGGACAAGAAAATT

GTGCCCAGGGATTGTGGTTGTAAGCCTTGCATATGTACAGTCCCAGAAGTATCATCTGTCTTCATCTTC

CCCCCAAAGCCCAAGGATGTGCTCACCATTACTCTGACTCCTAAGGTCACGTGTGTTGTGGTAGACATC

AGCAAGGATGATCCCGAGGTCCAGTTCAGCTGGTTTGTAGATGATGTGGAGGTGCACACAGCTCAGACG

CAACCCCGGGAGGAGCAGTTCAACAGCACTTTCCGCTCAGTCAGTGAACTTCCCATCATGCACCAGGAC

TGGCTCAATGGCAAGGAGCGATCGCTCACCATCACCATCACCATCACCATCACCATTAAAGGCCTATTT

TCTTTAGTTTGAATTTACTGTTATTCGGTGTGCATTTCTATGTTTGGTGAGCGGTTTTCTGTGCTCAGA

GTGTGTTTATTTTATGTAATTTAATTTCTTTGTGAGCTCCTGTTTAGCAGGTCGTCCCTTCAGCAAGGA

CACAAAAAGATTTTAATTTTATTAAAAAAAAAAAAAAAAAAAGACCGGGAATTCGATATCAAGCTTATCG

ACCTGCAGATCGTTCAAACATTTGGCAATAAAGTTTCTTAAGATTGAATCCTGTTGCCGGTCTTGCGAT

GATTATCATATAATTTCTGTTGAATTACGTTAAGCATGTAATAATTAACATGTAATGCATGACGTTATT

-continued

TATGAGATGGGTTTTTATGATTAGAGTCCCGCAATTATACATTTAATACGCGATAGAAAACAAAATATA

GCGCGCAAACTAGGATAAATTATCGCGCGCGGTGTCATCTATGTTACTAGATCTCTAGAGTCTCAAGCT

TGGCGCGCCCACGTGACTAGTGGCACTGGCCGTCGTTTTACAACGTCGTGACTGGGAAAACCCTGGCGT

TACCCAACTTAATCGCCTTGCAGCACATCCCCCTTTCGCCAGCTGGCGTAATAGCGAAGAGGCCCGCAC

CGATCGCCCTTCCCAACAGTTGCGCAGCCTGAATGGCGAATGCTAGAGCAGCTTGAGCTTGGATCAGAT

TGTCGTTTCCCGCCTTCAGTTTAAACTATCAGTGTTTGACAGGATATATTGGCGGGTAAACCTAAGAGA

AAAGAGCGTTTA

IF-H5ITMCT.s1-4r (SEQ ID NO: 67)

ACTAAAGAAAATAGGCCTTTAAATGCAAATTCTGCATTGTAACGATCCAT

PDI-H5 Indo DNA (SEQ ID NO: 68)

ATGGCGAAAAACGTTGCGATTTTCGGCTTATTGTTTTCTCTTCTTGTGTTGGTTCCTTCTCAGATCTTC

GCCGATCAGATTTGCATTGGTTACCATGCAAACAATTCAACAGAGCAGGTTGACACAATCATGGAAAAG

AACGTTACTGTTACACATGCCCAAGACATACTGGAAAAGACACACAACGGGAAGCTCTGCGATCTAGAT

GGAGTGAAGCCTCTAATTTTAAGAGATTGTAGTGTAGCTGGATGGCTCCTCGGGAACCCAATGTGTGAC

GAATTCATCAATGTACCGGAATGGTCTTACATAGTGGAGAAGGCCAATCCAACCAATGACCTCTGTTAC

CCAGGGAGTTTCAACGACTATGAAGAACTGAAACACCTATTGAGCAGAATAAACCATTTTGAGAAAATT

CAAATCATCCCCAAAAGTTCTTGGTCCGATCATGAAGCCTCATCAGGAGTTAGCTCAGCATGTCCATAC

CTGGGAAGTCCCTCCTTTTTTAGAAATGTGGTATGGCTTATCAAAAAGAACAGTACATACCCAACAATA

AAGAAAAGCTACAATAATACCAACCAAGAGGATCTTTTGGTACTGTGGGGAATTCACCATCCTAATGAT

GCGGCAGAGCAGACAAGGCTATATCAAAACCCAACCACCTATATTTCCATTGGGACATCAACACTAAAC

CAGAGATTGGTACCAAAAATAGCTACTAGATCCAAAGTAAACGGGCAAAGTGGAAGGATGGAGTTCTTC

TGGACAATTTTAAAACCTAATGATGCAATCAACTTCGAGAGTAATGGAAATTTCATTGCTCCAGAATAT

GCATACAAAATTGTCAAGAAAGGGGACTCAGCAATTATGAAAAGTGAATTGGAATATGGTAACTGCAAC

ACCAAGTGTCAAACTCCAATGGGGGCGATAAACTCTAGTATGCCATTCCACAACATACACCCTCTCACC

ATCGGGGAATGCCCCAAATATGTGAAATCAAACAGATTAGTCCTTGCAACAGGGCTCAGAAATAGCCCT

CAAAGAGAGAGCAGAAGAAAAAAGAGAGGACTATTTGGAGCTATAGCAGGTTTTATAGAGGGAGGATGG

CAGGGAATGGTAGATGGTTGGTATGGGTACCACCATAGCAATGAGCAGGGGAGTGGGTACGCTGCAGAC

AAAGAATCCACTCAAAAGGCAATAGATGGAGTCACCAATAAGGTCAACTCAATCATTGACAAAATGAAC

ACTCAGTTTGAGGCCGTTGGAAGGGAATTTAATAACTTAGAAAGGAGAATAGAGAATTTAAACAAGAAG

ATGGAAGACGGGTTTCTAGATGTCTGGACTTATAATGCCGAACTTCTGGTTCTCATGGAAAATGAGAGA

ACTCTAGACTTTCATGACTCAAATGTTAAGAACCTCTACGACAAGGTCCGACTACAGCTTAGGGATAAT

GCAAAGGAGCTGGGTAACGGTTGTTTCGAGTTCTATCACAAATGTGATAATGAATGTATGGAAAGTATA

AGAAACGGAACGTACAACTATCCGCAGTATTCAGAAGAAGCAAGATTAAAAAGAGAGGAAATAAGTGGG

GTAAAATTGGAATCAATAGGAACTTACCAAATACTGTCAATTTATTCAACAGTGGCGAGTTCCCTAGCA

CTGGCAATCATGATGGCTGGTCTATCTTTATGGATGTGCTCCAATGGATCGTTACAATGCAGAATTTGC

ATTTAA

PDI-H5 Indo AA (SEQ ID NO: 69)

MAKNVAIFGLLFSLLVLVPSQIFADQICIGYHANNSTEQVDTIMEKNVTVTHAQDILEKTHNGKLCDLD

GVKPLILRDCSVAGWLLGNPMCDEFINVPEWSYIVEKANPTNDLCYPGSFNDYEELKHLLSRINHFEKI

QIIPKSSWSDHEASSGVSSACPYLGSPSFFRNVVWLIKKNSTYPTIKKSYNNTNQEDLLVLWGIHHPND

AAEQTRLYQNPTTYISIGTSTLNQRLVPKIATRSKVNGQSGRMEFFWTILKPNDAINFESNGNFIAPEY

-continued

AYKIVKKGDSAIMKSELEYGNCNTKCQTPMGAINSSMPFHNIHPLTIGECPKYVKSNRLVLATGLRNSP

QRESRRKKRGLFGAIAGFIEGGWQGMVDGWYGYHHSNEQGSGYAADKESTQKAIDGVTNKVNSIIDKMN

TQFEAVGREFNNLERRIENLNKKMEDGELDVWTYNAELLVLMENERTLDFHDSNVKNLYDKVRLQLRDN

AKELGNGCFEFYHKCDNECMESIRNGTYNYPQYSEEARLKREEISGVKLESIGTYQILSIYSTVASSLA

LAIMMAGLSLWMCSNGSLQCRICI*

H5Ind(F393D).r (SEQ ID NO: 70)

CTTCCAACGGCCTCGTCCTGAGTGTTCATTTTGTCAATGATTGAGTTGA

H5Ind(F393D).c (SEQ ID NO: 71)

CAAAATGAACACTCAGGACGAGGCCGTTGGAAGGGAATTTAATAACTTA

PDI-H5 Indo-F393D DNA (SEQ ID NO: 72)

ATGGCGAAAAACGTTGCGATTTTCGGCTTATTGTTTTCTCTTCTTGTGTTGGTTCCTTCTCAGATCTTC

GCGGATCAGATTTGCATTGGTTACCATGCAAACAATTCAACAGAGCAGGTTGACACAATCATGGAAAAG

AACGTTACTGTTACACATGCCCAAGACATACTGGAAAAGACACACAACGGGAAGCTCTGCGATCTAGAT

GGAGTGAAGCCTCTAATTTTAAGAGATTGTAGTGTAGCTGGATGGCTCCTCGGGAACCCAATGTGTGAC

GAATTCATCAATGTACCGGAATGGTCTTACATAGTGGAGAAGGCCAATCCAACCAATGACCTCTGTTAC

CCAGGGAGTTTCAACGACTATGAAGAACTGAAACACCTATTGAGCAGAATAAACCATTTTGAGAAAATT

CAAATCATCCCCAAAAGTTCTTGGTCCGATCATGAAGCCTCATCAGGAGTTAGCTCAGCATGTCCATAC

CTGGGAAGTCCCTCCTTTTTTAGAAATGTGGTATGGCTTATCAAAAAGAACAGTACATACCCAACAATA

AAGAAAAGCTACAATAATACCAACCAAGAGGATCTTTTGGTACTGTGGGGAATTCACCATCCTAATGAT

GCGGCAGAGCAGACAAGGCTATATCAAAACCCAACCACCTATATTTCCATTGGGACATCAACACTAAAC

CAGAGATTGGTACCAAAAATAGCTACTAGATCCAAAGTAAACGGGCAAAGTGGAAGGATGGAGTTCTTC

TGGACAATTTTAAAACCTAATGATGCAATCAACTTCGAGAGTAATGGAAATTTCATTGCTCCAGAATAT

GCATACAAAATTGTCAAGAAAGGGGACTCAGCAATTATGAAAAGTGAATTGGAATATGGTAACTGCAAC

ACCAAGTGTCAAACTCCAATGGGGGCGATAAACTCTAGTATGCCATTCCACAACATACACCCTCTCACC

ATCGGGGAATGCCCCAAATATGTGAAATCAAACAGATTAGTCCTTGCAACAGGGCTCAGAAATAGCCCT

CAAAGAGAGAGCAGAAGAAAAAAGAGAGGACTATTTGGAGCTATAGCAGGTTTTATAGAGGGAGGATGG

CAGGGAATGGTAGATGGTTGGTATGGGTACCACCATAGCAATGAGCAGGGGAGTGGGTACGCTGCAGAC

AAAGAATCCACTCAAAAGGCAATAGATGGAGTCACCAATAAGGTCAACTCAATCATTGACAAAATGAAC

ACTCAGGACGAGGCCGTTGGAAGGGAATTTAATAACTTAGAAAGGAGAATAGAGAATTTAAACAAGAAG

ATGGAAGACGGGTTTCTAGATGTCTGGACTTATAATGCCGAACTTCTGGTTCTCATGGAAAATGAGAGA

ACTCTAGACTTTCATGACTCAAATGTTAAGAACCTCTACGACAAGGTCCGACTACAGCTTAGGGATAAT

GCAAAGGAGCTGGGTAACGGTTGTTTCGAGTTCTATCACAAATGTGATAATGAATGTATGGAAAGTATA

AGAAACGGAACGTACAACTATCCGCAGTATTCAGAAGAAGCAAGATTAAAAAGAGAGGAAATAAGTGGG

GTAAAATTGGAATCAATAGGAACTTACCAAATACTGTCAATTTATTCAACAGTGGCGAGTTCCCTAGCA

CTGGCAATCATGATGGCTGGTCTATCTTTATGGATGTGCTCCAATGGATCGTTACAATGCAGAATTTGC

ATTTAA

PDI-H5 Indo-F393D AA (SEQ ID NO: 73)

MAKNVAIFGLLFSLLVLVPSQIFADQICIGYHANNSTEQVDTIMEKNVTVTHAQDILEKTHNGKLCDLD

GVKPLILRDCSVAGWLLGNPMCDEFINVPEWSYIVEKANPTNDLCYPGSFNDYEELKHLLSRINHFEKI

QIIPKSSWSDHEASSGVSSACPYLGSPSFFRNVVWLIKKNSTYPTIKKSYNNTNQEDLLVLWGIHHPND

-continued

AAEQTRLYQNPTTYISIGTSTLNQRLVPKIATRSKVNGQSGRMEFFWTILKPNDAINFESNGNFIAPEY

AYKIVKKGDSAIMKSELEYGNCNTKCQTPMGAINSSMPFHNIHPLTIGECPKYVKSNRLVLATGLRNSP

QRESRRKKRGLFGAIAGFIEGGWQGMVDGWYGYHHSNEQGSGYAADKESTQKAIDGVTNKVNSIIDKMN

TQDEAVGREFNNLERRIENLNKKMEDGELDVWTYNAELLVLMENERTLDFHDSNVKNLYDKVRLQLRDN

AKELGNGCFEFYHKCDNECMESIRNGTYNYPQYSEEARLKREEISGVKLESIGTYQILSIYSTVASSLA

LAIMMAGLSLWMCSNGSLQCRICI*

IF-H5_Egy.r (SEQ ID NO: 74)

ACTAAAGAAAATAGGCCTTTAAATGCAAATTCTGCATTGTAGCGATCCATT

PDI-H5 Egypt DNA (SEQ ID NO: 75)

ATGGCGAAAAACGTTGCGATTTTCGGCTTATTGTTTTCTCTTCTTGTGTTGGTTCCTTCTCAGATCTTC

GCGGATCAGATTTGCATTGGTTACCATGCAAACAACTCGACAGAGCAGGTTGACACAATAATGGAAAAG

AATGTCACTGTTACACACGCCCAAGACATACTGGAAAAGACACACAACGGGAAACTCTGCAATCTAGAT

GGAGTGAAGCCTCTCATTTTGAGAGATTGTAGTGTAGCTGGATGGCTCCTCGGGAACCCAATGTGCGAT

GAATTCCTCAATGTGCCGGAATGGTCTTACATAGTGGAGAAAATCAATCCAGCCAATGACCTCTGTTAT

CCAGGGAATTTCAACGACTATGAAGAACTGAAACACCTATTGAGCAGAATAAACCATTTTGAGAAAATT

CAGATCATTCCCAAAGATTCTTGGTCAGATCATGAAGCCTCGGGAGTGAGCTCAGCATGCCCATACCAA

GGAAGATCCTCCTTTTTTAGAAATGTTGTATGGCTTACCAAAAAGAACGATGCATACCCAACAATAAAG

AAAAGTTACAATAATACTAACCAAGAAGATCTTTTGGTACTATGGGGGATTCACCATCCAAATGATGCT

GCAGAGCAGACAAGGCTTTATCAAAACCCAACTACCTATATCTCCGTTGGGACATCAACACTAAACCAG

AGATTGGTACCCAAAATAGCTACTAGATCTAAGGTAAACGGGCAAAGTGGAAGGATGGAGTTCTTTTGG

ACAATTTTAAAATCGAATGATGCAATAAACTTTGAGAGCAATGGAAACTTCATTGCTCCAGAAAATGCA

TACAAAATTGTCAAGAAAGGAGATTCAACAATTATGAAAAGTGAGTTGGAATATAGTAACTGCAACACC

AAGTGTCAGACTCCAATAGGGGCGATAAACTCCAGTATGCCATTCCACAACATCCACCCTCTCACCATC

GGGGAATGCCCCAAATATGTGAAATCAAACAGATTAGTCCTTGCTACTGGGCTCAGGAATAGCCCTCAA

GGAGAGAAAAGAAGAAAAAAGAGAGGACTATTCGGAGCCATAGCAGGCTTTATAGAGGGAGGATGGCAG

GGAATGGTAGATGGTTGGTATGGGTACCACCATAGCAACGAGCAGGGGAGTGGGTACGCTGCAGACAAA

GAATCCACTCAAAGGGCTATAGATGGAGTCACCAATAAGGTCAATTCGATCATTGACAAAATGAACACT

CAGTTTGAGGCTGTTGGAAGGGAATTTAATAACTTAGAAAGGAGAATAGAAAATTTAAACAAGAAGATG

GAAGACGGATTCCTAGATGTCTGGACTTATAATGCTGAACTTCTGGTTCTCATGGAAAATGAGAGAACT

CTAGACTTTCATGACTCAAATGTCAAGAATCTTTATGACAAGGTCCGACTACAGCTTAGGGATAATGCA

AAGGAGCTTGGTAACGGTTGTTTCGAGTTCTATCACAGATGTGATAATGAATGTATGGAAAGTGTAAGA

AACGGAACGTATGACTACCCTCAATATTCAGAAGAAGCAAGATTAAAAAGAGAGGAAATAAGTGGAGTA

AAATTGGAGTCAATAGGAACTTACCAAATACTGTCAATTTATTCAACAGTGGCGAGCTCCCTAGCACTG

GCAATCATGGTGGCTGGTCTATCTTTATGGATGTGCTCCAATGGATCGCTACAATGCAGAATTTGCATT

TAA

PDI-H5 Egypt AA (SEQ ID NO: 76)

MAKNVAIFGLLFSLLVLVPSQIFADQICIGYHANNSTEQVDTIMEKNVTVTHAQDILEKTHNGKLCNLD

GVKPLILRDCSVAGWLLGNPMCDEFLNVPEWSYIVEKINPANDLCYPGNENDYEELKHLLSRINHFEKI

QIIPKDSWSDHEASGVSSACPYQGRSSFFRNVVWLTKKNDAYPTIKKSYNNTNQEDLLVLWGIHHPNDA

AEQTRLYQNPTTYISVGTSTLNQRLVPKIATRSKVNGQSGRMEFFWTILKSNDAINFESNGNFIAPENA

YKIVKKGDSTIMKSELEYSNCNTKCQTPIGAINSSMPFHNIHPLTIGECPKYVKSNRLVLATGLRNSPQ

-continued

GEKRRKKRGLFGAIAGFIEGGWQGMVDGWYGYHHSNEQGSGYAADKESTQRAIDGVTNKVNSIIDKMNT

QFEAVGREENNLERRIENLNKKMEDGELDVWTYNAELLVLMENERTLDFHDSNVKNLYDKVRLQLRDNA

KELGNGCFEFYHRCDNECMESVRNGTYDYPQYSEEARLKREEISGVKLESIGTYQILSIYSTVASSLAL

AIMVAGLSLWMCSNGSLQCRICI*

H5Egy(F392D).r (SEQ ID NO: 77)

CTTCCAACAGCCTCGTCCTGAGTGTTCATTTTGTCAATGATCGAATTGA

H5Egy(F392D).c (SEQ ID NO: 78)

CAAAATGAACACTCAGGACGAGGCTGTTGGAAGGGAATTTAATAACTTA

PDI-H5 Egypt-F392D DNA (SEQ ID NO: 79)

ATGGCGAAAAACGTTGCGATTTTCGGCTTATTGTTTTCTCTTCTTGTGTTGGTTCCTTCTCAGATCTTC

GCGGATCAGATTTGCATTGGTTACCATGCAAACAACTCGACAGAGCAGGTTGACACAATAATGGAAAAG

AATGTCACTGTTACACACGCCCAAGACATACTGGAAAAGACACACAACGGGAAACTCTGCAATCTAGAT

GGAGTGAAGCCTCTCATTTTGAGAGATTGTAGTGTAGCTGGATGGCTCCTCGGGAACCCAATGTGCGAT

GAATTCCTCAATGTGCCGGAATGGTCTTACATAGTGGAGAAAATCAATCCAGCCAATGACCTCTGTTAT

CCAGGGAATTTCAACGACTATGAAGAACTGAAACACCTATTGAGCAGAATAAACCATTTTGAGAAAATT

CAGATCATTCCCAAAGATTCTTGGTCAGATCATGAAGCCTCGGGAGTGAGCTCAGCATGCCCATACCAA

GGAAGATCCTCCTTTTTTAGAAATGTTGTATGGCTTACCAAAAAGAACGATGCATACCCAACAATAAAG

AAAAGTTACAATAATACTAACCAAGAAGATCTTTTGGTACTATGGGGGATTCACCATCCAAATGATGCT

GCAGAGCAGACAAGGCTTTATCAAAACCCAACTACCTATATCTCCGTTGGGACATCAACACTAAACCAG

AGATTGGTACCCAAAATAGCTACTAGATCTAAGGTAAACGGGCAAAGTGGAAGGATGGAGTTCTTTTGG

ACAATTTTAAAATCGAATGATGCAATAAACTTTGAGAGCAATGGAAACTTCATTGCTCCAGAAAATGCA

TACAAAATTGTCAAGAAAGGAGATTCAACAATTATGAAAAGTGAGTTGGAATATAGTAACTGCAACACC

AAGTGTCAGACTCCAATAGGGGCGATAAACTCCAGTATGCCATTCCACAACATCCACCCTCTCACCATC

GGGGAATGCCCCAAATATGTGAAATCAAACAGATTAGTCCTTGCTACTGGGCTCAGGAATAGCCCTCAA

GGAGAGAAAAGAAGAAAAAAGAGAGGACTATTCGGAGCCATAGCAGGCTTTATAGAGGGAGGATGGCAG

GGAATGGTAGATGGTTGGTATGGGTACCACCATAGCAACGAGCAGGGGAGTGGGTACGCTGCAGACAAA

GAATCCACTCAAAGGGCTATAGATGGAGTCACCAATAAGGTCAATTCGATCATTGACAAAATGAACACT

CAGGACGAGGCTGTTGGAAGGGAATTTAATAACTTAGAAAGGAGAATAGAAAATTTAAACAAGAAGATG

GAAGACGGATTCCTAGATGTCTGGACTTATAATGCTGAACTTCTGGTTCTCATGGAAAATGAGAGAACT

CTAGACTTTCATGACTCAAATGTCAAGAATCTTTATGACAAGGTCCGACTACAGCTTAGGGATAATGCA

AAGGAGCTTGGTAACGGTTGTTTCGAGTTCTATCACAGATGTGATAATGAATGTATGGAAAGTGTAAGA

AACGGAACGTATGACTACCCTCAATATTCAGAAGAAGCAAGATTAAAAAGAGAGGAAATAAGTGGAGTA

AAATTGGAGTCAATAGGAACTTACCAAATACTGTCAATTTATTCAACAGTGGCGAGCTCCCTAGCACTG

GCAATCATGGTGGCTGGTCTATCTTTATGGATGTGCTCCAATGGATCGCTACAATGCAGAATTTGCATT

TAA

PDI-H5 Egypt-F392D AA (SEQ ID NO: 80)

MAKNVAIFGLLFSLLVLVPSQIFADQICIGYHANNSTEQVDTIMEKNVTVTHAQDILEKTHNGKLCNLD

GVKPLILRDCSVAGWLLGNPMCDEFLNVPEWSYIVEKINPANDLCYPGNENDYEELKHLLSRINHFEKI

QIIPKDSWSDHEASGVSSACPYQGRSSFFRNVVWLTKKNDAYPTIKKSYNNTNQEDLLVLWGIHHPNDA

AEQTRLYQNPTTYISVGTSTLNQRLVPKIATRSKVNGQSGRMEFFWTILKSNDAINFESNGNFIAPENA

-continued

YKIVKKGDSTIMKSELEYSNCNTKCQTPIGAINSSMPFHNIHPLTIGECPKYVKSNRLVLATGLRNSPQ

GEKRRKKRGLFGAIAGFIEGGWQGMVDGWYGYHHSNEQGSGYAADKESTQRAIDGVTNKVNSIIDKMNT

QDEAVGREENNLERRIENLNKKMEDGFLDVWTYNAELLVLMENERTLDFHDSNVKNLYDKVRLQLRDNA

KELGNGCFEFYHRCDNECMESVRNGTYDYPQYSEEARLKREEISGVKLESIGTYQILSIYSTVASSLAL

AIMVAGLSLWMCSNGSLQCRICI*

PDI-H3 Switz-N382A DNA (SEQ ID NO: 81)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

TACCCAGCATTAAACGTGACTATGCCAAACAATGAACAATTTGACAAATTGTACATTTGGGGGGTTCAC

CACCCGGGTACGGACAAGGACCAAATCTTCCTGTATGCACAATCATCAGGAAGAATCACAGTATCTACC

AAAAGAAGCCAACAAGCTGTAATCCCGAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGGCTCGATTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGGTGCAACATTTGCATTTGA

PDI-H3 Switz-N382A AA (SEQ ID NO: 82)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESENWAGVTQNGTSSSCIRGSNSSFFSRLNWLTHLNSKYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQSTLKLATGMR

NVPERQTRGIFGAIAGFIENGWEGMVDGWYGFRHQNSEGRGQAADLKSTQAAIDQINGKLARLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISCELLC

VALLGFIMWACQKGNIRCNICI*

-continued

PDI-H3 Switz-L384V DNA (SEQ ID NO: 83)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAGAAAACTGCACACTAATAGAT

GCTCTATTGGGAGACCCTCAGTGTGATGGCTTTCAAAATAAGAAATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACAATGAAAGCTTCAATTGGGCTGGAGTCACTCAAAACGGAACAAGTTCT

TCTTGCATAAGGGGATCTAATAGTAGTTTCTTTAGTAGATTAAATTGGTTGACCCACTTAAACTCCAAA

TACCCAGCATTAAACGTGACTATGCCAAACAATGAACAATTTGACAAATTGTACATTTGGGGGGTTCAC

CACCCGGGTACGGACAAGGACCAAATCTTCCTGTATGCACAATCATCAGGAAGAATCACAGTATCTACC

AAAAGAAGCCAACAAGCTGTAATCCCGAATATCGGATCTAGACCCAGAATAAGGGATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACGAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAGACAAACTAGAGGCATATTTGGCGCAATAGCGGGTTTCATAGAAAATGGTTGGGAG

GGAATGGTGGATGGTTGGTACGGCTTCAGGCATCAAAATTCTGAGGGAAGAGGACAAGCAGCAGATCTC

AAAAGCACTCAAGCAGCAATCGATCAAATCAATGGGAAGCTGAATCGAGTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCATTAAACAACCGGTTCCAGATCAAGGGAGTT

GAGCTGAAGTCAGGGTACAAAGATTGGATCCTATGGATTTCCTTTGCCATATCATGTTTTTTGCTTTGT

GTTGCTTTGTTGGGGTTCATCATGTGGGCCTGCCAAAAGGGCAACATTAGGTGCAACATTTGCATTTGA

PDI-H3 Switz-L384V AA (SEQ ID NO: 84)

MAKNVAIFGLLFSLLVLVPSQIFAQKLPGNDNSTATLCLGHHAVPNGTIVKTITNDRIEVTNATELVQN

SSIGEICDSPHQILDGENCTLIDALLGDPQCDGFQNKKWDLFVERSKAYSNCYPYDVPDYASLRSLVAS

SGTLEFNNESFNWAGVTQNGTSSSCIRGSNSSFFSRLNWLTHLNSKYPALNVTMPNNEQFDKLYIWGVH

HPGTDKDQIFLYAQSSGRITVSTKRSQQAVIPNIGSRPRIRDIPSRISIYWTIVKPGDILLINSTGNLI

APRGYFKIRSGKSSIMRSDAPIGKCKSECITPNGSIPNDKPFQNVNRITYGACPRYVKQSTLKLATGMR

NVPERQTRGIFGAIAGFIENGWEGMVDGWYGFRHQNSEGRGQAADLKSTQAAIDQINGKLNRVIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISCFLLC

VALLGFIMWACQKGNIRCNICI*

PDI-H3 Penn-CysTm DNA (SEQ ID NO: 85)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

-continued

TCCTCAATAGGTGAAATATGCGACAGTCCTCATCAGATCCTTGATGGAAAAAACTGCACTCTAATAGAT

GCTCTATTGGGAGACCCTCAGTGTGATGGCTTTCAAAATAAGAGATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACGATGAAAGCTTCAATTGGGCTGGAGTCACTCAAAACGGAACAAGTTCT

GCTTGCATAAGGGGATCTAATAGTAGTTTCTTTAGTAGATTAAATTGGTTGACCCACTCAAACTTCAAA

TACCCAGCATTGAACGTGACTATGCCAAACAATGAACAATTTGACAAATTGTACATTTGGGGGGTTCAC

CACCCGGGTACAGACAAGGACCAAATCTTCCTGTACGCTCAATCATCAGGAAGAATCACAGTATCTACC

AAAAGAAGCCAACAAGCTGTAATCCCGAATATCGGATCTAGACCCAGAATAAGGAATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACAAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGAAGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGATTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCTTTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Penn-CysTm AA (SEQ ID NO: 86)

MAKNVAIFGLLFSLLVLVPSQIFAQKLPGNDNSTATLCLGHHAVPNGTIVKTITNDRIEVTNATELVQN

SSIGEICDSPHQILDGKNCTLIDALLGDPQCDGFQNKRWDLFVERSKAYSNCYPYDVPDYASLRSLVAS

SGTLEFNDESFNWAGVTQNGTSSACIRGSNSSFFSRLNWLTHSNFKYPALNVTMPNNEQFDKLYIWGVH

HPGTDKDQIFLYAQSSGRITVSTKRSQQAVIPNIGSRPRIRNIPSRISIYWTIVKPGDILLINSTGNLI

APRGYFKIQSGKSSIMRSDAPIGKCKSECITPNGSIPNDKPFQNVNRITYGACPRYVKQSTLKLATGMR

NVPEKQTRGIFGAIAGFIENGWEGMKDGWYGFRHQNSEGRGQAADLKSTQAAIDQINGKLNRLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISSLVLL

VALLGFIMWACQKGNIRCNICI*

PDI-H3 Penn-N382A - CysTm DNA (SEQ ID NO: 87)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAAAAAACTGCACTCTAATAGAT

GCTCTATTGGGAGACCCTCAGTGTGATGGCTTTCAAAATAAGAGATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACGATGAAAGCTTCAATTGGGCTGGAGTCACTCAAAACGGAACAAGTTCT

GCTTGCATAAGGGGATCTAATAGTAGTTTCTTTAGTAGATTAAATTGGTTGACCCACTCAAACTTCAAA

-continued

TACCCAGCATTGAACGTGACTATGCCAAACAATGAACAATTTGACAAATTGTACATTTGGGGGGTTCAC

CACCCGGGTACAGACAAGGACCAAATCTTCCTGTACGCTCAATCATCAGGAAGAATCACAGTATCTACC

AAAAGAAGCCAACAAGCTGTAATCCCGAATATCGGATCTAGACCCAGAATAAGGAATATCCCTAGCAGA

ATAAGCATCTATTGGACAATAGTAAAACCGGGAGACATACTTTTGATTAACAGCACAGGGAATCTAATT

GCTCCTAGGGGTTACTTCAAAATACAAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGAAGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGGCTCGATTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCTTTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Penn-N382A - CysTm AA (SEQ ID NO: 88)

MAKNVAIFGLLFSLLVLVPSQIFAQKLPGNDNSTATLCLGHHAVPNGTIVKTITNDRIEVTNATELVQN

SSIGEICDSPHQILDGKNCTLIDALLGDPQCDGFQNKRWDLFVERSKAYSNCYPYDVPDYASLRSLVAS

SGTLEFNDESFNWAGVTQNGTSSACIRGSNSSFFSRLNWLTHSNFKYPALNVTMPNNEQFDKLYIWGVH

HPGTDKDQIFLYAQSSGRITVSTKRSQQAVIPNIGSRPRIRNIPSRISIYWTIVKPGDILLINSTGNLI

APRGYFKIQSGKSSIMRSDAPIGKCKSECITPNGSIPNDKPFQNVNRITYGACPRYVKQSTLKLATGMR

NVPEKQTRGIFGAIAGFIENGWEGMKDGWYGFRHQNSEGRGQAADLKSTQAAIDQINGKLARLIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISSLVLL

VALLGFIMWACQKGNIRCNICI*

PDI-H3 Penn-L384V - CysTm DNA (SEQ ID NO: 89)

ATGGCGAAAAACGTTGCGATTTTCGGCTTATTGTTTTCTCTTCTTGTGTTGGTTCCTTCTCAGATCTTC

GCGCAAAAACTTCCTGGAAATGACAATAGCACGGCAACGCTGTGCCTTGGGCACCATGCAGTACCAAAC

GGAACGATAGTGAAAACAATCACGAATGACCGAATTGAAGTTACTAATGCTACTGAGCTGGTTCAGAAT

TCCTCAATAGGTGAAATATGCGACAGTCCTCATCAGATCCTTGATGGAAAAAACTGCACTCTAATAGAT

GCTCTATTGGGAGACCCTCAGTGTGATGGCTTTCAAAATAAGAGATGGGACCTTTTTGTTGAACGAAGC

AAAGCCTACAGCAACTGTTACCCTTATGATGTGCCGGATTATGCCTCCCTTAGGTCACTAGTTGCCTCA

TCCGGCACACTGGAGTTTAACGATGAAAGCTTCAATTGGGCTGGAGTCACTCAAAACGGAACAAGTTCT

GCTTGCATAAGGGGATCTAATAGTAGTTTCTTTAGTAGATTAAATTGGTTGACCCACTCAAACTTCAAA

TACCCAGCATTGAACGTGACTATGCCAAACAATGAACAATTTGACAAATTGTACATTTGGGGGGTTCAC

CACCCGGGTACAGACAAGGACCAAATCTTCCTGTACGCTCAATCATCAGGAAGAATCACAGTATCTACC

AAAAGAAGCCAACAAGCTGTAATCCCGAATATCGGATCTAGACCCAGAATAAGGAATATCCCTAGCAGA

ATAAGCATCTATTGGACAATAGTAAAACCGGGAGACATACTTTTGATTAACAGCACAGGGAATCTAATT

-continued

GCTCCTAGGGGTTACTTCAAAATACAAAGTGGGAAAAGCTCAATAATGAGATCAGATGCACCCATTGGC

AAATGCAAGTCTGAATGCATCACTCCAAATGGAAGCATTCCCAATGACAAACCATTCCAAAATGTAAAC

AGGATCACATACGGGGCCTGTCCCAGATATGTTAAGCAAAGCACTCTGAAATTGGCAACAGGAATGCGA

AATGTACCAGAGAAACAAACTAGAGGCATATTTGGCGCAATAGCGGGTTTCATAGAAAATGGTTGGGAG

GGAATGAAGGATGGTTGGTACGGTTTCAGGCATCAAAATTCTGAGGGAAGAGGACAAGCAGCAGATCTC

AAAAGCACTCAAGCAGCAATCGATCAAATCAATGGGAAGCTGAATCGAGTGATCGGGAAAACCAACGAG

AAATTCCATCAGATTGAAAAAGAATTCTCAGAAGTAGAAGGGAGAATTCAGGACCTTGAGAAATATGTT

GAGGACACAAAAATAGATCTCTGGTCATACAACGCGGAGCTTCTTGTTGCCCTGGAGAACCAACATACA

ATTGATCTAACTGACTCAGAAATGAACAAACTGTTTGAAAAAACAAAGAAGCAACTGAGGGAAAATGCT

GAGGATATGGGCAATGGTTGTTTCAAAATATACCACAAATGTGACAATGCCTGCATAGGATCAATCAGA

AATGGAACTTATGACCACGATGTATACAGGGATGAAGCTTTAAACAACCGGTTCCAGATCAAGGGAGTT

GAGCTGAAGTCAGGGTACAAAGATTGGATCCTATGGATTTCCTTTGCCATATCATCCCTTGTACTGTTA

GTTGCTTTGTTGGGGTTCATCATGTGGGCCTGCCAAAAGGGCAACATTAGGTGCAACATTTGCATTTGA

PDI-H3 Penn-L384V - CysTm AA (SEQ ID NO: 90)

MAKNVAIFGLLFSLLVLVPSQIFAQKLPGNDNSTATLCLGHHAVPNGTIVKTITNDRIEVTNATELVQN

SSIGEICDSPHQILDGKNCTLIDALLGDPQCDGFQNKRWDLFVERSKAYSNCYPYDVPDYASLRSLVAS

SGTLEFNDESFNWAGVTQNGTSSACIRGSNSSFFSRLNWLTHSNFKYPALNVTMPNNEQFDKLYIWGVH

HPGTDKDQIFLYAQSSGRITVSTKRSQQAVIPNIGSRPRIRNIPSRISIYWTIVKPGDILLINSTGNLI

APRGYFKIQSGKSSIMRSDAPIGKCKSECITPNGSIPNDKPFQNVNRITYGACPRYVKQSTLKLATGMR

NVPEKQTRGIFGAIAGFIENGWEGMKDGWYGFRHQNSEGRGQAADLKSTQAAIDQINGKLNRVIGKTNE

KFHQIEKEFSEVEGRIQDLEKYVEDTKIDLWSYNAELLVALENQHTIDLTDSEMNKLFEKTKKQLRENA

EDMGNGCFKIYHKCDNACIGSIRNGTYDHDVYRDEALNNRFQIKGVELKSGYKDWILWISFAISSLVLL

VALLGFIMWACQKGNIRCNICI*

A/Bangkok/3007/15 (H3N2) (aa)

(SEQ ID NO: 91)

QKIPGNDNSTATLCLGHHAVPNGTIVKTITNDRIEVTNATELVQNSSIGEICDSPHQILDGENCTLIDA

LLGDPQCDGFQNKKWDLFVERSKAYSNCYPYDVPDYASLRSLVASSGTLEFNNESFNWTGVTQNGTSSA

CIRKSSSSFFSRLNWLTHLNYTYPALNVTVPNNEQFDKLYIWGVHHPGTDKDQIFLYARSSGRITVSTK

RSQQAVIPNIGSRPRIRDIPSRISIYWTIVKPGDILLINSTGNLIAPRGYFKIRSGKSSIMRSDAPIGK

CKSECITPNGSIPNDKPFQNVNRITYGACPRYVKHSTLKLATGMRNVPEKQTRGIFGAIAGFIENGWEG

MVDGWYGFRHQNSEGRGQAADLKSTQAAIDQINGKLNRLIGKTNEKFHQIEKEFSEVEGRIQDLEKYVE

DTKIDLWSYNAELLVALENQHTIDLTDSEMNKLFEKTKKQLRENAEDMGNGCFKIYHKCDNACIGSIRN

GTYDHNVYRDEALNNRFQIKGVELKSGYKDWILWISFAISCFLLCVALLGFIMWACQKGNIRCNICI

A/Hongkong/4801/14 (H3N2) (aa)

(SEQ ID NO: 92)

QKIPGNDNSTATLCLGHHAVPNGTIVKTITNDRIEVTNATELVQNSSIGEICDSPHQILDGENCTLIDA

LLGDPQCDGFQNKKWDLFVERSKAYSNCYPYDVPDYASLRSLVASSGTLEFNNESFNWTGVTQNGTSSA

CIRRSSSSFFSRLNWLTHLNYTYPALNVTMPNNEQFDKLYIWGVHHPGTDKDQIFLYAQSSGRITVSTK

RSQQAVIPNIGSRPRIRDIPSRISIYWTIVKPGDILLINSTGNLIAPRGYFKIRSGKSSIMRSDAPIGK

CKSECITPNGSIPNDKPFQNVNRITYGACPRYVKHSTLKLATGMRNVPEKQTRGIFGAIAGFIENGWEG

MVDGWYGFRHQNSEGRGQAADLKSTQAAIDQINGKLNRLIGKTNEKFHQIEKEFSEVEGRIQDLEKYVE

DTKIDLWSYNAELLVALENQHTIDLTDSEMNKLFEKTKKQLRENAEDMGNGCFKIYHKCDNACIGSIRN

GTYDHNVYRDEALNNRFQIKGVELKSGYKDWILWISFAISCFLLCVALLGFIMWACQKGNIRCNICI

-continued

A/Minnesota/40/15 (H3N2) (aa)

(SEQ ID NO: 93)

QKIPGNDNSTATLCLGHHAVPNGTIVKTITNDRIEVTNATELVQNSSIGEICDSPHQILDGENCTLIDA

LLGDPQCDGFQNKKWDLFVERSKAYSNCYPYDVPDYASLRSLVASSGTLEENNESFNWTGVTQNGTSSA

CIRRSSSSFFSRLNWLTHLNYTYPALNVTMPNKEQFDKLYIWGVHHPGTDKDQIFLYAQSSGRITVSTK

RSQQAVIPNIGSRPRIRDIPSRISIYWTIVKPGDILLINSTGNLIAPRGYFKIRSGKSSIMRSDAPIGK

CKSECITPNGSIPNDKPFQNVNRITYGACPRYVKHSTLKLATGMRNVPEKQTRGIFGAIAGFIENGWEG

MVDGWYGFRHQNSEGRGQAADLKSTQAAIDQINGKLNRLIGKTNEKFHQIEKEFSEVEGRVQDLEKYVE

DTKIDLWSYNAELLVALENQHTIDLTDSEMNKLFEKTKKQLRENAEDMGNGCFKIYHKCDNACIGSIRN

ETYDHNVYRDEALNNRFQIKGVELKSGYKDWILWISFAISCFLLCVALLGFIMWACQKGNIRCNICI

A/South Australia/1/16 (H3N2) (aa)

(SEQ ID NO: 94)

QKIPGNDNSTATLCLGHHAVPNGTIVKTITNDRIEVTNATELVQNSSIGEICDSPHQILDGENCTLIDA

LLGDPQCDGFQNKKWDLFVERSKAYSNCYPYDVPDYASLRSLVASSGTLEFKNESFNWTGVTQNGTSSA

CIRRSSSSFFSRLNWLTHLNYTYPALNVTMPNKEQFDKLYIWGVHHPGTDKDQIFLYAQSSGRITVSTK

RSQQAVIPNIGSRPRIRDIPSRISIYWTIVKPGDILLINSTGNLIAPRGYFKIRSGKSSIMRSDAPIGK

CKSECITPNGSIPNDKPFQNVNRITYGACPRYVKHSTLKLATGMRNVPEKQTRGIFGAIAGFIENGWEG

MVDGWYGFRHQNSEGRGQAADLKSTQAAIDQINGKLNRLIGKTNEKFHQIEKEFSEVEGRVQDLEKYVE

DTKIDLWSYNAELLVALENQHTIDLTDSEMNKLFEKTKKQLRENAEDMGNGCFKIYHKCDNACIGSIRN

ETYDHNVYRDEALNNRFQIKGVELKSGYKDWILWISFAISCFLLCVALLGFIMWACQKGNIRCNICI

A/Pennsylvania/09/15 (H3N2) (aa)

(SEQ ID NO: 95)

QKLPGNDNSTATLCLGHHAVPNGTIVKTITNDRIEVTNATELVQNSSIGEICDSPHQILDGKNCTLIDA

LLGDPQCDGFQNKRWDLFVERSKAYSNCYPYDVPDYASLRSLVASSGTLEENDESFNWAGVTQNGTSSA

CIRGSNSSFFSRLNWLTHSNFKYPALNVTMPNNEQFDKLYIWGVHHPGTDKDQIFLYAQSSGRITVSTK

RSQQAVIPNIGSRPRIRNIPSRISIYWTIVKPGDILLINSTGNLIAPRGYFKIQSGKSSIMRSDAPIGK

CKSECITPNGSIPNDKPFQNVNRITYGACPRYVKQSTLKLATGMRNVPEKQTRGIFGAIAGFIENGWEG

MKDGWYGFRHQNSEGRGQAADLKSTQAAIDQINGKLNRLIGKTNEKFHQIEKEFSEVEGRIQDLEKYVE

DTKIDLWSYNAELLVALENQHTIDLTDSEMNKLFEKTKKQLRENAEDMGNGCFKIYHKCDNACIGSIRN

GTYDHDVYRDEALNNRFQIKGVELKSGYKDWILWISFAISCFLLCVALLGFIMWACQKGNIRCNICI

A/Switzerland/9715293/13 (H3N2) (aa)

(SEQ ID NO: 96)

QKLPGNDNSTATLCLGHHAVPNGTIVKTITNDRIEVTNATELVQNSSIGEICDSPHQILDGENCTLIDA

LLGDPQCDGFQNKKWDLFVERSKAYSNCYPYDVPDYASLRSLVASSGTLEFNNESFNWAGVTQNGTSSS

CIRGSNSSFFSRLNWLTHLNSKYPALNVTMPNNEQFDKLYIWGVHHPGTDKDQIFLYAQSSGRITVSTK

RSQQAVIPNIGSRPRIRDIPSRISIYWTIVKPGDILLINSTGNLIAPRGYFKIRSGKSSIMRSDAPIGK

CKSECITPNGSIPNDKPFQNVNRITYGACPRYVKQSTLKLATGMRNVPERQTRGIFGAIAGFIENGWEG

MVDGWYGFRHQNSEGRGQAADLKSTQAAIDQINGKLNRLIGKTNEKFHQIEKEFSEVEGRIQDLEKYVE

DTKIDLWSYNAELLVALENQHTIDLTDSEMNKLFEKTKKQLRENAEDMGNGCFKIYHKCDNACIGSIRN

GTYDHDVYRDEALNNRFQIKGVELKSGYKDWILWISFAISCFLLCVALLGFIMWACQKGNIRCNICI

A/Mississippi/16/16 (H3N2) (aa)

(SEQ ID NO: 97)

QKLPGNDNSTATLCLGHHAVPNGTIVKTITNDRIEVTNATELVQNSSIGEICDSPHQILDGENCTLIDA

LLGDPQCDGFQNKKWDLFVERSRAYSNCYPYDVPDYASLRSLVASSGTLEFNNESENWAGVTQNGTSSS

CIRGSNSSFFSRLNWLTHLNSKYPALNVTMPNNEQFDKLYIWGVHHPGTDKDQIFLYAKPSGRITVSTK

-continued

RSQQAVIPNIGSRPRIRDIPSRISIYWTIVKPGDILLINSTGNLIAPRGYFKIRSGKSSIMRSDAPIGK

CKSECITPNGSIPNDKPFQNVNRITYGACPRYVKQNTLKLATGMRNVPERQTRGIFGAIAGFIENGWEG

MVDGWYGFRHQNSEGRGQAADLKSTQAAIDQINGKLNRLIGKTNEKFHQIEKEFSEVEGRIQDLEKYVE

DTKIDLWSYNAELLVALENQHTIDLTDSEMNKLFEKTKKQLRENAEDMGNGCFKIYHKCDNACIGSIRN

GTYDHDVYRDEALNNRFQIKGVELKSGYKDWILWISFAISCFLLCVALLGFIMWACQKGNIRCNICI

CysTM sequence (aa)

(SEQ ID NO: 98)

SLVLL

Native TMCT (aa)

SEQ ID NO: 99)

CFLLC

CysTM sequence (nt)

(SEQ ID NO: 100)

TCCCTTGTACTGTTA

Native TMCT (nt)

SEQ ID NO: 101)

TGTTTTTTGCTTTGT

A/Hong Kong/4801/14 (H3N2 (nt) - (Epiflu accession no EPI539576)

(SEQ ID NO: 102)

ATGAAGACTATCATTGCTTTGAGCTACATTCTATGTCTGGTTTTCGCTCAAAAAATTCCTGGAAATGAC

AATAGCACGGCAACGCTGTGCCTTGGGCACCATGCAGTACCAAACGGAACGATAGTGAAAACAATCACG

AATGACCGAATTGAAGTTACTAATGCTACTGAGCTGGTTCAGAATTCCTCAATAGGTGAAATATGCGAC

AGTCCTCATCAGATCCTTGATGGAGAAAACTGCACACTAATAGATGCTCTATTGGGAGACCCTCAGTGT

GATGGCTTTCAAAATAAGAAATGGGACCTTTTTGTTGAACGAAGCAAAGCCTACAGCAACTGTTACCCT

TATGATGTGCCGGATTATGCCTCCCTTAGGTCACTAGTTGCCTCATCCGGCACACTGGAGTTTAACAAT

GAAAGCTTCAATTGGACTGGAGTCACTCAAAACGGAACAAGTTCTGCTTGCATAAGGAGATCTAGTAGT

AGTTTCTTTAGTAGATTAAATTGGTTGACCCACTTAAACTACACATACCCAGCATTGAACGTGACTATG

CCAAACAATGAACAATTTGACAAATTGTACATTTGGGGGGTTCACCACCCGGGTACGGACAAGGACCAA

ATCTTCCTGTATGCTCAATCATCAGGAAGAATCACAGTATCTACCAAAAGAAGCCAACAAGCTGTAATC

CCAAATATCGGATCTAGACCCAGAATAAGGGATATCCCTAGCAGAATAAGCATCTATTGGACAATAGTA

AAACCGGGAGACATACTTTTGATTAACAGCACAGGGAATCTAATTGCTCCTAGGGGTTACTTCAAAATA

CGAAGTGGGAAAAGCTCAATAATGAGATCAGATGCACCCATTGGCAAATGCAAGTCTGAATGCATCACT

CCAAATGGAAGCATTCCCAATGACAAACCATTCCAAAATGTAAACAGGATCACATACGGGGCCTGTCCC

AGATATGTTAAGCATAGCACTCTGAAATTGGCAACAGGAATGCGAAATGTACCAGAGAAACAAACTAGA

GGCATATTTGGCGCAATAGCGGGTTTCATAGAAAATGGTTGGGAGGGAATGGTGGATGGTTGGTACGGT

TTCAGGCATCAAAATTCTGAGGGAAGAGGACAAGCAGCAGATCTCAAAAGCACTCAAGCAGCAATCGAT

CAAATCAATGGGAAGCTGAATCGATTGATCGGGAAAACCAACGAGAAATTCCATCAGATTGAAAAAGAA

TTCTCAGAAGTAGAAGGAAGAATTCAGGACCTTGAGAAATATGTTGAGGACACTAAAATAGATCTCTGG

TCATACAACGCGGAGCTTCTTGTTGCCCTGGAGAACCAACATACAATTGATCTAACTGACTCAGAAATG

AACAAACTGTTTGAAAAAACAAAGAAGCAACTGAGGGAAAATGCTGAGGATATGGGCAATGGTTGTTTC

AAAATATACCACAAATGTGACAATGCCTGCATAGGATCAATAAGAAATGGAACTTATGACCACAATGTG

TACAGGGATGAAGCATTAAACAACCGGTTCCAGATCAAGGGAGTTGAGCTGAAGTCAGGGTACAAAGAT

TGGATCCTATGGATTTCCTTTGCCATATCATGTTTTTTGCTTTGTGTTGCTTTGTTGGGGTTCATCATG

TGGGCCTGCCAAAAGGGCAACATTAGGTGCAACATTTGCATTTGA

-continued

Construct 2801 from 2X35S prom to NOS term (SEQ ID NO: 103)

GTCAACATGGTGGAGCACGACACACTTGTCTACTCCAAAAATATCAAAGATACAGTCTCAGAAGACCAA

AGGGCAATTGAGACTTTTCAACAAAGGGTAATATCCGGAAACCTCCTCGGATTCCATTGCCCAGCTATC

TGTCACTTTATTGTGAAGATAGTGGAAAAGGAAGGTGGCTCCTACAAATGCCATCATTGCGATAAAGGA

AAGGCCATCGTTGAAGATGCCTCTGCCGACAGTGGTCCCAAAGATGGACCCCCACCCACGAGGAGCATC

GTGGAAAAAGAAGACGTTCCAACCACGTCTTCAAAGCAAGTGGATTGATGTGATAACATGGTGGAGCAC

GACACACTTGTCTACTCCAAAAATATCAAAGATACAGTCTCAGAAGACCAAAGGGCAATTGAGACTTTT

CAACAAAGGGTAATATCCGGAAACCTCCTCGGATTCCATTGCCCAGCTATCTGTCACTTTATTGTGAAG

ATAGTGGAAAAGGAAGGTGGCTCCTACAAATGCCATCATTGCGATAAAGGAAAGGCCATCGTTGAAGAT

GCCTCTGCCGACAGTGGTCCCAAAGATGGACCCCCACCCACGAGGAGCATCGTGGAAAAAGAAGACGTT

CCAACCACGTCTTCAAAGCAAGTGGATTGATGTGATATCTCCACTGACGTAAGGGATGACGCACAATCC

CACTATCCTTCGCAAGACCCTTCCTCTATATAAGGAAGTTCATTTCATTTGGAGAGGTATTAAAATCTT

AATAGGTTTTGATAAAAGCGAACGTGGGGAAACCCGAACCAAACCTTCTTCTAAACTCTCTCTCATCTC

TCTTAAAGCAAACTTCTCTCTTGTCTTTCTTGCGTGAGCGATCTTCAACGTTGTCAGATCGTGCTTCGG

CACCAGTACAATGGCGAAAAACGTTGCGATTTTCGGCTTATTGTTTTCTCTTCTTGTGTTGGTTCCTTC

TCAGATCTTCGCGCAAAAACTTCCTGGAAATGACAATAGCACGGCAACGCTGTGCCTTGGGCACCATGC

AGTACCAAACGGAACGATAGTGAAAACAATCACGAATGACCGAATTGAAGTTACTAATGCTACTGAGCT

GGTTCAGAATTCCTCAATAGGTGAAATATGCGACAGTCCTCATCAGATCCTTGATGGAGAAAACTGCAC

ACTAATAGATGCTCTATTGGGAGACCCTCAGTGTGATGGCTTTCAAAATAAGAAATGGGACCTTTTTGT

TGAACGAAGCAAAGCCTACAGCAACTGTTACCCTTATGATGTGCCGGATTATGCCTCCCTTAGGTCACT

AGTTGCCTCATCCGGCACACTGGAGTTTAACAATGAAAGCTTCAATTGGGCTGGAGTCACTCAAAACGG

AACAAGTTCTTCTTGCATAAGGGGATCTAATAGTAGTTTCTTTAGTAGATTAAATTGGTTGACCCACTT

AAACTCCAAATACCCAGCATTAAACGTGACTATGCCAAACAATGAACAATTTGACAAATTGTACATTTG

GGGGGTTCACCACCCGGGTACGGACAAGGACCAAATCTTCCTGTATGCACAATCATCAGGAAGAATCAC

AGTATCTACCAAAAGAAGCCAACAAGCTGTAATCCCGAATATCGGATCTAGACCCAGAATAAGGGATAT

CCCTAGCAGAATAAGCATCTATTGGACAATAGTAAAACCGGGAGACATACTTTTGATTAACAGCACAGG

GAATCTAATTGCTCCTAGGGGTTACTTCAAAATACGAAGTGGGAAAAGCTCAATAATGAGATCAGATGC

ACCCATTGGCAAATGCAAGTCTGAATGCATCACTCCAAATGGAAGCATTCCCAATGACAAACCATTCCA

AAATGTAAACAGGATCACATACGGGGCCTGTCCCAGATATGTTAAGCAAAGCACTCTGAAATTGGCAAC

AGGAATGCGAAATGTACCAGAGAGACAAACTAGAGGCATATTTGGCGCAATAGCGGGTTTCATAGAAAA

TGGTTGGGAGGGAATGGTGGATGGTTGGTACGGCTTCAGGCATCAAAATTCTGAGGGAAGAGGACAAGC

AGCAGATCTCAAAAGCACTCAAGCAGCAATCGATCAAATCAATGGGAAGCTGAATCGATTGATCGGGAA

AACCAACGAGAAATTCCATCAGATTGAAAAAGAATTCTCAGAAGTAGAAGGGAGAATTCAGGACCTTGA

GAAATATGTTGAGGACACAAAAATAGATCTCTGGTCATACAACGCGGAGCTTCTTGTTGCCCTGGAGAA

CCAACATACAATTGATCTAACTGACTCAGAAATGAACAAACTGTTTGAAAAAACAAAGAAGCAACTGAG

GGAAAATGCTGAGGATATGGGCAATGGTTGTTTCAAAATATACCACAAATGTGACAATGCCTGCATAGG

ATCAATCAGAAATGGAACTTATGACCACGATGTATACAGGGATGAAGCATTAAACAACCGGTTCCAGAT

CAAGGGAGTTGAGCTGAAGTCAGGGTACAAAGATTGGATCCTATGGATTTCCTTTGCCATATCATGTTT

TTTGCTTTGTGTTGCTTTGTTGGGGTTCATCATGTGGGCCTGCCAAAAGGGCAACATTAGGTGCAACAT

TTGCATTTGAAGGCCTATTTTCTTTAGTTTGAATTTACTGTTATTCGGTGTGCATTTCTATGTTTGGTG

-continued

AGCGGTTTTCTGTGCTCAGAGTGTGTTTATTTTATGTAATTTAATTTCTTTGTGAGCTCCTGTTTAGCA

GGTCGTCCCTTCAGCAAGGACACAAAAAGATTTTAATTTTATTAAAAAAAAAAAAAAAAAAAGACCGGGA

ATTCGATATCAAGCTTATCGACCTGCAGATCGTTCAAACATTTGGCAATAAAGTTTCTTAAGATTGAAT

CCTGTTGCCGGTCTTGCGATGATTATCATATAATTTCTGTTGAATTACGTTAAGCATGTAATAATTAAC

ATGTAATGCATGACGTTATTTATGAGATGGGTTTTTATGATTAGAGTCCCGCAATTATACATTTAATAC

GCGATAGAAAACAAAATATAGCGCGCAAACTAGGATAAATTATCGCGCGCGGTGTCATCTATGTTACTA

GAT

Construct 3023 from 2X35S prom to NOS term (SEQ ID NO: 104)

GTCAACATGGTGGAGCACGACACACTTGTCTACTCCAAAAATATCAAAGATACAGTCTCAGAAGACCAA

AGGGCAATTGAGACTTTTCAACAAAGGGTAATATCCGGAAACCTCCTCGGATTCCATTGCCCAGCTATC

TGTCACTTTATTGTGAAGATAGTGGAAAAGGAAGGTGGCTCCTACAAATGCCATCATTGCGATAAAGGA

AAGGCCATCGTTGAAGATGCCTCTGCCGACAGTGGTCCCAAAGATGGACCCCCACCCACGAGGAGCATC

GTGGAAAAAGAAGACGTTCCAACCACGTCTTCAAAGCAAGTGGATTGATGTGATAACATGGTGGAGCAC

GACACACTTGTCTACTCCAAAAATATCAAAGATACAGTCTCAGAAGACCAAAGGGCAATTGAGACTTTT

CAACAAAGGGTAATATCCGGAAACCTCCTCGGATTCCATTGCCCAGCTATCTGTCACTTTATTGTGAAG

ATAGTGGAAAAGGAAGGTGGCTCCTACAAATGCCATCATTGCGATAAAGGAAAGGCCATCGTTGAAGAT

GCCTCTGCCGACAGTGGTCCCAAAGATGGACCCCCACCCACGAGGAGCATCGTGGAAAAAGAAGACGTT

CCAACCACGTCTTCAAAGCAAGTGGATTGATGTGATATCTCCACTGACGTAAGGGATGACGCACAATCC

CACTATCCTTCGCAAGACCCTTCCTCTATATAAGGAAGTTCATTTCATTTGGAGAGGTATTAAAATCTT

AATAGGTTTTGATAAAAGCGAACGTGGGGAAACCCGAACCAAACCTTCTTCTAAACTCTCTCTCATCTC

TCTTAAAGCAAACTTCTCTCTTGTCTTTCTTGCGTGAGCGATCTTCAACGTTGTCAGATCGTGCTTCGG

CACCAGTACAATGGCGAAAAACGTTGCGATTTTCGGCTTATTGTTTTCTCTTCTTGTGTTGGTTCCTTC

TCAGATCTTCGCGCAAAAACTTCCTGGAAATGACAATAGCACGGCAACGCTGTGCCTTGGGCACCATGC

AGTACCAAACGGAACGATAGTGAAAACAATCACGAATGACCGAATTGAAGTTACTAATGCTACTGAGCT

GGTTCAGAATTCCTCAATAGGTGAAATATGCGACAGTCCTCATCAGATCCTTGATGGAGAAAACTGCAC

ACTAATAGATGCTCTATTGGGAGACCCTCAGTGTGATGGCTTTCAAAATAAGAAATGGGACCTTTTTGT

TGAACGAAGCAAAGCCTACAGCAACTGTTACCCTTATGATGTGCCGGATTATGCCTCCCTTAGGTCACT

AGTTGCCTCATCCGGCACACTGGAGTTTAACAATGAAAGCTTCAATTGGGCTGGAGTCACTCAAAACGG

AACAAGTTCTTCTTGCATAAGGGGATCTAATAGTAGTTTCTTTAGTAGATTAAATTGGTTGACCCACTT

AAACTCCAAATACCCAGCATTAAACGTGACTATGCCAAACAATGAACAATTTGACAAATTGTACATTTG

GGGGGTTCACCACCCGGGTACGGACAAGGACCAAATCTTCCTGTATGCACAATCATCAGGAAGAATCAC

AGTATCTACCAAAAGAAGCCAACAAGCTGTAATCCCGAATATCGGATCTAGACCCAGAATAAGGGATAT

CCCTAGCAGAATAAGCATCTATTGGACAATAGTAAAACCGGGAGACATACTTTTGATTAACAGCACAGG

GAATCTAATTGCTCCTAGGGGTTACTTCAAAATACGAAGTGGGAAAAGCTCAATAATGAGATCAGATGC

ACCCATTGGCAAATGCAAGTCTGAATGCATCACTCCAAATGGAAGCATTCCCAATGACAAACCATTCCA

AAATGTAAACAGGATCACATACGGGGCCTGTCCCAGATATGTTAAGCAAAGCACTCTGAAATTGGCAAC

AGGAATGCGAAATGTACCAGAGAGACAAACTAGAGGCATATTTGGCGCAATAGCGGGTTTCATAGAAAA

TGGTTGGGAGGGAATGGTGGATGGTTGGTACGGCTTCAGGCATCAAAATTCTGAGGGAAGAGGACAAGC

AGCAGATCTCAAAAGCACTCAAGCAGCAATCGATCAAATCAATGGGAAGCTGGCTCGATTGATCGGGAA

AACCAACGAGAAATTCCATCAGATTGAAAAAGAATTCTCAGAAGTAGAAGGGAGAATTCAGGACCTTGA

GAAATATGTTGAGGACACAAAAATAGATCTCTGGTCATACAACGCGGAGCTTCTTGTTGCCCTGGAGAA

-continued

CCAACATACAATTGATCTAACTGACTCAGAAATGAACAAACTGTTTGAAAAAACAAAGAAGCAACTGAG

GGAAAATGCTGAGGATATGGGCAATGGTTGTTTCAAAATATACCACAAATGTGACAATGCCTGCATAGG

ATCAATCAGAAATGGAACTTATGACCACGATGTATACAGGGATGAAGCATTAAACAACCGGTTCCAGAT

CAAGGGAGTTGAGCTGAAGTCAGGGTACAAAGATTGGATCCTATGGATTTCCTTTGCCATATCATGTTT

TTTGCTTTGTGTTGCTTTGTTGGGGTTCATCATGTGGGCCTGCCAAAAGGGCAACATTAGGTGCAACAT

TTGCATTTGAAGGCCTATTTTCTTTAGTTTGAATTTACTGTTATTCGGTGTGCATTTCTATGTTTGGTG

AGCGGTTTTCTGTGCTCAGAGTGTGTTTATTTTATGTAATTTAATTTCTTTGTGAGCTCCTGTTTAGCA

GGTCGTCCCTTCAGCAAGGACACAAAAAGATTTTAATTTTATTAAAAAAAAAAAAAAAAAAAGACCGGGA

ATTCGATATCAAGCTTATCGACCTGCAGATCGTTCAAACATTTGGCAATAAAGTTTCTTAAGATTGAAT

CCTGTTGCCGGTCTTGCGATGATTATCATATAATTTCTGTTGAATTACGTTAAGCATGTAATAATTAAC

ATGTAATGCATGACGTTATTTATGAGATGGGTTTTTATGATTAGAGTCCCGCAATTATACATTTAATAC

GCGATAGAAAACAAAATATAGCGCGCAAACTAGGATAAATTATCGCGCGCGGTGTCATCTATGTTACTA

GAT

Construct 2811 from 2X35S prom to NOS term (SEQ ID NO: 105)

GTCAACATGGTGGAGCACGACACACTTGTCTACTCCAAAAATATCAAAGATACAGTCTCAGAAGACCAA

AGGGCAATTGAGACTTTTCAACAAAGGGTAATATCCGGAAACCTCCTCGGATTCCATTGCCCAGCTATC

TGTCACTTTATTGTGAAGATAGTGGAAAAGGAAGGTGGCTCCTACAAATGCCATCATTGCGATAAAGGA

AAGGCCATCGTTGAAGATGCCTCTGCCGACAGTGGTCCCAAAGATGGACCCCCACCCACGAGGAGCATC

GTGGAAAAAGAAGACGTTCCAACCACGTCTTCAAAGCAAGTGGATTGATGTGATAACATGGTGGAGCAC

GACACACTTGTCTACTCCAAAAATATCAAAGATACAGTCTCAGAAGACCAAAGGGCAATTGAGACTTTT

CAACAAAGGGTAATATCCGGAAACCTCCTCGGATTCCATTGCCCAGCTATCTGTCACTTTATTGTGAAG

ATAGTGGAAAAGGAAGGTGGCTCCTACAAATGCCATCATTGCGATAAAGGAAAGGCCATCGTTGAAGAT

GCCTCTGCCGACAGTGGTCCCAAAGATGGACCCCCACCCACGAGGAGCATCGTGGAAAAAGAAGACGTT

CCAACCACGTCTTCAAAGCAAGTGGATTGATGTGATATCTCCACTGACGTAAGGGATGACGCACAATCC

CACTATCCTTCGCAAGACCCTTCCTCTATATAAGGAAGTTCATTTCATTTGGAGAGGTATTAAAATCTT

AATAGGTTTTGATAAAAGCGAACGTGGGGAAACCCGAACCAAACCTTCTTCTAAACTCTCTCTCATCTC

TCTTAAAGCAAACTTCTCTCTTGTCTTTCTTGCGTGAGCGATCTTCAACGTTGTCAGATCGTGCTTCGG

CACCAGTACAATGGCGAAAAACGTTGCGATTTTCGGCTTATTGTTTTCTCTTCTTGTGTTGGTTCCTTC

TCAGATCTTCGCGCAAAAACTTCCTGGAAATGACAATAGCACGGCAACGCTGTGCCTTGGGCACCATGC

AGTACCAAACGGAACGATAGTGAAAACAATCACGAATGACCGAATTGAAGTTACTAATGCTACTGAGCT

GGTTCAGAATTCCTCAATAGGTGAAATATGCGACAGTCCTCATCAGATCCTTGATGGAGAAAACTGCAC

ACTAATAGATGCTCTATTGGGAGACCCTCAGTGTGATGGCTTTCAAAATAAGAAATGGGACCTTTTTGT

TGAACGAAGCAAAGCCTACAGCAACTGTTACCCTTATGATGTGCCGGATTATGCCTCCCTTAGGTCACT

AGTTGCCTCATCCGGCACACTGGAGTTTAACAATGAAAGCTTCAATTGGGCTGGAGTCACTCAAAACGG

AACAAGTTCTTCTTGCATAAGGGGATCTAATAGTAGTTTCTTTAGTAGATTAAATTGGTTGACCCACTT

AAACTCCAAATACCCAGCATTAAACGTGACTATGCCAAACAATGAACAATTTGACAAATTGTACATTTG

GGGGGTTCACCACCCGGGTACGGACAAGGACCAAATCTTCCTGTATGCACAATCATCAGGAAGAATCAC

AGTATCTACCAAAAGAAGCCAACAAGCTGTAATCCCGAATATCGGATCTAGACCCAGAATAAGGGATAT

CCCTAGCAGAATAAGCATCTATTGGACAATAGTAAAACCGGGAGACATACTTTTGATTAACAGCACAGG

GAATCTAATTGCTCCTAGGGGTTACTTCAAAATACGAAGTGGGAAAAGCTCAATAATGAGATCAGATGC

-continued

ACCCATTGGCAAATGCAAGTCTGAATGCATCACTCCAAATGGAAGCATTCCCAATGACAAACCATTCCA

AAATGTAAACAGGATCACATACGGGGCCTGTCCCAGATATGTTAAGCAAAGCACTCTGAAATTGGCAAC

AGGAATGCGAAATGTACCAGAGAGACAAACTAGAGGCATATTTGGCGCAATAGCGGGTTTCATAGAAAA

TGGTTGGGAGGGAATGGTGGATGGTTGGTACGGCTTCAGGCATCAAAATTCTGAGGGAAGAGGACAAGC

AGCAGATCTCAAAAGCACTCAAGCAGCAATCGATCAAATCAATGGGAAGCTGAATCGATTGATCGGGAA

AACCAACGAGAAATTCCATCAGATTGAAAAAGAATTCTCAGAAGTAGAAGGGAGAATTCAGGACCTTGA

GAAATATGTTGAGGACACAAAAATAGATCTCTGGTCATACAACGCGGAGCTTCTTGTTGCCCTGGAGAA

CCAACATACAATTGATCTAACTGACTCAGAAATGAACAAACTGTTTGAAAAAACAAAGAAGCAACTGAG

GGAAAATGCTGAGGATATGGGCAATGGTTGTTTCAAAATATACCACAAATGTGACAATGCCTGCATAGG

ATCAATCAGAAATGGAACTTATGACCACGATGTATACAGGGATGAAGCATTAAACAACCGGTTCCAGAT

CAAGGGAGTTGAGCTGAAGTCAGGGTACAAAGATTGGATCCTATGGATTTCCTTTGCCATATCATCCCT

TGTACTGTTAGTTGCTTTGTTGGGGTTCATCATGTGGGCCTGCCAAAAGGGCAACATTAGGTGCAACAT

TTGCATTTGAAGGCCTATTTTCTTTAGTTTGAATTTACTGTTATTCGGTGTGCATTTCTATGTTTGGTG

AGCGGTTTTCTGTGCTCAGAGTGTGTTTATTTTATGTAATTTAATTTCTTTGTGAGCTCCTGTTTAGCA

GGTCGTCCCTTCAGCAAGGACACAAAAAGATTTTAATTTTATTAAAAAAAAAAAAAAAAAAGACCGGGA

ATTCGATATCAAGCTTATCGACCTGCAGATCGTTCAAACATTTGGCAATAAAGTTTCTTAAGATTGAAT

CCTGTTGCCGGTCTTGCGATGATTATCATATAATTTCTGTTGAATTACGTTAAGCATGTAATAATTAAC

ATGTAATGCATGACGTTATTTATGAGATGGGTTTTTATGATTAGAGTCCCGCAATTATACATTTAATAC

GCGATAGAAAACAAAATATAGCGCGCAAACTAGGATAAATTATCGCGCGCGGTGTCATCTATGTTACTA

GAT

All citations are hereby incorporated by reference.

The present invention has been described with regard to one or more embodiments. However, it will be apparent to persons skilled in the art that a number of variations and modifications can be made without departing from the scope of the invention as defined in the claims.

The invention claimed is:

1. A modified influenza H3 hemagglutinin (HA) protein comprising an amino acid sequence comprising at least one amino acid substitution when compared to a corresponding wildtype amino acid sequence, said at least one amino acid substitution corresponding to positions 382, 384, 524, and 528 of reference sequence SEQ ID NO: 92, and optionally corresponding to positions 392, 431, 525 and/or 526 of reference sequence SEQ ID NO: 92, wherein:

the amino acid substitution corresponding to position 382 of reference sequence SEQ ID NO: 92 is to an alanine or a conserved substitution of alanine, the amino acid substitution corresponding to position 384 of reference sequence SEQ ID NO: 92 is to a valine or a conserved substitution of valine, the amino acid substitution corresponding to position 524 of reference sequence SEQ ID NO: 92 is to a serine or a conserved substitution of serine, the amino acid substitution corresponding to position 528 of reference sequence SEQ ID NO: 92 is to a leucine or a conserved substitution of leucine, the amino acid substitution corresponding to position 392 of reference sequence SEQ ID NO: 92 is to an aspartic acid or a conserved substitution of aspartic acid, the amino acid substitution corresponding to position 431 of reference sequence SEQ ID NO: 92 is to a methionine or a conserved substitution of methionine, the amino acid substitution corresponding to position 525 of reference sequence SEQ ID NO: 92 is to a leucine or a conserved substitution of leucine, and the amino acid substitution corresponding to position 526 of reference sequence SEQ ID NO: 92 is to a valine or a conserved substitution of valine.

2. The modified influenza H3 HA of claim 1, wherein the HA protein further comprises a substitution at amino acids corresponding to positions 525, 526, or 525 and 526 of reference sequence SEQ ID NO: 92.

3. The modified influenza H3 HA of claim 1, wherein:

the conserved substitution of alanine is serine, glycine, threonine, cysteine, or valine;

the conserved substitution of valine is isoleucine, methionine, alanine, or threonine;

the conserved substitution of serine is threonine, alanine, asparagine, aspartic acid, glutamine, glycine, glutamic acid, or lysine; and/or the conserved substitution of leucine is isoleucine, valine, methionine, phenylalanine, or valine.

4. The modified influenza H3 HA of claim 1, wherein:

the conserved substitution of aspartic acid is glutamic acid, glutamine, or serine.

5. The modified influenza H3 HA of claim 1, wherein:

the conserved substitution of methionine is isoleucine, glutamine, valine, or phenylalanine.

6. A nucleic acid encoding the modified influenza H3 HA protein of claim 1.

7. A virus-like particle (VLP) comprising the modified influenza H3 HA protein of claim 1.

8. A method of producing an influenza virus like particle (VLP) in a plant, portion of a plant, or a plant cell, comprising:

a) i) introducing the nucleic acid of claim 6 into the plant, portion of the plant, or plant cell, and optionally introducing a second nucleic acid encoding a proton channel protein; or ii) providing a plant, portion of a plant, or plant cell comprising the nucleic acid of claim 6, and optionally wherein the plant, portion of the plant, or plant cell further comprises a second nucleic acid encoding a proton channel protein;

b) incubating the plant, portion of the plant, or plant cell under conditions that permit expression of the HA protein encoded by the nucleic acid and optionally the proton channel protein encoded by the second nucleic acid, thereby producing the VLP; and c) optionally harvesting the plant, portion of the plant, or plant cell, and purifying the VLP.

9. A VLP produced by the method of claim 8, optionally further comprising one or more than one lipid derived from the plant, portion of the plant, or plant cell, plant-specific N-glycans, modified N-glycans or a combination thereof.

10. A plant, portion of the plant, or plant cell comprising the VLP of claim 7.

11. A composition for inducing an immune response comprising, an effective dose of the VLP of claim 7, and a pharmaceutically acceptable carrier, adjuvant, vehicle or excipient.

12. The VLP of claim 7, for use in inducing immunity to an influenza infection in a subject, wherein the VLP is optionally administered to the subject orally, intranasally, intramuscularly, intraperitoneally, intravenously or subcutaneously.

13. A method of increasing yield of production of an influenza virus like particle (VLP) in a plant, portion of a plant, or a plant cell, comprising:

a) introducing the nucleic acid of claim 6 into the plant, portion of the plant, or plant cell; or providing a plant, portion of a plant, or plant cell comprising the nucleic acid of claim 6;

b) incubating the plant, portion of the plant, or plant cell under conditions that permit expression of the modified influenza HA protein encoded by the nucleic acid, thereby producing the VLP at a higher yield compared to plant, portion of the plant, or plant cell expressing an unmodified influenza HA protein; and c) optionally harvesting the plant, portion of the plant, or plant cell, and purifying the VLP.

14. The method of claim 8, wherein the proton channel protein is an influenza A subtype M2 protein.

15. A modified influenza H3 hemagglutinin (HA) protein comprising amino acid substitutions corresponding to positions 382, 384, 524, and 528 of reference sequence SEQ ID NO: 92, wherein:

the amino acid substitution corresponding to position 382 is to alanine or a conserved substitution of alanine, the amino substitution corresponding to position 384 is to valine or a conserved substitution of valine;

the amino acid substitutions corresponding to position 524 is to serine or a conserved substitution of serine; and the amino acid substitutions corresponding to position 528 is to leucine or a conserved substitution of leucine.

* * * * *